US010443073B2

(12) United States Patent
Hooper

(10) Patent No.: US 10,443,073 B2
(45) Date of Patent: Oct. 15, 2019

(54) SIN NOMBRE VIRUS FULL-LENGTH M SEGMENT-BASED DNA VACCINES

(71) Applicant: The Government of the United States, as represented by the Secretary of the Army, Fort Detrick, MD (US)

(72) Inventor: Jay Hooper, New Market, MD (US)

(73) Assignee: The Government of the United States, as represented by the Secretary of the Army, Fort Detrick, MD (US)

( * ) Notice: Subject to any disclaimer, the term of this patent is extended or adjusted under 35 U.S.C. 154(b) by 0 days.

(21) Appl. No.: 15/081,218

(22) Filed: Mar. 25, 2016

(65) Prior Publication Data

US 2016/0346376 A1 Dec. 1, 2016

Related U.S. Application Data

(63) Continuation of application No. 13/982,606, filed as application No. PCT/US2011/023098 on Jan. 31, 2011, now Pat. No. 9,315,826.

(51) Int. Cl.
| | |
|---|---|
| A61K 39/12 | (2006.01) |
| C12N 15/86 | (2006.01) |
| C07K 14/005 | (2006.01) |
| C07K 16/10 | (2006.01) |
| C12N 7/00 | (2006.01) |
| A61K 39/00 | (2006.01) |

(52) U.S. Cl.
CPC ............ *C12N 15/86* (2013.01); *A61K 39/12* (2013.01); *C07K 14/005* (2013.01); *C07K 16/10* (2013.01); *C12N 7/00* (2013.01); *A61K 2039/53* (2013.01); *A61K 2039/575* (2013.01); *A61K 2039/70* (2013.01); *C12N 2760/12111* (2013.01); *C12N 2760/12121* (2013.01); *C12N 2760/12122* (2013.01); *C12N 2760/12134* (2013.01); *C12N 2760/12143* (2013.01); *C12N 2760/12151* (2013.01)

(58) Field of Classification Search
CPC .......... C12N 15/86; C12N 2760/12134; A61K 39/12
See application file for complete search history.

(56) References Cited

U.S. PATENT DOCUMENTS

| | | | |
|---|---|---|---|
| 4,945,050 | A | 7/1990 | Sanford |
| 5,853,980 | A | 12/1998 | Rollin |
| 5,916,754 | A | 6/1999 | Nichol |
| 5,945,277 | A | 8/1999 | Nichol |
| 6,316,250 | B1 | 11/2001 | Hjelle |
| 6,451,309 | B2 | 9/2002 | Hooper |
| 6,562,376 | B2 | 5/2003 | Hooper |
| 6,620,412 | B2 | 9/2003 | Hooper |
| 7,217,812 | B2 | 5/2007 | Hooper |
| 8,183,358 | B2 | 5/2012 | Hooper |
| 2002/0114818 | A1 | 8/2002 | Schmaljohn |
| 2004/0053216 | A1 | 3/2004 | Hooper |
| 2013/0273170 | A1 | 10/2013 | Hooper |

FOREIGN PATENT DOCUMENTS

| | | |
|---|---|---|
| WO | WO 95/19799 | 7/1995 |
| WO | WO 2004/058808 | 7/2004 |
| WO | WO 2008/100508 | 8/2008 |

OTHER PUBLICATIONS

Maes, P., et al., 2009, Recent approaches in hantavirus vaccine development, Exp. Rev. Vaccines 8(1):67-76.*
Schmaljohn, C., 2009, Vaccines for hantaviruses, Vaccine 27:D61-D64.*
International Search Report, dated Jan. 7, 2013, issued in parallel application PCT US2011/023098, 4 pages.
International Preliminary Report on Patentability, dated Sep. 3, 2013, issued in parallel application PCT US2011/023098, 5 pages.
Bjaradway, et al, "Intramuscular inoculation of Sin Nombre hantavirus cDNAs induces . . . ", Vaccine 17 (1999), pp. 2836-2843.
Bharadway et al., "Genetic vaccines protect against Sin Nombre hantavirus challenge in the deer mouse . . . ", J. General Virology (2002) 83, pp. 1745-1751.
Custer et al., "Active and Passive Vaccination against Hantavirus Pulmonary Syndrome with Andes Virus M Genome . . . ", J. Virology, Sep. 2003, vol. 77, No. 18, pp. 9894-9905.
Hooper et al., "DNA Vaccination with the Hantaan Virus M Gene Protects Hamsters . . . ", J. Virology, Sep. 2001, No. 75, Nov. 18, pp. 8469-8477.
Hooper et al., "Immuno Serum Produced by DNA Vaccination Protects Hamsters . . . ", J. Virology, Feb. 2008, vol. 82, No. 3, pp. 1332-1338.
Whal-Jensen et al., "Temporal Analysis of Andes Virus and Sin Nombre Virus . . . " J. Virology, 81(4), May 2, 2007, pp. 7449-7462.
Barry and Johnston, "Biological features of genetic immunization," Vaccine, vol. 15, No. 8, 1997, pp. 788-791.
Gurunathan et al., "DNA Vaccines: Immunology, Application, and Optimization," Annu. Rev.Immunol., 2000, 18:927-974.
Klinman et al., "Contribution of Cells at the Site of DNA Vaccination to the Generation . . . ", J. Immuno., 1998, 160:2388-2392.
Steele et al, "Cutaneous DNA Vaccination Against Ebola Virus", Veterinary Pathology 2001, 38:203-215.
Yoshida et al., "Advantage of gene gun-mediated over intramusculare inoculation of plasmid DNA . . . ", Vaccine 18 (2000) pp. 1725-1729.
Fuller et al., "Preclinical and clinical progress of particle-mediated DNA vaccines . . . ", Science Direct Methods 40 (2006), pp. 86-97.
Brocato et al., "Construction and Nonclinical Testing of a Pujmala Virus Sunthetic M Gene-Based . . . ", Clin. Vaccine Immunol. 2013, 20(2), 218 et seq.

(Continued)

*Primary Examiner* — Jeffrey S Parkin
(74) *Attorney, Agent, or Firm* — Nash and Titus, LLC

(57) ABSTRACT

The invention contemplates a new synthetic, codon-optimized Sin Nombre virus (SNV) full-length M gene open reading frame (ORF) that encodes a unique consensus amino acid sequence. The SNV ORF was cloned into a plasmid to form the first stable recombinant SNV full-length M gene that elicits neutralizing antibodies. The gene can be engineered into a vaccine system, and is useful to protect mammals against infection with Sin Nombre virus.

9 Claims, 14 Drawing Sheets

Specification includes a Sequence Listing.

(56) References Cited

OTHER PUBLICATIONS

Hammerbeck et al., Chap. 23—Hatavirus, in Vaccines for Biodefense and Emerging and Neglected Diseases, 2008, Elsevier Inc., pp. 377-409.
Hooper et al., "Hantaan/Andes virus DNA vaccine elecits a broadly cross-reactive . . . ", Virology 347 (2006), pp. 208-216.
Jonsson et al., "Treatment of hantavirus pulmonary syndrome", Science Direct Antiviral Research 78 (2008) pp. 162-169.
Hooper et al., "A novel Sin Nombre virus DNA vaccine and its inclusion in a candidate pan-hantavirus . . . ", Vaccine 31 (2013), pp. 4314-4321.
Hooper et al., "DNA Vaccination with Hantavirus M Segment Elecits Neutralizing Antibodies . . . ", Virology 255 (1999), pp. 269-278.
McElroy et al., "Andes virus M genome segment is not sufficient to confer the virulence . . . ", Science Direct Virology 326 (2004) pp. 130-139.
Brocato et al., "DNA Vaccine-Generated Duck Polyclonal Antibodies as a Postexposure . . . ", PLoS ONE, vol. 7, No. 4, Apr. 2012, pp. 1-11.
Ray et al., "Study of Andes virus entry and neutralization using a pseudoviron system", J. Virological Methods 163 (2010), pp. 416-423.
Schmaljohn and Hjelle, 1997, Emerg. Infect. Dis., vol. 3, pp. 95-104.
Schmaljohn et al., 1996, In the Bunyaviridae Ed. R. M. Elliott, New York Plenum Press, pp. 63-90.
Lee et al., 1990, Arch, Virol., Suppl 1, pp. 35-47.
Song et al., 1992, Vaccine 10, pp. 214-216.
Lu et al., 1996, J. Med. Virol., 49, pp. 333-335.
Schmaljohn et al., 1990, J. Virol. 64, pp. 3162-3170.
Schmaljohn et al., 1992, Vaccine 10, pp. 10-13.
Xu et al., 1992, Am. J. Trop. Med. Hyg., vol. 47, pp. 397-404.
Yoshimatsu et al., 1993, Arch. Virol., vol. 130, pp. 365-376.
Lundkvist et al., 1996, Virology 216, pp. 397-406.
Ulrich et al., 1998, Vaccine 16, pp. 272-280.
Schmaljohn and Nichols, 2001, Current Topics in Microbiology and Immunology, Hantaviruses, vol. 256, pp. 171-191.
Chu et al., 1995, J. Virol., vol. 69, pp. 6417-6423.
Arikawa et al., 1992, J. Gen. Virol., vol. 70, pp. 615-624.
Eisenbraun, et al., 1993, DNA Cell. Biol., vol. 12, pp. 791-797.
Fynan et al., 1993, PNAS USA, vol. 90, pp. 11478-11482.
Haynes et al., 1994, AIDS Res.Hum.Retrovirusues, vol. 10, Supple 2:S43.
Pertmer et al., 1995, Vaccine vol. 13, p. 1427 et seq.
Bos, J.D., 1997, Clin.Exp.Immunol., vol. 107, suppl. 1:3.
Labuda et al., 1996, Virology, 219:357.
Rambukkana et al., 1995, Lab. Invest. 73:521.
Stingl, G., 1993, Recent Results Cancer Res., 128:45.
Evans et al., Vaccine, 2009, vol. 27(18), pp. 2506-2512.
Yager et al., Expert Rev. Vaccines, 2009, vol. 8(9), pp. 1205-1220.
Robinson and Torres, 1997, Semin. Immunol. 9, pp. 271-283.
Gregoriadis, 1998, Pharm. Res. 15, pp. 661-670.
Van Drunen et al., Expert Rev. Vaccines, 2010, vol. 9(5), pp. 503-517.
Condon et al., DNA-based immunization by in vivo trasfection of dendritic cells, Nat. Med., 1996, 10:1122-1128.
Monteiro-Riviere et al., The pig as a model for . . . , In: tumbleson MD, Schook, LB (eds). Advances in Swine in Biomedical Res., vol. 2. New York, Plemum Press, 1996, 425-458.
Draize et al., Methods for the study of irritation . . . , J. Pharmacol. Exp. Ther., 1994, 82:377-390.
Charles River Lab., Arkansas Div., Assessment of the Local Skin Reactivity . . . ,Final Study report for Protocol No. JTA00001 (2005).
Pertmer et al., Vaccine, 1995, 219:357.
Maes et al., Viral Immunology, 2008, 21(1):49-60.
Maes et al., Expert Review Vaccines, 2009, 8(1):67-76.
Xu et al., Am. J. Trop. Med. Hyg., 47(4), 1992, pp. 397-404.
Hammerbeck, C.D., et al.,Hatavirus. In: Vaccines for Biodefense and Emerging and Neglected Diseases A.D.T. Barrett and L.R. Stanberry, Eds.) London, pp. 379-411 (2009).
Kwilas et al., A hantavirus pulmonary syndrome (HPS) DNA vaccine delivered . . . Curr.Gene Ther. 14(3):200-10 (2014).
Hooper et al., "DNA vaccine-derived human IgG produced in transchromosomal bovines protect in lethal models . . . " Sci Transl. Med. 6(264):264ra162 (2014).
Haese et al., "Antiviral biologic produced in DNA vaccine/goose platform . . . " PLoS Negl Trop Dis 9(6):e0003803 (2015).
Safronetz et al., "Pathophysiology of hantavirus pulmonary syndrome in rhesus macaques", PNAS vol. 111, No. 19 (2014).

\* cited by examiner

Fig. 1A

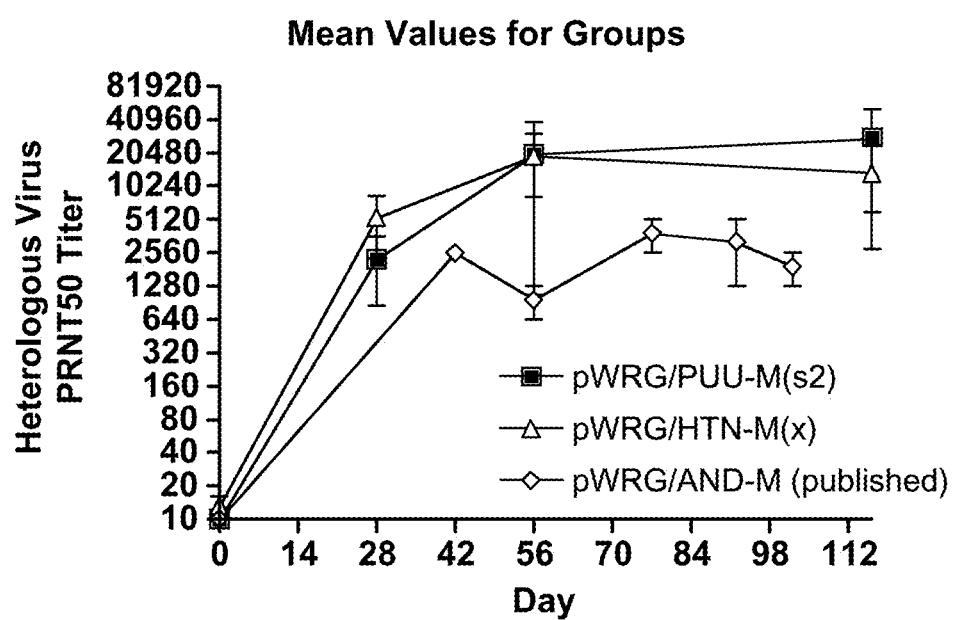

Fig. 1C plasmid: pWRG/SN-M(2a)

- 3244
- 3245
- 3246 plasmid: pWRG/SN-M(opt)

- 6281
- 6282
- 6283
- 6284

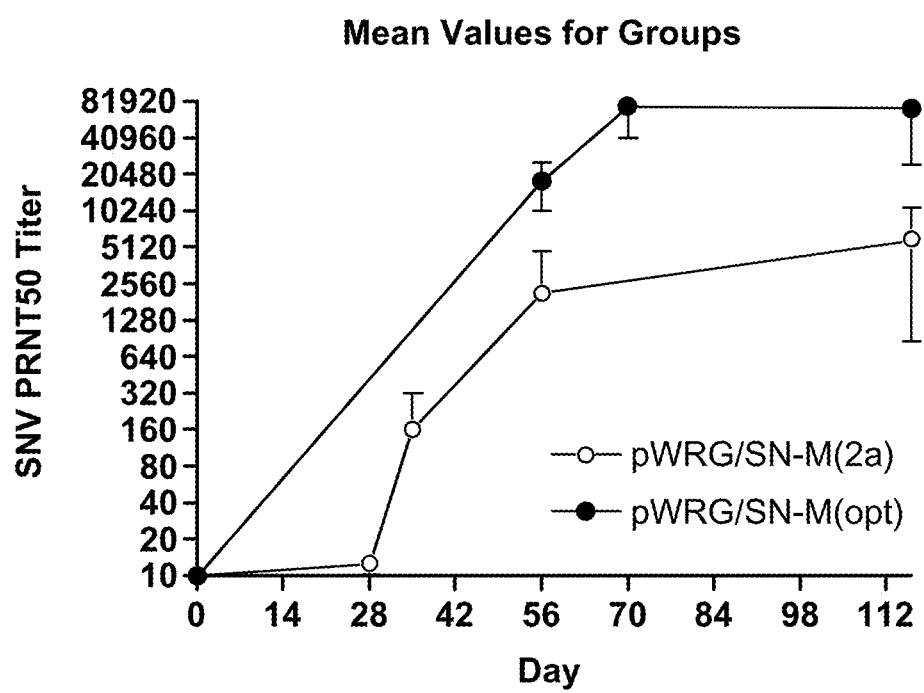

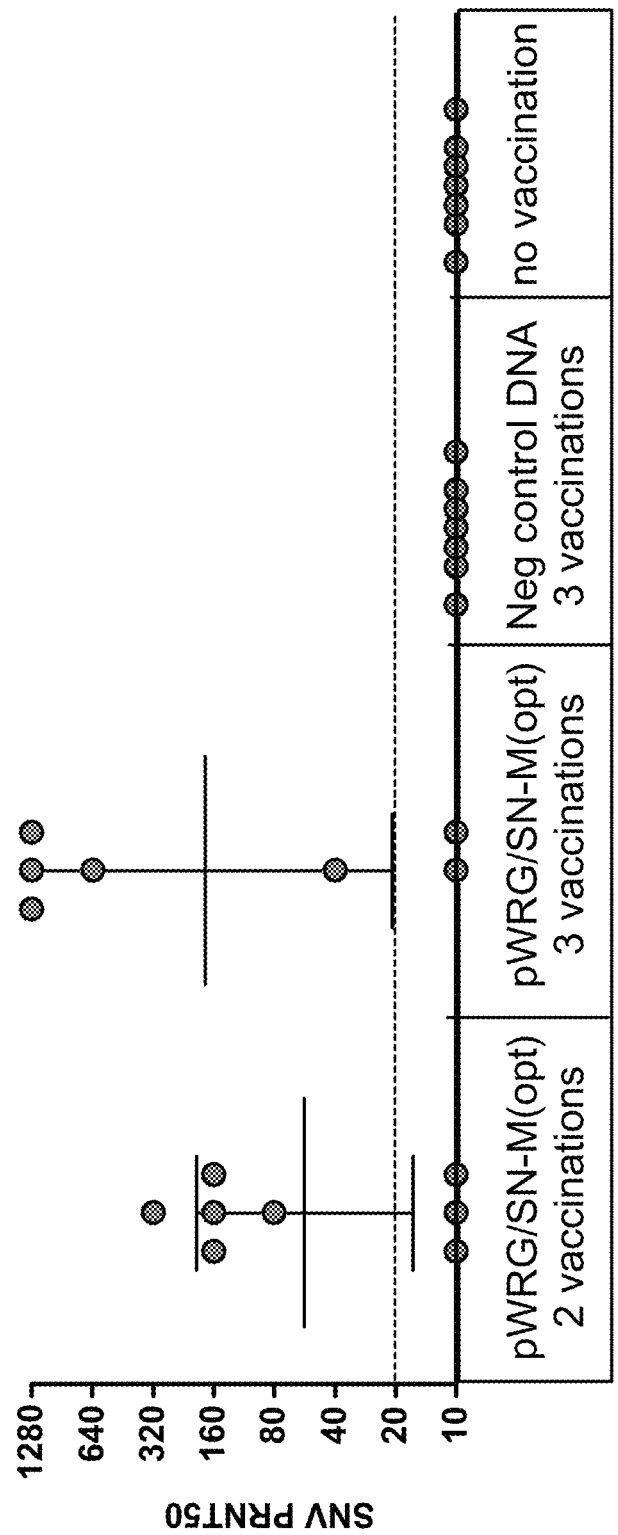

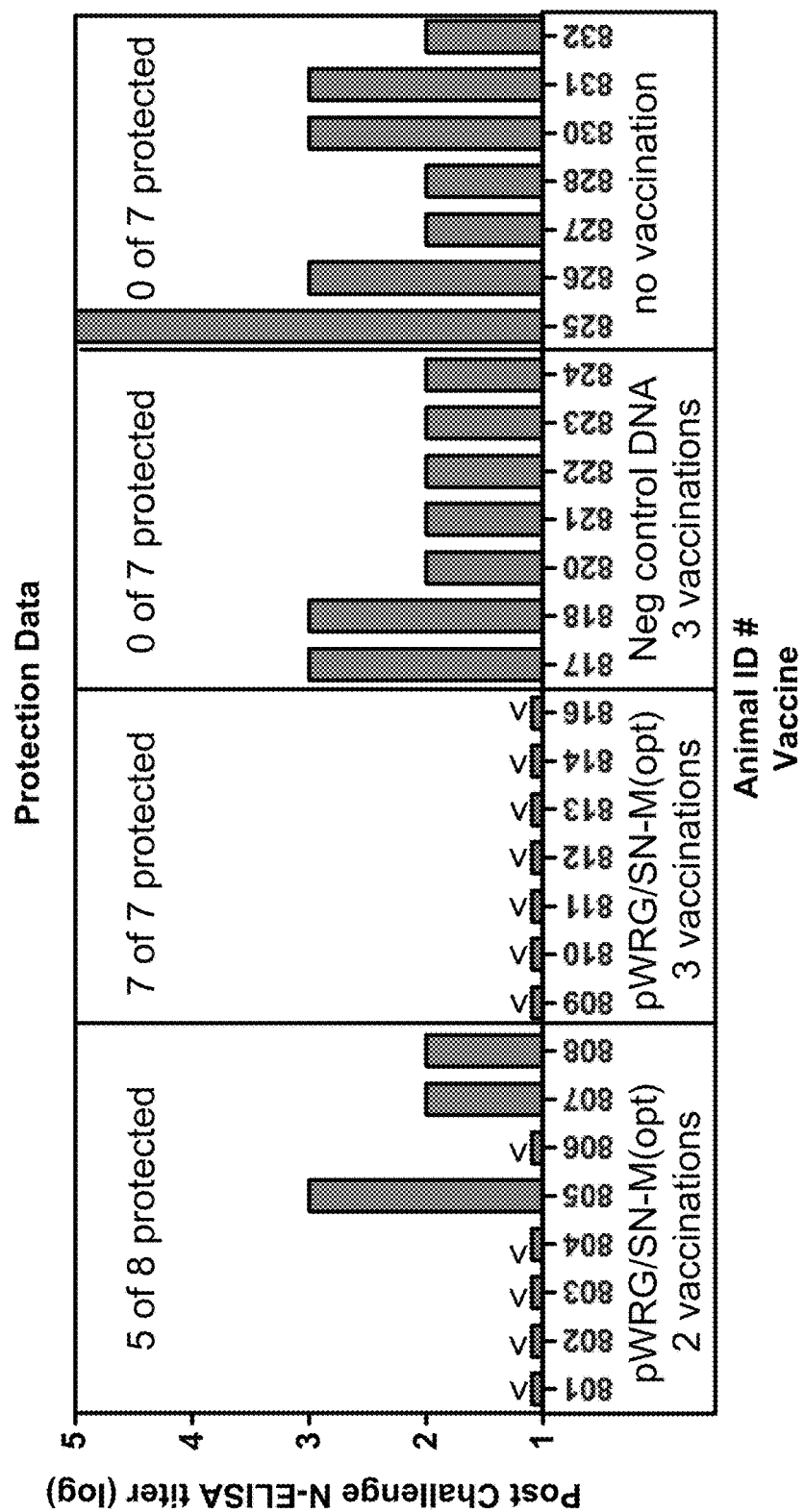

Fig. 7

Pseudovirons made with pWRG/SN-M(opt) are neutralized by SNV immune sera

- ■ Naive rabbit sera
- △ anti-VSV-G
- ○ anti-SNV rabbit sera

Pseudovirion prep 1

Pseudovirion prep 2

Reciprocal Antibody Dilution

SIN NOMBRE VIRUS FULL-LENGTH M SEGMENT-BASED DNA VACCINES

BACKGROUND OF THE INVENTION

Hantaviruses are considered Category A Priority Pathogens by the National Institute of Allergies and Infectious Disease. These viruses cause a spectrum of vascular-leak syndromes including hantavirus pulmonary syndrome (HPS) and hemorrhagic fever with renal syndrome (HFRS). Many HPS and HFRS hantaviruses pose a natural threat to persons working, living or traveling in endemic regions, including military personnel. There is one hantavirus (Andes virus) that has unique properties that make amenable to use as a biological weapon.

Andes virus (ANDV) and Sin Nombre virus (SNV) are the predominant causes of HPS in South and North America, respectively. These rodent-borne viruses were discovered in the early 1990's and have caused severe disease in several hundred persons.

Since the discovery of SNV in 1993, it has caused severe disease in ~500 persons in the United States and Canada, resulting in ~200 deaths (35% case-fatality rate). SNV is carried by the deer mouse and transmitted via inhalation or ingestion of contaminated secreta/excreta, or by rodent bite. Most of the fatalities occurred in previously healthy working-age males. HPS is a disease with rapid onset, and rapid progression from mild to severe disease (i.e., can occur over the weekend). The disease begins as an influenza-like illness including fever, headache, nausea, cough, and can progress rapidly to respiratory failure and cardiogenic shock. There is no specific therapeutic or vaccine to treat or prevent HPS. Hammerbeck, C. D., Wahl-Jensen, V., Hooper, J. W. Hantavirus. In: Vaccines for Biodefense and Emerging and Neglected Diseases (A. D. T. Barrett and L. R. Stanberry, Eds.), pp. 379-411. London: Academic Press, 2009; Jonsson C. B, J. Hooper, and G. Mertz (2008). Treatment of hantavirus pulmonary syndrome. Antiviral Res. Antiviral Res. 78:162-169.

There is no population with pre-existing immunity to SNV or ANDV and this virus is lethal in 35-40% of the people it infects. Note that this 35-40% case-fatality rate occurs despite treatment in modern intensive care units. All ages and both sexes are susceptible to ANDY and SNV. Most cases occur in previously healthy working-age males. The incubation period is approximately two weeks. Disease onset-to-death is rapid (over the weekend). In an animal model of HPS (Syrian hamsters), ANDY is highly lethal by all routes tested including the oral route. SNV is highly infectious (infectious dose 50% is 2 plaque forming units in Syrian hamsters but does cause lethal disease (Hooper et al., 2001). Thus, an infection model, rather than a lethal disease model, is used to evaluate medical countermeasures to prevent SNV infection.

New-World hantaviruses have been associated with outbreaks of a highly lethal disease, hantavirus pulmonary syndrome (HPS), in the Americas (reviewed in Schmaljohn and Hjelle, 1997, Emerg. Infect Dis. 3, 95-104). The disease is characterized by fever and vascular leakage resulting in non-cardiogenic pulmonary edema followed by shock. Case-fatality for HPS caused by the most prevalent North American and South American hantaviruses, Sin Nombre virus (SNV) and Andes virus (ANDY), respectively is 30-50%.

Currently, there are four known hantaviruses associated with hemorrhagic fever with renal syndrome (HFRS): Hantaan virus (HTNV), Dobrava-Belgrade virus (DOBV), Puumala virus (PUUV), and Seoul virus (SEOV). Because distinct hantaviruses are usually carried by only one principal rodent host species, their distribution is generally limited to the range of that host (reviewed in Schmaljohn and Hjelle, 1997, Emerg. Infect. Dis. 3, 95-104). HTNV, carried by *Apodemus agrarius*, is found in Asia; DOBV, carried by *Apodemus flavicollis*, and PUUV, carried by *Clethrionomys glareolus*, are found in Europe. SEOV is more widely disseminated than any other recognized hantaviruses because its host, the common urban rat (*Rattus norvegicus*), is found throughout the world.

There is an alarming paucity of existing medical countermeasures to prevent or treat HPS. There is no vaccine against SNV, ANDY or any other HPS-associated hantavirus. Moreover, aside from basic research, there are no funded HPS vaccine development efforts. There is no specific drug to prevent or treat HPS. The treatment for HPS is extracorporeal membrane oxygenation therapy (ECMO) with costs as much as $500,000 per patient. Expertise at performing adult ECMO resides at only a few hospitals in the world. Thus, we are poorly prepared to deal with naturally occurring HPS cases (there have been ~2500 cases including ~500 in the US since 1993), or the use of hantaviruses as biological weapons.

Viruses in the Hantavirus genus (family Bunyaviridae) are enveloped and contain a genome comprised of three single-stranded RNA segments designated large (L), medium (M), and small (S) based on size (reviewed in Schmaljohn, 1996, In *The Bunyaviridae* Ed. R. M. Elliott. New York, Plenum Press p. 63-90). The hantavirus L segment encodes the RNA dependent RNA polymerase, M encodes two envelope glycoproteins (G1 and G2, also known as $G_n$ and $G_c$), and S encodes the nucleocapsid protein (N).

A number of inactivated HFRS vaccines derived from cell culture or rodent brain were developed and tested in Asia (Lee et al., 1990, Arch. Virol., Suppl. 1, 35-47; Song et al., 1992, Vaccine 10, 214-216; Lu et al., 1996, J. Med. Virol. 49, 333-335). Drawbacks of these traditional killed-virus vaccines include a requirement for appropriate containment for the growth and manipulation of virus, and the necessity to ensure complete inactivation of infectivity without destroying epitopes on the virion important for protective immunity. In order to overcome these drawbacks, vaccine approaches involving recombinant DNA technology were developed including: vaccinia-vectored vaccines (Schmaljohn et al. 1990, J. Virol. 64, 3162-3170; Schmaljohn et al. 1992, Vaccine 10, 10-13; Xu et al. 1992, Am. J. Trop. Med. Hyg. 47, 397-404), protein subunit vaccines expressed in bacteria or insect cells (Schmaljohn et al. 1990, supra; Yoshimatsu et al., 1993, Arch. Virol. 130, 365-376; Lundkvist et al., 1996, Virology 216, 397-406), and a hepatitis core antigen-based recombinant vaccine (Ulrich et al., 1998, Vaccine 16, 272-280). For a review of hantavirus vaccine efforts see the review by Hooper and Li (Hooper and Li, 2001); Hammerbeck, C. D., Wahl-Jensen, V., Hooper, J. W. Hantavirus. In: Vaccines for Biodefense and Emerging and Neglected Diseases (A. D. T. Barrett and L. R. Stanberry, Eds.), pp. 379-411).

Vaccination with vaccinia recombinants expressing the M segment of either HTNV or SEOV elicited neutralizing antibodies and protected rodents against infection with both HTNV and SEOV, suggesting that an immune response to Gn-Gc alone can confer protection (Schmaljohn et al. 1990, supra; Xu et al. 1992, supra; Chu et al. 1995, J. Virol. 69, 6417-6423). Similarly, vaccination with Gn-Gc protein expressed in insect cells (baculovirus recombinant virus system) elicited neutralizing antibodies and protected hamsters from infection with HTNV (Schmaljohn et al. 1990, supra). In both the vaccinia and baculovirus systems, vaccination with Gn-Gc provided more complete protection than Gn or Gc alone (Schmaljohn et al. 1990, supra). There are reports that candidate DNA vaccines comprised of around 500 nucleotide stretches of the Sin Nombre virus (SNV) M gene, or the full-length S gene, are immunogenic in mice (Bharadwaj, et al., 1999, Vaccine 17, 2836, 43) and conferred some protection against infection with SNV in a deer mouse infection model (Bharadwaj, et al., 2002, J. Gen. Virol. 83, 1745-1751). The protection was surmised to be cell-mediated because there was no convincing evidence that these constructs elicited a neutralizing, or otherwise protective, antibody response.

There have been several publications reporting the successful use of plasmid DNA vaccines containing the full-length M gene of SEOV, HTNV, ANDV, including the following reports:
1. Hooper, J. W., K I Kamrud, F. Elgh, D. Custer, and C. S. Schmaljohn (1999). DNA vaccination with hantavirus M segment elicits neutralizing antibodies and protects against Seoul virus infection. Virology, 255:269-278.
2. Hooper, J. W., D. Custer, E. Thompson, and C. S. Schmaljohn (2001). DNA Vaccination with the Hantaan virus M gene protects hamsters against three of four HFRS hantaviruses and elicits a high-titer neutralizing antibody response in rhesus monkeys. Journal of Virology 75:8469-8477.
3. Custer, D. M., E. Thompson, C. S. Schmaljohn, T. G. Ksiazek, and J. W. Hooper (2003). Active and passive vaccination against hantavirus pulmonary syndrome using Andes virus M genome segment-based DNA vaccine. Journal of Virology 79:9894:9905.
4. Hooper, J. W., D. M. Custer, J. Smith, and Victoria Wahl-Jensen. Hantaan/Andes virus DNA vaccine elicits a broadly cross-reactive neutralizing antibody response in nonhuman primates (2006). Virology 347:208-216.

In all cases high titer neutralizing antibodies were detected in animals (including nonhuman primates) vaccinated with the full-length M gene DNA vaccines, and protection from infection was achieved in rodent models. Neutralizing antibody responses to Gn-Gc in the aforementioned vaccine studies correlated with protection, suggesting that neutralizing antibodies not only play an important role in preventing hantavirus infection, but also might be sufficient to confer protection. Passive transfer of neutralizing monoclonal antibodies (MAbs) specific to either Gn or Gc protected hamsters against HTNV infection (Schmaljohn et al., 1990, supra; Arikawa et al., 1992, *J. Gen. Virol.* 70, 615-624), supporting the idea that neutralizing antibodies alone can confer protection. This is further supported by the finding that serum from nonhuman primates vaccinated using a gene gun with DNA vaccines containing the HTNV or ANDY full-length M genes protected hamsters from infection with HTNV or lethal disease caused by ANDY Custer, D. M., E. Thompson, C. S. Schmaljohn, T. G. Ksiazek, and J. W. Hooper (2003). Active and passive vaccination against hantavirus pulmonary syndrome using Andes virus M genome segment-based DNA vaccine. Journal of Virology 79:9894:9905). Similarly, sera from rabbits vaccinated with the ANDY M gene-based DNA vaccine using electroporation protected hamsters from a lethal challenge with ANDY (Hooper J. W., A. M. Ferro, and V. Wahl-Jensen Immune Serum Produced by DNA Vaccination Protects Hamsters Against Lethal Respiratory Challenge with Andes Virus (2008). Journal of Virology 82:1332-1338.)

Hitherto, attempts to produce vaccines that produce neutralizing antibodies against SNV have been unsuccessful. For instance, Hjelle et al. (U.S. Pat. No. 6,316,250) attempted to vaccinate with the entire SNV Gn or fragments of G1 to generated antibodies. However, their vaccine did not produce high titer neutralizing antibodies. There are currently no serious efforts to develop an HPS vaccine anywhere in the world, including SNV vaccine. (refs 17, 18 below) NIH is currently funding a handful of academic laboratories working on hantavirus basic research.

The inventors have produced DNA vaccines against other hantaviruses including Seoul virus (SEOV), Hantaan virus, (HTNV) Puumala virus (PUUV) and Andes virus (ANDY) (refs 1, 5 and 6 below). There are a number of issued and pending patents related to these vaccines (refs 23-26 below). SEOV, HTNV, and PUUV cause hemorrhagic fever with renal syndrome (HFRS). All of these DNA vaccines are based on the full-length M gene open reading frame that encodes the Gn and Gc proteins, and all of these vaccines elicit neutralizing antibodies in animal models. Neutralizing antibodies produced by DNA vaccination have been shown to protect against infection and disease in passive transfer studies (refs 3,4 below). In addition, the Hantaan and Puumala DNA vaccines have been tested in a phase 1 clinical trial (ongoing). The immunogenicity data generated in this phase 1 trial demonstrates that DNA vaccines against hantaviruses were capable of eliciting neutralizing antibodies in humans. This was the first time hantavirus neutralizing antibodies have been produced in humans using plasmid DNA. The overall seroconversion rate in this phase 1 trial was 43% (12 of 28). One of the most notable findings was that very high titers of neutralizing antibodies were achievable. Two of the peak anti-Hantaan virus titers were >1,000 and four of the peak anti-Puumala virus titers were >1,000. Neutralizing antibody titers as high as 10,240 were achieved for both Hantaan virus and Puumala virus.

The antibody response elicited by the hantavirus M gene-based DNA vaccines have been shown to cross-neutralize some, but not other hantaviruses. For example, the HTNV DNA vaccine was shown to elicit neutralizing antibodies against Seoul virus and Dobrava virus (a major cause of HFRS in the Balkans)(ref 1 below). In some cases the cross-neutralizing antibody response is produced in certain species using certain delivery technologies, but not others. This was the case with our ANDY DNA vaccine. When nonhuman primates were vaccinated with the ANDY DNA vaccine using a gene gun the sera contained antibodies that not only neutralized ANDY but also neutralized SNV and Black Creek Canal virus (ref. 3 below). Based on those results we concluded that the development of a SNV-specific DNA vaccine was unnecessary. However, recently we found that when rabbits were vaccinated with the ANDY DNA vaccine using muscle electroporation the sera was unable to neutralize SNV despite exhibiting very high titer ANDY-neutralizing activity (ref 4 below). It is speculated that this could be due to antibody specificity differences, antibody avidity differences, or antibody isotype differences.

This finding prompted us to reinitiate the development of a SNV M gene-based DNA vaccine rather than depend on the ANDY DNA vaccine to cross-protect against SNV.

The inventor is named as an inventor on other U.S. patents and publications, related to vaccines for hantaviruses and poxviruses, namely U.S. Pat. Nos. 6,451,309; 6,620,412; 6,562,376, 7,217,812, and U.S. Patent application publication US-2010-03203024 A1. The entire contents of these patents are incorporated herein by reference.

SUMMARY OF THE INVENTION

Key to the invention is a novel synthetic, codon-optimized Sin Nombre virus full-length M gene open reading frame (ORF). To date, there are no reports of a full-length M gene, or SNV M gene ORF, being successfully engineered into a DNA vaccine plasmid or other mammalian expression vector. This SNV M gene DNA sequence has been altered (or optimized) in such a way as to increase the stability of the mRNA and to, theoretically, eliminate sequences that destabilize the plasmid in E. col. In addition, four amino acids that were unique to our full-length clone were changed to consensus amino acids based on alignments with five hantavirus M gene sequences from GeneBank. The ORF nucleic acid sequence was changed without altering the coded amino acid sequence of the Sin Nombre M gene product, other than the four aforementioned amino acids. This was accomplished by codon optimizing the ORF. The process of codon optimization not only changed the nucleic sequence, but also it was intended to allow more efficient codon usage and increased stability of the mRNA produced by the plasmid. An algorithm called GeneOptimizer (patent pending), owned by GeneArt was used to allow more efficient codon usage and stabilization of the mRNA. It is noted that, while the ORF was codon optimized, the flanking sequence was unchanged.

This synthetic M gene has been engineered into a plasmid-based vaccine system, (i.e, pWRG/SN-M(opt)), and is believed could be subcloned into a virus-vectored vaccine. The preferred DNA plasmid containing this sequence is designated pWRG/SN-M(opt), and its DNA sequence is described in detail below. pWRG/SN-M(opt) is capable of eliciting good neutralizing antibody responses against Sin Nombre virus. In fact, pWRG/SN-M(opt), as a DNA vaccine delivered by gene gun, is the first vaccine of any kind that has elicited convincing levels of neutralizing antibodies against Sin Nombre virus in animals.

The development of this novel SNV full-length M segment and its use as a vaccine can be summarized as follows. As mentioned above, it had been hoped that an Andes virus M gene-based DNA vaccine would cross—neutralize with the other HPS virus, Sin Nombre virus. In fact, early results gave indication that this would be the case. When nonhuman primates were vaccinated with the ANDY DNA vaccine using a gene gun the sera contained antibodies that not only neutralized ANDY but also neutralized SNV and Black Creek Canal virus (6). Based on those results the inventor concluded that the development of a SNV-specific DNA vaccine was unnecessary. However, recently the inventor found that when rabbits were vaccinated with the ANDY DNA vaccine using muscle electroporation the sera was unable to neutralize SNV despite exhibiting very high titer ANDY-neutralizing activity (11). The data is published in Hooper J. W., A. M. Ferro, and V. Wahl-Jensen Immune Serum Produced by DNA Vaccination Protects Hamsters Against Lethal Respiratory Challenge with Andes Virus (2008). Journal of Virology 82:1332-1338. The inventor realized that the ANDY DNA vaccine would not be suitable as a vaccine to cross-protect against SNV, so sought a vaccine specifically for SNV.

The inventor cloned the full-length M gene from SNV, strain CC107 into a DNA vaccine vector, producing a plasmid with an intact open reading frame—pWRG/SN-M (2a). pWRG/SNV-M(2a) was tested for immunogenicity in rabbits, and it was discovered that high-titer neutralizing antibodies were produced after 4 vaccinations. This represented the first time high-titer SNV neutralizing antibodies were ever produced by any vaccine.

However, it required more vaccinations than the inventor would have preferred, so pWRG/SNV-M(2a) was re-designed for optimization. It was found that the M gene sequence in pWRG/SNV-M(2a) produced amino acids that were unique to our clone (i.e., not in published GeneBank SNV M sequences). This is shown in the Table 1 below, by identifying possible cloning errors in pWRG/SN-M(2a) M gene ORF and determining consensus amino acid sequence. In Table 1, SN-M(2a) is the amino acid sequence of the SNV M open reading frame (ORF) cloned into pWRG/SN-M(2a). This sequence as aligned with several SNV M gene ORFs from Genebank: AAA68036 (SNV strain CC107), AAA68036 (SNV strain CC107 isolate 74), NP_941974 (SNV strain NMH10), 083887 (New York virus), AAC54561 (NY-2 virus), and AC54559 (Rhode Island 1 virus). The four amino acids so identified were changed to the consensus amino acids in the synthetic gene cloned into pWRG/SN-N(opt), see below.

These consensus amino acids were identified at these positions and then an optimized version of this gene was synthesized. Next, we cloned the synthetic M gene (SN-M (2a)) into a DNA vaccine vector and named the plasmid pWRG/SN-M(opt). This plasmid pWRG/SN-M(opt) was deposited on Jan. 26, 2011 in the American Type Culture Collection, located at 10801 University Blvd. Manassas, Va. 20110. The deposit was made under the terms of the Budapest Treaty.

Table 2 shows the nucleic acid differences between the original cloned M gene (SN-M[2a]) and the optimized M gene (SN-M[opt]).

TABLE 1

The amino acid sequence encoded by the ORF cloned into pWRG/SN-M(2a) was aligned with six SNV M sequences from genebank (accession numbers are shown). There were four positions (the first "Q" in line 1; the first "A" in the line beginning with nucleic acid 241; the first "G" in the line beginning with nucleic acid 421; and the third "P" in the line beginning with nucleic acid 481) that were unique to the cloned ORF (highlighted in bold type and underlined). These amino acids were changed to the consensus amino acids when the new gene was synthesized to produce pWRG/SN-M(opt).

```
SN-M(2a)    1   MVGWVCIFLVVLTTATAGLTRNLYELQIECPHTVGLGQGYVTGSVETTPILLTQVADLKI
AAA6800     1   ................................K...........................
AAA68036    1   ................................K...........................
NP_941974   1   ................................K....................I......
Q83887      1   .......S....A.T.................K..........................T....
AAC54561    1   ...F........A.T.................K..................G.........T....
```

TABLE 1-continued

The amino acid sequence encoded by the ORF cloned into pWRG/SN-M(2a) was aligned with six SNV M sequences from genebank (accession numbers are shown). There were four positions (the first "Q" in line 1; the first "A" in the line beginning with nucleic acid 241; the first "G" in the line beginning with nucleic acid 421; and the third "P" in the line beginning with nucleic acid 481) that were unique to the cloned ORF (highlighted in bold type and underlined). These amino acids were changed to the consensus amino acids when the new gene was synthesized to produce pWRG/SN-M(opt).

```
AAC54559    1   ...........A.T..........K.............................T....
consensus   1   ***.***.****.*.************.*******************.********.****

SN-M(2a)   61   ESSCNFDLHVPATTTQKYNQVDWTKKSSTTESTNAGATTFEAKTKEVNLKGTCNIPPTTF
AAA6800    61   ............................................................
AAA68036   61   ............................................................
NP_941974  61   .............................................I..............
Q83887     61   ...........S.SI......E.A.........S..............S........V...
AAC54561   61   ...........S.SI......E.A.........S..............S........V...
AAC54559   61   ...........S.SI......E.A.........S..............S........V...
consensus  61   ***********.*..******.*.*********.*************..********.***

SN-M(2a)  121   EAAYKSRKTVICYDLACNQTHCLPTVHLIAPVQTCMSVRSCMIGLLSSRIQVIYEKTYCV
AAA6800   121   ............................................................
AAA68036  121   ...F........................................................
NP_941974 121   ............................................................
Q83887    121   ............................................................
AAC54561  121   ............................................................
AAC54559  121   ...................Y........................................
consensus 121   ***.********************.***********************************

SN-M(2a)  181   TGQLIEGLCFIPTHTIALTQPGHTYDTMTLPVTCFLVAKKLGTQLKLAVELEKLITGVSC
AAA6800   181   ............................................................
AAA68036  181   ............................................................
NP_941974 181   ............................................................
Q83887    181   ....V.......................I...........I...........ASG.
AAC54561  181   ....V.......................I...........I...........AGG.
AAC54559  181   ....V.......................I...........I...........ASG.
consensus 181   ****.*************************.***************.*********...*

SN-M(2a)  241   AENSFQGYYICFIGKHSEPLFVPTMEDYRSAELFTRMVLNPRGEDHDPDQNGQGLMRIAG
AAA6800   241   T...........................................................
AAA68036  241   T...........................................................
NP_941974 241   T...........................................................
Q83887    241   T..........L..........M.D....................................
AAC54561  241   T..........L..........M.D....................................
AAC54559  241   T..........L........S..M.D....................................
consensus 241   .**********.*******.**.*********************************

SN-M(2a)  301   PVTAKVPSTETTETMQGIAFAGAPMYSSFSTLVRKADPEYVFSPGIIAESNHSVCDKKTV
AAA6800   301   ............................................................
AAA68036  301   ............................................................
NP_941974 301   ............................................................
Q83887    301   .I......................................D..................I
AAC54561  301   .I..........A...........................D..................I
AAC54559  301   .I..................T...................D..................AI
consensus 301   *.**********.**********.***************.******************..

SN-M(2a)  361   PLTWTGFLAVSGEIERITGCTVFCTLAGPGASCEAYSETGIFNISSPTCLVNKVQKFRGS
AAA6800   361   ............................................................
AAA68036  361   ............................................................
NP_941974 361   ..............K.............................................
Q83887    361   ..............K..............V..............................
AAC54561  361   ..............K..............V..............................
AAC54559  361   ..............K..............V......K......................
consensus 361   **************.***********.******.**************************

SN-M(2a)  421   EQRINFMCQRVDQGVVVYCNGQKKVILTKTLVIGQCIYTFTSLFSLIPGVAHSLAVELCV
AAA6800   421   .............D..............................................
AAA68036  421   .............D..............................................
NP_941974 421   .............D..............................................
Q83887    421   .............D.I.............................................
AAC54561  421   .............D.I.............................................
AAC54559  421   .............D.I................I............................
consensus 421   *************.*.*********************************************

SN-M(2a)  481   PGLHGWATTALLITTCFGWLLIPTVTLIILKILRLLITPCSHYSTESKFKVILERVKVEY
AAA6800   481   ..............................................S.............
AAA68036  481   ..............................................S.............
NP_941974 481   ...................A..........................S.............
Q83887    481   ........................I.M...................S...........A.
```

TABLE 1-continued

The amino acid sequence encoded by the ORF cloned into pWRG/SN-M(2a) was aligned with six SNV M sequences from genebank (accession numbers are shown). There were four positions (the first "Q" in line 1; the first "A" in the line beginning with nucleic acid 241; the first "G" in the line beginning with nucleic acid 421; and the third "P" in the line beginning with nucleic acid 481) that were unique to the cloned ORF (highlighted in bold type and underlined). These amino acids were changed to the consensus amino acids when the new gene was synthesized to produce pWRG/SN-M(opt).

```
AAC54561    481    ........................I.M...........S............A........
AAC54559    481    ........A...............I.M...........S............A........
consensus   481    *******.**************..*.***********.***********.*********

SN-M(2a)    541    QKTMGSMVCDICHHECETAKELETHKKSCPEGQCPYCMTITESTESALQAHFSICKLTNR
AAA6800     541    ............................................................
AAA68036    541    ............................................................
NP_941974   541    .....................................................A......
Q83887      541    ..........V...................................M............
AAC54561    541    ..........V...................................M............
AAC54559    541    ..........A...................................M........L...
consensus   541    **********.***********************************.********.***.*******

SN-M(2a)    601    FQENLKKSLKRPEVRKGCYRTLGVFRYKSRCYVGLVWGILLTTELIIWAASADTPLMESG
AAA6800     601    ...I........................................................
AAA68036    601    ...I........................................................
NP_941974   601    ............................................................
Q83887      601    ..............KQ......................V........V............
AAC54561    601    ..............KQ......................V........V............
AAC54559    601    ..............KQ.R....................V........V............
consensus   601    ***.**********..*.********************.*******.************

SN-M(2a)    661    WSDTAHGVGIVPMKTDLELDFALASSSSYSYRRKLVNPANQEETLPFHFQLDKQVVHAEI
AAA6800     661    ............................................................
AAA68036    661    ............................................................
NP_941974   661    ................I...........................................
Q83887      661    ..................................................K.........
AAC54561    661    ..............................................D...K.........
AAC54559    661    ..................................................K.........
consensus   661    **********.***********************.***.*******************

SN-M(2a)    721    QNLGHWMDGITNIKTAFHCYGECKKYAYPWQTAKCFFEKDYQYETSWGCNPPDCPGVGTG
AAA6800     721    ............................................................
AAA68036    721    ............................................................
NP_941974   721    ............................................................
Q83887      721    ............................................................
AAC54561    721    ............................................................
AAC54559    721    ............................................................
consensus   721    ************************************************************

SN-M(2a)    781    CTACGVYLDKLRSVGKAYKIVSLKYTRKVCIQLGTEQTCKHIDVNDCLVTPSVKVCMIGT
AAA6800     781    ............................................................
AAA68036    781    ............................................................
NP_941974   781    ............................................................
Q83887      781    ................................F..................L...
AAC54561    781    ................................F..................L...
AAC54559    781    ..............G.................F..................L...
consensus   781    **************.**********.*********************************.***

SN-M(2a)    841    ISKLQPGDTLLFLGPLEQGGIILKQWCTTSCVFGDPGDIMSTTSGMRCPEHTGSFRKICG
AAA6800     841    ............................................................
AAA68036    841    ............................................................
NP_941974   841    ............................................................
Q83887      841    .......................................................T..K............
AAC54561    841    .......................................................T..K............
AAC54559    841    .......................................................T..K............
consensus   841    *******************************************************.**.***********

SN-M(2a)    901    FATTPTCEYQGNTVSGFQRMMATRDSFQSFNVTEPHITSNRLEWIDPDSSIKDHINMVLN
AAA6800     901    ............................................................
AAA68036    901    ............................................................
NP_941974   901    ............................................................
Q83887      901    ...........I................................................
AAC54561    901    ...........I................................................
AAC54559    901    ...........I................................................
consensus   901    ***********.************************************************

SN-M(2a)    961    RDVSFQDLSDNPCKVDLHTQSIDGAWGSGVGFTLVCTVGLTECANFITSIKACDSAMCYG
AAA6800     961    ............................................................
AAA68036    961    ............................................................
NP_941974   961    ............................................................
```

TABLE 1-continued

The amino acid sequence encoded by the ORF cloned into pWRG/SN-M(2a) was aligned with six SNV M sequences from genebank (accession numbers are shown). There were four positions (the first "Q" in line 1; the first "A" in the line beginning with nucleic acid 241; the first "G" in the line beginning with nucleic acid 421; and the third "P" in the line beginning with nucleic acid 481) that were unique to the cloned ORF (highlighted in bold type and underlined). These amino acids were changed to the consensus amino acids when the new gene was synthesized to produce pWRG/SN-M(opt).

```
Q83887       961   ..............................................................
AAC54561     961   ..............................................................
AAC54559     961   ..............................................................
consensus    961   **************************************************************

SN-M(2a)    1021   ATVTNLLRGSNTVKVVGKGGHSGSLFKCCHDTDCITEGLAASPPHLDRVTGYNQIDSDKV
AAA6800     1021   ............................................................
AAA68036    1021   ............................................................
NP_941974   1021   ............................................................
Q83887      1021   ............................................................
AAC54561    1021   ............................................................
AAC54559    1021   ....................S.......................................
consensus   1021   ********************.***************************************

SN-M(2a)    1081   YDDGAPPCTIKCWFTKSGEWLLGILNGNWVVVAVLIVILILSILLFSFFCPVRNRKNKAN
AAA6800     1081   ..............R.............................................
AAA68036    1081   ............................................................
NP_941974   1081   ....................................................S.......
Q83887      1081   ..............................................I.G....S.
AAC54561    1081   ..............................................I.G....S.
AAC54559    1081   ..............................................I.G....S.
consensus   1081   **************.*********************************.*.****.*
```

TABLE 2

The sequence starts at the Not 1 site and ends at the BstB1 or BglII site depending on the construct (BstB1 for SN-M(2a) and BglII for SN-M(opt)).

```
SN-M(2a)       1   GCGGCCGCGGATCTGCAGGAATTCGGCACGAGAGTAGTAGACTCCGCACGAAGAAGCAAA
SN-M(opt)      1   ............................................................

SN-M(2a)      61   CACTGAATAAAGGATATACAGAATGGTAGGGTGGGTTTGCATCTTCCTCGTGGTCCTTAC
SN-M(opt)     61   ............................G..C.....G............G.....G..G..

SN-M(2a)     121   TACTGCAACTGCTGGATTGACACGGAATCTCTATGAATTACAGATAGAATGTCCACATAC
SN-M(opt)    121   C..C...C..A..C..CC....C.....C..G...C..GC.GA.....C..G...C..C...C..

SN-M(2a)     181   TGTGGGTCTAGGTCAAGGTTATGTGACAGGTTCTGTAGAAACTACACCTATTCTCTTAAC
SN-M(opt)    181   C.....C..G...C..G....C..C......C...CAGC..G...G..A...C..C..C...GC.G..

SN-M(2a)     241   ACAGGTAGCTGACCTCAAGATTGAGAGTTCTTGCAATTTTGACTTGCATGTCCCAGCCAC
SN-M(opt)    241   C......G..C.....G..........CAGC......C..C....C....C..G..C......

SN-M(2a)     301   TACTACTCAGAAATACAATCAAGTTGACTGGACTAAAAAAGTTCTACTACAGAAAGCAC
SN-M(opt)    301   C..C..C............C..G..G.........C..G..G..CAGC..C..C..G......

SN-M(2a)     361   GAATGCAGGTGCAACTACATTTGAGGCTAAAACAAAAGAGGTAAATTTAAAAGGCACATG
SN-M(opt)    361   C..C...C..A..C..C..C..C......C..G..C.....A..G..CC.G..G......C..

SN-M(2a)     421   TAATATTCCTCCAACTACGTTTGAGGCTGCATACAAGTCAAGGAAGACAGTGATTTGTTA
SN-M(opt)    421   C..C...C..C..C..C...A.........C..C......AGC...A......C.....C..C..

SN-M(2a)     481   TGATTTGGCCTGTAATCAAACACATTGTCTTCCTACAGTCCATCTGATTGCTCCTGTTCA
SN-M(opt)    481   C..CC.......C..C..G..C..C..C..G..C..C..G..C......C..C..C..G..

SN-M(2a)     541   AACATGTATGTCTGTACGGAGCTGTATGATAGGTCTGTTATCTAGCAGGATCCAGGTTAT
SN-M(opt)    541   G..C..C...AGC..G.........C......C..C....C.G..C....C..........G..

SN-M(2a)     601   CTACGAGAAGACATATTGTGTCACGGGTCAGTTAATAGAAGGGCTATGTTTCATTCCAAC
SN-M(opt)    601   .........A...C...C..C...G...C...C.....C.G...C..G...C..G..C..........C..C..

SN-M(2a)     661   ACATACAATTGCACTTACACAGCCTGGTCATACTTATGATACTATGACATTGCCTGTGAC
SN-M(opt)    661   C...C......C...C..G..C......C......C...C...C..C...C......CC....C......

SN-M(2a)     721   TTGTTTTTTAGTAGCCAAAAAGTTGGGGACGCAGCTTAAGCTGGCTGTTGAGTTAGAGAA
SN-M(opt)    721   C..C....C.G..G......G...C.....C..C......G.........C..G...C.G..A...
```

TABLE 2-continued

The sequence starts at the Not 1 site and ends at the BstB1 or BglII site depending on the construct (BstB1 for SN-M(2a) and BglII for SN-M(opt).

```
SN-M(2a)    781 ATTGATTACTGGTGTGAGCTGCGCAGAGAATAGCTTCCAAGGTTATTACATCTGTTTTAT
SN-M(opt)   781 GC....C..C..C.........A.C.....C........G..C..C........C..C..

SN-M(2a)    841 TGGAAAACATTCAGAGCCCTTATTTGTACCAACAATGGAAGATTATAGATCAGCTGAGTT
SN-M(opt)   841 C..C..G..CAGC......C.G..C..G..C..C...........C...AGC..C...C.

SN-M(2a)    901 ATTTACTCGTATGGTTTTAAATCCAAGAGGTGAAGATCATGACCCTGATCAAAATGGACA
SN-M(opt)   901 G..C..C..G.....GC.G..C..C..G..C..G..C..C.....C..C..G..C..C..

SN-M(2a)    961 AGGGTTGATGAGAATAGCTGGACCTGTTACTGCCAAGGTACCATCTACAGAAACGACTGA
SN-M(opt)   961 G..CC.....C.G..C..C.....C..G..C........G..CAGC..C..G..A..C..

SN-M(2a)   1021 AACAATGCAAGGAATTGCATTTGCTGGGGCACCAATGTATAGTTCATTCTCAACTCTTGT
SN-M(opt)  1021 ...C.....G..C.....C..C..C..A..C..C.....C..CAGC...AGC..C..G..

SN-M(2a)   1081 GAGAAAAGCTGATCCTGAATATGTCTTTTCTCCAGGTATAATTGCAGAATCAAATCATAG
SN-M(opt)  1081 .C.G..G..C..C..C..G..C..G..CAGC..C..C..C.....C..GAGC..C..C..

SN-M(2a)   1141 TGTTTGTGATAAAAAGACAGTGCCCCTAACATGGACTGGGTTTCTAGCAGTTTCAGGAGA
SN-M(opt)  1141 C..G..C..C..G..A..C........G..C.....C..C..C..G..C..GAGC..C..

SN-M(2a)   1201 GATAGAAAGGATAACAGGCTGTACAGTTTTCTGTACATTGGCTGGACCTGGTGCCAGTTG
SN-M(opt)  1201 ...C..GC....C..C.....C..C..G.....C..CC....C........C.....C..

SN-M(2a)   1261 TGAAGCATACTCAGAAACAGGAATCTTCAACATAAGCTCCCCAACTTGCTTGGTAAATAA
SN-M(opt)  1261 C..G..C..AGC..G.....C...........C...AG..C..C...C....G..C..

SN-M(2a)   1321 AGTCCAAAAATTTAGAGGTTCAGAACAAAGAATTAATTTTATGTGTCAAAGGGTTGATCA
SN-M(opt)  1321 G..G..G..G..CC.G..CAGC..G..GC.G..C..C..C.....C..GC....G..C..

SN-M(2a)   1381 AGGTGTTGTGGTTTACTGTAATGGACAGAAGAAAGTCATTCTTACCAAAACCCTAGTAAT
SN-M(opt)  1381 G.AC..G.....G.....C..C..C.....A.....G..C..C.....G.....G..G..

SN-M(2a)   1441 AGGTCAATGTATCTACACATTTACTAGTCTGTTTTCACTGATCCCTGGAGTTGCTCATTC
SN-M(opt)  1441 C..C..G..C........C..C..C..C.....CAGC...........C...G......AG SN-M(2a)   1501 CCTTGCTGTGGAGTTATGTGTTCCAGGTCTTCATGGCTGGGCTACAACAGCACTACTTAT
SN-M(opt)  1501 ...G..A..C..AC.G..C..G..T..C..G..C..A......C..C..C..C..G..G..

SN-M(2a)   1561 TACTTTCTGCTTTGGCTGGCTTCTCATACCAACAGTTACTTTAATTATACTAAAAATCTT
SN-M(opt)  1561 C..C........C........G..G..C..C.....G..CC.G..C..C..G..G...C.

SN-M(2a)   1621 AAGGCTATTGACCTTCCCATGCTCGCACTATTCTACAGAATCAAAATTCAAAGTCATTTT
SN-M(opt)  1621 GC....GC........AGC...AGC.....CAGC..C..G..C..G........G..C.

SN-M(2a)   1681 AGAAAGAGTCAAGGTGGAGTATCAAAAGACAATGGGTTCAATGGTGTGTGACATTTGTCA
SN-M(opt)  1681 G...C.C..G...........C..G..A..C.....CAGC........C.....C..C..

SN-M(2a)   1741 CCATGAATGTGAGACGGCAAAAGAGCTCGAAACACATAAGAAAAGTTGCCCAGAAGGTCA
SN-M(opt)  1741 ...C..G..C.....A..C........G.....C..C.....G..C.....C..G..C..

SN-M(2a)   1801 ATGCCCATACTGCATGACAATAACTGAGTCCACTGAGAGTGCATTACAAGCTCATTTTTC
SN-M(opt)  1801 G.....C...........C..C..A...AG...C.....C..CC.G..G..C..C..CAG SN-M(2a)   1861 AATCTGTAAGCTAACGAACAGGTTCCAGGAAAATCTAAAAAAATCATTAAAACGTCCAGA
SN-M(opt)  1861 C.....C.....G..C...C.............C..G..G..GAGCC.G..G..G..C..

SN-M(2a)   1921 AGTAAGGAAAGGTTGTTACAGGACATTAGGAGTATTCCGCTACAAGAGCAGGTGCTATGT
SN-M(opt)  1921 ...GC....G..C..C.....C....CC.G..C..G.....G..........C.........

SN-M(2a)   1981 TGGCTTAGTATGGGGGATCCTCTTGACGACAGAGCTGATTATATGGGCTGCTAGTGCAGA
SN-M(opt)  1981 G...C.G..G.....C...T..GC.....C...........C..C..C...C..C..C..

SN-M(2a)   2041 TACCCCTCTAATGGAGTCTGGTTGGTCAGATACAGCACATGGTGTAGGTATAGTCCCTAT
SN-M(opt)  2041 C.....C..G.....AAGC..G...AGC..C..C..T.....C..G..A..C..G..C..

SN-M(2a)   2101 GAAAACAGATTTAGAGCTTGACTTTGCCTTGGCCTCATCATCTTCTTATAGTTATAGAAG
SN-M(opt)  2101 ......C..CC.G..A...G.....C...C.....AGCAGCAGCAGC..C..C..CC.GC.

SN-M(2a)   2161 AAAGCTTGTAAACCCTGCCAATCAAGAGGAGACACTCCCTTTTCATTTCCAGTTAGATAA
SN-M(opt)  2161 G.....G..G.....C.....C..G..A........G..C..C..C.....AC.G..C..

SN-M(2a)   2221 GCAAGTAGTGCATGCAGAAATACAGAACCTAGGGCATTGGATGGATGGCACATTCAACAT
SN-M(opt)  2221 ...G..G.....C..C..G..C........G..C..C........C.....C.....T..

SN-M(2a)   2281 AAAGACTGCTTTCCATTGCTATGGAGAATGTAAAAAATATGCCTATCCTTGGCAGACAGC
SN-M(opt)  2281 C.....C..C........C..C..C..G..C..G..G..C.....C..C........C..
```

TABLE 2-continued

The sequence starts at the Not 1 site and ends at the BstB1 or BglII site
depending on the construct (BstB1 for SN-M(2a) and BglII for SN-M(opt)).

```
SN-M(2a)    2341  CAAGTGTTTCTTTGAAAAAGATTATCAGTATGAAACAAGCTGGGGCTGTAACCCACCAGA
SN-M(opt)   2341  ......C.....C..G..G..C..C.....C..G...............C.....C..C...

SN-M(2a)    2401  TTGCCCAGGAGTAGGGACAGGTTGTACAGCCTGTGGGGTATACTTAGACAAGCTCCGTTC
SN-M(opt)   2401  C..T..T..C..G..C..C..C.....C.....C..C..G...C.G........G..GAG SN-M(2a)    2461  AGTTGGGAAAGCCTATAAAATTGTATCACTCAAATACACGCGAAAGGTGTGTATTCAATT
SN-M(opt)   2461  C..G..C..G.....C..G..C..G..C..G..G.....C..G..A.....C..C..GC.

SN-M(2a)    2521  GGGGACAGAACAAACCTGTAAACATATAGATGTTAATGATTGTTTGGTCACCCCGTCTGT
SN-M(opt)   2521  ...C.....G..G..A..C..G..C..C..C..G..C.....CC....G.....CAGC..

SN-M(2a)    2581  TAAAGTTTGCATGATAGGTACCATCTCGAAGCTTCAGCCAGGTGACACCTTATTGTTTTT
SN-M(opt)   2581  G.....C..T.....T..C......AGC.....G.....C..C..T...C.GC....CC.

SN-M(2a)    2641  GGGCCCTTTAGAGCAAGGTGGGATTATTCTAAAACAATGGTGCACAACATCATGTGTGTT
SN-M(opt)   2641  ......CC.G..A..G..C..C..C.....G..G..G.....T..C..C..C..C.....

SN-M(2a)    2701  TGGAGACCCTGGTGATATCATGTCAACAACAAGTGGGATGAGATGCCCTGAGCACACAGG
SN-M(opt)   2701  C..C.....C..C..C......AGC..C..CTCC..C...C.G.....C.........C..

SN-M(2a)    2761  GTCTTTTAGAAAAATCTGTGGATTTGCTACAACACCTACATGTGAATATCAAGGTAATAC
SN-M(opt)   2761  CAGC..CC.G..G..T.....C..C..C..C..C.....C..C..G..C..G..C..C..

SN-M(2a)    2821  AGTGTCTGGATTCCAACGCATGATGGCAACTCGAGATTCTTTTCAATCATTCAATGTGAC
SN-M(opt)   2821  C.....C..C.....G..G........C..C..G...AGC..C..GAGC.....C.....

SN-M(2a)    2881  AGAACCACATATTACCAGCAATCGACTGGAATGGATTGATCCAGATAGTAGTATTAAAGA
SN-M(opt)   2881  C..G..C..C..C........C..G...........C..C..C..C..C..C..C..G..

SN-M(2a)    2941  CCATATCAACATGGTTTTGAATAGAGATGTTTCCTTCCAAGATCTAAGTGATAATCCATG
SN-M(opt)   2941  ...C..........GC.C...C.G..C...GAG......G..C..G..C..C..C..C..

SN-M(2a)    3001  TAAGGTTGATTTGCATACACAATCTATTGATGGGGCTTGGGGATCAGGAGTGGGCTTTAC
SN-M(opt)   3001  C.....G..CC....C..C..GAGC..C..C..C..C.....CAGC..C.........C..

SN-M(2a)    3061  ATTAGTATGTACTGTAGGTCTTACAGAGTGTGCAAATTTCATAACTTCAATTAAGGCGTG
SN-M(opt)   3061  .C.G..G..C..A..G..C..G..C.....C..C..C.....C..C..C..C.....C..

SN-M(2a)    3121  TGATTCTGCTATGTGTTATGGGGCCACAGTTACAAATCTACTCAGAGGGTCTAACACAGT
SN-M(opt)   3121  C..CAGC..C.....C..C..C.....C..G..C..C..G..GC.G..C..C........

SN-M(2a)    3181  TAAAGTTGTCGGTAAAGGTGGGCATTCTGGGTCCTTGTTCAAGTGCTGCCATGATACTGA
SN-M(opt)   3181  G..G..G..G..C..G..C..C..CAGC..CAG.C....T...........C..C..C..

SN-M(2a)    3241  CTGTACTGAAGAAGGTTTAGCAGCATCACCACCTCATTTAGATAGGGTTACTGGTTACAA
SN-M(opt)   3241  ...C..C..G.....CC.G..C..CAGC..C.....CC.G..C..A..G..C..C.....

SN-M(2a)    3301  TCAAATAGATTCTGATAAGGTTTATGATGACGGTGCACCGCCCTGTACAATTAAATGTTG
SN-M(opt)   3301  C..G..C..CAGC..C.....G..C..C..T..C..C..T.....C..C..C..G..C..

SN-M(2a)    3361  GTTCACAAAGTCAGGTGAGTGGTTGCTAGGAATTCTTAATGGCAATTGGGTAGTAGTTGC
SN-M(opt)   3361  ......C...AGC..C......C....G..C..C..G..C.....C.....C..C..G..

SN-M(2a)    3421  TG1TTTGATTGTAATTTTGATACTATCAATACTCCTGTTCAGCTTCTTTTGTCCTGTTAG
SN-M(opt)   3421  C..GC....C..G..CC....C..G..T..C..G...........C..C..C..GC.

SN-M(2a)    3481  AAATAGAAAAAATAAGGCCAATTAGCAAACATATATGTAAGTAAGGGTATGATCATATTA
SN-M(opt)   3481  G..CC.G..G..C.......C...........................

SN-M(2a)    3541  TATCATTATGCGTATACTCTTATATCTATAATATCTATGTATCCTTATACTCTAACTATT
SN-M(opt)   3541  ............................................................

SN-M(2a)    3601  TATATTAATTTTTACTTTTATACAAGTATTAACTAACCCATTACCAGCTAAAAAAACAA
SN-M(opt)   3601  ............................................................

SN-M(2a)    3661  ACCCTTAACACCTATATAATCCCATTTGCTTATTACGAGGCTTTTGTTCCTGCGGAGTCT
SN-M(opt)   3661  ............................................................

SN-M(2a)    3721  ACTACTATTCGAA
SN-M(opt)   3721  .......AGATCT
```

This new SNV vaccine was tested for a capacity to elicit neutralzing antibodies by vaccinating rabbits with the pWRG/SN-M(opt) using muscle electroporation. Very high titers of SNV neutralizing antibodies were produced after only a single vaccination.

The term "antibody" is art-recognized terminology and is intended to include molecules or active fragments of molecules that bind to known antigens. These active fragments can be derived from an antibody of the present invention by a number of techniques. For further description of general techniques for the isolation of active fragments of antibodies, see for example, Khaw, B. A. et al. *J. Nucl. Med.* 23:1011-1019 (1982). The term "antibody" also includes bispecific and chimeric antibodies and antibodies in non-mammalian species.

By neutralizing antibodies, or NAb, it is meant an antibody which defends a cell from an antigen or infectious body by inhibiting or neutralizing any effect it has biologically. For instance, a neutralizing antibody for SNV is an antibody which can inhibit or reduce the biological effects of SNV infection, that is, it binds to the virus and interferes with its ability to infect a cell.

By "high titer" it is meant neutralizing antibody titers similar to those produced in individuals that were infected with the virus and survived. As described in greater detail in the examples, the present inventors have found that serum from a vaccine immunized with a DNA vaccine comprising the M segment of Sin Nombre virus contains antibodies able to neutralize Sin Nombre virus.

As used herein the term "immunogenically active" designates the ability to stimulate an immune response, i.e., to stimulate the production of antibodies, particularly humoral antibodies, or to stimulate a cell-mediated response. For example, the ability to stimulate the production of circulating or secretory antibodies or the production of a cell-mediated response in local mucosal regions, (e.g., intestinal mucosa), peripheral blood, cerebral spinal fluid or the like. The effective immunizing amount of the immunogenically active component(s) of this invention may vary and may be any amount sufficient to evoke an immune response and provide immunological protection against Sin Nombre virus infection. Amounts where a dosage unit comprises at least about 5 micrograms to about 5 milligrams of plasmid DNA are contemplated. At least one dosage unit per patient is contemplated herein as a vaccination regimen. In some embodiments, two or more dosage units may be especially useful. The skilled artisan will quickly recognize that a particular quantity of vaccine composition per dosage unit, as well as the total number of dosage units per vaccination regimen, may be optimized, so long as an effective immunizing amount of the virus or a component thereof is ultimately delivered to the animal.

We next combined the SNV DNA vaccine with an Andes virus construct, pWRG/AND-M, and a mixture of the two plasmids was used to vaccinate rabbits using muscle electroporation. High titer neutralizing antibodies against both SNV and ANDY were produced after 1 or 2 vaccinations. The SNV neutralizing activity was especially potent (titers>10,000 after 1 vaccination). Thus, the combination of the pWRG/SN-M(opt) DNA vaccine and pWRG/AND-M DNA vaccine effectively elicited high-titer neutralizing antibodies against the most prevalent and lethal hantavirus in North and South America. The novelty and potency of this SNV DNA vaccine and its utility in alone or in combination with other hantavirus DNA vaccine plasmids is a main focus of this application.

The amino acid one letter code is defined as the following: A=Alanine (Ala), I=Isoleucine (Ile), L=Leucine (Leu), M=Methionine (Met), F=Phenylalanine (Phe), P=Proline (Pro), W=Tryptophan (Trp), V=Valine (Val), N=Asparagine (Asn), C=Cysteine (Cys), Q=Glutamine (Q), G=Glycine (Gly), S=Serine (Ser), T=Threonine (Thr), Y=Tyrosine (Tyr), R=Arginine (Arg), H=Histidine (His), K=Lysine (Lys), D=Aspartic acid (Asp), and E=Glutamic acid (Glu).

As would be understood by someone having skill in this art, this invention covers sequences that are not necessarily physically derived from the nucleotide sequence itself, but may be generated in any manner, including for example, chemical synthesis or DNA replication or reverse transcription or transcription, which are based on the information provided by the sequence bases in the region(s) from which the polynucleotide is derived. In addition, combinations of regions corresponding to that of the designated sequence may be modified in ways known in the art to be consistent with an intended use.

It is also understood in the art that certain changes to the nucleotide sequence employed in a genetic construct have little or no bearing on the proteins encoded by the construct, for example due to the degeneracy of the genetic code. Such changes result either from silent point mutations or point mutations that encode different amino acids that do not appreciably alter the behavior of the encoded protein. It is understood that portions of the coding region can be eliminated without affecting the ability of the construct to achieve the desired effect, namely induction of a protective immune response against Sin Nombre virus. It is further understood in the art that certain advantageous steps can be taken to increase the antigenicity of an encoded protein by modifying its amino acid composition. Such changes in amino acid composition can be introduced by modifying the genetic sequence encoding the protein. It is contemplated that all such modifications and variations of the M segment of Sin Nombre virus are equivalents within the scope of the present invention.

The DNA encoding the desired antigen can be introduced into the cell in any suitable form including, a linearized plasmid, a circular plasmid, a plasmid capable of replication, an episome, RNA, etc. Preferably, the gene is contained in a plasmid. In a particularly preferred embodiment, the plasmid is an expression vector, such as pWRG7077. In another embodiment, the DNA encoding the desired antigen can be introduced into virus-based vaccine vectors such as recombinant adenovirus, recombinant vesicular stomatitis virus, or alphavirus replicons. Individual expression vectors capable of expressing the genetic material can be produced using standard recombinant techniques.

This invention entails new recombinant SNV DNA sequences which are useful to elicit neutralizing antibodies against SNV. The DNA sequences include the codon-optimized full-length M segment [designated SN-M(opt)] (SEQ ID NO:1), the optimized ORF plus M gene flanking sequences (SEQ ID NO:2), and the optimized open reading frame (ORF) (SEQ ID NO:3).

Thus in one embodiment the invention entails an isolated nucleic acid sequence set forth in SEQ ID NO:1, which is as follows. The Sin Nombre virus M gene (optimized) open reading frame is underlined. The synthetic open reading frame and flanking sequence was cloned into the Not I, Bgl II site of pWRG7077 (published). The Not 1 cloning site (GCGGCCGCGG) (SEQ ID NO:7) and the Bg1 II cloning site (GATCT) (SEQ ID NO:8) are in bold. An extraneous sequence having the sequence "ATCTGCAGGAATTCG-GCACGAG" (SEQ ID NO:9) is in italics. The flanking sequences include 5' and 3' non-translated sequence from the SNV M genome segment, and a 24-base sequence (the extraneous sequence) between the Not I site and position +2 of the M gene (not +1 because the first nucleotide is missing). This sequence was found to be essential for expression of the Gn protein from the Hantaan virus and Seoul virus full-length M gene-based DNA vaccine plasmids, pWRG/HTN-M(x) and pWRG/SEO-M, respectably. (See U.S. Pat. No. 7,217,812) It is noted that experiments demonstrated that this 24-base sequence was not essential for expression of Gn from the Puumala M gene-based DNA vaccine plasmid or the Andes M gene-based DNA vaccine plasmid, but was retained in those constructs (See US Patent Application Publication No. 20100323024 and U.S. Pat. No. 7,217,812, respectively).

Two SNV M segment nontranslated regions are indicated by wavy underline, and are between the extraneous sequence and the beginning of the ORF, and between the end of the ORF and the Bg1 II cloning site.

GGGGGGGGGGGGCGCTGAGGTCTGCCTCGTGAAGAAGGTGTTGCTGACTCA

TACCAGGCCTGAATCGCCCCATCATCCAGCCAGAAAGTGAGGGAGCCACGG

TTGATGAGAGCTTTGTTGTAGGTGGACCAGTTGGTGATTTTGAACTTTTGC

TTTGCCACGGAACGGTCTGCGTTGTCGGGAAGATGCGTGATCTGATCCTTC

AACTCAGCAAAAGTTCGATTTATTCAACAAAGCCGCCGTCCCGTCAAGTCA

GCGTAATGCTCTGCCAGTGTTACAACCAATTAACCAATTCTGATTAGAAAA

ACTCATCGAGCATCAAATGAAACTGCAATTTATTCATATCAGGATTATCAA

TACCATATTTTTGAAAAAGCCGTTTCTGTAATGAAGGAGAAAACTCACCGA

GGCAGTTCCATAGGATGGCAAGATCCTGGTATCGGTCTGCGATTCCGACTC

GTCCAACATCAATACAACCTATTAATTTCCCCTCGTCAAAAATAAGGTTAT

CAAGTGAGAAATCACCATGAGTGACGACTGAATCCGGTGAGAATGGCAAAA

GCTTATGCATTTCTTTCCAGACTTGTTCAACAGGCCAGCCATTACGCTCGT

CATCAAAATCACTCGCATCAACCAAACCGTTATTCATTCGTGATTGCGCCT

GAGCGAGACGAAATACGCGATCGCTGTTAAAAGGACAATTACAAACAGGAA

TCGAATGCAACCGGCGCAGGAACACTGCCAGCGCATCAACAATATTTTCAC

CTGAATCAGGATATTCTTCTAATACCTGGAATGCTGTTTTCCCGGGGATCG

CAGTGGTGAGTAACCATGCATCATCAGGAGTACGGATAAAATGCTTGATGG

TCGGAAGAGGCATAAATTCCGTCAGCCAGTTTAGTCTGACCATCTCATCTG

TAACATCATTGGCAACGCTACCTTTGCCATGTTTCAGAAACAACTCTGGCG

CATCGGGCTTCCCATACAATCGATAGATTGTCGCACCTGATTGCCCGACAT

TATCGCGAGCCCATTTATACCCATATAAATCAGCATCCATGTTGGAATTTA

ATCGCGGCCTCGAGCAAGACGTTTCCCGTTGAATATGGCTCATAACACCCC

TTGTATTACTGTTTATGTAAGCAGACAGTTTTATTGTTCATGATGATATAT

TTTTATCTTGTGCAATGTAACATCAGAGATTTTGAGACACAACGTGGCTTT

CCCCCCCCCCCGGCATGCCTGCAGGTCGACAATATTGGCTATTGGCCATT

GCATACGTTGTATCTATATCATAATATGTACATTTATATTGGCTCATGTCC

AATATGACCGCCATGTTGACATTGATTATTGACTAGTTATTAATAGTAATC

AATTACGGGGTCATTAGTTCATAGCCCATATATGGAGTTCCGCGTTACATA

ACTTACGGTAAATGGCCCGCCTGGCTGACCGCCCAACGACCCCCGCCCATT

GACGTCAATAATGACGTATGTTCCCATAGTAACGCCAATAGGGACTTTCCA

TTGACGTCAATGGGTGGAGTATTTACGGTAAACTGCCCACTTGGCAGTACA

TCAAGTGTATCATATGCCAAGTCCGCCCCCTATTGACGTCAATGACGGTAA

ATGGCCCGCCTGGCATTATGCCCAGTACATGACCTTACGGGACTTTCCTAC

TTGGCAGTACATCTACGTATTAGTCATCGCTATTACCATGGTGATGCGGTT

TTGGCAGTACACCAATGGGCGTGGATAGCGGTTTGACTCACGGGGATTTCC

AAGTCTCCACCCCATTGACGTCAATGGGAGTTTGTTTTGGCACCAAAATCA

ACGGGACTTTCCAAAATGTCGTAATAACCCCGCCCCGTTGACGCAAATGGG

CGGTAGGCGTGTACGGTGGGAGGTCTATATAAGCAGAGCTCGTTTAGTGAA

CCGTCAGATCGCCTGGAGACGCCATCCACGCTGTTTTGACCTCCATAGAAG

ACACCGGGACCGATCCAGCCTCCGCGGCCGGGAACGGTGCATTGGAACGCG

GATTCCCCGTGCCAAGAGTGACGTAAGTACCGCCTATAGACTCTATAGGCA

CACCCCTTTGGCTCTTATGCATGCTATACTGTTTTTGGCTTGGGGCCTATA

CACCCCCGCTTCCTTATGCTATAGGTGATGGTATAGCTTAGCCTATAGGTG

TGGGTTATTGACCATTATTGACCACTCCCCTATTGGTGACGATACTTTCCA

TTACTAATCCATAACATGGCTCTTTGCCACAACTATCTCTATTGGCTATAT

GCCAATACTCTGTCCTTCAGAGACTGACACGGACTCTGTATTTTTACAGGA

TGGGGTCCCATTTATTATTTACAAATTCACATATACAACAACGCCGTCCCC

CGTGCCCGCAGTTTTTATTAAACATAGCGTGGGATCTCCACGCGAATCTCG

GGTACGTGTTCCGGACATGGGCTCTTCTCCGGTAGCGGCGGAGCTTCCACA

TCCGAGCCCTGGTCCCATGCCTCCAGCGGCTCATGGTCGCTCGGCAGCTCC

TTGCTCCTAACAGTGGAGGCCAGACTTAGGCACAGCACAATGCCCACCACC

ACCAGTGTGCCGCACAAGGCCGTGGCGGTAGGGTATGTGTCTGAAAATGAG

CTCGGAGATTGGGCTCGCACCGCTGACGCAGATGGAAGACTTAAGGCAGCG

GCAGAAGAAGATGCAGGCAGCTGAGTTGTTGTATTCTGATAAGAGTCAGAG

GTAACTCCCGTTGCGGTGCTGTTAACGGTGGAGGGCAGTGTAGTCTGAGCA

GTACTCGTTGCTGCCGCGCGCGCCACCAGACATAATAGCTGACAGACTAAC

AGACTGTTCCTTTCCATGGGTCTTTTCTGCAGTCACCGTCCAAGCTT

GCGGCCGCGGATCTGCAGGAATTCGGCACGAGAGTAGTAGACTCCGCACGA

AGAAGCAAACACTGAATAAAGGATATACAGAATGGTGGGCTGGGTGTGCA

TCTTCCTGGTGGTGCTGACCACCGCCACAGCCGGCCTGACCCGGAACCTGT

ACGAGCTGAAGATCGAGTGCCCCCACACCGTGGGCCTGGGCCAGGGCTAC

GTGACCGGCAGCGTGGAGACAACCCCCATCCTGCTGACCCAGGTGGCCGAC

CTGAAGATTGAGAGCAGCTGCAACTTCGACCTGCACGTGCCCGCCACCACC

ACCCAGAAATACAACCAGGTGGACTGGACCAAGAAGAGCAGCACCACCGA

GAGCACCAACGCCGGAGCCACCACCTTCGAGGCCAAGACCAAAGAAGTGA

ACCTGAAGGGCACCTGCAACATCCCCCCCACCACATTTGAGGCCGCCTACA

AGAGCAGAAAGACCGTGATCTGCTACGACCTGGCCTGCAACCAGACCCACT

GCCTGCCCACCGTGCACCTGATCGCCCCCGTGCAGACCTGCATGAGCGTGC

GGAGCTGCATGATCGGCCTGCTGTCCAGCCGGATCCAGGTGATCTACGAGA
AAACCTACTGCGTGACCGGCCAGCTGATCGAGGGCCTGTGCTTCATCCCCA
CCCACACAATCGCCCTGACCCAGCCCGGCCACACCTACGACACCATGACCC
TGCCCGTGACCTGCTTTCTGGTGGCCAAGAAGCTGGGCACCCAGCTGAAGC
TGGCCGTGGAGCTGGAAAAGCTGATCACCGGCGTGAGCTGCACCGAGAAC
AGCTTCCAGGGCTACTACATCTGCTTCATCGGCAAGCACAGCGAGCCCCTG
TTCGTGCCCACCATGGAAGATTACAGAAGCGCCGAGCTGTTCACCCGGATG
GTGCTGAACCCCAGGGGCGAGGACCACGACCCCGACCAGAACGGCCAGGG
CCTGATGCGGATCGCCGGACCCGTGACCGCCAAGGTGCCCAGCACCGAGAC
AACCGAAACCATGCAGGGCATTGCCTTCGCCGGAGCCCCCATGTACAGCAG
CTTCAGCACCCTGGTGCGGAAGGCCGACCCCGAGTACGTGTTCAGCCCCGG
CATCATTGCCGAGAGCAACCACAGCGTGTGCGACAAGAAAACCGTGCCCCT
GACCTGGACCGGCTTCCTGGCCGTGAGCGGCGAGATCGAGCGGATCACCGG
CTGCACCGTGTTCTGCACCCTGGCCGGACCTGGCGCCAGCTGCGAGGCCTA
CAGCGAGACAGGCATCTTCAACATCAGCAGCCCCACCTGCCTGGTGAACAA
GGTGCAGAAGTTCCGGGGCAGCGAGCAGCGGATCAACTTCATGTGCCAGC
GGGTGGACCAGGACGTGGTGGTGTACTGCAACGGCCAGAAAAAGTGATC
CTGACCAAGACCCTGGTGATCGGCCAGTGCATCTACACCTTCACCAGCCTG
TTCAGCCTGATCCCTGGCGTGGCTCATAGCCTGGCAGTCGAACTGTGCGTG
CCTGGCCTGCACGGATGGGCCACCACCGCCCTGCTGATCACCTTCTGCTTC
GGCTGGCTGCTGATCCCCACAGTGACCCTGATCATCCTGAAGATCCTGCGG
CTGCTGACCTTCAGCTGCAGCCACTACAGCACCGAGTCCAAGTTCAAAGTG
ATTCTGGAACGCGTGAAGGTGGAGTACCAGAAAACCATGGGCAGCATGGTG
TGCGACATCTGCCACCACGAGTGCGAGACAGCCAAAGAGCTGGAAACCCAC
AAGAAGAGCTGCCCCGAGGGCCAGTGCCCCTACTGCATGACCATCACAGA
GAGCACCGAGAGCGCCCTGCAGGCCCACTTCAGCATCTGCAAGCTGACCAA
CCGGTTCCAGGAAAACCTGAAGAAGAGCCTGAAGCGGCCCGAAGTGCGGA
AGGGCTGCTACCGGACCCTGGGCGTGTTCCGGTACAAGAGCCGGTGCTATG
TGGGCCTGGTGTGGGCATTCTGCTGACCACAGAGCTGATCATCTGGGCCG
CCAGCGCCGACACCCCCCTGATGGAAAGCGGGTGGAGCGACACCGCTCAT
GGCGTGGGAATCGTGCCCATGAAAACCGACCTGGAACTGGACTTCGCCCTG
GCCAGCAGCAGCAGCTACAGCTACCGGCGGAAGCTGGTGAACCCCGCCAA
CCAGGAAGAGACACTGCCCTTCCACTTCCAACTGGACAAGCAGGTGGTGCA
CGCCGAGATCCAGAACCTGGGCCACTGGATGGACGGCACCTTCAATATCAA
GACCGCCTTCCACTGCTACGGCGAGTGCAAGAAGTACGCCTACCCCTGGCA
GACCGCCAAGTGCTTCTTCGAGAAGGACTACCAGTACGAGACAAGCTGGG
GCTGCAACCCCCCCGACTGTCCTGGCGTGGGCACCGGCTGTACCGCCTGCG
GCGTGTACCTGGACAAGCTGCGGAGCGTGGGCAAGGCCTACAAGATCGTGT
CCCTGAAGTACACCCGGAAAGTGTGCATCCAGCTGGGCACAGAGCAGACA
TGCAAGCACATCGACGTGAACGATTGCCTGGTGACCCCCAGCGTGAAAGTC
TGTATGATTGGCACCATCAGCAAGCTGCAGCCCGGCGATACCCTGCTGTTC

CTGGGCCCCCTGGAACAGGGCGGCATCATTCTGAAGCAGTGGTGTACCACC
TCCTGCGTGTTCGGCGACCCCGGCGACATCATGAGCACCACCTCCGGCATG
CGGTGCCCCGAGCACACCGGCAGCTTCCGGAAGATTTGTGGCTTCGCCACC
ACCCCTACCTGCGAGTACCAGGGCAACACCGTGTCCGGCTTCCAGCGGATG
ATGGCCACCCGGGATAGCTTCCAGAGCTTCAACGTGACCGAGCCCCACATC
ACCAGCAACCGGCTGGAATGGATCGACCCCGACAGCAGCATCAAGGACCA
CATCAACATGGTGCTCAATCGGGACGTGAGCTTCCAGGACCTGAGCGACAA
CCCCTGCAAGGTGGACCTGCACACCCAGAGCATCGACGGCGCCTGGGGCA
GCGGCGTGGGCTTCACACTGGTGTGCACAGTGGGCCTGACCGAGTGCGCCA
ACTTCATCACCTCCATCAAGGCCTGCGACAGCGCCATGTGCTACGGCGCCA
CCGTGACCAACCTGCTGCGGGGCTCCAACACAGTGAAGGTGGTGGGCAAG
GGCGGCCACAGCGGCAGCCTGTTTAAGTGCTGCCACGACACCGACTGCACC
GAGGAAGGCCTGGCCGCCAGCCCCCCCTCACCTGGACAGAGTGACCGGCTAC
AACCAGATCGACAGCGACAAGGTGTACGACGATGGCGCCCCTCCCTGCACC
ATCAAGTGCTGGTTCACCAAGAGCGGCGAGTGGCTGCTGGGCATCCTGAAC
GGCAACTGGGTCGTCGTGGCCGTGCTGATCGTGATCCTGATCCTGTCTATC
CTGCTGTTCAGCTTCTTCTGCCCCGTGCGGAACCGGAAGAACAAGGCCAAC
TAGCAAACATATATGTAAGTAAGGGTATGATCATATTTATATCATTATGCG
TATACTCTTATATCTATAATATCTATGTATCCTTATACTCTAACTATTTA
TATTAATTTTTACTTTTATACAAGTATTAACTAACCCATTACCAGCTAAAA
AAAACAAACCCTTAACACCTATATAATCCCATTTGCTTATTACGAGGCTTT
TGTTCCTGCGGAGTCTACTACTAAGATCT
ACGTATGATCAGCCTCGACTGTGCCTTCTAGTTGCCAGCCATCTGTTGTTT
GCCCCTCCCCCGTGCCTTCCTTGACCCTGGAAGGTGCCACTCCCACTGTCC
TTTCCTAATAAAATGAGGAAATTGCATCGCATTGTCTGAGTAGGTGTCATT
CTATTCTGGGGGGTGGGGTGGGGCAGGACAGCAAGGGGGAGGATTGGGAAG
ACAATAGCAGGCATGCTGGGGATGCGGTGGGCTCTATGGCTTCTGAGGCGG
AAAGAACCAGCTGGGGCTCGACAGCTCGACTCTAGAATTGCTTCCTCGCTC
ACTGACTCGCTGCGCTCGGTCGTTCGGCTGCGGCGAGCGGTATCAGCTCAC
TCAAAGGCGGTAATACGGTTATCCACAGAATCAGGGGATAACGCAGGAAAG
AACATGTGAGCAAAAGGCCAGCAAAAGGCCAGGAACCGTAAAAAGGCCGCG
TTGCTGGCGTTTTTCCATAGGCTCCGCCCCCCTGACGAGCATCACAAAAAT
CGACGCTCAAGTCAGAGGTGGCGAAACCCGACAGGACTATAAAGATACCAG
GCGTTTCCCCCTGGAAGCTCCCTCGTGCGCTCTCCTGTTCCGACCCTGCCG
CTTACCGGATACCTGTCCGCCTTTCTCCCTTCGGGAAGCGTGGCGCTTTCT
CATAGCTCACGCTGTAGGTATCTCAGTTCGGTGTAGGTCGTTCGCTCCAAG
CTGGGCTGTGTGCACGAACCCCCCGTTCAGCCCGACCGCTGCGCCTTATCC
GGTAACTATCGTCTTGAGTCCAACCCGGTAAGACACGACTTATCGCCACTG
GCAGCAGCCACTGGTAACAGGATTAGCAGAGCGAGGTATGTAGGCGGTGCT
ACAGAGTTCTTGAAGTGGTGGCCTAACTACGGCTACACTAGAAGAACAGTA

TTTGGTATCTGCGCTCTGCTGAAGCCAGTTACCTTCGGAAAAAGAGTTGGT

AGCTCTTGATCCGGCAAACAAACCACCGCTGGTAGCGGTGGTTTTTTTGTT

TGCAAGCAGCAGATTACGCGCAGAAAAAAAGGATCTCAAGAAGATCCTTTG

ATCTTTTCTACGGGGTCTGACGCTCAGTGGAACGAAAACTCACGTTAAGGG

ATTTTGGTCATGAGATTATCAAAAAGGATCTTCACCTAGATCCTTTTAAAT

TAAAAATGAAGTTTTAAATCAATCTAAAGTATATATGAGTAAACTTGGTCT

GACAGTTACCAATGCTTAATCAGTGAGGCACCTATCTCAGCGATCTGTCTA

TTTCGTTCATCCATAGTTGCCTGACTC

This is the full-length optimized SNV M gene of pWRG/SN-M(opt). The nucleic acids outside the Not 1 and Bgl II cloning sites are not considered significant to the use of the SNV M gene.

Another valuable sequence is the isolated nucleic acid sequence of the SNV M gene (optimized) open reading frame plus the flanking sequence, as shown in SEQ ID NO:2, as follows:

GCGGCCGCGGATCTGCAGGAATTCGGCACGAGAGTAGTAGACTCCGCACG

AAGAAGCAAACACTGAATAAAGGATATACAGAATGGTGGGCTGGGTGTGC

ATCTTCCTGGTGGTGCTGACCACCGCCACAGCCGGCCTGACCCGGAACCT

GTACGAGCTGAAGATCGAGTGCCCCCACACCGTGGGCCTGGGCCAGGGCT

ACGTGACCGGCAGCGTGGAGACAACCCCCATCCTGCTGACCCAGGTGGCC

GACCTGAAGATTGAGAGCAGCTGCAACTTCGACCTGCACGTGCCCGCCAC

CACCACCCAGAAATACAACCAGGTGGACTGGACCAAGAAGAGCAGCACCA

CCGAGAGCACCAACGCCGGAGCCACCACCTTCGAGGCCAAGACCAAAGAA

GTGAACCTGAAGGGCACCTGCAACATCCCCCCCACCACATTTGAGGCCGC

CTACAAGAGCAGAAAGACCGTGATCTGCTACGACCTGGCCTGCAACCAGA

CCCACTGCCTGCCCACCGTGCACCTGATCGCCCCCGTGCAGACCTGCATG

AGCGTGCGGAGCTGCATGATCGGCCTGCTGTCCAGCCGGATCCAGGTGAT

CTACGAGAAACCTACTGCGTGACCGGCCAGCTGATCGAGGGCCTGTGCT

TCATCCCCACCCACACAATCGCCCTGACCCAGCCCGGCCACACCTACGAC

ACCATGACCCTGCCCGTGACCTGCTTTCTGGTGGCCAAGAAGCTGGGCAC

CCAGCTGAAGCTGGCCGTGGAGCTGGAAAAGCTGATCACCGGCGTGAGCT

GCACCGAGAACAGCTTCCAGGGCTACTACATCTGCTTCATCGGCAAGCAC

AGCGAGCCCCTGTTCGTGCCCACCATGGAAGATTACAGAAGCGCCGAGCT

GTTCACCCGGATGGTGCTGAACCCCAGGGGCGAGGACCACGACCCCGACC

AGAACGGCCAGGGCCTGATGCGGATCGCCGGACCCGTGACCGCCAAGGTG

CCCAGCACCGAGACAACCGAAACCATGCAGGGCATTGCCTTCGCCGGAGC

CCCCATGTACAGCAGCTTCAGCACCCTGGTGCGGAAGGCCGACCCCGAGT

ACGTGTTCAGCCCCGGCATCATTGCCGAGAGCAACCACAGCGTGTGCGAC

AAGAAAACCGTGCCCCTGACCTGGACCGGCTTCCTGGCCGTGAGCGGCGA

GATCGAGCGGATCACCGGCTGCACCGTGTTCTGCACCCTGGCCGGACCTG

GCGCCAGCTGCGAGGCCTACAGCGAGACAGGCATCTTCAACATCAGCAGC

CCCACCTGCCTGGTGAACAAGGTGCAGAAGTTCCGGGGCAGCGAGCAGCG

GATCAACTTCATGTGCCAGCGGGTGGACCAGGACGTGGTGGTGTACTGCA

ACGGCCAGAAAAAGTGATCCTGACCAAGACCCTGGTGATCGGCCAGTGC

ATCTACACCTTCACCAGCCTGTTCAGCCTGATCCCTGGCGTGGCTCATAG

CCTGGCAGTCGAACTGTGCGTGCCTGGCCTGCACGGATGGGCCACCACCG

CCCTGCTGATCACCTTCTGCTTCGGCTGGCTGCTGATCCCCACAGTGACC

CTGATCATCCTGAAGATCCTGCGGCTGCTGACCTTCAGCTGCAGCCACTA

CAGCACCGAGTCCAAGTTCAAAGTGATTCTGGAACGCGTGAAGGTGGAGT

ACCAGAAAACCATGGGCAGCATGGTGTGCGACATCTGCCACCACGAGTGC

GAGACAGCCAAAGAGCTGGAAACCCACAAGAAGAGCTGCCCCGAGGGCCA

GTGCCCCTACTGCATGACCATCACAGAGAGCACCGAGAGCGCCCTGCAGG

CCCACTTCAGCATCTGCAAGCTGACCAACCGGTTCCAGGAAAACCTGAAG

AAGAGCCTGAAGCGGCCCGAAGTGCGGAAGGGCTGCTACCGGACCCTGGG

CGTGTTCCGGTACAAGAGCCGGTGCTATGTGGGCCTGGTGTGGGGCATTC

TGCTGACCACAGAGCTGATCATCTGGGCCGCCAGCGCCGACACCCCCCTG

ATGGAAAGCGGGTGGAGCGACACCGCTCATGGCGTGGGAATCGTGCCCAT

GAAAACCGACCTGGAACTGGACTTCGCCCTGGCCAGCAGCAGCAGCTACA

GCTACCGGCGGAAGCTGGTGAACCCCGCCAACCAGGAAGAGACACTGCCC

TTCCACTTCCAACTGGACAAGCAGGTGGTGCACGCCGAGATCCAGAACCT

GGGCCACTGGATGGACGGCACCTTCAATATCAAGACCGCCTTCCACTGCT

ACGGCGAGTGCAAGAAGTACGCCTACCCCTGGCAGACCGCCAAGTGCTTC

TTCGAGAAGGACTACCAGTACGAGACAAGCTGGGGCTGCAACCCCCCCGA

CTGTCCTGGCGTGGGCACCGGCTGTACCGCCTGCGGCGTGTACCTGGACA

AGCTGCGGAGCGTGGGCAAGGCCTACAAGATCGTGTCCCTGAAGTACACC

CGGAAAGTGTGCATCCAGCTGGGCACAGAGCAGACATGCAAGCACATCGA

CGTGAACGATTGCCTGGTGACCCCCAGCGTGAAAGTCTGTATGATTGGCA

CCATCAGCAAGCTGCAGCCCGGCGATACCCTGCTGTTCCTGGGCCCCCTG

GAACAGGGCGGCATCATTCTGAAGCAGTGGTGTACCACCTCCTGCGTGTT

CGGCGACCCCGGCGACATCATGAGCACCACCTCCGGCATGCGGTGCCCCG

AGCACACCGGCAGCTTCCGGAAGATTTGTGGCTTCGCCACCACCCCTACC

TGCGAGTACCAGGGCAACACCGTGTCCGGCTTCCAGCGGATGATGGCCAC

CCGGGATAGCTTCCAGAGCTTCAACGTGACCGAGCCCCACATCACCAGCA

ACCGGCTGGAATGGATCGACCCCGACAGCAGCATCAAGGACCACATCAAC

ATGGTGCTCAATCGGGACGTGAGCTTCCAGGACCTGAGCGACAACCCCTG

CAAGGTGGACCTGCACACCCAGAGCATCGACGGCGCCTGGGGCAGCGGCG

TGGGCTTCACACTGGTGTGCACAGTGGGCCTGACCGAGTGCGCCAACTTC

ATCACCTCCATCAAGGCCTGCGACATGGCCATGTGCTACGGCGCCACCGT

GACCAACCTGCTGCGGGGCTCCAACACAGTGAAGGTGGTGGGCAAGGGCG

GCCACAGCGGCAGCCTGTTTAAGTGCTGCCACGACACCGACTGCACCGAG

GAAGGCCTGGCCGCCAGCCCCCCTCACCTGGACAGAGTGACCGGCTACAA

CCAGATCGACAGCGACAAGGTGTACGACGATGGCGCCCCTCCCTGCACCA

TCAAGTGCTGGTTCACCAAGAGCGGCGAGTGGCTGCTGGGCATCCTGAAC

GGCAACTGGGTCGTCGTGGCCGTGCTGATCGTGATCCTGATCCTGTCTAT

CCTGCTGTTCAGCTTCTTCTGCCCCGTGCGGAACCGGAAGAACAAGGCCA

AGCAAACATATATGTAAGTAAGGGTATGATCATATTATATCATTATGCGT

ACTATACTCTTATATCTATAATATCTATGTATCCTTATACTCTAACTATT

TATATTAATTTTTACTTTTATACAAGTATTAACTAACCCATTACCAGCTA

AAAAAAACAAACCCTTAACACCTATATAATCCCATTTGCTTATTACGAGG

CTTTTGTTCCTGCGGAGTCTACTACTAAGATCT

The flanking sequences are the cloning sites plus the SNV M segment non-translated regions of SEQ ID NO:1, and also includes the "extraneous sequence" at the 5' end. The first flanking sequence is:

(SEQ ID: NO 5)
ATCTGCAGGAATTCGGCACGAGAGTAGTAGACTCCGCACGAAGAAGCAAA
CACTGAATAAAGGATATACAGA; the second flanking
sequence is (SEQ ID NO: 6)
CAAACATATATGTAAGTAAGGGTATGATCATATTATATCATTATGCGTAT

ACTCTTATATCTATAATATCTATGTATCCTTATACTCTAACTATTTATAT

TAATTTTTACTTTTATACAAGTATTAACTAACCCATTACCAGCTAAAAAA

AACAAACCCTTAACACCTATATAATCCCATTTGCTTATTACGAGGCTTTT

GTTCCTGCGGAGTCTACTACTAA

Another valuable sequence is the isolated nucleic acid sequence of the SNV M gene (optimized) open reading frame by itself, as shown in SEQ ID NO:3. As a point of reference, the ORF begins with the ATG start codon and ends with the TAG stop codon. SEQ ID NO:3 is as follows:

ATGGTGGGCTGGGTGTGCATCTTCCTGGTGGTGCTGACCACCGCCACAGC

CGGCCTGACCCGGAACCTGTACGAGCTGAAGATCGAGTGCCCCCACACCG

TGGGCCTGGGCCAGGGCTACGTGACCGGCAGCGTGGAGACAACCCCCATC

CTGCTGACCCAGGTGGCCGACCTGAAGATTGAGAGCAGCTGCAACTTCGA

CCTGCACGTGCCCGCCACCACCACCCAGAAATACAACCAGGTGGACTGGA

CCAAGAAGAGCAGCACCACCGAGAGCACCAACGCCGGAGCCACCACCTTC

GAGGCCAAGACCAAAGAAGTGAACCTGAAGGGCACCTGCAACATCCCCCC

CACCACATTTGAGGCCGCCTACAAGAGCAGAAAGACCGTGATCTGCTACG

ACCTGGCCTGCAACCAGACCCACTGCCTGCCCACCGTGCACCTGATCGCC

CCCGTGCAGACCTGCATGAGCGTGCGGAGCTGCATGATCGGCCTGCTGTC

CAGCCGGATCCAGGTGATCTACGAGAAAACCTACTGCGTGACCGGCCAGC

TGATCGAGGGCCTGTGCTTCATCCCCACCCACACAATCGCCCTGACCCAG

CCCGGCCACACCTACGACACCATGACCCTGCCCGTGACCTGCTTTCTGGT

GGCCAAGAAGCTGGGCACCCAGCTGAAGCTGGCCGTGGAGCTGGAAAAGC

TGATCACCGGCGTGAGCTGCACCGAGAACAGCTTCCAGGGCTACTACATC

TGCTTCATCGGCAAGCACAGCGAGCCCCTGTTCGTGCCCACCATGGAAGA

-continued

TTACAGAAGCGCCGAGCTGTTCACCCGGATGGTGCTGAACCCCAGGGGCG

AGGACCACGACCCCGACCAGAACGGCCAGGGCCTGATGCGGATCGCCGGA

CCCGTGACCGCCAAGGTGCCCAGCACCGAGACAACCGAAACCATGCAGGG

CATTGCCTTCGCCGGAGCCCCCATGTACAGCAGCTTCAGCACCCTGGTGC

GGAAGGCCGACCCCGAGTACGTGTTCAGCCCCGGCATCATTGCCGAGAGC

AACCACAGCGTGTGCGACAAGAAAACCGTGCCCCTGACCTGGACCGGCTT

CCTGGCCGTGAGCGGCGAGATCGAGCGGATCACCGGCTGCACCGTGTTCT

GCACCCTGGCCGGACCTGGCGCCAGCTGCGAGGCCTACAGCGAGACAGGC

ATCTTCAACATCAGCAGCCCCACCTGCCTGGTGAACAAGGTGCAGAAGTT

CCGGGGCAGCGAGCAGCGGATCAACTTCATGTGCCAGCGGGTGGACCAGG

ACGTGGTGGTGTACTGCAACGGCCAGAAAAAAGTGATCCTGACCAAGACC

CTGGTGATCGGCCAGTGCATCTACACCTTCACCAGCCTGTTCAGCCTGAT

CCCTGGCGTGGCTCATAGCCTGGCAGTCGAACTGTGCGTGCCTGGCCTGC

ACGGATGGGCCACCACCGCCCTGCTGATCACCTTCTGCTTCGGCTGGCTG

CTGATCCCCACAGTGACCCTGATCATCCTGAAGATCCTGCGGCTGCTGAC

CTTCAGCTGCAGCCACTACAGCACCGAGTCCAAGTTCAAAGTGATTCTGG

AACGCGTGAAGGTGGAGTACCAGAAAACCATGGGCAGCATGGTGTGCGAC

ATCTGCCACCACGAGTGCGAGACAGCCAAAGAGCTGGAAACCCACAAGAA

GAGCTGCCCCGAGGGCCAGTGCCCCTACTGCATGACCATCACAGAGAGCA

CCGAGAGCGCCCTGCAGGCCCACTTCAGCATCTGCAAGCTGACCAACCGG

TTCCAGGAAAACCTGAAGAAGAGCCTGAAGCGGCCCGAAGTGCGGAAGGG

CTGCTACCGGACCCTGGGCGTGTTCCGGTACAAGAGCCGGTGCTATGTGG

GCCTGGTGTGGGGCATTCTGCTGACCACAGAGCTGATCATCTGGGCCGCC

AGCGCCGACACCCCCCTGATGGAAAGCGGGTGGAGCGACACCGCTCATGG

CGTGGGAATCGTGCCCATGAAAACCGACCTGGAACTGGACTTCGCCCTGG

CCAGCAGCAGCAGCTACAGCTACCGGCGGAAGCTGGTGAACCCCGCCAAC

CAGGAAGAGACACTGCCCTTCCACTTCCAACTGGACAAGCAGGTGGTGCA

CGCCGAGATCCAGAACCTGGGCCACTGGATGGACGGCACCTTCAATATCA

AGACCGCCTTCCACTGCTACGGCGAGTGCAAGAAGTACGCCTACCCCTGG

CAGACCGCCAAGTGCTTCTTCGAGAAGGACTACCAGTACGAGACAAGCTG

GGGCTGCAACCCCCCCGACTGTCCTGGCGTGGGCACCGGCTGTACCGCCT

GCGGCGTGTACCTGGACAAGCTGCGGAGCGTGGGCAAGGCCTACAAGATC

GTGTCCCTGAAGTACACCCGGAAAGTGTGCATCCAGCTGGGCACAGAGCA

GACATGCAAGCACATCGACGTGAACGATTGCCTGGTGACCCCCAGCGTGA

AAGTCTGTATGATTGGCACCATCAGCAAGCTGCAGCCCGGCGATACCCTG

CTGTTCCTGGGCCCCCTGGAACAGGGCGGCATCATTCTGAAGCAGTGGTG

TACCACCTCCTGCGTGTTCGGCGACCCCGGCGACATCATGAGCACCACCT

CCGGCATGCGGTGCCCCGAGCACACCGGCAGCTTCCGGAAGATTTGTGGC

TTCGCCACCACCCCTACCTGCGAGTACCAGGGCAACACCGTGTCCGGCTT

CCAGCGGATGATGGCCACCCGGGATAGCTTCCAGAGCTTCAACGTGACCG

AGCCCCACATCACCAGCAACCGGCTGGAATGGATCGACCCCGACAGCAGC

```
ATCAAGGACCACATCAACATGGTGCTCAATCGGGACGTGAGCTTCCAGGA

CCTGAGCGACAACCCCTGCAAGGTGGACCTGCACACCCAGAGCATCGACG

GCGCCTGGGGCAGCGGCGTGGGCTTCACACTGGTGTGCACAGTGGGCCTG

ACCGAGTGCGCCAACTTCATCACCTCCATCAAGGCCTGCGACAGCGCCAT

GTGCTACGGCGCCACCGTGACCAACCTGCTGCGGGGCTCCAACACAGTGA

AGGTGGTGGGCAAGGGCGGCCACAGCGGCAGCCTGTTTAAGTGCTGCCAC

GACACCGACTGCACCGAGGAAGGCCTGGCCGCCAGCCCCCCTCACCTGGA

CAGAGTGACCGGCTACAACCAGATCGACAGCGACAAGGTGTACGACGATG

GCGCCCCTCCCTGCACCATCAAGTGCTGGTTCACCAAGAGCGGCGAGTGG

CTGCTGGGCATCCTGAACGGCAACTGGGTCGTCGTGGCCGTGCTGATCGT

GATCCTGATCCTGTCTATCCTGCTGTTCAGCTTCTTCTGCCCCGTGCGGA

ACCGGAAGAACAAGGCCAACTAG
```

SEQ ID NO:2 and SEQ ID NO:3 are especially useful as a DNA cassette. The preferred cassette is the SNV optimized M gene cassette in the SNV-M (opt) (preferably taken from the Not 1 site to the BglII site, or minimally the ORF (SEQ ID NO:3) operably linked to a promoter) which can be subcloned into any other vaccine/expression system available, and used to generate active or passive immunity against SN virus. The DNA cassette specifically includes at least SEQ ID NO:2 linked to a promoter operable in a eukaryotic expression system. Alternatively, the DNA cassette includes the sequence in SEQ ID NO:3 (within pWRG/SN-M(opt)) from the ATG start codon to the TAG stop codon.

The peptide encoded by DNA sequence SEQ ID NO:3 is as follows: SN-M(opt) amino acid sequence

```
MVGWVCIFLVVLTTATAGLTRNLYELKIECPHTVGLGQGYVTGSVETTPI

LLTQVADLKIESSCNFDLHVPATTTQKYNQVDWTKKSSTTESTNAGATTF

EAKTKEVNLKGTCNIPPTTFEAAYKSRKTVICYDLACNQTHCLPTVHLIA

PVQTCMSVRSCMIGLLSSRIQVIYEKTYCVTGQLIEGLCFIPTHTIALTQ

PGHTYDTMTLPVTCFLVAKKLGTQLKLAVELEKLITGVSCTENSFQGYYI

CFIGKHSEPLFVPTMEDYRSAELFTRMVLNPRGEDHDPDQNGQGLMRIAG

PVTAKVPSTETTETMQGIAFAGAPMYSSFSTLVRKADPEYVFSPGIIAES

NHSVCDKKTVPLTWTGFLAVSGEIERITGCTVFCTLAGPGASCEAYSETG

IFNISSPTCLVNKVQKFRGSEQRINFMCQRVDQDVVVYCNGQKKVILTKT

LVIGQCIYTFTSLFSLIPGVAHSLAVELCVPGLHGWATTALLITFCFGWL

LIPTVTLIILKILRLLTFSCSHYSTESKFKVILERVKVEYQKTMGSMVCD

ICHHECETAKELETHKKSCPEGQCPYCMTITESTESALQAHFSICKLTNR

FQENLKKSLKRPEVRKGCYRTLGVFRYKSRCYVGLVWGILLTTELIIWAA

SADTPLMESGWSDTAHGVGIVPMKTDLELDFALASSSSYSYRRKLVNPAN

QEETLPFHFQLDKQVVHAEIQNLGHWMDGTFNIKTAFHCYGECKKYAYPW

QTAKCFFEKDYQYETSWGCNPPDCPGVGTGCTACGVYLDKLRSVGKAYKI

VSLKYTRKVCIQLGTEQTCKHIDVNDCLVTPSVKVCMIGTISKLQPGDTL

LFLGPLEQGGIILKQWCTTSCVFGDPGDIMSTTSGMRCPEHTGSFRKICG

FATTPTCEYQGNTVSGFQRMMATRDSFQSFNVTEPHITSNRLEWIDPDSS

IKDHINMVLNRDVSFQDLSDNPCKVDLHTQSIDGAWGSGVGFTLVCTVGL

TECANFITSIKACDSAMCYGATVTNLLRGSNTVKVVGKGGHSGSLFKCCH

DTDCTEEGLAASPPHLDRVTGYNQIDSDKVYDDGAPPCTIKCWFTKSGEW

LLGILNGNWVVVAVLIVILILSILLFSFFCPVRNRKNKAN
```

There are four residues that are altered in the M(opt) from the M(2a): K at position 27, T at position 241, D at position 434, and S at position 519. The enhanced immunogenicity of pWRG/SN-M(opt) vs pWRG/SN-M(2a) is speculated to be due to the nucleic acid changes, one or more of the four amino acid changes, or a combination thereof.

In another embodiment, the invention entails a recombinant DNA construct comprising:

(i) a vector, and (ii) the DNA fragment comprising the nucleic acid sequence set forth in SEQ ID NO:1, SEQ ID NO:2 or SEQ ID NO:3, or a DNA fragment comprising a nucleic acid sequence that encodes the amino acid sequence set forth in SEQ ID NO:4, operably linked to a promoter sequence.

As would be understood by someone having skill in this art, the DNA constructs of our invention will have all necessary structural components for expression of the DNA fragment of interest (e.g., promoters functional in mammals, and the like). The vector can take the form of a plasmid such as pCRII (Invitrogen) or pJW4303 (Konishi, E. et al., 1992, *Virology* 188:714), or any expression vector such as viral vectors e.g. adenovirus or Venezuelan equine encephalitis virus and others known in the art. Preferably the vector is a recombinant adenovirus or recombinant vesicular stomatitis virus, or alphavirus replicon. Preferably, a promoter sequence operable in the target cell is operably linked to the DNA sequence. Several such promoters are known for mammalian systems which may be joined 5', or upstream, of the coding sequence for the encoded protein to be expressed. A suitable and preferred promoter is the human cytomegalovirus immediate early promoter, preferably operably linked to intron A. Another preferred promoter is the beta-actin promoter or the SV40 promoter. A downstream transcriptional terminator, or polyadenylation sequence, such as the polyA addition sequence of the bovine growth hormone gene, may also be added 3' to the protein coding sequence.

Preferably, the construct is the pWRG/SN-M(opt) DNA vaccine plasmid, whose sequence is set forth above and referred to as SEQ ID NO:1.

In a further embodiment, the present invention relates to host cells stably transformed or transfected with the above-described recombinant DNA constructs. The host cell can be prokaryotic such as *Bacillus* or *E. coli*, or eukaryotic such a *Saccharomyces* or *Pichia*, or mammalian cells or insect cells. The vector containing the Sin Nombre virus M gene sequence is expressed in the bacteria and the expressed product used for diagnostic procedures or as a vaccine. Please see e.g., Maniatis et al., 1985 *Molecular Cloning: A Laboratory Manual* or *DNA Cloning*, Vol. I and II (D. N. Glover, ed., 1985) for general cloning methods. The DNA sequence can be present in the vector operably linked to a highly purified IgG molecule, an adjuvant, a carrier, or an agent for aid in purification of Sin Nombre virus proteins or peptides. The transformed or transfected host cells can be used as a source of DNA sequences described above. When the recombinant molecule takes the form of an expression system, the transformed or transfected cells can be used as a source of the protein or peptide encoded by the DNA. The DNA can be used as circular or linear, or linearized plasmid as long as the Sin Nombre virus sequences are operably linked to a promoter which can be expressed in the transfected cell.

In another embodiment, the invention entails vaccines against infection with Sin Nombre virus. In a method for eliciting in a subject an immune response against Sin Nombre virus, the method comprises administering to a subject a DNA fragment comprising a genome segment of hantavirus. In one preferred embodiment, the vaccine composition comprises an effective immunizing amount of SNV plasmid DNA, which plasmid DNA comprises one or more of the recombinant DNA constructs described above, and a pharmacologically acceptable carrier. That is, the recombinant DNA construct should minimally include (i) a vector, and (ii) the DNA fragment comprising the nucleic acid sequence set forth in SEQ ID NO:1, SEQ ID NO:2 or SEQ ID NO:3, or a DNA fragment comprising a nucleic acid sequence that encodes the amino acid sequence set forth in SEQ ID NO:4. The DNA fragment is operably linked to a promoter sequence. The pharmacologically acceptable carrier may be any carrier that is known in the art, which is safe and effective for a SNV DNA vaccine. Examples of such carriers include PBS, water, saline, Tris-EDTA, and mixtures of these.

The vaccine composition may which further comprise an adjuvant. The adjuvant may be any one that is known in the art, which is safe and effective for a SNV DNA vaccine. As used herein the term "adjuvant" refers to any component which improves the body's response to a vaccine. The adjuvant will typically comprise about 0.1 to 50% vol/vol of the vaccine formulation of the invention, more preferably about 1 to 50% of the vaccine, and even more desirably about 1 to 20% thereof. Examples of such adjuvants include CpG (cystein-phosphate-guanine) oligodeoxynucleic acid, or plasmid DNA-encoded heat labile enterotoxins, or alum.

The immunizing amount of SNV plasmid DNA is preferably between about 5 micrograms (e.g., with gene gun administration) and about 5 milligrams (e.g., electroporation or other forms of administration). By "immunizing amount", it is meant the amount of vaccine or immunogenic composition that is needed to raise high titers of neutralizing antibodies in response to the composition.

One unique aspect of our invention is that it can further comprise one or more additional vaccine components of other hantaviruses, to make a bi-valent, tri-valent, multivalent or pan-virus vaccine. In one embodiment, a DNA vaccine is contemplated that elicits an immune response against multiple HPS-associated hantaviruses and protects against more than one HPS virus. Such a DNA vaccine comprises one of the SNV sequences described above (SEQ ID NO:1, SEQ ID NO:2 or SEQ ID NO:3), in combination with an HPS hantavirus M gene DNA vaccine (such as M gene DNA vaccine from one or more of Black Creek Canal virus, Bayou virus, New York virus, Andes virus and Laguna Negra virus) such that each M gene is expressed in the subject. The respective M gene DNA sequences may each be part of respective recombinant constructs that each include (i) a vector and (ii) the desired DNA fragment that is operably linked to a promoter sequence. A preferred HPS virus is Andes virus.

In another embodiment, a DNA vaccine elicits an immune response against both HFRS and HPS hantavirus and protects against all the hantaviruses causing severe disease by providing to a subject a DNA vaccine comprising one of the SNV sequences described above (SEQ ID NO:1, SEQ ID NO:2 or SEQ ID NO:3), in combination with at least one HFRS hantavirus M gene DNA vaccine (such as Hantaan M gene DNA vaccine, Puumala M gene DNA vaccine, Seoul M gene DNA vaccine and Dobrava M gene DNA) such that each M gene is expressed in the subject. Furthermore, the M gene DNA vaccine from one or more of another HPS-associated virus (such as Black Creek Canal virus, Bayou virus, New York virus, Andes virus and Laguna Negra virus) may be included, to strengthen the HPS component. The respective M gene DNA sequences may each be part of respective recombinant constructs that each include (i) a vector and (ii) the desired DNA fragment that is operably linked to a promoter sequence.

The SNV M gene or the other HPS or HFRS M gene may be administered separately, i.e. on seperate vectors, or may be combined on the same vector as is described in one aspect of this invention. For instance, a pan-HPS virus vaccine can include any of SEQ ID NO:1, SEQ ID NO:2, or SEQ ID NO:3, and a suitable Andes M gene sequence (in whole, or an ORF with flanking sequences, or simply the ORF). A preferred Andes M gene sequence is SEQ ID NO:10, which is the full-length ANDY M gene described in U.S. Pat. No. 7,217,812 (and the sequence is referred to as SEQ ID NO:8 therein).

A preferred Puumala M gene sequence is SEQ ID NO:11, which is the full-length PUUV M gene described in U.S. patent publication number 20100323024 (and the sequence is referred to as SEQ ID NO: 1 therein). A preferred Hantaan M gene sequence is SEQ ID NO:12, which is the full-length HNTV M gene described in U.S. Pat. No. 7,217,812 (and the sequence is referred to as SEQ ID NO:7 therein). A preferred Seoul M gene sequence is SEQ ID NO:13, which is the full-length Seoul M gene described in U.S. Pat. No. 7,217,812 (and the sequence is referred to as SEQ ID NO:3 therein). The preferred HPS/HFRS vaccine combination includes Hantaan, Puumala, Andes, and Sin Nombre DNA vaccines, although Seoul DNA vaccine is also a good component for the combined vaccine. Any of these M genes can be used in full-length, or just the ORF with flanking sequences, or simply the ORF. As someone skilled in this art would understand, this invention entailing the combination of hantavirus M genes is not limited at all to these specific M genes—these are merely examples, and any M gene isolated or derived or improved or otherwise altered from the hantavirus (e.g., an altered Seoul M gene, or a non-optimized Puumala M gene).

The vaccine may involve the delivery of pWRG/SN-M (opt) DNA (SEQ ID NO:1), or the DNA of SEQ ID NO:2 or SEQ ID NO:3 (or, if a multivalent vaccine is employed, one or more of the above-described sequences of the other HPS- or HFRS-associated viruses) by any of several platforms used to deliver gene-based vaccines. For example, the vaccine could comprise a composition comprising inert particles and a nucleic acid coated onto the inert particles producing nucleic acid coated particles. The nucleic acid will comprise a promoter operative in the cells of a mammal and further comprise (or even consist essentially of or consist of) SEQ ID NO:1, SEQ ID NO:2 or SEQ ID NO:3. As would be understood by someone having skill in this art, the ORF sequence (SEQ ID NO:3) is essential (and for the other HPS- or HFRS-associated viruses, the ORF of the respective M gene). The flanking region between the cloning sites and the ORF are preferably included, as they may be helpful for efficient expression. The inert particle may be gold particles, silver particles, platinum particles, tungsten particles, polystyrene particles, polypropylene particles, polycarbonate particles, and the like, as would be understood by someone having ordinary skill in this art. In particular, it is preferred that the inert particle is suitable for use in a gene gun.

The invention further encompasses a method for inducing a protective immune response against Sin Nombre virus infection in a mammal, comprising the step of accelerating into epidermal cells of the mammal in vivo a composition comprising inert particles and a nucleic acid coated onto the inert particles producing nucleic acid coated particles, such that said nucleic acid is expressed (e.g., gene gun administration). The nucleic acid will comprise a promoter effective and functional in the cells of a mammal and SEQ ID NO:1, SEQ ID NO:2 or SEQ ID NO:3.

Electroporation is another method of administration. Electroporation involves injecting plasmid DNA into a tissue (e.g. muscle or skin) and then applying micropulses of an electric field causing transient permeability of the cells of the vaccine. This transient permeability allows for a more efficient take-up of the DNA vaccine plasmid.

In a more general method for inducing a protective immune response against Sin Nombre virus infection in a mammal, a composition is administered to a mammal comprising a nucleic acid comprising a promoter operative in the cells of a mammal and one of SEQ ID NO: 1, SEQ ID NO:2 or SEQ ID NO:3. It is generally preferred that the chosen sequence be inserted into a plasmid, and the plasmid administered. To that end, preferably the nucleic acid is a component of one of the above-referenced DNA constructs. However, it is known that a linear piece of DNA consisting of only a promoter and the gene-of-interest can elicit an immune response. Thus, one option for the composition is that it comprises SEQ ID NO: 1, SEQ ID NO:2 or SEQ ID NO:3 plus an appropriate promoter. One preferred method comprises the step of administering a composition comprising an effective immunizing amount of SNV plasmid DNA, which plasmid DNA comprises one of the recombinant DNA construct described above; and a pharmacologically acceptable carrier. Another preferred method comprises the step of administering a composition comprising an effective immunizing amount of EQ ID NO: 1, SEQ ID NO:2 or SEQ ID NO:3 operably linked to a promoter operative in the cells of a mammal plus an appropriate promoter; and a pharmacologically acceptable carrier. Appropriate pharmacologically acceptable carriers are discussed elsewhere in this document. Preferably, the immunizing amount of SNV plasmid DNA is between about 5 micrograms and about 5 milligrams.

In another embodiment, this invention provides a method for raising high titers of neutralizing antibodies against Sin Nombre virus in a mammal or a bird. The method comprises the step of administering a composition comprising a SNV plasmid DNA which comprises one or more of the recombinant DNA constructs described above (including SEQ ID NO:1, SEQ ID NO:2 or SEQ ID NOT:3); and a pharmacologically acceptable carrier. Preferably, the titers are at least 100, and more preferably are at least 10,000. As someone having ordinary skill in this art would recognize, in the context of hantavirus infection, titers with a level of at least 100 are significant, and considered "high" because they are 10 times higher than the minimal titer of 10 that has been used to evaluate vaccines against HFRS (a titer of 10 indicates there was a 50% reduction in plaque forming units when virus was combined with serum for a final dilution of 1:10). Titers of >10,000 are similar to those produced in person who have developed HPS and survived.

High titers are obtained even with only one dose or administration of the composition, although additional doses or vaccinations can boost titers even higher. The pharmacologically acceptable carrier can be any such carrier known in the art which is safe and does not hamper effectiveness of the composition. Examples are mentioned above, and throughout this document. The amount of the composition required for raising high titers of neutralizing antibodies is between about 5 micrograms and about 5 milligrams. The inventors discovered that the composition was effective in both mammals and birds.

The invention also encompasses post-exposure prophylactics, or passive vaccines, for treating or preventing Sin Nombre virus infections, for someone who has already been exposed to Sin Nombre virus and may be infected. Polyclonal antibodies may be obtained using methods known in the art, from a population of vaccines (human or animal) vaccinated with a Sin Nombre virus DNA vaccine comprised of a plasmid expressing SEQ ID NO:1, SEQ ID NO:2 or SEQ ID NO; 3, such as pWRG/SN-M(opt). Alternatively, polyclonal or monoclonal antibodies could be produced in animals using the pWRG/SN-M(opt) plasmid, or a plasmid containing SEQ ID NO:2 or SEQ ID NO:3, operably associated with a promoter and any other elements needed for expression of the sequence. The methods entail administration of a therapeutically or prophylactically effective amount of the antibodies which protect against Sin Nombre virus disease in combination with a pharmaceutically acceptable carrier or excipient. For instance, a therapeutic composition for ameliorating symptoms of Sin Nombre virus infection may comprise a composition comprising these polyclonal antibodies, and a pharmaceutically acceptable excipient. For instance, pWRG/SN-M(opt) may be used to vaccinate ducks, sheep, or transgenic cows or rabbits to produce polyclonal neutralizing antibodies for use in humans.

The invention also entails a method for diagnosis of Sin Nombre virus infection by assaying for the presence of Sin Nombre virus in a sample using the above-described antibodies. For instance, a method for the diagnosis of Sin Nombre virus infection may comprise the steps of:

(i) contacting a sample from an individual suspected of having Sin Nombre virus infection with a composition comprising the polyclonal antibodies (e.g., the pWRG/SN-M(opt) plasmid could be used to produce diagnostic antibodies in any of several species of animals—goats, rabbits, etc.); and (ii) detecting the presence or absence of Sin Nombre virus infection by detecting the presence or absence of a complex formed between Sin Nombre virus antigens and antibodies specific therefor.

In addition, the invention encompasses novel immunoprobes and test kits for detection of Sin Nombre virus infection comprising antibodies according to the present invention. For immunoprobes, the antibodies are directly or indirectly attached to a suitable reporter molecule, e.g., and enzyme or a radionuclide. The test kit includes a container holding one or more antibodies according to the present invention and instructions for using the antibodies for the purpose of binding to Sin Nombre virus to form an immunological complex and detecting the formation of the immunological complex such that presence or absence of the immunological complex correlates with presence or absence of Sin Nombre virus. For instance, the kit may include kit may include a container holding one or more polyclonal antibodies of the present invention which binds a Sin Nombre virus antigen, and ancillary reagents suitable for use in detecting Sin Nombre virus antigens, and instructions for using any of the antibodies or polyclonal antibodies described herein for the purpose of binding to SNV antigen to form an immunological complex and detecting the formation of the immunological complex such that the presence or absence of the immunological complex correlates with presence or absence of Sin Nombre virus antigens in the sample. Examples of containers include multiwell plates which allow simultaneous detection of Sin Nombre virus in multiple samples.

Further, the invention contemplates a method for producing pseudotyped viruses for use in serologic assays or delivery of gene therapies to endothelial cells targeted by hantavirus glycoproteins. The invention as used for this purpose would comprise the following steps. The plasmid pWRG/SN-M(opt) or derivative thereof would be used to transfect cells or stably transform cells. Cells expressing the Sin Nombre glycoproteins could then be infected with viruses engineered to produce progeny that incorporate the Sin Nombre glycoproteins into progeny virus surface envelopes. Pseudotype virus systems include retrovirus systems and vesicular stomatitis virus systems. Pseudotypes have been produced using the hantavirus full-length M gene plasmids, including pWRG/SN-M(opt). The pseudotypes can be used for testing for neutralizing antibodies. They also may be used to deliver genes to endothelial cells in a clinical setting. For example, gene therapy viruses containing the Sin Nombre glycoproteins on their surface will target to certain endothelial cells.

The invention also entails a therapeutic composition for ameliorating symptoms of Sin Nombre virus infection. The composition includes polyclonal or monoclonal antibodies specifically raised against one of SEQ ID NO:1, SEQ ID NO:2 or SEQ ID NO:3. The composition may be combined with a pharmaceutically acceptable carrier and/or an adjuvant, such as the examples as described herein.

Other embodiments are discussed below. The invention is described in further detail by the non-limiting examples and text below.

BRIEF DESCRIPTION OF THE FIGURES

FIG. 1A-1D. Hantavirus neutralizing antibodies produced in rabbits vaccinated with full-length hantavirus M gene-based DNA vaccines using muscle electroporation. FIG. 1A: Hantaan, Puumala, and Andes DNA vaccines. Groups of 3 rabbits were vaccinated with either the Hantaan DNA vaccine, pWRG/HTN-M(x) (described in U.S. Pat. No. 7,217,812), or the Puumala DNA vaccine, pWRG/PUU-M(s2) (described in U.S. Patent Publication No. 20100323024) on days 0, 14, 28, and 32 by muscle electroporation (Invoio Elgen device, dose was 0.4 mg of DNA per injection. Sera were collected on weeks 0, 28, 56, and 116 and tested in homotypic PRNT. Symbols represent the mean of two separate PRNT±SE. FIG. 1B: The same data from panel A were combined to show mean titers for the groups. In addition, published data from rabbits vaccinated with the Andes DNA vaccine, pWRG/AND-M, are included. Note the vaccination days were different for the Andes DNA vaccine (shown in grey arrows). FIG. 1C: Sin Nombre DNA vaccines. The first generation SNV full-length M gene based DNA vaccine, pWRG/SNV-M(2a), was tested in three rabbits. The animals were vaccinated four times (arrows) and sera were tested for SNV neutralizing antibodies. High-titer neutralizing antibody could be produced after multiple vaccinations. The second generation plasmid, pWRG/SN-M (opt), was tested in rabbits. Rabbits were vaccinated on days 0, 28, 56 and 84. Sera collected on the indicated days were tested for SNV neutralizing antibodies. High-titers were achieved after 2, or fewer, vaccinations (sera from day 28 was not collected). FIG. 1D: The same data from panel C were combined to show mean titers for the groups±SE.

FIG. 2A. The titers are the reciprocal of the highest dilution reducing the number of plaques in the media alone wells by 80%. FIG. 2B. Raw plaque numbers for one representative rabbit are shown before vaccination, after 2 (day 56) and after 3 (day 70). Note that there is 100% neutralization out to a 1:10,240 dilution for the day 70 serum. The numbers 6281, 6282, 6283, and 5284 are designations for the different rabbits vaccinated.

FIGS. 3A and 3B. HPS vaccine. Plasmid mixtures were tested in rabbits using muscle electroporation (EP). Three rabbits were vaccinated by muscle EP on day 0, 21, and 42 with a 1:1 mixture of the pWRG/SN-M(opt) and pWRG/AND-M DNA (described in U.S. Pat. No. 7,217,812) vaccine plasmids. Sera were collected at the indicated time points and plaque reduction neutralization tests (PRNT) were performed. Neutralizing antibodies were produced against both SNV and ANDY after a single vaccination. Overall, the neutralizing antibody titers were greater against SNV (shown in FIG. 3A) than ANDY (shown in FIG. 3B) Device=Ichor Tri-grid device; Dose=2.0 mg mixed DNA/injection, 1 injection per vaccination. (Unpublished) The numbers 6214, 6215, and 6216 are designations for the different rabbits vaccinated.

Figure 4B:
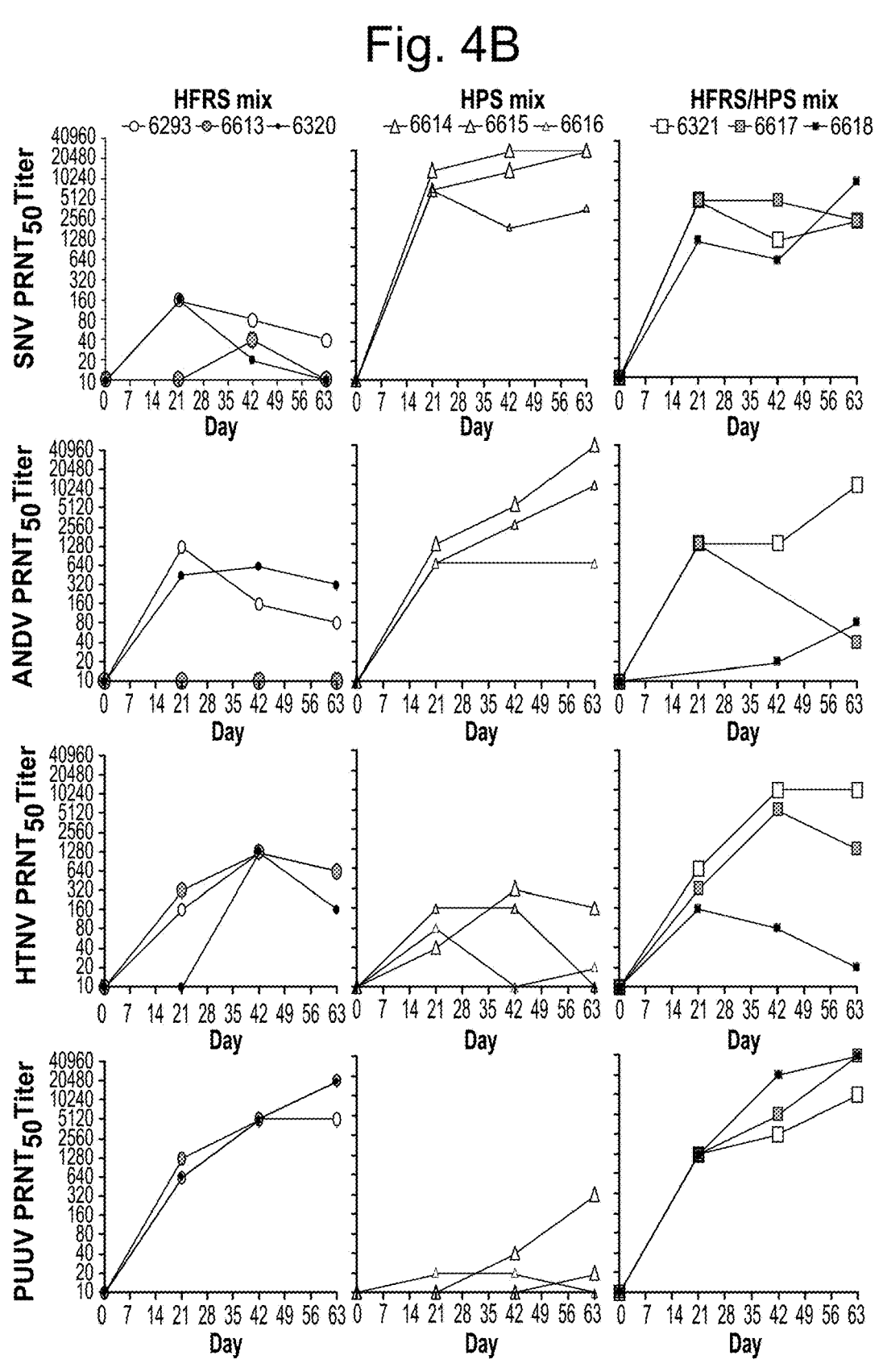
Figure 4C:
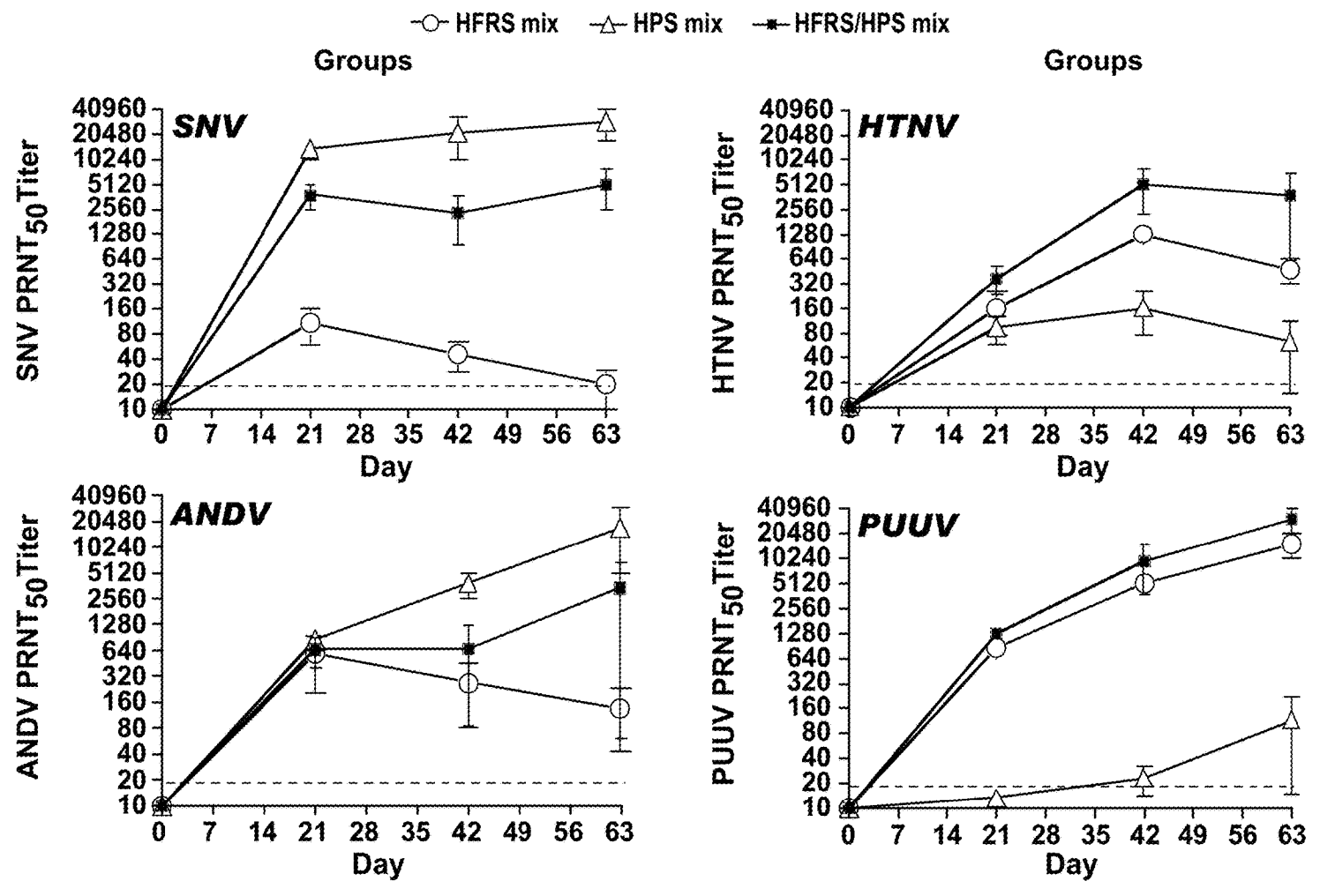

FIG. 4A-4C. Mixed hantavirus DNA vaccines are feasible. Three mixtures of hantavirus DNA vaccine plasmids delivered by muscle electroporation were tested in rabbits. FIG. 4A: Experimental design. Groups of three rabbits were vaccinated three times by muscle electroporation using the Ichor Tri-grid at three-week intervals. The HFRS mixture was comprised of equal volumes of Hantaan and Puumala DNA vaccine plasmids, pWRG/HTN-M(x) and pWRG/PUU-M(s2), respectively. The HPS mixture was comprised of equal volumes of Andes and Sin Nombre DNA vaccine plasmids, pWRG/AND-M and pWRG/SN-M(opt), respectively. The HFRS/HPS mixture was comprised of equal volumes of the Hantaan, Puumala, Andes, and Sin Nombre DNA vaccine plasmids. The mixtures contained 1 mg of each plasmid per dose. FIG. 4B: Neutralizing antibody titers for individual rabbits are shown. The virus used in the neutralization test is shown on the y-axis. Sera from days 0, 21, 42, and 63 were tested. FIG. 4C: Mean neutralizing titers for each group plus/minus standard error. The data demonstrate that it is possible to mix hantavirus DNA vaccines into a single-injection vaccine and produce neutralizing antibodies against multiple hantaviruses. The HFRS DNA vaccine was more effective at neutralizing Puumala virus and Hantaan virus and the HPS DNA vaccine was more effective at neutralizing Andes virus and Sin Nombre virus. The HFRS/HPS DNA vaccine elicited neutralizing antibodies against all four hantaviruses after a single vaccination for all but one rabbit.

Figure 5:
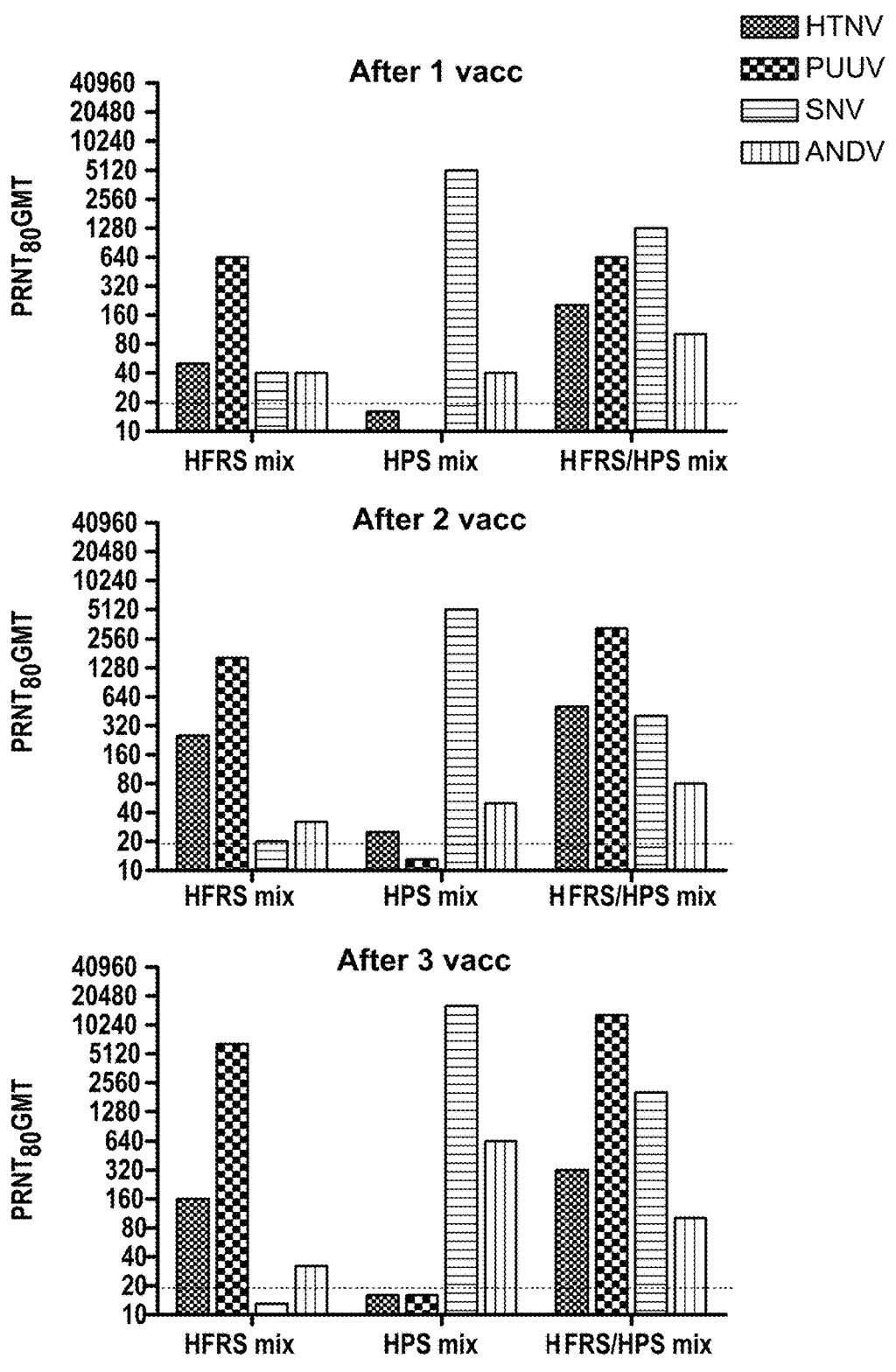

FIG. 5. PRNT80 GMT against HTNV, PUUV, SNV, and ANDY for each DNA vaccine formulation after 1, 2, or 3 vaccinations are shown. These data are from the same experiment shown in FIG. 2; however PRNT80 GMT are shown here. PRNT80 titers are a more stringent measure of neutralizing antibodies that PRNT50. The HFRS mix (pWRG/HTN-M[x] and pWRG/PUU-M[s2]) produced GMTs>100 against HTNV and PUUV. The HPS mix (pWRG/SN-M[opt] and pWRG/AND-M) produced GMTs>100 against SNV and ANDY. And the HFRS/HPS mix "pan-hantavirus" produced GMTs>100 against all four hantaviruses. PUUV PRNT endpoints after 1 vaccination were not determined beyond 640 (indicated by ≥). < indicates GMT was below detection. These data demonstrate the utility of using the SN DNA vaccine as part of HPS vaccine or a pan-hantavirus DNA vaccine.

FIGS. 6A and 6B. pWRG/SN-M(opt) DNA vaccine is immunogenic and protective in hamsters. Groups of 7-8 hamsters received 2 vaccinations (week 0, 3), or three vaccinations (week 0, 3, 6) with pWRG/SN-M(opt), or 3 vaccinations with a negative control DNA vaccine, or no vaccine. Vaccinations were performed using a gene gun. FIG. 6A: Sera collected on week 9 were tested for SNV neutralizing antibody by SNV PRNT. Each symbol represents the PRNT50 titer of an individual hamster. The geometric mean titer and 95% confidence interval for each group are shown. The limit of detection was a titer of 20 (dashed line). Seroconversion rates after 2 or 3 vaccinations were 62.5% (5 of 8) and 71.4% (5 of 7), respectively. The immune response was lower than what we observed in rabbits using electroporation, but was nevertheless evidence that the pWRG/SN-M(opt) plasmid was immunogenic in hamsters. FIG. 6B: The hamsters were challenged with 200 pfu of SNV by the intramuscular route on week 11. Sera were collected on week 16 and tested by ELISA for evidence of SNV infection (note that SNV infects hamsters but is not lethal). A positive ELISA indicates the hamsters were infected with SNV (i.e., not protected). 2 vaccinations with pWRG/SN-M(opt) protected 62.5% of the hamsters and 3 vaccinations protected 100% of the hamsters. All of the negative control hamsters were infected. < indicates titer was below level of detection.

FIG. 7. The pWRG/SN-M(opt) plasmid was used to make pseudovirions that were specifically neutralized by rabbit sera containing SNV neutralizing antibodies. 293T cells were transfected with pWRG/SN-M(opt) and then, after 24 hr, were "infected" with recombinant vesicular stomatitis virus (VSV) that had the G protein deleted and replaced with the Renilla luciferase gene (VSV deltaG luciferase reporter core virus system was provided by Robert Doms, University of Pennsylvania). After 48 hr at 37 C, the supernatant was harvested and pseudovirion particles were purified on a sucrose gradient. Two different preparations of pseudovirions (prep 1, top panel; prep 2, bottom panel) where then mixed with serial dilutions of naïve rabbit sera, anti-SNV rabbit sera, or anti-VSV-G antibody (as control) and incubated for 1 hr at 37 C. The mixtures were then used to infect BHK cells in a 96-well format for 24 hours. Cell lysates were harvested, combined with luciferase substrate, and the luciferase reporter activity in Relative Luminescent Units (RLU) was measured using a luminometer. Symbols represent the average value of duplicates. The data demonstrate that the anti-SNV rabbit sera, but not the other sera, reduced the RLU activity (neutralized the pseudovirions) in a dose dependent manor. This assay can be used to measure SNV neutralizing antibodies in any sera including humans vaccinated with candidate HPS vaccines, or naturally infected with hantaviruses FIG. 8. The nonoptimized version of the Sin Nombre DNA vaccine, pWRG/SN-M(2a), was tested for the capacity to produce neutralizing antibodies in an avian species. Ducks were vaccinated with 0.4 mg of plasmid DNA using muscle electroporation on days 0, 14, and 42. Sera was collected on days 0, 28, and 56 and tested for SNV neutralizing antibodies by PRNT. Higher titers are expected using the optimized pWRG/SN-M(opt) plasmid. These data demonstrate that the Sin Nombre DNA vaccine can be used to produce high titer neutralizing antibodies in avian species. This antibody is reasonably expected to be purified from eggs and may be used in humans or other mammals as post-exposure prophylactics or therapeutics, or as diagnostic reagents. The duck IgY naturally loses the Fc fragment of the antibody and this, it is believed, will make the molecule less reactogenic when used in a human as a therapeutic or post-exposure prophylactic.

DETAILED DESCRIPTION OF THE INVENTION

Supplemental to the previous description of the invention, the following further details are provided.

The inventor has created a novel, synthetic codon optimized Sin Nombre virus full-length M gene, ORF plus flanking sequences, and ORF, that are each stably maintained in a DNA vaccine plasmid, and elicit good neutralizing antibodies in animal models. Heretofore, there was no full length Sin Nombre M gene clone stably inserted it on an expression plasmid, which could be successfully expressed. Likewise, this is the first time any vaccine, of any kind, has been shown to elicit high titer neutralizing antibodies and protect against SNV infection in an animal model.

Figure 1A:
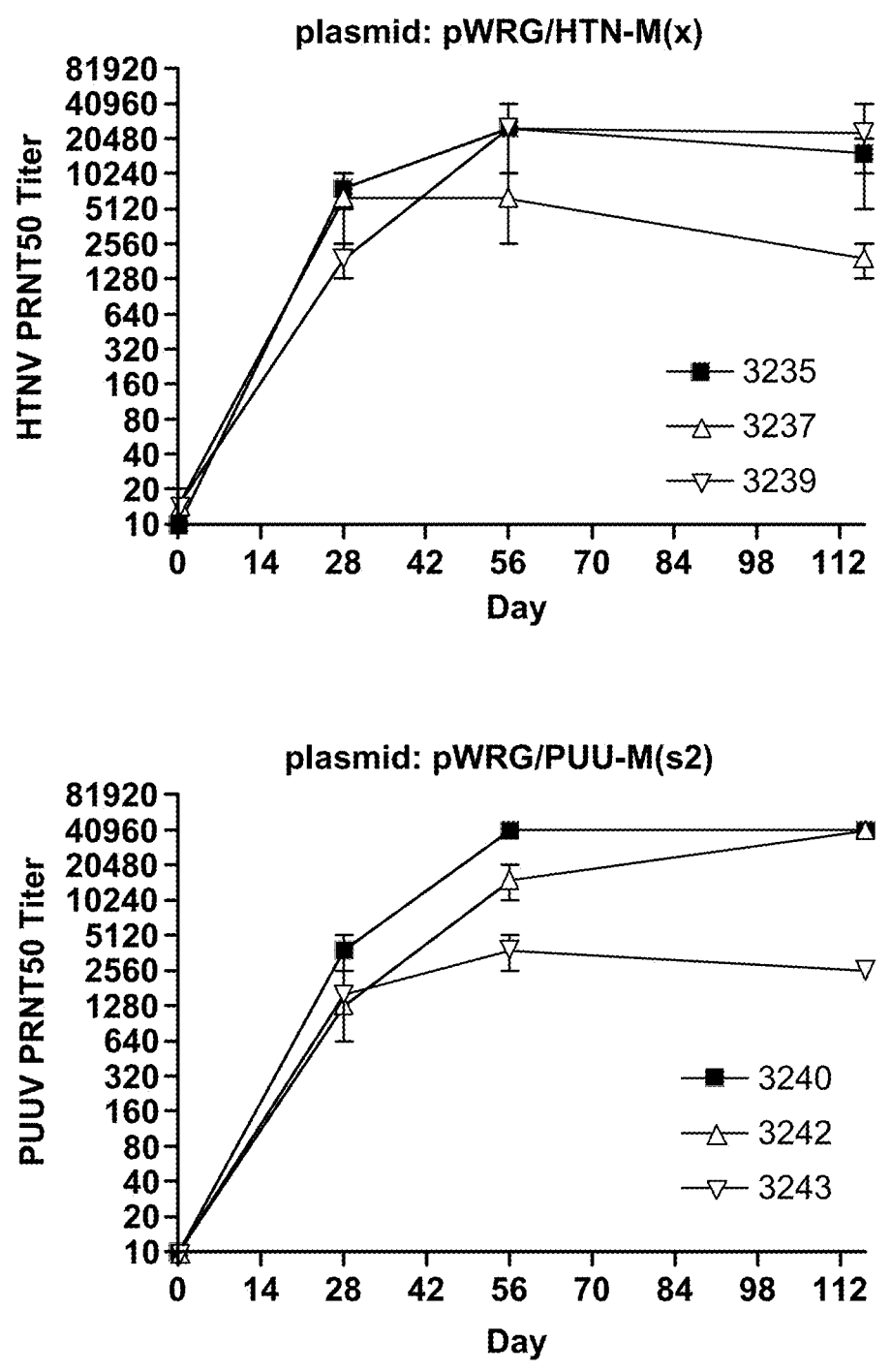

The inventor cloned the full-length M gene from SNV, strain CC107 into a DNA vaccine vector (i.e., RNA was purified, reverse transcribed to cDNA, PCR amplified, and cloned into a DNA vaccine plasmid [pWRG7077]). Ultimately, the inventor was able to produce a unique plasmid with an intact open reading frame (designated pWRG/SN-M(2a) or "M(2a)"). It was confirmed that this plasmid could produce the Gn and Gc protein in cell culture. pWRG/SN-M(2a) was tested for immunogenicity in rabbits using muscle electroporation technology. Three rabbits were vaccinated on weeks 0, 2, 4, 6 with 0.4 mg of DNA per vaccination. Sera were collected on weeks 0, 4, and 8. PRNT were performed to detect SNV neutralizing antibodies. The data demonstrated that high-titer neutralizing antibody were produced after 4 vaccinations (FIG. 1). The titers reached were over 10,000, which is considered are similar to those produced in person who have developed HPS and survived. In the art of immunology, and especially regarding hantaviruses, any titer over 100 would be considered good, and useful for vaccine purposes. This was the first time high-titer SNV neutralizing antibodies were ever produced by any vaccine, confirming the uniqueness of the M(2a) plasmid. Nevertheless, one undesirable result was that the M(2a) required more vaccinations to raise high-titers than the inventor's previous hantavirus vaccines, namely the HTNV, PUUV, or ANDY M gene-based DNA vaccines.

Figure 2A:
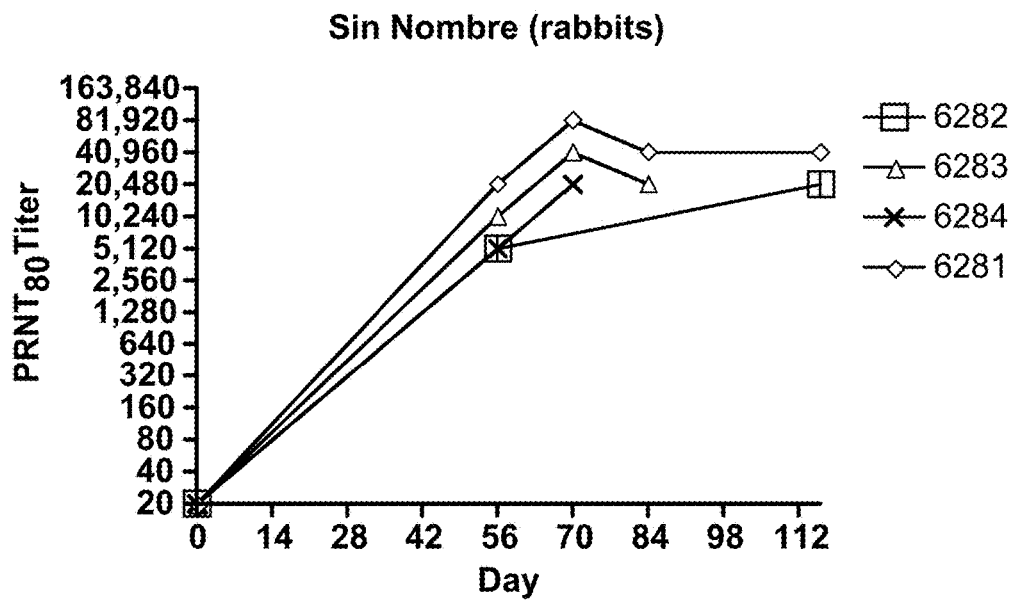
FIGS. 2A and 2B. Neutralizing antibody data from rabbits vaccinated with pWRG/SN-M(opt) (also designated as pWRG/SN-M(opt)). Rabbits were vaccinated on days 0, 28, 56 and 84. Sera collected on days 0, 56, and 70 where tested for Sin Nombre virus neutralizing antibodies by plaque reduction neutralization test (PRNT). The neutralizing antibody titers are shown.
Figure 2B:
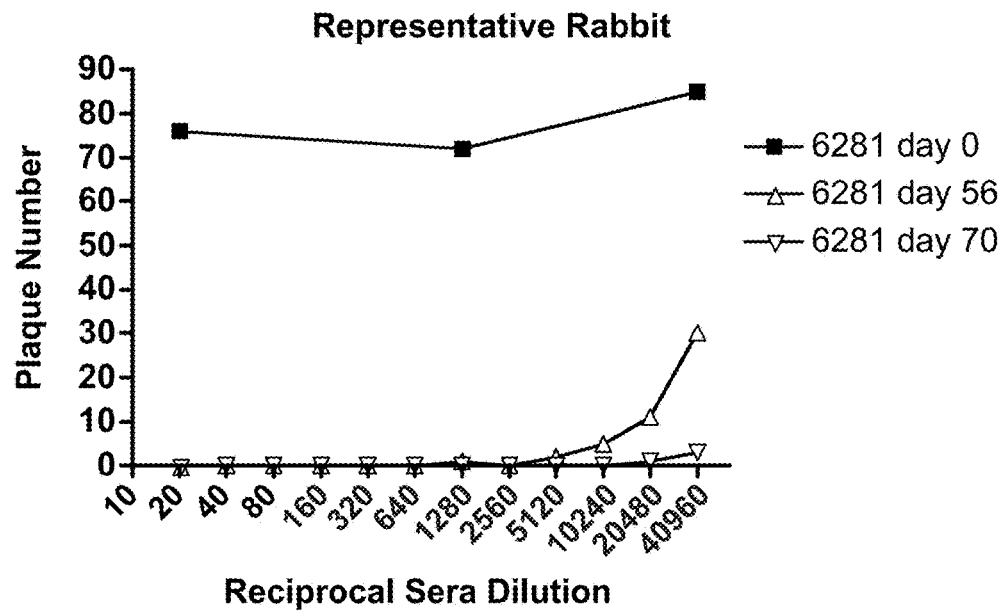
Figure 4A:
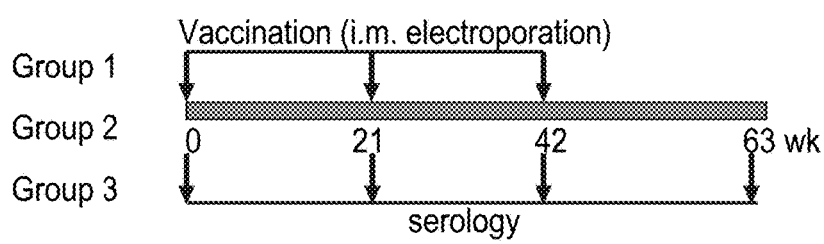
Figure 8:
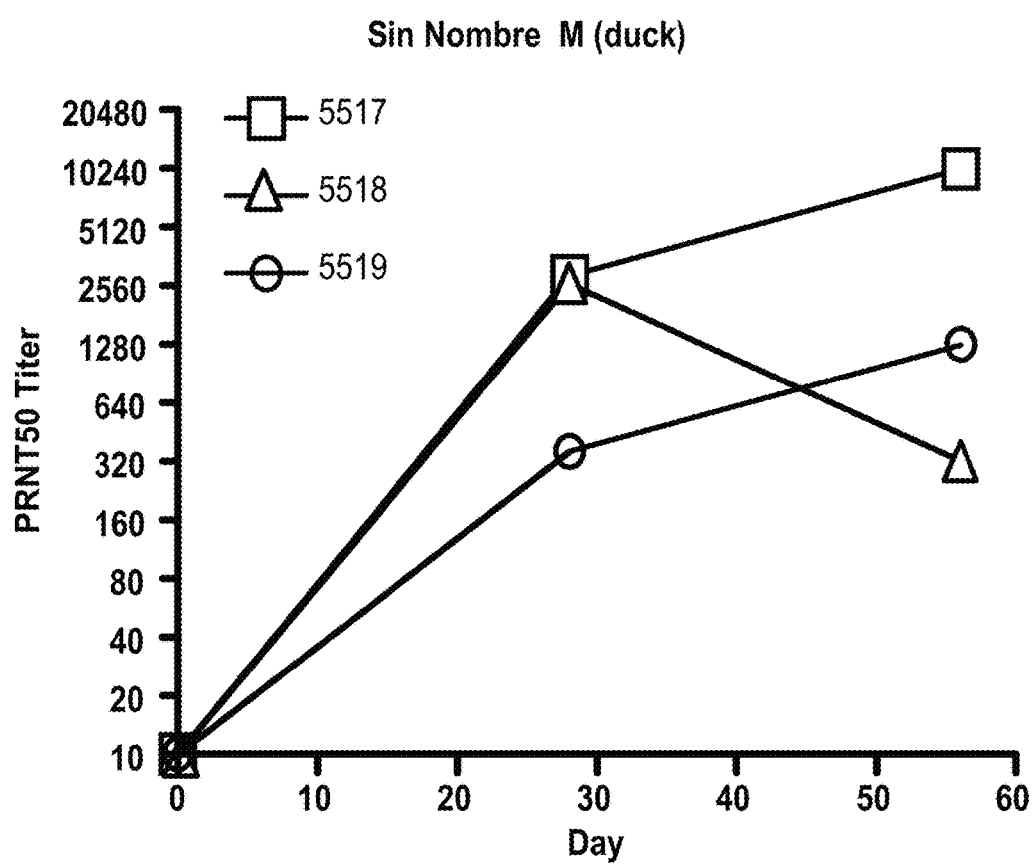

In an attempt to improve immunogenicity and potency, the M(2a) plasmid was refined by (1) first determining any possible flaws in the open reading frame and (2) obtaining the synthesis of a codon-optimized version of the SNV M gene. The inventor analyzed the M gene sequence in pWRG/SN-M(2a) and discovered amino acids that were unique to the clone (i.e., not in published GeneBank SNV M sequences) (Table 1). He identified consensus amino acids at these positions and then had an optimized version of this gene synthesized (work contracted to GeneArt)(Table 2). Next, the synthetic M gene was cloned into a DNA vaccine vector and the resultant plasmid was named pWRG/SN-M(opt) (or "M(opt)"). The sequence of the pWRG/SN-M(opt) plasmid is given in SEQ ID NO:1. M(opt) was tested for a capacity to elicit neutralizing antibodies by vaccinating rabbits with the pWRG/SN-(opt) using muscle electroporation. Four rabbits were vaccinated on weeks 0, 4, and 8 with 1 mg of DNA per vaccination. Sera were collected on weeks 0, 8 and 10. PRNT were performed to detect SNV neutralizing antibodies. Very high titers of SNV neutralizing antibodies were produced after only 2 vaccinations (week 8 sera) with pWRG/SN-M(opt) (FIG. 2) After 3 vaccinations (week 10 sera) there was 100% neutralization in all four rabbits even when the sera was diluted ≥1:5,000. This was a significant improvement over the M(2a) results—2 vaccinations is considered acceptable to be convenient enough for human or animal use.

Figures 3A, 3B:
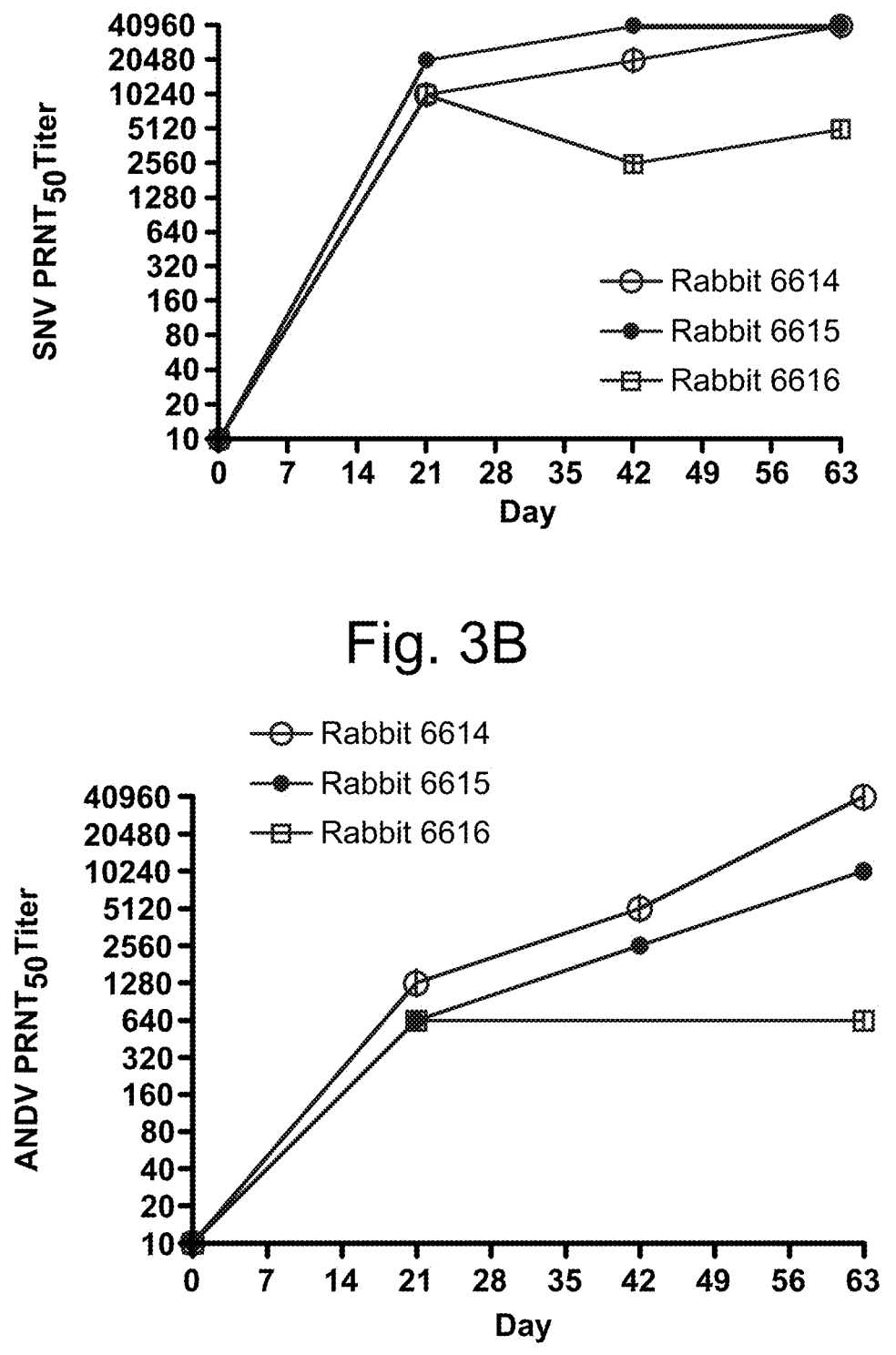

Having found the pWRG/SN-M(opt) to be a potent DNA vaccine, the inventor next combined the SNV DNA vaccine with the pWRG/AND-M. A mixture of the two plasmids was used to vaccinate rabbits using muscle electroporation. High titer neutralizing antibodies against both SNV and ANDY were produced after 1 or 2 vaccinations (FIG. 3). The SNV neutralizing activity was especially potent (titers>10,000 after 1 vaccination). Thus, the combination of the pWRG/SN-M(opt) DNA vaccine and pWRG/AND-M DNA vaccine effectively elicited high-titer neutralizing antibodies against the most prevalent and lethal hantavirus in North and South America. The novelty and potency of this SNV DNA vaccine was surprising and unexpected.

In summary, the inventor produced two plasmids that elicited high titer neutralizing antibodies against SNV in animal models. Thus, one point of novelty of the invention is that it elicits Sin Nombre virus neutralizing antibodies, and with significantly high titers. To the best of the inventor's knowledge, there is no other SNV vaccine that elicits antibodies that directly neutralize Sin Nombre virus.

Vaccines and Immunogenic Compositions

To summarize, the vaccines and immunogenic compositions comtemplated by this invention include: (1) Sin Nombre virus vaccines and immunogenic compositions; (2) Sin Nombre virus+other HPS viruses (e.g., Andes virus) vaccines and immunogenic compositions; (3) Sin Nombre virus vaccines and immunogenic compositions+HFRS viruses (e.g., Puumula and Hantaan viruses) vaccines and immunogenic compositions; and (4) Sin Nombre virus+other HPS viruses (e.g., Andes virus) vaccines and immunogenic compositions+HFRS viruses (e.g., Puumula and Hantaan viruses) vaccines and immunogenic compositions. These vaccines and immunogenic compositions, when transfected into mammalian cells, result in the expression of proteins that mimic the Gn and Gc surface glycoproteins of SNV and the other hantaviruses targeted. When these DNA vaccines or immunogenic compositions are introduced into the cells of a vaccine, the vaccine produces a neutralizing antibody response against SNV, and, if relevant, the other hantavirus(es). Neutralizing antibody responses are sufficient to confer protection against SNV and the other hantaviruses. Thus, SEQ ID NO:1, SEQ ID NO:2 and SEQ ID NO:3, and derivatives thereof, represent a candidate vaccine for the prevention of HPS caused by SNV. Moreover, these novel sequences, and derivatives thereof, can be used to generate anti-SNV immunotherapeutics and diagnostic antibodies in animals. (The term transfected is used herein to refer to cells which have incorporated the delivered foreign DNA vaccine, whichever delivery technique is used.)

As noted above, there is no vaccine or drug to prevent or treat HPS. One of the embodiments of the invention described herein is a DNA vaccine based on the M-gene segment of Sin Nombre virus. The M genome segment encodes the two proteins found on the virus surface.

One embodiment of the invention encompasses DNA vaccines. DNA vaccination involves administering antigen-encoding polynucleotides in vivo to induce the production of a correctly folded antigen(s) within the target cells. The introduction of the DNA vaccine will cause to be expressed within those cells the structural protein determinants associated with the pathogen protein or proteins. The processed structural proteins will be displayed on the cellular surface of the transfected cells in conjunction with the Major Histocompatibility Complex (MHC) antigens of the normal cell. Even when cell-mediated immunity is not the primary means of preventing infection, it is likely important for resolving established infections. Furthermore, the structural proteins released by the expressing transfected cells can also be picked up by antigen-presenting cells to trigger systemic humoral antibody responses.

The DNA vaccine according to the present invention is inherently safe, is not painful to administer, and should not result in adverse side effects to the vaccinated individual. In addition, the invention does not require growth or use of Sin Nombre virus, which is a biosafety level 3 (BSL-3) virus, and is a BSL-4 virus if the virus is grown to high levels or used in animals.

In order to achieve the immune response sought, a DNA vaccine construct capable of causing transfected cells of the vaccinated individual to express one or more major viral antigenic determinant is necessary. This can be done by identifying regions of the viral genome which code for viral glycoproteins or capsid components, and joining such coding sequences to promoters capable of expressing the sequences in cells of the vaccine. Alternatively, the viral genome itself, or parts of the genome, can be used.

In a preferred embodiment, the vaccine is a plasmid based codon-optimized Sin Nombre virus (SNV) M gene open reading frame. The M gene encodes for two proteins that form a part of the viral capsid. In nature these are glycosylated during synthesis in mammalian cells which would occur after vaccination. SNV is one of several viruses that cause Hantavirus Pulmonary Syndrome, a disease with high mortality (20-50%). There have been several hundred cases in the Americas over the past several years. This vaccine has been shown to induce high neutralizing antibody titers in animals and therefore would be useful for a human vaccine. Two hantavirus DNA vaccines—Hantaan and Puumala—have been shown to induce neutralizing antibodies in human clinical trials. (Presentation given: "Preclinical and Phase 1 Clinical Studies of a DNA Vaccine for HFRS Caused by Hantaviruses" J. Hooper, to the American Society of Microbiology Biodefense Meeting, held in Baltimore, February, 2010)

As noted above, attempts to produce SNV vaccine that produce neutralizing antibodies against SNV have been unsuccessful. Here, for the first time, the inventor has synthesized a codon-optimized full-length M gene open reading frame and cloned it into a DNA vaccine expression vector (e.g., pWRG-SN-M(opt)). The nucleotide sequences are completely unique because the ORF has been optimized. Regarding the preferred embodiment pWRG/SN-M(opt), hamsters and rabbits vaccinated with pWRG/SN-M(opt) using a gene gun developed neutralizing antibodies as measured by plaque reduction neutralization test (PRNT) with PRNT50 titers ranging from 10,240-over 81,920 in rabbits by electroporation; in hamsters, less than 20-1,280 by gene gun. This is believed to be the first candidate SNV vaccine that successfully elicits neutralizing antibodies against SNV.

In its preferred vaccine embodiment, the SNV virus M gene-based DNA vaccine is a plasmid that consists of a well-characterized backbone that enables expression of the above-described synthetic, codon-optimized, SNV virus full-length M gene, or the ORF with or without flanking sequences. Preferred examples are SEQ ID NO:1, SEQ ID NO:2 and SEQ ID NO:3. It can be used in other vaccine systems and systems for generating SNV neutralizing antibodies.

In this application we describe the elicitation of protective immunity to SNV alone or with other hantaviruses by DNA vaccines. The gene(s) of interest, in our case, a synthetic Sin Nombre virus M gene having at least one of the sequences identified herein as SEQ ID NO:1, SEQ ID NO:2, and SEQ ID NO:3, is controlled by a mammalian or virus promoter (e.g., the cytomegalovirus immediate early promoter followed by intron A) that facilitates expression of the naked DNA gene product(s) within the vaccine's cells. Preferably, Intron A is included. It is preferred even to use pWRG/SN-M(opt) as the DNA vaccine plasmid. This intracellular expression can elicit both humoral and cell-mediated immune responses (Robinson and Torres, 1997, supra; and Gregoriadis, 1998, supra). Methods of DNA delivery include needle inoculation, needle-free jet injection, oral or pulmonary delivery, and inoculation by particle bombardment (i.e., gene gun) and electroporation—by well-known methods for each. Needle inoculation and needle-free jet injection may be made with or without electroporation. Delivery may be intramuscular or intradermal, as appropriate.

A suitable construct for use in the method of the present invention is pWRG7077 (4326 bp)(PowderJect Vaccines, Inc., Madison, Wis.). pWRG7077 includes a human cytomegalovirus (hCMV) immediate early promoter (IE) and a bovine growth hormone polyA addition site. Between the promoter and the polyA addition site is Intron A, a sequence that naturally occurs in conjunction with the hCMV IE promoter that has been demonstrated to increase transcription when present on an expression plasmid. Downstream from Intron A, and between Intron A and the polyA addition sequence, are unique cloning sites into which the hantavirus M DNA can be cloned. Also provided on pWRG7077 is a gene that confers bacterial host-cell resistance to kanamycin. Any of the fragments that encode hantavirus Gn and/or Gc or nucleocapsid peptides can be cloned into one of the cloning sites in pWRG7077, using methods known to the art.

The DNA can be delivered by injection into the tissue of the recipient, oral or pulmonary delivery and inoculation by particle bombardment (i.e., gene gun). Any of these methods can be used to deliver DNA as long as the DNA is expressed and the desired antigen is made in the cell. Two methods are exemplified in this application, both shown to be successful in eliciting a protective immune response in the vaccine.

In one aspect of the invention, the DNA vaccine is delivered by coating a small carrier particle with the DNA vaccine and delivering the DNA-coated particle into an animal's epidermal tissue via particle bombardment. This method may be adapted for delivery to either epidermal or mucosal tissue, or delivery into peripheral blood cells, and thus may be used to induce humoral, cell-mediated, and secretory immune reponses in the vaccinated individual.

To deliver DNA vaccines by particle bombardment, we chose to use the PowderJect-XR™ gene gun device described in WO 95/19799, 27 Jul. 1995. Other instruments are available and known to people in the art. This instrument, which delivers DNA-coated gold beads directly into epidermal cells by high-velocity particle bombardment, was shown to more efficiently induce both humoral and cell-mediated immune responses, with smaller quantities of DNA, than inoculation of the same DNAs by other parenteral routes (Eisenbraun, M. et al., 1993, DNA Cell. Biol. 12: 791; Fynan, E. F. et al., 1993, Proc. Natl. Acad. Sci. USA 90: 11478; Haynes, J. R. et al., 1994, AIDS Res. Hum. Retroviruses 10: Suppl. 2:S43; Pertmer, T. M. et al., 1995, Vaccine 13: 1427). Epidermal inoculation of the DNA candidate vaccines also offers the advantages of gene expression in an immunologically active tissue that is generally exfoliated within 15 to 30 days, and which is an important natural focus of viral replication after tick-bite (Bos, J. D., 1997, Clin. Exp. Immunol. 107 Suppl. 1:3; Labuda, M. et al., 1996, Virology 219:357; Rambukkana, A. et al., 1995, Lab. Invest. 73:521; Stingl, G., 1993, Recent Results Cancer Res. 128: 45; Evans et al., Vaccine, 2009, Vol. 27(18), pp. 2506-2512; Yager et al., Expert Rev. Vaccines, 2009, Vol. 8(9), pp. 1205-1220).

The technique of accelerated particles gene delivery or particle bombardment is based on the coating of DNA to be delivered into cells onto extremely small carrier particles, which are designed to be small in relation to the cells sought to be transformed by the process. The DNA sequence containing the desired gene can be simply dried onto a small inert particle. The particle may be made of any inert material such as an inert metal (gold, silver, platinum, tungsten, etc.) or inert plastic (polystyrene, polypropylene, polycarbonate, etc.). Preferably, the particle is made of gold, platinum or tungsten. Most preferably, the particle is made of gold. suitably, the particle is spherical and has a diameter of 0.5 to 5 microns, preferably 1 to 3 microns.

The DNA sequence containing the desired gene prepared in the form suitable for gene introduction can be simply dried onto naked gold or tungsten pellets. However, DNA molecules in such a form may have a relatively short period of stability and may tend to degrade rather rapidly due to chemical reactions with the metallic or oxide substrate of the particle itself. Thus, if the carrier particles are first coated with an encapsulating agent, the DNA strands have greatly improved stability and do not degrade significantly even over a time period of several weeks. A suitable encapsulating agent is polylysine (molecular weight 200,000) which can be applied to the carrier particles before the DNA molecules are applied. Other encapsulating agents, polymeric or otherwise, may also be useful as similar encapsulating agents, including spermidine. The polylysine is applied to the particles by rinsing the gold particles in a solution of 0.02% polylysine and then air drying or heat drying the particles thus coated. Once the metallic particles coated with polylysine were properly dried, DNA strands are then loaded onto the particles.

The DNA is loaded onto the particles at a rate of between 0.5 and 30 micrograms of DNA per milligram of gold bead spheres. A preferable ratio of DNA to gold is 0.5 5.0 ug of DNA per milligram of gold. A sample procedure begins with gamma irradiated (preferably about 30 kGy) tefzel tubing. The gold is weighed out into a microfuge tube, spermidine (free base) at about 0.05 M is added and mixed, and then the DNA is added. A 10% CaCl solution is incubated along with the DNA for about 10 minutes to provide a fine calcium precipitate. The precipitate carries the DNA with it onto the beads. The tubes are microfuged and the pellet resuspended and washed in 100% ethanol and the final product resuspended in 100% ethanol at 0.0025 mg/ml PVP. The gold with the DNA is then applied onto the tubing and dried.

The general approach of accelerated particle gene transfection technology is described in U.S. Pat. No. 4,945,050 to Sanford. An instrument based on an improved variant of that approach is available commercially from PowderJect Vaccines, Inc., Madison Wis., and is described in WO 95/19799. All documents cited herein supra and infra are hereby incorporated in their entirety by reference thereto. Briefly, the DNA-coated particles are deposited onto the interior surface of plastic tubing which is cut to a suitable length to form sample cartridges. A sample cartridge is placed in the path of a compressed gas (e.g., helium at a pressure sufficient to dislodge the particles from the cartridge e.g., 350 400 psi). The particles are entrained in the gas stream and are delivered with sufficient force toward the target tissue to enter the cells of the tissue. Further details are available in the published apparatus application.

The coated carrier particles are physically accelerated toward the cells to be transformed such that the carrier particles lodge in the interior of the target cells. This technique can be used either with cells in vitro or in vivo. At some frequency, the DNA which has been previously coated onto the carrier particles is expressed in the target cells. This gene expression technique has been demonstrated to work in prokaryotes and eukaryotes, from bacteria and yeasts to higher plants and animals. Thus, the accelerated particle method provides a convenient methodology for delivering genes into the cells of a wide variety of tissue types, and offers the capability of delivering those genes to cells in situ and in vivo without any adverse impact or effect on the treated individual. Therefore, the accelerated particle method is also preferred in that it allows a DNA vaccine capable of eliciting an immune response to be directed both to a particular tissue, and to a particular cell layer in a tissue, by varying the delivery site and the force with which the particles are accelerated, respectively. This technique is thus particularly suited for delivery of genes for antigenic proteins into the epidermis.

A DNA vaccine can be delivered in a non-invasive manner to a variety of susceptible tissue types in order to achieve the desired antigenic response in the individual. Most advantageously, the genetic vaccine can be introduced into the epidermis. Such delivery, it has been found, will produce a systemic humoral immune response.

To obtain additional effectiveness from this technique, it may also be desirable that the genes be delivered to a mucosal tissue surface, in order to ensure that mucosal, humoral and cellular immune responses are produced in the vaccinated individual. There are a variety of suitable delivery sites available including any number of sites on the epidermis, peripheral blood cells, i.e. lymphocytes, which could be treated in vitro and placed back into the individual, and a variety of oral, upper respiratory, and genital mucosal surfaces.

Gene gun-based DNA immunization achieves direct, intracellular delivery of DNA, elicits higher levels of protective immunity, and requires approximately three orders of magnitude less DNA than methods employing standard inoculation.

Moreover, gene gun delivery allows for precise control over the level and form of antigen production in a given epidermal site because intracellular DNA delivery can be controlled by systematically varying the number of particles delivered and the amount of DNA per particle. This precise control over the level and form of antigen production may allow for control over the nature of the resultant immune response.

The invention further covers passive vaccines for treating or preventing Sin Nombre virus infections comprising a therapeutically or prophylactically effective amount of the antibodies of the present invention which protect against Sin Nombre virus disease in combination with a pharmaceutically acceptable carrier or excipient. As described in greater detail herein, the present inventor has found that serum from a vaccine immunized with a DNA vaccine comprising the Sin Nombre virus M segment described above contains antibodies able to neutralize Sin Nombre virus and display in vitro and in vivo Sin Nombre virus neutralization properties.

The invention also contemplates a new recombinant DNA vaccine approach that involves vaccination with naked DNA expressing individual Sin Nombre virus genome segment cDNAs. Naked DNA vaccination involves delivery of plasmid DNA constructs with a gene(s) of interest into the tissue of the vaccine (reviewed in Robinson and Torres, 1997, *Semin. Immunol.* 9, 271-283; and Gregoriadis, 1998, *Pharm. Res.* 15, 661-670). DNA vaccination mimicks the de novo antigen production and MHC class I-restricted antigen presentation obtainable with live vaccines, without the risks of pathogenic infection. Also, this DNA vaccine approach allows delivery to mucosal tissues which may aid in conferring resistance to viral introduction since entry of the virus may be through mucosal tissues.

This vaccine was also tested for a capacity to elicit neutralizing antibodies in rabbits using muscle electroporation as the means of vaccine delivery. The electroporation device and dose of DNA delivered is compatible with human use (Ichor Tri-grid device). Well-known methods of electroporation are effective for this DNA vaccine. For instance, Hooper et al. (February 2008), describes methods useful for this. (Hooper et al., "Immune Serum Produced by DNA Vaccination Protects Hamsters against Lethal Respiratory Challenge with Andes Virus", J. Virology, February 2008, Vol. 82, No. 3, pp. 1332-1338; also see, van Drunen, et al., Expert Rev. Vaccines, 2010, Vol. 9(5), pp. 503-517). In addition, mammals such as rabbits can be vaccinated by muscle electroporation with a DNA vaccine plasmid such as pWRG/SN-M(opt) to rapidly generate sera containing high-titer SNV neutralizing antibodies. Sera can be collected and tested for neutralizing antibodies by PRNT.

Vaccination with the SNV M gene-based DNA vaccine, called pWRG/SN-M(opt), elicits high-titer neutralizing antibodies. It is widely believed in the field that neutralizing antibodies are surrogate endpoints of protective immunity, so any vaccine that elicits high-titer neutralizing antibodies has utility as a vaccine. This vaccine could be used to immunize against North American HPS. In addition, it could be combined with other hantavirus DNA vaccines to create a pan-hantavirus vaccine. In short, the plasmid containing the synthetic codon-optimized SNV M gene is exceedingly effective at eliciting neutralizing antibodies.

For a HPS vaccine composition or immunogenic composition, the composition will have at least one of the above-described SNV sequences (SEQ ID NO:1, SEQ ID NO:2 or SEQ ID NO:3), plus at least one other M-gene (e.g., whole full-length or ORF or ORF plus flanking sequences) from a different (non-SNV) HPS. Examples of other HPS viruses include Black Creek Canal virus, Bayou virus, New York virus, Andes virus, and Laguna Negra virus. A preferred HPS vaccine or immunogenic composition comprises at least one of the above-described SNV sequences, and the Andes M-gene—preferably plasmid pWRG/AND-M(x) (SEQ ID NO:10), below:

```
gggggggggg ggcgctgagg tctgcctcgt gaagaaggtg      40
ttgctgactc ataccaggcc tgaatcgccc catcatccag      80
ccagaaagtg agggagccac ggttgatgag agctttgttg     120
taggtggacc agttggtgat tttgaactt tgctttgcca      160
cggaacggtc tgcgttgtcg ggaagatgcg tgatctgatc     200
cttcaactca gcaaaagttc gatttattca acaaagccgc     240
cgtcccgtca agtcagcgta atgctctgcc agtgttacaa     280
ccaattaacc aattctgatt agaaaaactc atcgagcatc     320
aaatgaaact gcaatttatt catatcagga ttatcaatac     360
catattttg aaaaagccgt ttctgtaatg aaggagaaaa      400
ctcaccgagg cagttccata ggatggcaag atcctggtat     440
cggtctgcga ttccgactcg tccaacatca atacaaccta     480
ttaatttccc ctcgtcaaaa ataaggttat caagtgagaa     520
atcaccatga gtgacgactg aatccggtga atggcaaa       560
agcttatgca ttttctttcca gacttgttca acaggccagc    600
cattacgctc gtcatcaaaa tcactcgcat caaccaaacc     640
gttattcatt cgtgattgcg cctgagcgag acgaaatacg     680
cgatcgctgt taaaaggaca attacaaaca ggaatcgaat     720
gcaaccggcg caggaacact gccagcgcat caacaatatt     760
ttcacctgaa tcaggatatt cttctaatac ctggaatgct     800
gttttccgg ggatcgcagt ggtgagtaac catgcatcat      840
caggagtacg gataaaatgc ttgatggtcg gaagaggcat     880
aaattccgtc agccagttta gtctgaccat ctcatctgta     920
acatcattgg caacgctacc tttgccatgt tcagaaaca     960
actctggcgc atcgggcttc ccatacaatc gatagattgt    1000
cgcacctgat tgcccgacat tatcgcgagc ccatttatac    1040
ccatataaat cagcatccat gttggaattt aatcgcggcc    1080
tcgagcaaga cgtttccgt tgaatatggc tcataacacc     1120
ccttgtatta ctgtttatgt aagcagacag ttttattgtt    1160
catgatgata tattttatc ttgtgcaatg taacatcaga     1200
gattttgaga cacaacgtgg ctttcccccc cccccggca     1240
tgcctgcagg tcgacaatat tggctattgg ccattgcata    1280
cgttgtatct atatcataat atgtacatt atattggctc     1320
atgtccaata tgaccgccat gttgacattg attattgact    1360
agttattaat agtaatcaat tacggggtca ttagttcata    1400
gcccatatat ggagttccgc gttacataac ttacggtaaa    1440
tggcccgcct ggctgaccgc ccaacgaccc cgcccattg     1480
acgtcaataa tgacgtatgt tcccatagta acgccataag    1520
ggactttcca ttgacgtcaa tgggtggagt atttacggta    1560
aactgcccac ttggcagtac atcaagtgta tcatatgcca    1600
agtccgcccc ctattgacgt caatgacggt aaatggcccg    1640
```

```
cctggcatta tgcccagtac atgaccttac gggactttcc    1680
tacttggcag tacatctacg tattagtcat cgctattacc    1720
atggtgatgc ggttttggca gtacaccaat gggcgtggat    1760
agcggtttga ctcacgggga tttccaagtc tccaccccat    1800
tgacgtcaat gggagtttgt tttggcacca aaatcaacgg    1840
gactttccaa aatgtcgtaa taaccccgcc ccgttgacgc    1880
aaatgggcgg taggcgtgta cggtgggagg tctatataag    1920
cagagctcgt ttagtgaacc gtcagatcgc ctggagacgc    1960
catccacgct gttttgacct ccatagaaga caccgggacc    2000
gatccagcct ccgcggccgg gaacggtgca ttggaacgcg    2040
gattccccgt gccaagagtg acgtaagtac cgcctataga    2080
ctctataggc acacccctt ggctcttatg catgctatac     2120
tgttttggc ttggggccta tacacccccg cttccttatg     2160
ctataggtga tggtatagct tagcctatag gtgtgggtta    2200
ttgaccatta ttgaccactc ccctattggt gacgatactt    2240
tccattacta atccataaca tggctctttg ccacaactat    2280
ctctattggc tatatgccaa tactctgtcc ttcagagact    2320
gacacggact ctgtatttt acaggatggg gtcccattta     2360
ttatttacaa attcacatat acaacaacgc cgtccccgt     2400
gcccgcagtt tttattaaac atagcgtggg atctccacgc    2440
gaatctcggg tacgtgttcc ggacatgggc tcttctccgg    2480
tagcggcgga gcttccacat ccgagccctg gtcccatgcc    2520
tccagcggct catggtcgct cggcagctcc ttgctcctaa    2560
cagtggaggc cagacttagg cacagcacaa tgcccaccac    2600
caccagtgtg ccgcacaagg ccgtggcggt agggtatgtg    2640
tctgaaaatg agctcggaga ttgggctcgc accgctgacg    2680
cagatggaag acttaaggca gcggcagaag aagatgcagg    2720
cagctgagtt gttgtattct gataagagtc agaggtaact    2760
cccgttgcgg tgctgttaac ggtggagggc agtgtagtct    2800
gagcagtact cgttgctgcc gcgcgcgcca ccagacataa    2840
tagctgacag actaacgac tgttcctttc catgggtctt     2880
ttctgcagtc agggtccaag cttgcggccg cggatctgca    2920
ggaattcggc acgagagtag tagactccgc acgaagaagc    2960
aaaaaattaa agaagtgagt ttaaaatgga agggtggtat    3000
ctggttgttc ttggagtctg ctatacgctg acactggcaa    3040
tgcccaagac catttatgag cttaaaatgg aatgcccgca    3080
cactgtgggt ctcggtcaag gttacatcat tggctcaaca    3120
gaactaggtt tgatctcaat tgaggctgca tctgatataa    3160
agctcgagag ctcttgcaat tttgatcttc atacaacatc    3200
tatggcccag aagagtttca cccaagttga atggagaaag    3240
```

-continued

```
aaaagtgaca caactgatac cacaaatgct gcgtccacta    3280
cctttgaagc acaaactaaa actgttaacc ttagagggac    3320
ttgtatactg gcacctgaac tctatgatac attgaagaaa    3360
gtaaaaaaga cagtcctgtg ctatgatcta acatgtaatc    3400
aaacacattg tcagccaact gtctatctga ttgcacctgt    3440
attgacatgc atgtcaataa gaagttgtat ggctagtgtg    3480
tttacaagca ggattcaggt gatttatgaa aagacacatt    3520
gtgtaacagg tcagctgatt gagggtcagt gtttcaaccc    3560
agcacacaca ttgacattat ctcagcctgc tcacacttat    3600
gatactgtca cccttcctat ctcttgtttt ttcacaccaa    3640
agaagtcgga gcaactaaaa gttataaaaa catttgaagg    3680
aattctgacg aagacaggtt gcacggagaa tgcattgcag    3720
ggttattatg tgtgtttttt agggagtcat tcagaacctt    3760
taattgttcc gagtttggag acatacggt ctgctgaagt    3800
tgttagtagg atgcttgtac accctagggg agaagaccat    3840
gatgccatac agaattcaca aagtcactta agaatagtgg    3880
gacctatcac agcaaaagtg ccatcaacta gttccacaga    3920
taccctaaag gggacagcct ttgcaggcgt cccaatgtat    3960
agctctttat ctacactagt cagaaatgca gacccagaat    4000
ttgtattttc tccaggtata gtacctgaat ctaatcacag    4040
tacatgtgat aagaagacag tacctatcac atggacaggc    4080
tacctaccaa tatcaggtga gatggaaaaa gtgactggat    4120
gtacagtttt ttgtacacta gcaggacctg gtgctagttg    4160
tgaggcctat tctgaaaatg gtatatttaa catcagttct    4200
ccaacatgtc ttgtaaacaa agtccaagaa tttcgtggat    4240
ctgaacagaa aataaatttt atctgtcagc gggtagatca    4280
ggatgttgtt gtatactgca atgggcaaaa gaaagtcata    4320
ttaaccaaaa ctttggttat tgggcagtgt atttatacat    4360
tcacaagcct attttcattg atgcctgatg tagcccactc    4400
attggctgta gaattatgtg tcccgggatt acatgggtgg    4440
gccactgtca tgcttctatc aacattctgc tttgggtggg    4480
tcttgattcc tgcggtcaca ttaataatat taaagtgtct    4520
aagggttttg acgttttctt gttcccatta cactaatgag    4560
tcaaaattta aattcatcct ggaaaaagtt aaaattgaat    4600
accaaaagac tatgggatca atggtgtgcg atgtatgtca    4640
tcatgagtgt gaaacagcaa aagaacttga atcacataga    4680
cagagttgta tcaatggaca atgtcctttat tgcatgacaa    4720
taactgaagc aactgaaagt gccttgcaag cccattattc    4760
catttgtaaa ttggcaggaa gatttcagga ggcactgaaa    4800
aagtcactta aaaagccaga ggtaaaaaaa ggttgttaca    4840
gaacactcgg ggtatttaga tataaaagta gatgttatgt    4880
```

```
gggtttggta tggtgcctat tgttgacatg tgaaattgtt    4920
atttgggccg caagtgcaga gactccacta atggagtcag    4960
gctggtcaga tacggctcat ggtgttggtg agattccaat    5000
gaagacagac ctcgagctgg acttttcact gccttcttca    5040
tcctcttaca gttataggag aaagctcaca aacccagcca    5080
ataaagaaga gtctattccc ttccacttcc agatggaaaa    5120
acaagtaatt catgctgaaa tccaacccct gggtcattgg    5160
atggatgcga catttaatat taagactgca tttcattgtt    5200
atggtgcatg ccagaaatac tcttatccat ggcagacatc    5240
taagtgcttc tttgaaaagg actaccagta tgaaacaggc    5280
tggggctgta atcctggtga ctgcccaggg gttgggactg    5320
gatgcactgc ttgtggtgtt tatctcgata aactaaaatc    5360
tgttgggaag gcctataaga taatttcttt aaaatatacc    5400
agaaaggttt gtattcagtt aggaacagaa caaacttgca    5440
agcatattga tgcaaatgat tgtttagtga caccatctgt    5480
gaaagtttgc atagtgggca cagtttcaaa acttcaacca    5520
tctgatactc ttttgttctt aggtccacta gaacaagggg    5560
gaatcattct taagcaatgg tgcacaacat catgtgcatt    5600
tggggaccct ggtgatatca tgtccactcc cagtggtatg    5640
aggtgtccag agcacactgg atcatttagg aaaatttgcg    5680
gttttgctac tacaccagtt tgtgaatatc aaggaaatac    5720
catttctgga tataaaagaa tgatggcaac aaaagattca    5760
ttccaatcat ttaacttaac agaacctcac atcacaacaa    5800
acaagcttga atggatcgac ccagatggga atacaagaga    5840
ccacgtaaac cttgtcttaa atagagatgt ctcatttcag    5880
gatttaagtg ataaccctg taaagtagac ctacacacac    5920
aagcaataga aggggcatgg ggttctggtg tagggtttac    5960
actcacatgt actgtcggat taacagagtg cccaagtttt    6000
atgacatcaa ttaaggcatg tgacctagct atgtgttatg    6040
gatcaacagt aacaaacctt gccaggggct ctaatacagt    6080
gaaagtagtt ggtaaggag gccattcagg gtcctcattt    6120
aaatgctgtc atgatacaga ttgctcctct gaaggtttac    6160
ttgcatcagc ccctcatctt gagagggtaa caggattcaa    6200
tcaaattgat tcagataagg tttatgatga tggtgcacca    6240
ccttgcacat tcaaatgctg gttcactaag tcaggtgagt    6280
ggcttcttgg gatcttaaac gggaattgga ttgttgttgt    6320
agtgcttgtt gtgatactca ttctctctat cataatgttc    6360
agtgttttgt gtcccaggag agggcacaag aaaactgtct    6400
aagcattgac ctcaactcct acattagatc atatacattt    6440
atgcacttcc tcatatttag ctgcactaag atattaataa    6480
```

```
actctagtta ttgactttat aagattatta tggaactaac    6520
ctcacttaaa aaaaacaaat actttactca tatataactc    6560
catattctct taccgaggat tttgttcctg cggagcatac    6600
tactaggatc tacgtatgat cagcctcgac tgtgccttct    6640
agttgccagc catctgttgt ttgcccctcc cccgtgcctt    6680
ccttgaccct ggaaggtgcc actcccactg tcctttccta    6720
ataaaatgag gaaattgcat cgcattgtct gagtaggtgt    6760
cattctattc tgggggtgg ggtggggcag gacagcaagg    6800
gggaggattg ggaagacaat agcaggcatg ctggggatgc    6840
ggtgggctct atggcttctg aggcggaaag aaccagctgg    6880
ggctcgacag ctcgactcta gaattgcttc ctcgctcact    6920
gactcgctgc gctcggtcgt tcggctgcgg cgagcggtat    6960
cagctcactc aaaggcggta atacggttat ccacagaatc    7000
aggggataac gcaggaaaga acatgtgagc aaaaggccag    7040
caaaaggcca ggaaccgtaa aaaggccgcg ttgctggcgt    7080
ttttccatag gctccgcccc cctgacgagc atcacaaaaa    7120
tcgacgctca agtcagaggt ggcgaaaccc gacaggacta    7160
taaagatacc aggcgtttcc ccctggaagc tccctcgtgc    7200
gctctcctgt tccgaccctg ccgcttaccg gatacctgtc    7240
cgcctttctc ccttcgggaa gcgtggcgct ttctcatagc    7280
tcacgctgta ggtatctcag ttcggtgtag gtcgttcgct    7320
ccaagctggg ctgtgtgcac gaaccccccg ttcagcccga    7360
ccgctgcgcc ttatccggta actatcgtct tgagtccaac    7400
ccggtaagac acgacttatc gccactggca gcagccactg    7440
gtaacaggat tagcagagcg aggtatgtag gcggtgctac    7480
agagttcttg aagtggtggc ctaactacgg ctacactaga    7520
agaacagtat ttggtatctg cgctctgctg aagccagtta    7560
ccttcgaaaa aagagttggt agctcttgat ccggcaaaca    7600
aaccaccgct ggtagcggtg ttttttttgt ttgcaagcag    7640
cagattacgc gcagaaaaaa aggatctcaa gaagatcctt    7680
tgatcttttc tacggggtct gacgctcagt ggaacgaaaa    7720
ctcacgttaa gggattttgg tcatgagatt atcaaaaagg    7760
atcttcacct agatcctttt aaattaaaaa tgaagtttta    7800
aatcaatcta aagtatatat gagtaaactt ggtctgacag    7840
ttaccaatgc ttaatcagtg aggcacctat ctcagcgatc    7880
tgtctatttc gttcatccat agttgcctga ctc           7913
```

For a HPS+HFRS, or pan-hantavirus, vaccine composition or immunogenic composition, the composition will have at least one of the above-described SNV sequences (SEQ ID NO:1, SEQ ID NO:2 or SEQ ID NO:3), plus at least one other M-gene (e.g., whole full-length or ORF or ORF plus flanking sequences) from an HFRS virus. Examples of HFRS viruses include Seoul virus, Hantaan virus, Pumuula virus, and Dobrava virus. In addition, the vaccine composition or immunogenic composition may further include one or more of the above-described other HPS M-genes (e.g., whole full-length or ORF or ORF plus flanking sequences). A preferred HPS+HFRS vaccine or immunogenic composition comprises at least one of the above-described SNV sequences, and one or more of Puumala M-gene plasmid (preferably plasmid pWRG/PUU-M(s2) shown below as SEQ ID NO:11 or the ORF shown below as SEQ ID NO:14), Hantaan M-gene plasmid (preferably plasmid pWRG/HTN-M(x) shown below as SEQ ID NO:12), and Seoul (preferably plasmid pWRG-SEO-M which is Seoul hantavirus M segment, strain SR-11, subcloned into DNA vector pWRG7077, and shown below as SEQ ID NO:13).

```
pWRG/PUU-M(s2) DNA vaccine plasmid (SEQ ID NO: 11)
(the underlined section indicates the ORF)-
GGGGGGGGGGGGCGCTGAGGTCTGCCTCGTGAAGAAGGTGTTGCTGACTC
ATACCAGGCCTGAATCGCCCCATCATCCAGCCAGAAAGTGAGGGAGCCAC
GGTTGATGAGAGCTTTGTTGTAGGTGGACCAGTTGGTGATTTTGAACTTT
TGCTTTGCCACGGAACGGTCTGCGTTGTCGGGAAGATGCGTGATCTGATC
CTTCAACTCAGCAAAAGTTCGATTTATTCAACAAAGCCGCCGTCCCGTCA
AGTCAGCGTAATGCTCTGCCAGTGTTACAACCAATTAACCAATTCTGATT
AGAAAAACTCATCGAGCATCAAATGAAACTGCAATTTATTCATATCAGGA
TTATCAATACCATATTTTTGAAAAAGCCGTTTCTGTAATGAAGGAGAAAA
CTCACCGAGGCAGTTCCATAGGATGGCAAGATCCTGGTATCGGTCTGCGA
TTCCGACTCGTCCAACATCAATACAACCTATTAATTTCCCCTCGTCAAAA
ATAAGGTTATCAAGTGAGAAATCACCATGAGTGACGACTGAATCCGGTGA
GAATGGCAAAAGCTTATGCATTTCTTTCCAGACTTGTTCAACAGGCCAGC
CATTACGCTCGTCATCAAAATCACTCGCATCAACCAAACCGTTATTCATT
CGTGATTGCGCCTGAGCGAGACGAAATACGCGATCGCTGTTAAAAGGACA
ATTACAAACAGGAATCGAATGCAACCGGCGCAGGAACACTGCCAGCGCAT
CAACAATATTTTCACCTGAATCAGGATATTCTTCTAATACCTGGAATGCT
GTTTTCCCGGGGATCGCAGTGGTGAGTAACCATGCATCATCAGGAGTACG
GATAAAATGCTTGATGGTCGGAAGAGGCATAAATTCCGTCAGCCAGTTTA
GTCTGACCATCTCATCTGTAACATCATTGGCAACGCTACCTTTGCCATGT
TTCAGAAACAACTCTGGCGCATCGGGCTTCCCATACAATCGATAGATTGT
CGCACCTGATTGCCCGACATTATCGCGAGCCCATTTATACCCATATAAAT
CAGCATCCATGTTGGAATTTAATCGCGGCCTCGAGCAAGACGTTTCCCGT
TGAATATGGCTCATAACACCCCTTGTATTACTGTTTATGTAAGCAGACAG
TTTTATTGTTCATGATGATATATTTTTATCTTGTGCAATGTAACATCAGA
GATTTTGAGACACAACGTGGCTTTCCCCCCCCCCCGGCATGCCTGCAGG
TCGACAATATTGGCTATTGGCCATTGCATACGTTGTATCTATATCATAAT
ATGTACATTTATATTGGCTCATGTCCAATATGACCGCCATGTTGACATTG
ATTATTGACTAGTTATTAATAGTAATCAATTACGGGGTCATTAGTTCATA
GCCCATATATGGAGTTCCGCGTTACATAACTTACGGTAAATGGCCCGCCT
GGCTGACCGCCCAACGACCCCCGCCCATTGACGTCAATAATGACGTATGT
```

```
TCCCATAGTAACGCCAATAGGGACTTTCCATTGACGTCAATGGGTGGAGT
ATTTACGGTAAACTGCCCACTTGGCAGTACATCAAGTGTATCATATGCCA
AGTCCGCCCCCTATTGACGTCAATGACGGTAAATGGCCCGCCTGGCATTA
TGCCCAGTACATGACCTTACGGGACTTTCCTACTTGGCAGTACATCTACG
TATTAGTCATCGCTATTACCATGGTGATGCGGTTTTGGCAGTACACCAAT
GGGCGTGGATAGCGGTTTGACTCACGGGGATTTCCAAGTCTCCACCCCAT
TGACGTCAATGGGAGTTTGTTTTGGCACCAAAATCAACGGGACTTTCCAA
AATGTCGTAATAACCCCGCCCCGTTGACGCAAATGGGCGGTAGGCGTGTA
CGGTGGGAGGTCTATATAAGCAGAGCTCGTTTAGTGAACCGTCAGATCGC
CTGGAGACGCCATCCACGCTGTTTTGACCTCCATAGAAGACACCGGGACC
GATCCAGCCTCCGCGGCCGGGAACGGTGCATTGGAACGCGGATTCCCCGT
GCCAAGAGTGACGTAAGTACCGCCTATAGACTCTATAGGCACACCCCTTT
GGCTCTTATGCATGCTATACTGTTTTTGGCTTGGGGCCTATACACCCCCG
CTTCCTTATGCTATAGGTGATGGTATAGCTTAGCCTATAGGTGTGGGTTA
TTGACCATTATTGACCACTCCCCTATTGGTGACGATACTTTCCATTACTA
ATCCATAACATGGCTCTTTGCCACAACTATCTCTATTGGCTATATGCCAA
TACTCTGTCCTTCAGAGACTGACACGGACTCTGTATTTTTACAGGATGGG
GTCCCATTTATTATTTACAAATTCACATATACAACAACGCCGTCCCCCGT
GCCCGCAGTTTTTATTAAACATAGCGTGGGATCTCCACGCGAATCTCGGG
TACGTGTTCCGGACATGGGCTCTTCTCCGGTAGCGGCGGAGCTTCCACAT
CCGAGCCCTGGTCCCATGCCTCCAGCGGCTCATGGTCGCTCGGCAGCTCC
TTGCTCCTAACAGTGGAGGCCAGACTTAGGCACAGCACAATGCCCACCAC
CACCAGTGTGCCGCACAAGGCCGTGGCGGTAGGGTATGTGTCTGAAAATG
AGCTCGGAGATTGGGCTCGCACCGCTGACGCAGATGGAAGACTTAAGGCA
GCGGCAGAAGAAGATGCAGGCAGCTGAGTTGTTGTATTCTGATAAGAGTC
AGAGGTAACTCCCGTTGCGGTGCTGTTAACGGTGGAGGGCAGTGTAGTCT
GAGCAGTACTCGTTGCTGCCGCGCGCCACCAGACATAATAGCTGACAG
ACTAACAGACTGTTCCTTTCCATGGGTCTTTTCTGCAGTCACCGTCCAAG
CTTGCGGCCGCGGATCTGCAGGAATTCGGCACAGAGTAGTAGAC
TCCGCAAGAAACAGCAAACACAGATAAATATGGGCGAGCTGTCCCTGTG
TGCCTGTACCTGCTGCTGCAGGGCCTGCTGCTGTGTAACACCGGAGCCGC
CAGGAACCTGAACGAGCTGAAGATGGAGTGCCCCCACACCATCAGACTGG
GCCAGGGCCTGGTGGTGGGCAGCGTGGAGCTGCCCAGCCTGCCCATCCAG
CAGGTGGAGACCCTGAAGCTGGAGAGCAGCTGTAACTTCGACCTGCACAC
CAGCACAGCCGGCCAGCAGAGCTTCACCAAGTGGACCTGGGAGATCAAGG
GCGACCTGGCCGAGAACACCCAGGCCAGCAGCACCAGCTTCCAGACCAAG
AGCAGCGAGGTGAACCTGAGAGGCCTGTGCCTGATCCCCACACTGGTGGT
GGAGACCGCCGCCAGAATGAGAAAGACCATCGCCTGCTACGACCTGAGCT
GTAACCAGACCGTGTGTCAGCCTACCGTGTACCTGATGGGCCCTATCCAG
ACCTGTATCACCACCAAGAGCTGCCTGCTGTCCCTGGGCGATCAGAGAAT
CCAGGTGAACTACGAGAAAACCTACTGTGTGAGCGGCCAGCTGGTGGAGG
GCATCTGCTTCAACCCCCATCCACACCATGGCCCTGAGCCAGCCTAGCCAC
ACCTACGACATCATGACCATGATGGTGAGATGCTTTCTGGTGATCAAGAA
GGTGACCAGCGGCGACAGCATGAAGATCGAGAAGAACTTCGAGACCCTGG
TGCAGAAGAATGGCTGTACCGCCAACAACTTCCAGGGCTACTACATCTGC
CTGATCGGCAGCAGCAGCGAGCCCCTGTACGTGCCCGCCCTGGACGACTA
CAGAAGCGCCGAGGTGCTGTCCAGAATGGCCTTCGCCCCCCACGGCGAGG
ACCACGACATCGAGAAAAACGCCGTGTCCGCCATGAGAATCGCCGGCAAG
GTGACCGGCAAGGCCCCCAGCACCGAGTCCAGCGACACCGTGCAGGGCAT
CGCCTTCAGCGGCAGCCCCCTGTACACCTCCACCGGCGTGCTGACCAGCA
AGGACGACCCCGTGTACATCTGGGCCCCTGGCATCATCATGGAGGGCAAC
CACAGCATCTGTGAGAAGAAACCCTGCCCCTGACCTGGACCGGCTTCAT
CAGCCTGCCCGGCGAGATCGAGAAAACCACCCAGTGTACCGTGTTCTGTA
CCCTGGCCGGACCTGGCGCCGACTGTGAGGCCTACAGCGAGACCGGCATC
TTCAACATCAGCAGCCCCACCTGCCTGATCAACCGGGTGCAGAGGTTCAG
AGGCAGCGAGCAGCAGATCAAGTTTGTGTGCCAGCGGGTGGACATGGACA
TCACCGTGTACTGTAACGGCATGAAGAAGGTGATCCTGACCAAGACACTG
GTGATCGGCCAGTGTATCTACACCTTCACCAGCATCTTCTCCCTGATCCC
CGGCGTGGCCCACAGCCTGGCCGTGGAGCTGTGTGTGCCCGGCCTGCACG
GCTGGGCCACCATGCTGCTGCTGCTGACCTTCTGCTTCGGCTGGGTGCTG
ATCCCTACCATCACCATGATCCTGCTGAAGATCCTGATCGCCTTCGCCTA
CCTGTGCTCCAAGTACAACACCGACAGCAAGTTCAGAATCCTGATCGAGA
AAGTGAAGCGGGAGTACCAGAAAACCATGGGCAGCATGGTGTGTGAAGTG
TGCCAGTACGAGTGTGAGACCGCCAAGGAGCTGGAGTCCCACAGAAAGAG
CTGCTCCATCGGCAGCTGCCCCTACTGCCTGAACCCCAGCGAGGCCACCA
CCTCCGCCCTGCAGGCCCACTTCAAAGTGTGTAAGCTGACCAGCCGGTTC
CAGGAGAACCTGAGGAAGTCCCTGACCGTGTACGAGCCCATGCAGGGCTG
CTACAGAACCCTGAGCCTGTTCCGGTACAGGAGCCGGTTCTTTGTGGGCC
TGGTGTGGTGTGTGCTGCTGGTGCTGGAGCTGATTGTGTGGGCCGCCAGC
GCCGAGACCCAGAACCTGAATGCCGGCTGGACCGACACCGCCCACGGCAG
CGGCATCATCCCCATGAAAACCGACCTGGAGCTGGACTTCAGCCTGCCTA
GCAGCGCCTCCTACACCTACAGGCGGCAGCTGCAGAATCCTGCCAACGAG
CAGGAGAAGATCCCCTTCCACCTGCAGCTGTCCAAGCAGGTGATCCACGC
CGAGATTCAGCACCTGGGCCACTGGATGGACGCCACCTTCAACCTGAAAA
CCGCCTTCCACTGCTACGGCAGCTGTGAAGTACGCCTACCCTTGGCAG
ACCGCCGGCTGCTTCATCGAGAAGGACTACGAGTACGAGACCGGCTGGGG
CTGTAATCCTCCTGATTGCCCCGGAGTGGGCACCGGCTGTACTGCATGTG
GCGTGTACCTGGACAAGCTGAAGTCTGTGGGCAAGGTGTTCAAGATCGTG
TCCCTGAGGTACACCCGGAAAGTGTGTATCCAGCTGGGCACCGAGCAGAC
CTGTAAGACCGTGGACAGCAACGATTGCCTGATCACAACCAGCGTGAAAG
TGTGTCTGATCGGCACCATCAGCAAGTTCCAGCCCAGCGATACCCTGCTG
```

-continued

TTTCTGGGCCCCCTGCAGCAGGGCGGCCTGATCTTCAAGCAGTGGTGTAC
CACCACCTGCCAGTTCGGCGATCCCGGCGATATCATGAGCACCCCCACCG
GCATGAAGTGCCCTGAGCTGAACGGCAGCTTCCGGAAGAAGTGTGCCTTC
GCCACCACCCCTGTGTGTCAGTTCGACGGCAACACCATCAGCGGCTACAA
GCGGATGATCGCCACCAAGGACAGCTTCCAGTCCTTCAACGTGACCGAGC
CCCACATCAGCACCAGCGCCCTGGAGTGGATCGATCCCGACAGCAGCCTG
AGGGACCACATCAACGTGATCGTGTCCAGGGACCTGAGCTTCCAGGACCT
GAGCGAGACCCCCTGCCAGATCGACCTGGCCACCGCCAGCATCGATGGCG
CCTGGGGCAGCGGAGTGGGCTTCAACCTGGTGTGTACAGTGAGCCTGACC
GAGTGTAGCGCCTTCCTGACCAGCATCAAAGCCTGTGACGCCGCCATGTG
TTACGGCAGCACCACCGCCAACCTGGTGAGAGGCCAGAACACCATCCACA
TTGTGGGCAAAGGCGGCCACAGCGGCAGCAAGTTTATGTGCTGCCACGAC
ACCAAGTGTAGCAGCACCGGCCTGGTGGCCGCTGCCCCCCACCTGGACAG
AGTGACCGGCTACAACCAGGCCGACAGCGACAAGATTTTCGACGACGGAG
CCCCTGAGTGTGGCATGAGTTGCTGGTTCAAGAAGAGCGGCGAGTGGATT
CTGGGCGTGCTGAACGGGAATTGGATGGTGGTGGCCGTGCTGGTCGTGCT
GCTGATCCTGAGCATCCTGCTGTTCACCCTGTGCTGCCCTAGGAGACCCA
GCTACCGGAAGGAGCACAAGCCCTGAGTTTTGCTTACTAACATAATTATT
GTATTCTGTTTATTGACACAATTACCATATGATTAACTGTATTCCCCCAT
CTTATATCTTATATAATATTCTTTATTTAATCACTATATAGAAAAAAAAC
TAGCACTTTACTAATTAAATTACCCCATACCGATTATGCCTGGACTTTTG
TTCCTGCGGAGCATACTACTAGGATCTACGTATGATCAGCCTCGACTGTG
CCTTCTAGTTGCCAGCCATCTGTTGTTTGCCCCTCCCCCGTGCCTTCCTT
GACCCTGGAAGGTGCCACTCCCACTGTCCTTTCCTAATAAAATGAGGAAA
TTGCATCGCATTGTCTGAGTAGGTGTCATTCTATTCTGGGGGGTGGGGTG
GGGCAGGACAGCAAGGGGAGGATTGGGAAGACAATAGCAGGCATGCTGG
GGATGCGGTGGGCTCTATGGCTTCTGAGGCGGAAAGAACCAGCTGGGGCT
CGACAGCTCGACTCTAGAATTGCTTCCTCGCTCACTGACTCGCTGCGCTC
GGTCGTTCGGCTGCGGCGAGCGGTATCAGCTCACTCAAAGGCGGTAATAC
GGTTATCCACAGAATCAGGGGATAACGCAGGAAAGAACATGTGAGCAAAA
GGCCAGCAAAAGGCCAGGAACCGTAAAAAGGCCGCGTTGCTGGCGTTTTT
CCATAGGCTCCGCCCCCCTGACGAGCATCACAAAAATCGACGCTCAAGTC
AGAGGTGGCGAAACCCGACAGGACTATAAAGATACCAGGCGTTTCCCCCT
GGAAGCTCCCTCGTGCGCTCTCCTGTTCCGACCCTGCCGCTTACCGGATA
CCTGTCCGCCTTTCTCCCTTCGGGAAGCGTGGCGCTTTCTCATAGCTCAC
GCTGTAGGTATCTCAGTTCGGTGTAGGTCGTTCGCTCCAAGCTGGGCTGT
GTGCACGAACCCCCCGTTCAGCCCGACCGCTGCGCCTTATCCGGTAACTA
TCGTCTTGAGTCCAACCCGGTAAGACACGACTTATCGCCACTGGCAGCAG
CCACTGGTAACAGGATTAGCAGAGCGAGGTATGTAGGCGGTGCTACAGAG
TTCTTGAAGTGGTGGCCTAACTACGGCTACACTAGAAGAACAGTATTTGG
TATCTGCGCTCTGCTGAAGCCAGTTACCTTCGGAAAAAGAGTTGGTAGCT

-continued

CTTGATCCGGCAAACAAACCACCGCTGGTAGCGGTGGTTTTTTTGTTTGC
AAGCAGCAGATTACGCGCAGAAAAAAAGGATCTCAAGAAGATCCTTTGAT
CTTTTCTACGGGGTCTGACGCTCAGTGGAACGAAAACTCACGTTAAGGGA
TTTTGGTCATGAGATTATCAAAAAGGATCTTCACCTAGATCCTTTTAAAT
TAAAAATGAAGTTTTAAATCAATCTAAAGTATATATGAGTAAACTTGGTC
TGACAGTTACCAATGCTTAATCAGTGAGGCACCTATCTCAGCGATCTGTC
TATTTCGTTCATCCATAGTTGCCTGACTC

Puumala synthetic full-length M-segment ORF-
SEQ ID NO: 14
ATGGGCGAGCTGTCCCCTGTGTGCCTGTACCTGCTGCTGCAGGGCCTGCT
GCTGTGTAACACCGGAGCCGCCAGGAACCTGAACGAGCTGAAGATGGAGT
GCCCCCACACCATCAGACTGGGCCAGGGCCTGGTGGTGGGCAGCGTGGAG
CTGCCCAGCCTGCCCATCCAGCAGGTGGAGACCCTGAAGCTGGAGAGCAG
CTGTAACTTCGACCTGCACACCAGCACAGCCGGCAGCAGAGCTTCACCA
AGTGGACCTGGAGATCAAGGGCGACCTGGCCGAGAACACCCAGGCCAGC
AGCACCAGCTTCCAGACCAAGAGCAGCGAGGTGAACCTGAGAGGCCTGTG
CCTGATCCCCACACTGGTGGTGGAGACCGCCGCCAGAATGAGAAAGACCA
TCGCCTGCTACGACCTGAGCTGTAACCAGACCGTGTGTCAGCCTACCGTG
TACCTGATGGGCCCTATCCAGACCTGTATCACCACCAAGAGCTGCCTGCT
GTCCCTGGGCGATCAGAGAATCCAGGTGAACTACGAGAAAACCTACTGTG
TGAGCGGCCAGCTGGTGGAGGGCATCTGCTTCAACCCCATCCACACCATG
GCCCTGAGCCAGCCTAGCCACACCTACGACATCATGACCATGATGGTGAG
ATGCTTTCTGGTGATCAAGAAGGTGACCAGCGGCGACAGCATGAAGATCG
AGAAGAACTTCGAGACCCTGGTGCAGAAGAATGGCTGTACCGCCAACAAC
TTCCAGGGCTACTACATCTGCCTGATCGGCAGCAGCAGCGAGCCCCTGTA
CGTGCCCGCCCTGGACGACTACAGAAGCGCCGAGGTGCTGTCCAGAATGG
CCTTCGCCCCCACGGCGAGGACCACGACATCGAGAAAACGCCGTGTCC
GCCATGAGAATCGCCGGCAAGGTGACCGGCAAGGCCCCCAGCACCGAGTC
CAGCGACACCGTGCAGGGCATCGCCTTCAGCGGCAGCCCCCTGTACACCT
CCACCGGCGTGCTGACCAGCAAGGACGACCCCGTGTACATCTGGGCCCCT
GGCATCATCATGGAGGGCAACCACAGCATCTGTGAGAAGAAACCCTGCC
CCTGACCTGGACCGGCTTCATCAGCCTGCCCGGCGAGATCGAGAAACCA
CCCAGTGTACCGTGTTCTGTACCCTGGCCGGACCTGGCGCCGACTGTGAG
GCCTACAGCGAGACCGGCATCTTCAACATCAGCAGCCCCACCTGCCTGAT
CAACCGGGTGCAGAGGTTCAGAGGCAGCGAGCAGCAGATCAAGTTTGTGT
GCCAGCGGGTGGACATGGACATCACCGTGTACTGTAACGGCATGAAGAAG
GTGATCCTGACCAAGACACTGGTGATCGGCCAGTGTATCTACACCTTCAC
CAGCATCTTCTCCCTGATCCCCGGCGTGGCCCACAGCCTGGCCGTGGAGC
TGTGTGTGCCCGGCCTGCACGGCTGGGCCACCATGCTGCTGCTGCTGACC
TTCTGCTTCGGCTGGGTGCTGATCCCTACCATCACCATGATCCTGCTGAA
GATCCTGATCGCCTTCGCCTACCTGTGCTCCAAGTACAACACCGACAGCA -continued

AGTTCAGAATCCTGATCGAGAAAGTGAAGCGGGAGTACCAGAAAACCATG
GGCAGCATGGTGTGTGAAGTGTGCCAGTACGAGTGTGAGACCGCCAAGGA
GCTGGAGTCCCACAGAAAGAGCTGCTCCATCGGCAGCTGCCCCTACTGCC
TGAACCCCAGCGAGGCCACCACCTCCGCCCTGCAGGCCCACTTCAAAGTG
TGTAAGCTGACCAGCCGGTTCCAGGAGAACCTGAGGAAGTCCCTGACCGT

GTACGAGCCCATGCAGGGCTGCTACAGAACCCTGAGCCTGTTCCGGTACA

GGAGCCGGTTCTTTGTGGGCCTGGTGTGGTGTGTGCTGCTGGTGCTGGAG
CTGATTGTGTGGGCCGCCAGCGCCGAGACCCAGAACCTGAATGCCGGCTG
GACCGACACCGCCCACGGCAGCGGCATCATCCCCATGAAAACCGACCTGG
AGCTGGACTTCAGCCTGCCTAGCAGCGCCTCCTACACCTACAGGCGGCAG
CTGCAGAATCCTGCCAACGAGCAGGAGAAGATCCCCTTCCACCTGCAGCT
GTCCAAGCAGGTGATCCACGCCGAGATTCAGCACCTGGGCCACTGGATGG
ACGCCACCTTCAACCTGAAAACCGCCTTCCACTGCTACGGCAGCTGTGAG
AAGTACGCCTACCCTTGGCAGACCGCCGGCTGCTTCATCGAGAAGGACTA
CGAGTACGAGACCGGCTGGGGCTGTAATCCTCCTGATTGCCCCGGAGTGG
GCACCGGCTGTACTGCATGTGGCGTGTACCTGGACAAGCTGAAGTCTGTG
GGCAAGGTGTTCAAGATCGTGTCCCTGAGGTACACCCGGAAAGTGTGTAT
CCAGCTGGGCACCGAGCAGACCTGTAAGACCGTGGACAGCAACGATTGCC
TGATCACAACCAGCGTGAAAGTGTGTCTGATCGGCACCATCAGCAAGTTC
CAGCCCAGCGATACCCTGCTGTTTCTGGGCCCCCTGCAGCAGGGCGGCCT
GATCTTCAAGCAGTGGTGTACCACCACCTGCCAGTTCGGCGATCCCGGCG
ATATCATGAGCACCCCCACCGGCATGAAGTGCCCTGAGCTGAACGGCAGC
TTCCGGAAGAAGTGTGCCTTCGCCACCACCCCTGTGTGTCAGTTCGACGG

CAACACCATCAGCGGCTACAAGCGGATGATCGCCACCAAGGACAGCTTCC

AGTCCTTCAACGTGACCGAGCCCCACATCAGCACCAGCGCCCTGGAGTGG
ATCGATCCCGACAGCAGCCTGAGGGACCACATCAACGTGATCGTGTCCAG
GGACCTGAGCTTCCAGGACCTGAGCGAGACCCCCTGCCAGATCGACCTGG
CCACCGCCAGCATCGATGGCGCCTGGGGCAGCGGAGTGGGCTTCAACCTG
GTGTGTACAGTGAGCCTGACCGAGTGTAGCGCCTTCCTGACCAGCATCAA
AGCCTGTGACGCCGCCATGTGTTACGGCAGCACCACCGCCAACCTGGTGA
GAGGCCAGAACACCATCCACATTGTGGGCAAAGGCGGCCACAGCGGCAGC
AAGTTTATGTGCTGCCACGACACCAAGTGTAGCAGCACCGGCCTGGTGGC
CGCTGCCCCCCACCTGGACAGAGTGACCGGCTACAACCAGGCCGACAGCG
ACAAGATTTTCGACGACGGAGCCCCTGAGTGTGGCATGAGTTGCTGGTTC
AAGAAGAGCGGCGAGTGGATTCTGGGCGTGCTGAACGGGAATTGGATGGT
GGTGGCCGTGCTGGTCGTGCTGCTGATCCTGAGCATCCTGCTGTTCACCC
TGTGCTGCCCTAGGAGACCCAGCTACCGGAAGGAGCACAAGCCCTGA

Plasmid pWRG/HTN-M(x)

SEQ ID NO: 12

```
gggggggggg ggcgctgagg tctgcctcgt gaagaaggtg     40
ttgctgactc ataccaggcc tgaatcgccc catcatccag     80
ccagaaagtg agggagccac ggttgatgag agctttgttg    120
```

-continued

```
taggtggacc agttggtgat tttgaacttt tgctttgcca    160
cggaacggtc tgcgttgtcg ggaagatgcg tgatctgatc    200
cttcaactca gcaaaagttc gatttattca acaaagccgc    240
cgtcccgtca agtcagcgta atgctctgcc agtgttacaa    280
ccaattaacc aattctgatt agaaaaactc atcgagcatc    320
aaatgaaact gcaatttatt catatcagga ttatcaatac    360
catatttttg aaaaagccgt ttctgtaatg aaggagaaaa    400
ctcaccgagg cagttccata ggatggcaag atcctggtat    440
cggtctgcga ttccgactcg tccaacatca atacaaccta    480
ttaatttccc ctcgtcaaaa ataaggttat caagtgagaa    520
atcaccatga gtgacgactg aatccggtga gaatggcaaa    560
agcttatgca tttctttcca gacttgttca acaggccagc    600
cattacgctc gtcatcaaaa tcactcgcat caaccaaacc    640
gttattcatt cgtgattgcg cctgagcgag acgaaatacg    680
cgatcgctgt taaaaggaca attacaaaca ggaatcgaat    720
gcaaccggcg caggaacact gccagcgcat caacaatatt    760
ttcacctgaa tcaggatatt cttctaatac ctggaatgct    800
gttttcccgg ggatcgcagt ggtgagtaac catgcatcat    840
caggagtacg gataaaatgc ttgatggtcg gaagaggcat    880
aaattccgtc agccagttta gtctgaccat ctcatctgta    920
acatcattgg caacgctacc tttgccatgt ttcagaaaca    960
actctggcgc atcgggcttc ccatacaatc gatagattgt   1000
cgcacctgat tgcccgacat tatcgcgagc ccatttatac   1040
ccatataaat cagcatccat gttggaattt aatcgcggcc   1080
tcgagcaaga cgtttcccgt tgaatatggc tcataacacc   1120
ccttgtatta ctgtttatgt aagcagacag ttttattgtt   1160
catgatgata tatttttatc ttgtgcaatg taacatcaga   1200
gattttgaga cacaacgtgg ctttcccccc cccccggca    1240
tgcctgcagg tcgacaatat tggctattgg ccattgcata   1280
cgttgtatct atatcataat atgtacattt atattggctc   1320
atgtccaata tgaccgccat gttgacattg attattgact   1360
agttattaat agtaatcaat tacggggtca ttagttcata   1400
gcccatatat ggagttccgc gttacataac ttacggtaaa   1440
tggcccgcct ggctgaccgc ccaacgaccc ccgcccattg   1480
acgtcaataa tgacgtatgt tcccatagta acgccaatag   1520
ggactttcca ttgacgtcaa tgggtggagt atttacggta   1560
aactgcccac ttggcagtac atcaagtgta tcatatgcca   1600
agtccgcccc ctattgacgt caatgacggt aaatggcccg   1640
cctggcatta tgcccagtac atgaccttac gggactttcc   1680
tacttggcag tacatctacg tattagtcat cgctattacc   1720
```

-continued

```
atggtgatgc ggttttggca gtacaccaat gggcgtggat       1760
agcggtttga ctcacgggga tttccaagtc tccaccccat       1800
tgacgtcaat gggagtttgt tttggcacca aaatcaacgg       1840
gactttccaa aatgtcgtaa taccccgccc ccgttgacgc       1880
aaatgggcgg taggcgtgta cggtggGagg tctatataag       1920
cagagctcgt ttagtgaacc gtcagatcgc ctggagacgc       1960
catccacgct gttttgacct gcatcgaaga caccgggacc       2000
gatccagcct ccgcgccgg gaacggtgca ttggaacgcg        2040
gattccccgt gccaagagtg acgtaagtac cgcctataga      2080
ctctataggc acacccnttt ggctcttatg catgctatac      2120
tgttttggc ttggggccta tacaccccg cttccttatg       2160
ctataggtga tggtatagct tagcctatag gtgtgggtta      2200
ttgaccatta ttgaccactc ccctattggt gacgatactt      2240
tccattacta atccataaca tggctctttg ccacaactat      2280
ctctattggc tatatgccaa tactctgtcc ttcagagact      2320
gacacggact ctgtattttt acaggatggg gtcccattta      2360
ttatttacaa attcacatat acaacaacgc cgtcccccgt      2400
gcccgcagtt tttattaaac atagcgtggg atctccacgc      2440
gaatctcggg tacgtgttcc ggacatggc tcttctccgg       2480
tagcggcgga gcttccacat ccgagccctg gtcccatgcc      2520
tccagcggct catggtcgct cggcagctcc ttgctcctaa      2560
cagtggaggc cagacttagg cacagcacaa tgcccaccac      2600
caccagtgtg ccgcacaagg ccgtggcggt agggtatgtg      2640
tctgaaaatg agctcggaga ttgggctcgc accgctgacg      2680
cagatggaag acttaaggca gcggcagaag aagatgcagg      2720
cagctgagtt gttgtattct gataagagtc agaggtaact      2760
cccgttgcgc tgctgttaac ggtggagggc agtgtagtct      2800
gagcagtact cgttgctgcc gcgcgcgcca ccagacataa      2840
tagctgacag actaacagac tgttcctttc catgggtctt      2880
ttctgcagtc accgtccaag cttgcggccg cggatctgca      2920
ggaattcggc acgagagtag tagactccgc aagaaacagc      2960
agtcaatcag caacatgggg atatggaagt ggctagtgat      3000
ggccagttta gtatggcctg ttttgacact gagaaatgtc      3040
tatgacatga aaattgagtg ccccCatACa gtaagttttg      3080
gggaaaacag tgtgataggt tatgtagaat tacccccCgt      3120
gccattggcc gacacagcac agatggtgcc tgagagttct      3160
tgtagcatgg ataatcacca atcgttgaat acaataacaa      3200
aatatacCca gtaagttgg agaggaaagg ctgatcagtc       3240
acagtctagt caaaattcat ttgagacagt gtccactgaa      3280
gttgacttga aaggaacatg tgctctaaaa cacaaaatgg      3320
tggaagaatc ataccgtagt aggaaatcag taacctgtta      3360
cgacctgtct tgcaatagca cttactgcaa gccaacacta      3400
tacatgattg taccaattca tgcatgcaat atgatgaaaa      3440
gctgtttgat tgcattggga ccatacagag tacaggtggt      3480
ttatgagaga tcttattgca tgacaggagt cctgattgaa      3520
gggaaatgct tgtcccaga tcaaagtgtg gtcagtatta       3560
tcaagcatgg gatctttgat attgcaagtt ttcatattgt      3600
atgtttcttt gttgcagtta agggaatac ttataaaatt       3640
tttgaacagg ttaagaaatc ctttgaatca acatgcaatg      3680
atacagagaa taaagtgcaa ggatattata tttgtattgt      3720
agggggaaac tctgcaccaa tatatgttcc aacacttgat      3760
gatttcagat ccatggaagc atttacagga atcttcagat      3800
caccacatgg ggaagatcat gatctggctg gagaagaaat      3840
tgcatcttat tctatagtcg gacctgccaa tgcaaaagtt      3880
cctcatagtg ctagctcaga tacattgagc ttgattgcct      3920
attcaggtat accatcttat tcttccctta gcatcctaac      3960
aagttcaaca gaagctaagc atgtattcag ccctgggttg      4000
ttcccaaaac ttaatcacac aaattgtgat aaaagtgcca      4040
taccactcat atggactggg atgattgatt tacctggata      4080
ctacgaagct gtccaccctt gtacagtttt ttgcgtatta      4120
tcaggtcctg gggcatcatg tgaagccttt tctgaaggcg      4160
ggattttcaa cataacctct cccatgtgct tagtgtcaaa      4200
acaaaatcga ttccggttaa cagaacagca agtgaatttt      4240
gtgtgtcagc gagtggacat ggacattgtt gtgtactgca      4280
acgggcagag gaaagtaata ttaacaaaaa ctctagttat      4320
tggacagtgt atatatacta taacaagctt attctcatta      4360
ctacctggag tagcacattc tattgctgtt gaattgtgtg      4400
tacctgggtt ccatggttgg gccacagctg ctctgcttgt      4440
tacattctgt ttcggatggg ttcttatacc agcaattaca      4480
tttatcatac taacagtcct aaagttcatt gctaatattt      4520
ttcacacaag taatcaagag aataggctaa aatcagtact      4560
tagaaagata aaggaagagt ttgaaaaaac aaaaggctca      4600
atggtatgtg atgtctgcaa gtatgagtgt gaaacctata      4640
aagaattaaa ggcacacggg gtatcatgcc cccaatctca      4680
atgtccttac tgttttactc attgtgaacc cacagaagca      4720
gcattccaag ctcattacaa ggtatgccaa gttactcaca      4760
gattcaggga tgatctaaag aaaactgtta ctcctcaaaa      4800
ttttacacca ggatgttacc ggacactaaa tttatttaga      4840
tacaaaagca ggtgctacat ctttacaatg tggatatttc      4880
ttcttgtctt agaatccata ctgtgggctg caagtgcatc      4920
agagacacca ttaactcctg tctggaatga caatgcccat      4960
```

```
ggggtaggtt ctgttcctat gcatacagat ttagagcttg    5000
atttctcttt aacatccagt tccaagtata cataccgtag    5040
gaggttaaca aacccacttg aggaagcaca atccattgac    5080
ctacatattg aaatagaaga acagacaatt ggtgttgatg    5120
tgcatgctct aggacactgg tttgatggtc gtcttaacct    5160
taaaacatcc tttcactgtt atggtgcttg tacaaagtat    5200
gaatacccct ggcatactgc aaagtgccac tatgaaagag    5240
attaccaata tgagacgagc tggggttgta atccatcaga    5280
ttgtcctggg gtgggcacag gctgtacagc atgtggttta    5320
tacctagatc aactgaaacc agttggtagt gcttataaaa    5360
ttatcacaat aaggtacagc aggagagtct gtgttcagtt    5400
tggggaggaa aacctttgta agataataga catgaatgat    5440
tgttttgtat ctaggcatgt taaggtctgc ataattggta    5480
cagtatctaa attctctcag ggtgatacct tattgttttt    5520
tggaccgctt gaaggtggtg gtctaatatt taaacactgg    5560
tgtacatcca catgtcaatt tggtgaccca ggagatatca    5600
tgagtccaag agacaaaggt ttttatgcc ctgagtttcc    5640
aggtagtttc aggaagaaat gcaactttgc tactacccct    5680
atttgtgagt atgatggaaa tatggtctca ggttacaaga    5720
aagtgatggc cacaattgat tccttccaat cttttaatac    5760
aagcactatg cacttcactg atgaaaggat agagtggaaa    5800
gaccctgatg gaatgctaag ggaccatata aacatttag    5840
taacgaagga cattgacttt gataaccttg gtgaaaatcc    5880
ttgcaaaatt ggcctacaaa catcttctat tgagggggcc    5920
tggggttctg gtgtgggggtt cacattaaca tgtctggtat    5960
cactaacaga atgtcctacc ttttgacct caataaaggc    6000
ttgtgataag gctatctgtt atggtgcaga gagtgtaaca    6040
ttgacaagag acaaaatac agtcaaggta tcagggaaag    6080
gtggccatag tggttcaaca tttaggtgtt gccatgggga    6120
ggactgttca caaattggac tccatgctgc tgcacctcac    6160
cttgacaagg taaatgggat ttctgagata gaaaatagta    6200
aagtatatga tgatggggca ccgcaatgtg ggataaaatg    6240
ttggtttgtt aaatcagggg aatggatttc agggatattc    6280
agtggtaatt ggattgtact cattgtcctc tgtgtatttc    6320
tattgttctc cttggttttta ctaagcattc tctgtcccgt    6360
aaggaagcat aaaaaatcat agctaaattc tgtgactatc    6400
ctgttcttat gtatagcttt aacatatata ctaattttta    6440
tattccagta tactctatct aacacactaa aaaaatagt    6480
agctttctaa ccacaaaacg gatctacgta tgatcagcct    6520
cgactgtgcc ttctagttgc cagccatctg ttgtttgccc    6560
ctccccccgtg ccttccttga ccctggaagg tgccactccc    6600
```

```
actgtccttt cctaataaaa tgaggaaatt gcatcgcatt    6640
gtctgagtag gtgtcattct attctgggg gtggggtggg    6680
gcaggacagc aaggggagg attgggaaga caatagcagg    6720
catgctgggg atgcggtggg ctctatggct tctgaggcgg    6760
aaagaaccag ctggggctcg acagctcgac tctagaattg    6800
cttcctcgct cactgactcg ctgcgctcgg tcgttcggct    6840
gcggcgagcg gtatcagctc actcaaaggc ggtaatacgg    6880
ttatccacag aatcagggga taacgcagga agaacatgt    6920
gagcaaaagg ccagcaaaag gccaggaacc gtaaaaaggc    6960
cgcgttgctg gcgttttcc ataggctccg ccccctgac    7000
gagcatcaca aaaatcgacg ctcaagtcag aggtggcgaa    7040
acccgacagg actataaaga taccaggcgt ttccccctgg    7080
aagctccctc gtgcgctctc ctgttccgac cctgccgctt    7120
accggatacc tgtccgcctt tctcccttcg ggaagcgtgg    7160
cgctttctca tagctcacgc tgtaggtatc tcagttcggt    7200
gtaggtcgtt cgctccaagc tgggctgtgt gcacgaaccc    7240
cccgttcagc ccgaccgctg cgccttatcc ggtaactatc    7280
gtcttgagtc caacccggta agacacgact tatcgccact    7320
ggcagcagcc actggtaaca ggattagcag agcgaggtat    7360
gtaggcggtg ctacagagtt cttgaagtgg tggcctaact    7400
acgctacac tagaagaaca gtatttggta tctgcgctct    7440
gctgaagcca gttaccttcg gaaaaagagt tggtagctct    7480
tgatccggca aacaaaccac cgctggtagc ggtggttttt    7520
ttgtttgcaa gcagcagatt acgcgcagaa aaaaaggatc    7560
tcaagaagat cctttgatct tttctacggg gtctgacgct    7600
cagtggaacg aaaactcacg ttaagggatt ttggtcatga    7640
gattatcaaa aaggatcttc acctagatcc ttttaaatta    7680
aaaatgaagt tttaaatcaa tctaaagtat atatgagtaa    7720
acttggtctg acagttacca atgcttaatc agtgaggcac    7760
ctatctcagc gatctgtcta tttcgttcat ccatagttgc    7800
``` pWRG-SEO-M (Seoul hantavirus M segment, strain SR-11, subcloned into DNA vector pWRG7077)
                                          SEQ ID NO: 13

```
ggggggggggg ggcgctgagg tctgcctcgt gaagaaggtg    40
ttgctgactc ataccaggcc tgaatcgccc catcatccag    80
ccagaaagtg agggagccac ggttgatgag agctttgttg    120
taggtggacc agttggtgat tttgaacttt gctttgcca    160
cggaacggtc tgcgttgtcg ggaagatgcg tgatctgatc    200
cttcaactca gcaaaagttc gatttattca acaaagccga    240
cgtcccgtca gtcagcgta atgctctgcc agtgttacaa    280
ccaattaacc aattctgatt agaaaactc atcgagcatc    320
aaatgaaact gcaatttatt catatcagga ttatcaatac    360
```

-continued

```
catattttg aaaaagccgt tctgtaatg aaggagaaaa      400
ctcaccgagg cagttccata ggatggcaag atcctggtat    440
cggtctgcga ttccgactcg tccaacatca atacaaccta    480
ttaatttccc ctcgtcaaaa ataaggttat caagtgagaa    520
atcaccatga gtgacgactg aatccggtga gaatggcaaa    560
agcttatgca tttctttcca gacttgttca acaggccagc    600
cattacgctc gtcatcaaaa tcactcgcat caaccaaacc    640
gttattcatt cgtgattgcg cctgagcgag acgaaatacg    680
cgatcgctgt taaaaggaca attacaaaca ggaatcgaat    720
gcaaccggcg caggaacact gccagcgcat caacaatatt    760
ttcacctgaa tcaggatatt cttctaatac ctggaatgct    800
gttttccgg gatcgcagt ggtgagtaac catgcatcat       840
caggagtacg gataaaatgc ttgatggtcg gaagaggcat    880
aaattccgtc agccagttta gtctgaccat ctcatctgta    920
acatcattgg caacgctacc tttgccatgt ttcagaaaca    960
actctggcgc atcgggcttc ccatacaatc gatagattgt   1000
cgcacctgat tgccccacat tatcgcgagc ccatttatac   1040
ccatataaat cagcatccat gttggaattt aatcgcggcc   1080
tcgagcaaga cgtttcccgt tgaatatggc tcataacacc   1120
ccttgtatta ctgtttatgt aagcagacag ttttattgtt   1160
catgatgata tattttatc ttgtgcaatg taacatcaga    1200
gattttgaga cacaacgtgg cttccccccc cccccggca    1240
tgcctgcagg tcgacataaa tcaatattgg ctattggcca   1280
ttgcatacgt tgtatctata tcataatatg tacatttata   1320
ttggctcatg tccaatatga ccgccatgtt gacattgatt   1360
attgactagt tattaatagt aatcaattac ggggtcatta   1400
gttcatagcc catatatgga gttccgcgtt acataactta   1440
cggtaaatgg cccgcctcgt gaccgcccaa cgaccccgc    1480
ccattgacgt caataatgac gtatgttccc atagtaacgc   1520
caatagggac tttccattga cgtcaatggg tggagtattt   1560
acggtaaact gcccacttgg cagtacatca agtgtatcat   1600
atgccaagtc cggcccccta ttgacgtcaa tgacggtaaa   1640
tggcccgcct ggcattatgc ccagtacatg accttacggg   1680
actttcctac ttggcagtac atctacgtat tagtcatcgc   1720
tattaccatg gtgatgcggt tttggcagta caccaatggg   1760
cgtggatagc ggtttgactc acggggattt ccaagtctcc   1800
accccattga cgtcaatggg agtttgtttt ggcaccaaaa   1840
tcaacgggac tttccaaaat gtcgtaataa ccccgccccg   1880
ttgacgcaaa tgggcggtag gcgtgtacgg tgggaggtct   1920
atataagcag agctcgttta gtgaaccgtc agatcgcctg   1960
```

```
gagacgccat ccacgctgtt ttgacctcca tagaagacac   2000
cgggaccgat ccagcctccg cggccgggaa cggtgcattg   2040
gaacgcggat tccccgtgcc aagagtgacg taagtaccgc   2080
ctatagactc tataggcaca ccccttggc tcttatgcat     2120
gctatactgt ttttggcttg gggcctatac accccgctc    2160
cttatgctat aggtgatggt atagcttagc ctataggtgt   2200
gggttattga ccattattga ccactcccct attggtgacg   2240
atactttcca ttactaatcc ataacatggc tctttgccac   2280
aactatctct attggctata tgccaatact ctgtccttca   2320
gagactgaca cggactctgt atttttacag gatggggtcc   2360
catttattat ttacaaattc acatatacaa caacgccgtc   2400
ccccgtgccc gcagttttta ttaaacatag cgtgggatct   2440
ccacgcgaat ctcgggtacg tgttccggac atgggctctt   2480
ctccggtagc ggcggagctt ccacatccga gccctggtcc   2520
catgcctcca gcggctcatg gtcgctcgg agctccttgc    2560
tcctaacagt ggaggccaga cttaggcaca gcacaatgcc   2600
caccaccacc agtgtgccgc acaaggccgt ggcggtaggg   2640
tatgtgtctg aaaatgagct cggagattgg gctcgcaccg   2680
tgacgcagat ggaagactta aggcagcggc agaagaagat   2720
gcaggcagct gagttgttgt attctgataa gagtcagagg   2760
taactcccgt tgcggtgctg ttaacggtgg agggcagtgt   2800
agtctgagca gtactcgttg ctgccgcgcg cgccaccaga   2840
cataatagct gacagactaa cagactgttc ctttccatgg   2880
gtctttttctg cagtcaccgt ccaagcttgc ggccgcggat   2920
ctgcaggaat tcggcacgag agtagtagac tccgcaagaa   2960
acagcagtta aagaacaata ggatcatgtg gagtttgcta   3000
ttactggccg ctttagttgg ccaaggcttt gcattaaaaa   3040
atgtatttga catgagaatt cagttgcccc actcagtcaa   3080
ctttggggaa acaagtgtgt caggctatac agaatttccc   3120
ccactctcat tacaggaggc agaacagcta gtgccagaga   3160
gctcatgcaa catggacaac caccagtcac tctcaacaat   3200
aaataaatta accaaggtca tatggcggaa aaaagcaaat   3240
caggaatcag caaaccagaa ttcatttgaa gttgtggaaa   3280
gtgaagtcag ctttaagggg ttgtgtatgt taaagcatag   3320
aatggttgaa gaatcatata gaaataggag atcagtaatc   3360
tgttatgatc tagcctgtaa tagtacattc tgtaaaccaa   3400
ctgtttatat gattgttcct atacatgctt gcaacatgat   3440
gaaaagctgt ttgattggcc ttggccccta cagaatccag   3480
gttgtctatg aaaggacata ctgcactacg ggtatattga   3520
cagaaggaaa atgctttgtc cctgacaagc tgttgtcag    3560
tgcattgaaa agaggcatgt atgctatagc aagcatagag   3600
```

-continued

```
acaatctgct tttttattca tcagaaaggg aatacatata    3640
agatagtgac tgccattaca tcagcaatgg gctccaaatg    3680
taataataca gatactaaag ttcaaggata ttatatctgt    3720
attattggtg gaaactccgc ccctgtatat gcccctgctg    3760
gtgaagactt cagagcaatg gaggttttt ctgggattat     3800
tacatcacca catggagaag accatgacct acccggcgaa    3840
gaaatcgcaa cgtaccagat ttcagggcag atagaggcaa    3880
aaatccctca tacagtgagc tccaaaaact taaaattgac    3920
tgcttttgca ggtattccat catactcatc aactagtata    3960
ttggctgctt cagaagatgg tcgtttcata tttagtcctg    4000
gtttatttcc taacctaaat cagtcagtct gtgacaacaa    4040
tgcactccct ttaatctgga ggggcctaat tgatttaacg    4080
ggatactatg aggcagtcca cccttgcaat gtgttctgtg    4120
tcttatcagg accaggtgct tcatgtgagg ccttttcaga    4160
aggaggtatt ttcaatatta cttctccaat gtgtctggtg    4200
tctaagcaaa atagatttag agcagctgag cagcagatta    4240
gctttgtctg ccaaagagtt gatatggata ttatagtgta    4280
ctgtaatggt cagaaaaaaa caatcctaac aaaaacatta    4320
gttataggcc aatgtattta tactattaca agtctctttt    4360
cactgttacc aggggttgcc cattctattg ctattgagtt    4400
gtgtgttcca gggtttcatg gctgggccac agctgcactt    4440
ttgattacat tctgcttcgg ctgggtattg attcctgcat    4480
gtacattagc tattcttta gtccttaagt tctttgcaaa     4520
tatccttcat acaagcaatc aagagaaccg attcaaagcc    4560
attctacgga aaataaagga ggagtttgaa aaaacaaagg    4600
gttccatggt ttgtgagatc tgtaagtatg agtgtgaaac    4640
attaaaggaa ttgaaggcac ataacctatc atgtgttcaa    4680
ggagagtgcc catattgctt tacccactgt gaaccgacag    4720
aaactgcaat tcaggcacat tacaaagttt gtcaagccac    4760
ccaccgattc agagaagatt taaaaaagac tgtaactcct    4800
caaaatattg ggccaggctg ttaccgaaca ctaaatcttt    4840
ttaggtataa aagtaggtgt tatattctga caatgtggac    4880
tcttcttctc attattgaat ccatcctctg gcagcaagt     4920
gcagcagaaa tccccttgt ccctctctgg acagataatg     4960
ctcatggcgt tgggagtgtt cctatgcata cggatcttga    5000
attagacttc tctttgccat ccagttctaa gtacacatac    5040
aaaagacatc tcacaaaccc agttaatgac caacagagtg    5080
tctcattgca tatagaaatt gaaagtcaag gcattggtgc    5120
tgctgttcat catcttggac attggtatga tgcaagattg    5160
aatctaaaaa cctcatttca ttgttatggt gcctgcacaa    5200
aatatcaata cccatggcac actgcaaaat gccattttga    5240
gaaagattat gagtatgaaa atagctgggc ttgcaacccc    5280
ccagattgcc caggggttgg tacaggttgt actgcttgtg    5320
gattatatct agatcaattg aagccggtag gaacagcctt    5360
taaaattata agtgtaagat acagtagaaa agtgtgcgtg    5400
cagtttggtg aagaacacct ttgtaaaaca attgatatga    5440
atgattgctt tgtgactagg catgccaaaa tatgtataat    5480
tgggactgta tctaagtttt ctcaaggtga cactctacta    5520
tttctggggc ccatggaagg aggtggtata atctttaaac    5560
actggtgtac atctacctgt cactttggag accctggtga    5600
tgtcatgggt ccaaaagata aaccatttat ttgccctgaa    5640
ttcccaggc aatttaggaa aaaatgtaac tttgccacaa     5680
ctccagtttg tgaatatgat ggaaacatta tcaggcta      5720
taagaaagta cttgcaacaa ttgattcttt ccaatcattt    5760
aacacaagca atatacactt cactgatgag agaattgaat    5800
ggagagaccc tgatggcatg cttcgggatc atattaatat    5840
tgttatttct aaagatattg attttgaaaa tttggctgag    5880
aatccttgta agtagggct ccaggcagca aacatagaag     5920
gtgcctgggg ttcaggtgtc gggtttacac tcacatgcaa    5960
ggtgtctctc acagaatgcc caacatttct tacatcaata    6000
aaggcctgtg acatggcaat ttgttatggt gcagaaagtg    6040
tgacactctc acgaggacaa aatactgtca aaattaccgg    6080
gaaaggtggc catagtggtt cttcattcaa atgctgtcat    6120
gggaaagaat gttcatcaac tggcctccaa gccagtgcac    6160
cacatctgga taaggtaaat ggtatctctg agttagaaaa    6200
cgagaaagtt tatgatgacg gtgcacctga atgtggcatt    6240
acttgttggt ttaaaaaatc aggtgaatgg gttatgggta    6280
taatcaatgg gaactgggtt gtcctaattg tcttgtgtgt    6320
actgctgctc ttttctctta tcctgttgag catcttgtgt    6360
cctgttagaa agcataaaaa atcataaatc ccacctaaca    6400
atcttcacat catgtatcga ttttcaaaca ctttatcatt    6440
tagaacttaa cttggcacta ctatctgata actgactttc    6480
attttattt ttatatggat taattactaa aaaaaatact     6520
ctctcgtgcc gaattcgata tcaagcttat cgataccgtc    6560
gacctcgagg gggggcccgg tacccgggat cctcgcaatc    6600
cctaggagga ttaggcaagg gcttgagctc acgctcttgt    6640
gagggacaga aatacaatca ggggcagtat atgaatactc    6680
catggagaaa cccagatcta cgtatgatca gcctcgactg    6720
tgccttctag ttgccagcca tctgttgttt gcccctcccc    6760
cgtgccttcc ttgaccctgg aaggtgccac tcccactgtc    6800
ctttcctaat aaaatgagga aattgcatcg cattgtctga    6840
```

```
gtaggtgtca ttctattctg gggggtgggg tggggcagga    6880
cagcaagggg gaggattggg aagacaatag caggcatgct    6920
ggggatgcgg tgggctctat ggcttctgag gcggaaagaa    6960
ccagctgggg ctcgacagct cgactctaga attgcttcct    7000
cgctcactga ctcgctgcgc tcggtcgttc ggctgcggcg    7040
agcggtatca gctcactcaa aggcggtaat acggttatcc    7080
acagaatcag gggataacgc aggaaagaac atgtgagcaa    7120
aaggccagca aaaggccagg aaccgtaaaa aggccgcgtt    7160
gctggcgttt ttccataggc tccgcccccc tgacgagcat    7200
cacaaaaatc gacgctcaag tcagaggtgg cgaaacccga    7240
caggactata aagataccag gcgtttcccc ctggaagctc    7280
cctcgtgcgc tctcctgttc cgaccctgcc gcttaccgga    7320
tacctgtccg cctttctccc ttcgggaagc gtggcgcttt    7360
ctcaatgctc acgctgtagg tatctcagtt cggtgtaggt    7400
cgttcgctcc aagctgggct gtgtgcacga accccccgtt    7440
cagcccgacc gctgcgcctt atccggtaac tatcgtcttg    7480
agtccaaccc ggtaagacac gacttatcgc cactggcagc    7520
agccactggt aacaggatta gcagagcgag gtatgtaggc    7560
ggtgctacag agttcttgaa gtggtggcct aactacggct    7600
acactagaag gacagtattt ggtatctgcg ctctgctgaa    7640
gccagttacc ttcggaaaaa gagttggtag ctcttgatcc    7680
ggcaaacaaa ccaccgctgg tagcggtggt tttttgttt    7720 gcaagcagca gattacgcgc agaaaaaaag gatctcaaga    7760
agatcctttg atcttttcta cggggtctga cgctcagtgg    7800
aacgaaaact cacgttaagg gattttggtc atcagattat    7840 caaaaggat cttcacctag atccttttaa attaaaaatg    7880
aagttttaaa tcaatctaaa gtatatatga gtaaacttgg    7920
tctgacagtt accaatgctt aatcagtgag gcacctatct    7960
cagcgatctg tctatttcgt tcatccatag ttgcctgact    8000
c                                              8001
```

More preferably, it further includes the Andes M-gene construct pWRG/AND-M(x) (SEQ ID NO:10), which strengthens the HPS component.

Where gene-gun delivery is contemplated, the DNA segments from different viruses can be on different particles or on the same particle, whichever results in the desired immune response. The vaccine is designed to protect against pathologies resulting from exposure to one or several hantaviruses. The vaccine can also be combined with reagents which increase the antigenicity of the vaccine, or reduce its side effects. As shown above, the delivery of a combination of vaccines by electroporation involves mixtures of DNA. This demonstrates that plasmids can be mixed and any interference from the respective DNA with each other can be overcome—another advantage of this invention.

For DNA vaccinations described here, as appropriate, when inducing cellular, humoral, and protective immune responses after DNA vaccination the preferred target cells are epidermal cells, rather than cells of deeper skin layers such as the dermis. Epidermal cells are preferred recipients of DNA vaccines because they are the most accessible cells of the body and may, therefore, be immunized non-invasively. Secondly, in addition to eliciting a humoral immune response, DNA immunized epidermal cells also elicit a cytotoxic immune response that is stronger than that generated in sub-epidermal cells. Delivery to epidermis also has the advantages of being less invasive and delivering to cells which are ultimately sloughed by the body.

Although it can be desirable to induce an immune response by delivering genetic material to a target animal, merely demonstrating an immune response is not necessarily sufficient to confer protective advantage on the animal. What is important is to achieve a protective immune response that manifests itself in a clinical difference. That is, a method is effective only if it prevents infection or reduces the severity of the disease symptoms. It is preferred that the immunization method be at least 20% effective in preventing death in an immunized population after challenge with SNV or, if a multivalent vaccine is used, at least one of the other targeted hantaviruses. More preferably, the vaccination method is 50% or more effective, and most preferably 70 100% effective, in preventing death in an immunized population. The vaccination method is shown herein to be 100% effective in the hamster models for hantavirus. Hamsters have been used extensively as the laboratory models of choice for assessment of protective immune responses to hantaviruses. In contrast, unimmunized animals are uniformly infected by challenge with hantavirus. The inventor's results indicate that vaccination with our SNV vaccines protects against infection with SNV. As is well known, high titer antibody such as achieved by the inventor is predictive of protection.

Generally, the DNA vaccine administered may be in an amount of about 5 ug-5 mg of DNA per dose and will depend on the delivery technology, subject to be treated, capacity of the subject's immune system to develop the desired immune response, and the degree of protection desired. Precise amounts of the vaccine to be administered may depend on the judgement of the practitioner and may be peculiar to each subject and antigen. Delivery technology plays an important role in determining dosage—e.g., an adjuvant may change the dosage or number of vaccinations needed.

The vaccine for eliciting an immune response against one or more viruses, may be given in a single dose schedule, or if deemed necessary or desirable, a multiple dose schedule in which a primary course of vaccination may be with 1-8 separate doses, followed by other doses given at subsequent time intervals required to maintain and or reinforce the immune response, for example, at 14 months for a second dose, and if needed, a subsequent dose(s) after several months. Examples of suitable immunization schedules include: (i) 0, 1 months and 6 months, (ii) 0, 7 days and 1 month, (iii) 0 and 1 month, (iv) 0 and 6 months, or other schedules sufficient to elicit the desired immune responses expected to confer protective immunity, or reduce disease symptoms, or reduce severity of disease.

In a related embodiment, this invention provides a method for raising high titers of neutralizing antibodies against Sin Nombre virus in a mammal or a bird. The method comprises the step of administering a composition comprising a SNV plasmid DNA which comprises one or more of the recombinant DNA constructs described above (including SEQ ID NO:1, SEQ ID NO:2 or SEQ ID NOT:3); and a pharmacologically acceptable carrier. The step of administering may need to be repeated as desired in order to achieve the level of titer targeted. Preferably the titer is measured to be between 100 and 10,000.

Therapeutic Use of Polyclonal and Monoclonal Antibodies

In another embodiment, the present invention relates to polyclonal antibodies from vaccines receiving the DNA vaccines described above. A composition comprising the polyclonal antibodies can be used as a prophylactic or therapeutic effective in preventing onset of Sin Nombre virus infection after exposure to it, and/or in treating Sin Nombre virus disease. For example, the composition of the present invention is composed of polyclonal antiserum from a population of animals or humans vaccinated with a DNA vaccine comprised of a plasmid expressing the above-described synthetic Sin Nombre virus M gene. The polyclonal serum would contain neutralizing antibodies against Sin Nombre virus. Unlike conventional polyclonal immune serum products, the process used to make this invention (DNA vaccination to produce antibody in vaccines) does not involve live virus and does not require the identification of patients who have survived Sin Nombre virus disease.

Similarly, animals or humans vaccinated with one of the above-described DNA vaccines can produce SNV-neutralizing monoclonal antibodies (Mab), which Mab can then be engineered into expression systems.

In one embodiment of this method, the invention contemplates a method to treat or prevent or ameliorate symptoms after onset of Sin Nombre virus infection by administering a therapeutically or prophylactically effective amount of serum of the present invention or a mixture of antibodies of the present invention to a subject in need of such treatment. The antibodies are specific for peptides encoded by the nucleic acids described herein—e.g., where the Gn and Gc are encoded by the nucleic acid of one of SEQ ID NO:1, SEQ ID NO:2 and/or SEQ ID NO:3.

The polyclonal antibodies described herein are characterized in that the antibody binds to the appropriate immunogen, i.e. Gn and Gc, as measured by assays such as ELISA, immunoprecipitation, or immunofluorescence. Also, the antibodies must neutralize Sin Nombre virus as measured by plaque reduction neutralization test (PRNT). Any antibody retaining these characteristics is related to the present invention. The polyclonal antibody may be concentrated, irradiated, and tested for a capacity to neutralize Sin Nombre virus. Serum lots with sufficiently high neutralizing antibody titers, i.e., high enough to give a detectable response in the recipient after transfer, can be pooled. The product can then be lyophilized for storage and reconstituted for use.

As described in greater detail in the examples, the present inventor has found that serum from a vaccine immunized with a DNA vaccine comprising one of the above-described SNV sequences, contains antibodies able to neutralize hantavirus.

Given these results, polyclonal antibodies according to the present invention are suitable both as therapeutic and prophylactic agents for treating or preventing SNV infection or disease in susceptible SNV-exposed subjects. Subjects include rodents such as mice or guinea pigs, avian, and mammals (including transgenic animals), including humans.

Any active form of the antibodies can be administered. Antibodies of the present invention can be produced in any system, including insect cells, baculovirus expression systems, chickens, rabbits, goats, cows, or plants such as tomato, potato, banana or strawberry. Methods for the production of antibodies in these systems are known to a person with ordinary skill in the art. Preferably, the antibodies used are compatible with the recipient species such that the immune response to the antibodies does not result in clearance of the antibodies before virus can be controlled, and the induced immune response to the antibodies in the subject does not induce "serum sickness" in the subject.

Treatment of individuals having SNV infection may comprise the administration of a therapeutically effective amount of anti-SNV antibodies of the present invention. The antibodies can be provided in a kit as described below. In providing a patient with antibodies, or fragments thereof, capable of binding to SNV, or an antibody capable of protecting against SNV in a recipient patient, the dosage of administered agent will vary depending upon such factors as the patient's age, weight, height, sex, general medical condition, previous medical history, etc.

In general, it is desirable to provide the recipient with a dosage of antibody which is in the range of from about 1 pg/kg 100 pg/kg, 100 pg/kg 500 pg/kg, 500 pg/kg 1 ng/kg, 1 ng/kg 100 ng/kg, 100 ng/kg 500 ng/kg, 500 ng/kg 1 ug/kg, 1 ug/kg 100 ug/kg, 100 ug/kg 500 ug/kg, 500 ug/kg 1 mg/kg, 1 mg/kg 50 mg/kg, 50 mg/kg 100 mg/kg, 100 mg/kg 500 mg/kg, 500 mg/kg 1 g/kg, 1 g/kg 5 g/kg, 5 g/kg 10 g/kg (body weight of recipient), although a lower or higher dosage may be administered.

The antibodies capable of protecting against hantavirus are intended to be provided to recipient subjects in an amount sufficient to effect a reduction in the SNV infection symptoms. An amount is said to be sufficient to "effect" the reduction of infection symptoms if the dosage, route of administration, etc. of the agent are sufficient to influence such a response. Responses to antibody administration can be measured by analysis of subject's vital signs.

A composition is said to be "pharmacologically acceptable" if its administration can be tolerated by a recipient patient. Such an agent is said to be administered in a "therapeutically effective amount" if the amount administered is physiologically significant. An agent is physiologically significant if its presence results in a detectable change in the physiology of a recipient patient.

The compounds of the present invention can be formulated according to known methods to prepare pharmaceutically useful compositions, whereby these materials, or their functional derivatives, are combined in admixture with a pharmaceutically acceptable carrier vehicle. Suitable vehicles and their formulation, inclusive of other human proteins, e.g., human serum albumin, are described, for example, in Remington's Pharmaceutical Sciences (16th ed., Osol, A. ed., Mack Easton Pa. (1980)). In order to form a pharmaceutically acceptable composition suitable for effective administration, such compositions will contain an effective amount of the above-described compounds together with a suitable amount of carrier vehicle.

Additional pharmaceutical methods may be employed to control the duration of action. Control release preparations may be achieved through the use of polymers to complex or absorb the compounds. The controlled delivery may be exercised by selecting appropriate macromolecules (for example polyesters, polyamino acids, polyvinyl, pyrrolidone, ethylenevinylacetate, methylcellulose, carboxymethylcellulose, or protamine sulfate) and the concentration of macromolecules as well as the method of incorporation in order to control release. Another possible method to control the duration of action by controlled release preparations is to incorporate the compounds of the present invention into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, interfacial polymerization, for example, hydroxymethylcellulose or gelatin-microcapsules and poly (methylmethacylate)-microcapsules, respectively, or in colloidal drug delivery systems, for example, liposomes, albumin microspheres, microemulsions, nanoparticles, and nanocapsules or in macroemulsions. Such techniques are disclosed in Remington's Pharmaceutical Sciences (1980).

Administration of the antibodies disclosed herein may be carried out by any suitable means, including parenteral injection (such as intraperitoneal, subcutaneous, or intramuscular injection), in ovo injection of birds, orally, or by topical application of the antibodies (typically carried in a pharmaceutical formulation) to an airway surface. Topical application of the antibodies to an airway surface can be carried out by intranasal administration (e.g., by use of dropper, swab, or inhaler which deposits a pharmaceutical formulation intranasally). Topical application of the antibodies to an airway surface can also be carried out by inhalation administration, such as by creating respirable particles of a pharmaceutical formulation (including both solid particles and liquid particles) containing the antibodies as an aerosol suspension, and then causing the subject to inhale the respirable particles. Methods and apparatus for administering respirable particles of pharmaceutical formulations are well known, and any conventional technique can be employed. Oral administration may be in the form of an ingestable liquid or solid formulation.

The treatment may be given in a single dose schedule, or preferably a multiple dose schedule in which a primary course of treatment may be with 1-10 separate doses, followed by other doses given at subsequent time intervals required to maintain and or reinforce the response, for example, at 1-4 months for a second dose, and if needed, a subsequent dose(s) after several months. Examples of suitable treatment schedules include: (i) 0, 1 month and 6 months, (ii) 0, 7 days and 1 month, (iii) 0 and 1 month, (iv) 0 and 6 months, or other schedules sufficient to elicit the desired responses expected to reduce disease symptoms, or reduce severity of disease.

Diagnostic Methods

The present invention still further pertains to a method for detecting SNV in a sample suspected of containing SNV. The method includes contacting the sample with polyclonal antibodies of the present invention which bind SNV antigens, allowing the antibody to bind to the SNV antigen(s) to form an immunological complex, detecting the formation of the immunological complex and correlating the presence or absence of the immunological complex with the presence or absence of SNV antigen in the sample. The sample can be biological, environmental or a food sample.

The language "detecting the formation of the immunological complex" is intended to include discovery of the presence or absence of SNV antigen in a sample. The presence or absence of SNV antigen can be detected using an immunoassay. A number of immunoassays used to detect and/or quantitate antigens are well known to those of ordinary skill in the art. See Harlow and Lane, Antibodies: A Laboratory Manual (Cold Spring Harbor Laboratory, New York 1988 555 612). Such immunoassays include antibody capture assays, antigen capture assays, and two-antibody sandwich assays. These assays are commonly used by those of ordinary skill in the art.

In an antibody capture assay, the antigen is attached to solid support, and labeled antibody is allowed to bind. After washing, the assay is quantitated by measuring the amount of antibody retained on the solid support. A variation of this assay is a competitive ELISA wherein the antigen is bound to the solid support and two solutions containing antibodies which bind the antigen, for example, serum from a SNV virus vaccine and the polyclonal antibodies of the present invention, are allowed to compete for binding of the antigen. The amount of polyclonal antibody bound is then measured, and a determination is made as to whether the serum contains anti SNV antigen antibodies. This competitive ELISA can be used to indicate immunity to known protective epitopes in a vaccine following vaccination.

In an antigen capture assay, the antibody is attached to a solid support, and labeled antigen is allowed to bind. The unbound proteins are removed by washing, and the assay is quantitated by measuring the amount of antigen that is bound. In a two-antibody sandwich assay, one antibody is bound to a solid support, and the antigen is allowed to bind to this first antibody. The assay is quantitated by measuring the amount of a labeled second antibody that can bind to the antigen.

These immunoassays typically rely on labeled antigens, antibodies, or secondary reagents for detection. These proteins can be labeled with radioactive compounds, enzymes, biotin, or fluorochromes. Of these, radioactive labeling can be used for almost all types of assays and with most variations. Enzyme-conjugated labels are particularly useful when radioactivity must be avoided or when quick results are needed. Biotin-coupled reagents usually are detected with labeled streptavidin. Streptavidin binds tightly and quickly to biotin and can be labeled with radioisotopes or enzymes. Fluorochromes, although requiring expensive equipment for their use, provide a very sensitive method of detection. Antibodies useful in these assays include monoclonal antibodies, polyclonal antibodies, and affinity purified polyclonal antibodies. Those of ordinary skill in the art will know of other suitable labels which may be employed in accordance with the present invention. The binding of these labels to antibodies or fragments thereof can be accomplished using standard techniques commonly known to those of ordinary skill in the art. Typical techniques are described by Kennedy, J. H., et al., 1976 (Clin. Chim Acta 70:1 31), and Schurs, A. H. W. M., et al. 1977 (Clin Chim Acta 81:1 40). Coupling techniques mentioned in the latter are the glutaraldehyde method, the periodate method, the dimaleimide method, and others, all of which are incorporated by reference herein.

The language "biological sample" is intended to include biological material, e.g. cells, tissues, or biological fluid. By "environmental sample" is meant a sample such as soil and water. Food samples include canned goods, meats, and others.

Yet another aspect of the present invention is a kit for detecting hantavirus in a biological sample. The kit includes a container holding one or more polyclonal antibodies of the present invention which binds a SNV antigen and instructions for using the antibody for the purpose of binding to SNV antigen to form an immunological complex and detecting the formation of the immunological complex such that the presence or absence of the immunological complex correlates with presence or absence of SNV in the sample. Examples of containers include multiwell plates which allow simultaneous detection of SNV in multiple samples.

Production of Pseudotyped Virions

Another use of the invention is a method for producing pseudotyped virions. One of the above-described DNA constructs is used to transfect cells, under conditions that pseudotyped virions or SNV glycoprotein is produced. The pseudotyped viruses are useful in serologic assays or delivery of gene therapies to endothelial cells targeted by hantavirus glycoproteins.

REFERENCES

1. Hooper J W, Custer D M, Thompson E, Schmaljohn C S. DNA vaccination with the hantaan virus m gene protects hamsters against three of four HFRS hantaviruses and elicits a high-titer neutralizing antibody response in rhesus monkeys. *J Virol* 2001; 75(18): 8469-8477.
2. Fuller D H, Loudon P, Schmaljohn C. Preclinical and clinical progress of particle-mediated DNA vaccines for infectious diseases. *Methods* 2006:40:86-97.
3. Custer D M, Thompson E, Schmaljohn C S, et al. Active and passive vaccination against hantavirus pulmonary syndrome with Andes virus M genome segment-based DNA vaccine. *J Virol* 2003; 77(18):9894-9905.
4. Hooper J W, Ferro A M, and Wahl-Jensen V Immune Serum Produced by DNA Vaccination Protects Hamsters Against Lethal Respiratory Challenge with Andes Virus. *Journal of Virology* 2008 82:1332-1338.
5. Hooper J W, Kamrud K I, Elgh F, et al. DNA vaccination with hantavirus M segment elicits neutralizing antibodies and protects against Seoul virus infection. *Virology* 1999; 255:269-278.
6. Hooper J W, Custer D M, Smith J., and Wahl-Jensen W. Hantaan/Andes virus DNA vaccine elicits a broadly cross-reactive neutralizing antibody response in nonhuman primates. *Virology* 2006; 347:208-216.
7. Condon C, Watkins S C, Celluzzi C M, et al. DNA-based immunization by in vivo transfection of dendritic cells. *Nat Med* 1996; 10:1122-1128.
8. Barry M A, Johnston S A. Biological features of genetic immunization. *Vaccine* 1997; 15:788-791.
9. Yoshida A, Nagata T, Uchijima M, et al. Advantage of gene gun-mediated over intramuscular inoculation of plasmid DNA vaccine in reproducible induction of specific immune responses. *Vaccine* 2000; 18:1725-1729.
10. Steele K E, Stabler K, VanderZanden L. Cutaneous DNA vaccination against Ebola virus by particle bombardment: histopathology and alteration of CD3-positive dendritic epidermal cells. *Vet Path* 2001; 38:203-215.
11. Monteiro-Riviere N A, Riviere J. The pig as a model for cutaneous pharmacology and toxicology research. In: Tumbleson M E, Schook L B (eds). *Advances in Swine in Biomedical Research*, Vol. 2, New York, Plenum Press, 1996, pp. 425-458.
12. Draize J H, Woodward G, Calvery H O. Methods for the study of irritation and toxicity of substances applied topically to the skin and mucous membranes. *J Pharmacol Exp Ther* 1944; 82, 377-390.
13. Klinman D M, Sechler J M G, Conover J, et al. Contribution of cells at the site of DNA vaccination to the generation of antigen-specific immunity and memory. *J Immunol* 1998; 160: 2388-2392.
14. Gurunathan S, Klinman D, Seder R. DNA vaccines. 2000 *Ann Rev Immunol* 2000; 7-74.
15. McElroy A K, Smith J M, Hooper J W, Schmaljohn C S. Andes virus M genome segment is not sufficient to confer the virulence associated with Andes virus in Syrian hamsters. Virology 2004; 326(1):130-139.
16. Charles River Laboratories—Arkansas Division. Assessment of the Local Skin Reactivity and Systemic Toxicity of Hantaan Virus DNA Vaccine pWRG/HTN-M(x) following PowderJect® Delivery to Syrian Hamster Skin. Final Study Report for Protocol Number JTA00001. 2005.
17 Hammerbeck, C. D., Wahl-Jensen, V., Hooper, J. W. Hantavirus. In: Vaccines for Biodefense and Emerging and Neglected Diseases (A. D. T. Barrett and L. R. Stanberry, Eds.), pp. 379-411. London: Academic Press, 2009.
18. Jonsson C. B, J. Hooper, and G. Mertz (2008). Treatment of hantavirus pulmonary syndrome. Antiviral Res. Antiviral Res. 78:162-169.
23. Schmaljohn, C. S., and J. W. Hooper (Jan. 27, 2000). U.S. patent application Ser. No. 09/491,974; publication number 2002/0114818, published Aug. 22, 2002, entitled "DNA vaccines against hantavirus infections"
24. Hooper, J. W., C. S. Schmaljohn and M. Custer. "Extraneous DNA sequence that facilitates hantavirus gene expression. U.S. Pat. No. 7,217,812. Issued May 15, 2007.
25. Hooper, J. W., C. S. Schmaljohn. DNA Vaccines Against Hantavirus. Korean Patent 660040. Issued December 2006, and European Patent EPO 00908388.2, issued January 2007
26. Hooper, J. W. Puumala virus full-length M segment-based DNA vaccines. U.S. application Ser. No. 12/449, 504, filed Aug. 11, 2009; PCT/US2008/001847, published Jan. 15, 2009

The contents of all cited references (including literature references, issued patents, published patent applications, and co-pending patent applications) cited throughout this application are hereby expressly incorporated by reference.

What is claimed is:

1. An immunizing composition capable of inducing a high titer neutralizing antibody response against Sin Nombre Virus Gc and Gn glycoproteins, which composition comprises
   (i) a recombinant plasmid DNA capable of expressing the SNV Gc and Gn glycoproteins,
      wherein the plasmid DNA contains a modified codon optimized M gene selected
      from the group consisting of SEQ ID NO:1, 2 or 3, operably linked to a promoter
      that results in expression of the Gc and Gn glycoproteins, and
   (ii) a pharmacologically acceptable carrier.

2. The immunizing composition of claim 1, wherein the pharmacologically acceptable carrier is selected from the group consisting of PBS, water, saline, TRIS-EDTA, and mixtures of these.

3. The immunizing composition of claim 1, wherein the amount of SNV plasmid DNA in the composition is between about 5 micrograms and about 5 milligrams.

4. The immunizing composition of claim 1, which further comprises the additional component of an Andes M gene sequence, operably linked to a promoter that results in expression of the Andes M gene sequence.

5. The immunizing composition of claim 4, wherein the Andes M gene sequence is SEQ ID NO:10.

6. The immunizing composition of claim 1, which further comprises the additional component of a Puumala M gene sequence, or a Hantaan M gene sequence, or a Seoul M gene sequence, or a combination of these, wherein each additional component is operably linked to a promoter that results in expression of the respective M gene sequence.

7. The immunizing composition of claim 6, wherein Puumala M gene sequence is SEQ ID NO:11, the Hantaan M gene sequence is SEQ ID NO:12, and/or the Seoul M gene sequence is SEQ ID NO:13.

8. The immunizing composition of claim 4, which further comprises the additional component of a Puumala M gene sequence, or a Hantaan M gene sequence, or a Seoul M gene sequence, or a combination of these, wherein each additional component is operably linked to a promoter that results in expression of the respective M gene sequence.

9. The immunizing composition of claim 8, wherein the Andes M gene sequence is SEQ ID NO:10, the Puumala M gene sequence is SEQ ID NO:11, the Hantaan M gene sequence is SEQ ID NO:12, and/or the Seoul M gene sequence is SEQ ID NO:13.

* * * * *

SEQUENCE LISTING

```
<160> NUMBER OF SEQ ID NOS: 22

<210> SEQ ID NO 1
<211> LENGTH: 7938
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
gggggggggg ggcgctgagg tctgcctcgt gaagaaggtg ttgctgactc ataccaggcc      60
tgaatcgccc catcatccag ccagaaagtg agggagccac ggttgatgag agctttgttg     120
taggtggacc agttggtgat tttgaacttt tgctttgcca cggaacggtc tgcgttgtcg     180
```

-continued

| | |
|---|---|
| ggaagatgcg tgatctgatc cttcaactca gcaaaagttc gatttattca acaaagccgc | 240 |
| cgtcccgtca agtcagcgta atgctctgcc agtgttacaa ccaattaacc aattctgatt | 300 |
| agaaaaactc atcgagcatc aaatgaaact gcaatttatt catatcagga ttatcaatac | 360 |
| catattttg aaaaagccgt ttctgtaatg aaggagaaaa ctcaccgagg cagttccata | 420 |
| ggatggcaag atcctggtat cggtctgcga ttccgactcg tccaacatca atacaaccta | 480 |
| ttaatttccc ctcgtcaaaa ataaggttat caagtgagaa atcaccatga gtgacgactg | 540 |
| aatccggtga gaatggcaaa agcttatgca tttctttcca gacttgttca acaggccagc | 600 |
| cattacgctc gtcatcaaaa tcactcgcat caaccaaacc gttattcatt cgtgattgcg | 660 |
| cctgagcgag acgaaatacg cgatcgctgt taaaaggaca attacaaaca ggaatcgaat | 720 |
| gcaaccggcg caggaacact gccagcgcat caacaatatt ttcacctgaa tcaggatatt | 780 |
| cttctaatac ctggaatgct gtttttcccgg ggatcgcagt ggtgagtaac catgcatcat | 840 |
| caggagtacg gataaaatgc ttgatggtcg aagaggcat aaattccgtc agccagttta | 900 |
| gtctgaccat ctcatctgta acatcattgg caacgctacc tttgccatgt ttcagaaaca | 960 |
| actctggcgc atcgggcttc ccatacaatc gatagattgt cgcacctgat tgcccgacat | 1020 |
| tatcgcgagc ccatttatac ccatataaat cagcatccat gttggaattt aatcgcggcc | 1080 |
| tcgagcaaga cgtttcccgt tgaatatggc tcataacacc ccttgtatta ctgtttatgt | 1140 |
| aagcagacag ttttattgtt catgatgata tatttttatc ttgtgcaatg taacatcaga | 1200 |
| gattttgaga cacaacgtgg ctttccccc ccccggca tgcctgcagg tcgacaatat | 1260 |
| tggctattgg ccattgcata cgttgtatct atatcataat atgtacattt atattggctc | 1320 |
| atgtccaata tgaccgccat gttgacattg attattgact agttattaat agtaatcaat | 1380 |
| tacggggtca ttagttcata gcccatatat ggagttccgc gttacataac ttacggtaaa | 1440 |
| tggcccgcct ggctgaccgc ccaacgaccc ccgcccattg acgtcaataa tgacgtatgt | 1500 |
| tcccatagta acgccaatag ggactttcca ttgacgtcaa tgggtggagt atttacggta | 1560 |
| aactgcccac ttggcagtac atcaagtgta tcatatgcca agtccgcccc ctattgacgt | 1620 |
| caatgacggt aaatggcccg cctggcatta tgcccagtac atgaccttac gggactttcc | 1680 |
| tacttggcag tacatctacg tattagtcat cgctattacc atggtgatgc ggttttggca | 1740 |
| gtacaccaat gggcgtggat agcggtttga ctcacgggga tttccaagtc tccaccccat | 1800 |
| tgacgtcaat gggagtttgt tttggcacca aaatcaacgg gactttccaa aatgtcgtaa | 1860 |
| taaccccgcc ccgttgacgc aaatgggcgg taggcgtgta cggtgggagg tctatataag | 1920 |
| cagagctcgt ttagtgaacc gtcagatcgc ctggagacgc catccacgct gttttgacct | 1980 |
| ccatagaaga caccgggacc gatccagcct ccgcggccgg gaacggtgca ttggaacgcg | 2040 |
| gattccccgt gccaagagtg acgtaagtac cgcctataga ctctataggc acaccccttt | 2100 |
| ggctcttatg catgctatac tgttttggc ttggggccta tacaccccg cttccttatg | 2160 |
| ctataggtga tggtatagct tagcctatag gtgtgggtta ttgaccatta ttgaccactc | 2220 |
| ccctattggt gacgatactt tccattacta atccataaca tggctctttg ccacaactat | 2280 |
| ctctattggc tatatgccaa tactctgtcc ttcagagact gacacggact ctgtattttt | 2340 |
| acaggatggg gtcccatttta ttatttacaa attcacatat acaacaacgc cgtccccgt | 2400 |
| gcccgcagtt tttattaaac atagcgtggg atctccacgc gaatctcggg tacgtgttcc | 2460 |
| ggacatgggc tcttctccgg tagcggcgga gcttccacat ccgagccctg gtcccatgcc | 2520 |
| tccagcggct catggtcgct cggcagctcc ttgctcctaa cagtggaggc cagacttagg | 2580 |

```
cacagcacaa tgcccaccac caccagtgtg ccgcacaagg ccgtggcggt agggtatgtg    2640
tctgaaaatg agctcggaga ttgggctcgc accgctgacg cagatggaag acttaaggca    2700
gcggcagaag aagatgcagg cagctgagtt gttgtattct gataagagtc agaggtaact    2760
cccgttgcgg tgctgttaac ggtggagggc agtgtagtct gagcagtact cgttgctgcc    2820
gcgcgcgcca ccagacataa tagctgacag actaacagac tgttcctttc catgggtctt    2880
ttctgcagtc accgtccaag cttgcggccg cggatctgca ggaattcggc acgagagtag    2940
tagactccgc acgaagaagc aaacactgaa taaaggatat acagaatggt gggctgggtg    3000
tgcatcttcc tggtggtgct gaccaccgcc acagccggcc tgacccggaa cctgtacgag    3060
ctgaagatcg agtgccccca caccgtgggc ctgggccagg gctacgtgac cggcagcgtg    3120
gagacaaccc ccatcctgct gacccaggtg gccgacctga agattgagag cagctgcaac    3180
ttcgacctgc acgtgcccgc caccaccacc cagaaataca accaggtgga ctggaccaag    3240
aagagcagca ccaccgagag caccaacgcc ggagccacca ccttcgaggc caagaccaaa    3300
gaagtgaacc tgaagggcac ctgcaacatc ccccccacca catttgaggc cgcctacaag    3360
agcagaaaga ccgtgatctg ctacgacctg gcctgcaacc agacccactg cctgcccacc    3420
gtgcacctga tcgcccccgt gcagacctgc atgagcgtgc ggagctgcat gatcggcctg    3480
ctgtccagcc ggatccaggt gatctacgag aaaacctact gcgtgaccgg ccagctgatc    3540
gagggcctgt gcttcatccc cacccacaca atcgccctga cccagcccgg ccacacctac    3600
gacaccatga ccctgcccgt gacctgcttt ctggtggcca agaagctggg cacccagctg    3660
aagctggccg tggagctgga aaagctgatc accggcgtga gctgcaccga aacagcttc    3720 cagggctact acatctgctt catcggcaag cacagcgagc ccctgttcgt gcccaccatg    3780
gaagattaca aagcgccga ctgttcacc cggatggtgc tgaaccccag gggcgaggac    3840
cacgaccccg accagaacgg ccagggcctg atgcggatcg ccggaccgt gaccgccaag    3900 gtgcccagca ccgagacaac cgaaaccatg cagggcattg ccttcgccgg agccccatg    3960 tacagcagct tcagcaccct ggtgcggaag gccgaccccg agtacgtgtt cagccccggc    4020
atcattgccg agagcaacca cagcgtgtgc gacaagaaaa ccgtgcccct gacctggacc    4080
ggcttcctgg ccgtgagcgg cgagatcgag cggatcaccg gctgcaccgt gttctgcacc    4140
ctggccggac ctggcgccag ctgcgaggcc tacagcgaga caggcatctt caacatcagc    4200
agccccacct gcctggtgaa caaggtgcag aagttccggg gcagcgagca gcggatcaac    4260
ttcatgtgcc agcgggtgga ccaggacgtg gtggtgtact gcaacggcca gaaaaaagtg    4320
atcctgacca agaccctggt gatcggccag tgcatctaca ccttcaccag cctgttcagc    4380
ctgatccctg gcgtggctca tagcctggca gtcgaactgt gcgtgcctgg cctgcacgga    4440
tgggccacca ccgccctgct gatcaccttc tgcttcggct ggctgctgat ccccacagtg    4500
accctgatca tcctgaagat cctgcggctg ctgaccttca gctgcagcca ctacagcacc    4560
gagtccaagt tcaaagtgat tctggaacgc gtgaaggtgg agtaccagaa aaccatgggc    4620
agcatggtgt gcgacatctg ccaccacgag tgcgagacag ccaaagagct ggaaacccac    4680
aagaagagct gccccgaggg ccagtgcccc tactgcatga ccatcacaga gagcaccgag    4740
agcgccctgc aggcccactt cagcatctgc aagctgacca accggttcca ggaaaacctg    4800
aagaagagct gaagcggcc cgaagtgcgg aagggctgct accggaccct gggcgtgttc    4860
cggtacaaga gccggtgcta tgtgggcctg gtgtggggca ttctgctgac cacagagctg    4920
```

```
atcatctggg ccgccagcgc cgacaccccc ctgatggaaa gcgggtggag cgacaccgct    4980
catggcgtgg gaatcgtgcc catgaaaacc gacctggaac tggacttcgc cctggccagc    5040
agcagcagct acagctaccg gcggaagctg gtgaaccccg ccaaccagga agagacactg    5100
cccttccact tccaactgga caagcaggtg gtgcacgccg agatccagaa cctgggccac    5160
tggatggacg gcaccttcaa tatcaagacc gccttccact gctacggcga gtgcaagaag    5220
tacgcctacc cctggcagac cgccaagtgc ttcttcgaga aggactacca gtacgagaca    5280
agctggggct gcaaccccccc cgactgtcct ggcgtgggca ccggctgtac cgcctgcggc    5340
gtgtacctgg acaagctgcg gagcgtgggc aaggcctaca gatcgtgtc cctgaagtac    5400 acccggaaag tgtgcatcca gctgggcaca gagcagacat gcaagcacat cgacgtgaac    5460
gattgcctgg tgaccccag cgtgaaagtc tgtatgattg caccatcag caagctgcag    5520 cccggcgata ccctgctgtt cctgggcccc ctggaacagg gcggcatcat tctgaagcag    5580
tggtgtacca cctcctgcgt gttcggcgac cccggcgaca tcatgagcac cacctccggc    5640
atgcggtgcc ccgagcacac cggcagcttc cggaagattt gtggcttcgc caccacccct    5700
acctgcgagt accagggcaa caccgtgtcc ggcttccagc ggatgatggc caccgggat    5760 agcttccaga gcttcaacgt gaccgagccc cacatcacca gcaaccggct ggaatggatc    5820
gaccccgaca gcagcatcaa ggaccacatc aacatggtgc tcaatcggga cgtgagcttc    5880
caggacctga gcgacaaccc ctgcaaggtg gacctgcaca cccagagcat cgacggcgcc    5940
tggggcagcg gcgtgggctt cacactggtg tgcacagtgg gcctgaccga gtgcgccaac    6000
ttcatcacct ccatcaaggc ctgcgacagc gccatgtgct acggcgccac cgtgaccaac    6060
ctgctgcggg gctccaacac agtgaaggtg gtgggcaagg gcggccacag cggcagcctg    6120
tttaagtgct gccacgacac cgactgcacc gaggaaggcc tggccgccag ccccccctcac    6180 ctggacagag tgaccggcta caaccagatc gacagcgaca aggtgtacga cgatggcgcc    6240 cctcccctgca ccatcaagtg ctggttcacc aagagcggcg agtggctgct gggcatcctg    6300
aacggcaact gggtcgtcgt ggccgtgctg atcgtgatcc tgatcctgtc tatcctgctg    6360
ttcagcttct tctgccccgt gcggaaccgg aagaacaagg ccaactagca acatatatg    6420 taagtaaggg tatgatcata ttatatcatt atgcgtatac tcttatatct ataatatcta    6480
tgtatcctta tactctaact attttatatta atttttactt ttatacaagt attaactaac    6540
ccattaccag ctaaaaaaaa caaacccctta acacctatat aatcccattt gcttattacg    6600
aggcttttgt tcctgcggag tctactacta agatctacgt atgatcagcc tcgactgtgc    6660
cttctagttg ccagccatct gttgtttgcc cctcccccgt gccttccttg accctggaag    6720
gtgccactcc cactgtcctt tcctaataaa atgaggaaat tgcatcgcat tgtctgagta    6780
ggtgtcattc tattctgggg ggtggggtgg gcaggacag caaggggag gattgggaag    6840 acaatagcag gcatgctggg gatgcggtgg gctctatggc ttctgaggcg gaaagaacca    6900 gctgggctc gacagctcga ctctagaatt gcttcctcgc tcactgactc gctgcgctcg    6960
gtcgttcggc tgcggcgagc ggtatcagct cactcaaagg cggtaatacg gttatccaca    7020
gaatcagggg ataacgcagg aaagaacatg tgagcaaaag gccagcaaaa ggccaggaac    7080
cgtaaaaagg ccgcgttgct ggcgtttttc cataggctcc gcccccctga cgagcatcac    7140
aaaaatcgac gctcaagtca gaggtggcga aacccgacag gactataaag ataccaggcg    7200
tttccccctg gaagctccct cgtgcgctct cctgttccga ccctgccgct taccggatac    7260
ctgtccgcct ttctcccttc gggaagcgtg gcgctttctc atagctcacg ctgtaggtat    7320
```

```
ctcagttcgg tgtaggtcgt tcgctccaag ctgggctgtg tgcacgaacc ccccgttcag    7380
cccgaccgct gcgccttatc cggtaactat cgtcttgagt ccaacccggt aagcacgac    7440 ttatcgccac tggcagcagc cactggtaac aggattagca gagcgaggta tgtaggcggt    7500
gctacagagt tcttgaagtg gtggcctaac tacggctaca ctagaagaac agtatttggt    7560
atctgcgctc tgctgaagcc agttaccttc ggaaaagag ttggtagctc ttgatccggc    7620
aaacaaacca ccgctggtag cggtggtttt tttgtttgca agcagcagat tacgcgcaga    7680
aaaaaaggat ctcaagaaga tcctttgatc ttttctacgg ggtctgacgc tcagtggaac    7740
gaaaactcac gttaagggat tttggtcatg agattatcaa aaaggatctt cacctagatc    7800
cttttaaatt aaaaatgaag ttttaaatca atctaaagta tatatgagta aacttggtct    7860
gacagttacc aatgcttaat cagtgaggca cctatctcag cgatctgtct atttcgttca    7920
tccatagttg cctgactc                                                 7938

<210> SEQ ID NO 2
<211> LENGTH: 3733
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
gcggccgcgg atctgcagga attcggcacg agagtagtag actccgcacg aagaagcaaa      60
cactgaataa aggatataca gaatggtggg ctgggtgtgc atcttcctgg tggtgctgac     120
caccgccaca gccggcctga cccggaacct gtacgagctg aagatcgagt gcccccacac     180
cgtgggcctg ggccagggct acgtgaccgg cagcgtggac acaaccccca tcctgctgac     240
ccaggtggcc gacctgaaga ttgagagcag ctgcaacttc gacctgcacg tgcccgccac     300 caccaccccag aaatacaacc aggtggactg gaccaagaag agcagcacca ccgagagcac     360
caacgccgga gccaccacct tcgaggccaa gaccaaagaa gtgaacctga agggcacctg     420
caacatcccc cccaccacat tgaggccgc ctacaagagc agaaagaccg tgatctgcta     480
cgacctggcc tgcaaccaga cccactgcct gccaccgtg cacctgatcg ccccgtgca     540 gacctgcatg agcgtgcgga gctgcatgat cggcctgctg ccagccggga tccaggtgat     600
ctacgagaaa acctactgcg tgaccggcca gctgatcgag ggcctgtgct tcatccccac     660
ccacacaatc gccctgaccc agcccggcca cacctacgac accatgaccc tgcccgtgac     720
ctgctttctg gtggccaaga agctgggcac ccagctgaag ctggccgtgg agctggaaaa     780
gctgatcacc ggcgtgagct gcaccgagaa cagcttccag ggctactaca tctgcttcat     840
cggcaagcac agcgagcccc tgttcgtgcc caccatggaa gattacagaa gcgccgagct     900
gttcacccgg atggtgctga cccagggggc gaggaccac gacccgacc agaacggcca     960 gggcctgatg cggatcgccg acccgtgac cgccaaggtg cccagcaccg agacaaccga    1020
aaccatgcag gcattgcct tcgccggagc ccccatgtac agcagcttca gcaccctggt    1080
gcggaaggcc gacccccgagt acgtgttcag ccccggcatc attgccgaga gcaaccacag    1140
cgtgtgcgac aagaaaaccg tgccctgac ctggaccggc ttcctggccg tgagcggcga    1200
gatcgagcgg atcaccggct gcaccgtgtt ctgcaccctg gccggacctg cgccagctg    1260 cgaggcctac agcgagacag gcatcttcaa catcagcagc cccacctgcc tggtgaacaa    1320
ggtgcagaag ttccggggca gcgagcagcg gatcaacttc atgtgccagc gggtggacca    1380
```

| | |
|---|---|
| ggacgtggtg gtgtactgca acggccagaa aaaagtgatc ctgaccaaga ccctggtgat | 1440 |
| cggccagtgc atctacacct tcaccagcct gttcagcctg atccctggcg tggctcatag | 1500 |
| cctggcagtc gaactgtgcg tgcctggcct gcacggatgg ccaccaccg ccctgctgat | 1560 |
| caccttctgc ttcggctggc tgctgatccc cacagtgacc ctgatcatcc tgaagatcct | 1620 |
| gcggctgctg accttcagct gcagccacta cagcaccgag tccaagttca agtgattct | 1680 |
| ggaacgcgtg aaggtggagt accagaaaac catgggcagc atggtgtgcg acatctgcca | 1740 |
| ccacgagtgc gagacagcca aagagctgga aacccacaag aagagctgcc ccgagggcca | 1800 |
| gtgcccctac tgcatgacca tcacagagag caccgagagc ccctgcagg cccacttcag | 1860 |
| catctgcaag ctgaccaacc ggttccagga aaacctgaag aagagcctga gcggcccga | 1920 |
| agtgcggaag ggctgctacc ggaccctggg cgtgttccgg tacaagagcc ggtgctatgt | 1980 |
| gggcctggtg tggggcattc tgctgaccac agagctgatc atctgggccg ccagcgccga | 2040 |
| cacccccctg atggaaagcg gtggagcga caccgctcat ggcgtgggaa tcgtgcccat | 2100 |
| gaaaaccgac ctggaactgg acttcgccct ggccagcagc agcagctaca gctaccggcg | 2160 |
| gaagctggtg aaccccgcca accaggaaga cactgccc ttccacttcc aactggacaa | 2220 |
| gcaggtggtg cacgccgaga tccagaacct gggccactgg atggacggca ccttcaatat | 2280 |
| caagaccgcc ttccactgct acggcgagtg caagaagtac gcctacccct ggcagaccgc | 2340 |
| caagtgcttc ttcgagaagg actaccagta cgagacaagc tggggctgca ccccccga | 2400 |
| ctgtcctggc gtgggcaccg gctgtaccgc ctgcggcgtg tacctggaca gctgcggag | 2460 |
| cgtgggcaag gcctacaaga tcgtgtccct gaagtacacc cggaaagtgt gcatccagct | 2520 |
| gggcacagag cagacatgca agcacatcga cgtgaacgat tgcctggtga cccccagcgt | 2580 |
| gaaagtctgt atgattggca ccatcagcaa gctgcagccc ggcgatacc tgctgttcct | 2640 |
| gggccccctg aacagggcg gcatcattct gaagcagtgg tgtaccacct cctgcgtgtt | 2700 |
| cggcgacccc ggcgacatca tgagcaccac ctccggcatg cggtgccccg agcacaccgg | 2760 |
| cagcttccgg aagatttgtg gcttcgccac caccctacc tgcgagtacc agggcaacac | 2820 |
| cgtgtccggc ttcagcgga tgatggccac ccgggatagc ttccagagct caacgtgac | 2880 |
| cgagccccac atcaccagca accggctgga atggatcgac cccgacagca gcatcaagga | 2940 |
| ccacatcaac atggtgctca atcgggacgt gagcttccag gacctgagcg acaacccctg | 3000 |
| caaggtggac ctgcacaccc agagcatcga cggcgcctgg ggcagcggcg tgggcttcac | 3060 |
| actggtgtgc acagtgggcc tgaccgagtg cgccaacttc atcacctcca tcaaggcctg | 3120 |
| cgacagcgcc atgtgctacg cgccaccgt gaccaacctg ctgcggggct ccaacacagt | 3180 |
| gaaggtggtg ggcaagggcg ccacagcgg cagcctgttt aagtgctgcc acgacaccga | 3240 |
| ctgcaccgag gaaggcctgg ccgccagccc cctcacctg gacagagtga ccggctacaa | 3300 |
| ccagatcgac agcgacaagg tgtacgacga tggcgcccct ccctgcacca tcaagtgctg | 3360 |
| gttcaccaag agcggcgagt ggctgctggg catcctgaac ggcaactggg tcgtcgtggc | 3420 |
| cgtgctgatc gtgatcctga tcctgtctat cctgctgttc agcttcttct gccccgtgcg | 3480 |
| gaaccggaag aacaaggcca actagcaaac atatatgtaa gtaagggtat gatcatatta | 3540 |
| tatcattatg cgtatactct tatatctata atatctatgt atccttatac tctaactatt | 3600 |
| tatattaatt tttacttta tacaagtatt aactaaccca ttaccagcta aaaaaaacaa | 3660 |
| acccttaaca cctatataat cccatttgct tattacgagg cttttgttcc tgcggagtct | 3720 |

| | |
|---|---|
| actactaaga tct | 3733 |

<210> SEQ ID NO 3
<211> LENGTH: 3423
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 3

| | |
|---|---|
| atggtgggct gggtgtgcat cttcctggtg gtgctgacca ccgccacagc cggcctgacc | 60 |
| cggaacctgt acgagctgaa gatcgagtgc ccccacaccg tgggcctggg ccagggctac | 120 |
| gtgaccggca gcgtggagac aaccccatc ctgctgaccc aggtggccga cctgaagatt | 180 |
| gagagcagct gcaacttcga cctgcacgtg ccgccacca ccacccagaa atacaaccag | 240 |
| gtggactgga ccaagaagag cagcaccacc gagagcacca cgccggagc caccaccttc | 300 |
| gaggccaaga ccaaagaagt gaacctgaag gcacctgca acatcccccc caccacattt | 360 |
| gaggccgcct acaagagcag aaagaccgtg atctgctacg acctggcctg caaccagacc | 420 |
| cactgcctgc caccgtgca cctgatcgcc ccgtgcaga cctgcatgag cgtgcggagc | 480 |
| tgcatgatcg gcctgctgtc cagccggatc caggtgatct acgagaaaac ctactgcgtg | 540 |
| accggccagc tgatcgaggg cctgtgcttc atccccaccc acacaatcgc cctgacccag | 600 |
| cccggccaca cctacgacac catgaccctg cccgtgacct gctttctggt ggccaagaag | 660 |
| ctgggcaccc agctgaagct ggccgtggag ctggaaaagc tgatcaccgg cgtgagctgc | 720 |
| accgagaaca gcttccaggg ctactacatc tgcttcatcg gcaagcacag cgagcccctg | 780 |
| ttcgtgccca ccatggaaga ttacagaagc gccgagctgt tcacccggat ggtgctgaac | 840 |
| cccagggggcg aggaccacga cccccgaccag aacggccagg gcctgatgcg gatcgccgga | 900 |
| cccgtgaccg ccaaggtgcc cagcaccgag acaaccgaaa ccatgcaggg cattgccttc | 960 |
| gccggagccc ccatgtacag cagcttcagc accctggtgc ggaaggccga ccccgagtac | 1020 |
| gtgttcagcc ccggcatcat tgccgagagc aaccacagcg tgtgcgacaa gaaaaccgtg | 1080 |
| cccctgacct ggaccggctt cctggccgtg agcggcgaga tcgagcggat caccggctgc | 1140 |
| accgtgttct gcaccctggc cggacctggc gccagctgcg aggcctacag cgagacaggc | 1200 |
| atcttcaaca tcagcagccc cacctgcctg gtgaacaagg tgcagaagtt ccggggcagc | 1260 |
| gagcagcgga tcaacttcat gtgccagcgg gtggaccagg acgtggtggt gtactgcaac | 1320 |
| ggccagaaaa aagtgatcct gaccaagacc ctggtgatcg ccagtgcat ctacaccttc | 1380 |
| accagcctgt tcagcctgat ccctggcgtg gctcatagcc tggcagtcga actgtgcgtg | 1440 |
| cctggcctgc acgatgggc caccaccgcc tgctgatca ccttctgctt cggctggctg | 1500 |
| ctgatcccca cagtgaccct gatcatcctg aagatcctgc ggctgctgac cttcagctgc | 1560 |
| agccactaca gcaccgagtc caagttcaaa gtgattctgg aacgcgtgaa ggtggagtac | 1620 |
| cagaaaacca tgggcagcat ggtgtgcgac atctgccacc acgagtgcga cagccaaaa | 1680 |
| gagctggaaa cccacaagaa gagctgcccc gagggccagt gcccctactg catgaccatc | 1740 |
| acagagagca ccgagagcgc cctgcaggcc cacttcagca tctgcaagct gaccaaccgg | 1800 |
| ttccaggaaa acctgaagaa gagcctgaag cggcccgaag tgcggaaggg ctgctaccgg | 1860 |
| accctgggcg tgttccggta caagagccgg tgctatgtgg gcctggtgtg gggcattctg | 1920 |
| ctgaccacag agctgatcat ctgggccgcc agcgccgaca cccccctgat ggaaagcggg | 1980 |

```
tggagcgaca ccgctcatgg cgtgggaatc gtgcccatga aaaccgacct ggaactggac    2040
ttcgccctgg ccagcagcag cagctacagc taccggcgga agctggtgaa ccccgccaac    2100
caggaagaga cactgcccct ccacttccaa ctggacaagc aggtggtgca cgccgagatc    2160
cagaacctgg ccactggat ggacggcacc ttcaatatca agaccgcctt ccactgctac    2220
ggcgagtgca agaagtacgc ctaccctgg cagaccgcca agtgcttctt cgagaaggac    2280
taccagtacg agacaagctg gggctgcaac ccccccgact gtcctggcgt gggcaccggc    2340
tgtaccgcct gcggcgtgta cctggacaag ctgcggagcg tgggcaaggc ctacaagatc    2400
gtgtccctga agtacacccg gaaagtgtgc atccagctgg gcacagagca gacatgcaag    2460
cacatcgacg tgaacgattg cctggtgacc cccagcgtga agtctgtat gattggcacc    2520 atcagcaagc tgcagcccgg cgataccctg ctgttcctgg ccccctgga acagggcggc    2580 atcattctga agcagtggtg taccacctcc tgcgtgttcg gcgaccccgg cgacatcatg    2640
agcaccacct ccggcatgcg cgtgccccgag cacaccggca gcttccggaa gatttgtggc    2700
ttcgccacca cccctacctg cgagtaccag ggcaacaccg tgtccggctt ccagcggatg    2760
atggccaccc gggatagctt ccagagcttc aacgtgaccg agccccacat caccagcaac    2820
cggctggaat ggatcgaccc cgacagcagc atcaaggacc acatcaacat ggtgctcaat    2880
cgggacgtga gcttccagga cctgagcgac aaccccctgca aggtggacct gcacacccag    2940
agcatcgacg cgcctggggg cagcggcgtg ggcttcacac tggtgtgcac agtgggcctg    3000
accgagtgcg ccaacttcat cacctccatc aaggcctgcg acagcgccat gtgctacggc    3060
gccaccgtga ccaacctgct gcggggctcc aacacagtga aggtggtggg caagggcggc    3120
cacagcggca gcctgtttaa gtgctgccac gacaccgact gcaccgagga aggcctggcc    3180
gccagccccc ctcacctgga cagagtgacc ggctacaacc agatcgacag cgacaaggtg    3240
tacgacgatg gcgcccctcc ctgcaccatc aagtgctggt tcaccaagag cggcgagtgg    3300
ctgctgggca tcctgaacgg caactgggtc gtcgtggccg tgctgatcgt gatcctgatc    3360
ctgtctatcc tgctgttcag cttcttctgc cccgtgcgga accggaagaa caaggccaac    3420
tag                                                                  3423
```

<210> SEQ ID NO 4  
<211> LENGTH: 1140  
<212> TYPE: PRT  
<213> ORGANISM: Artificial Sequence  
<220> FEATURE:  
<223> OTHER INFORMATION: Description of Artificial Sequence: Synthetic polypeptide

<400> SEQUENCE: 4

```
Met Val Gly Trp Val Cys Ile Phe Leu Val Val Leu Thr Thr Ala Thr
1               5                   10                  15

Ala Gly Leu Thr Arg Asn Leu Tyr Glu Leu Lys Ile Glu Cys Pro His
                20                  25                  30

Thr Val Gly Leu Gly Gln Gly Tyr Val Thr Gly Ser Val Glu Thr Thr
            35                  40                  45

Pro Ile Leu Leu Thr Gln Val Ala Asp Leu Lys Ile Glu Ser Ser Cys
        50                  55                  60

Asn Phe Asp Leu His Val Pro Ala Thr Thr Thr Gln Lys Tyr Asn Gln
65                  70                  75                  80

Val Asp Trp Thr Lys Lys Ser Ser Thr Thr Glu Ser Thr Asn Ala Gly
                85                  90                  95
```

-continued

```
Ala Thr Thr Phe Glu Ala Lys Thr Lys Glu Val Asn Leu Lys Gly Thr
                100                 105                 110
Cys Asn Ile Pro Pro Thr Thr Phe Glu Ala Ala Tyr Lys Ser Arg Lys
            115                 120                 125
Thr Val Ile Cys Tyr Asp Leu Ala Cys Asn Gln Thr His Cys Leu Pro
        130                 135                 140
Thr Val His Leu Ile Ala Pro Val Gln Thr Cys Met Ser Val Arg Ser
145                 150                 155                 160
Cys Met Ile Gly Leu Leu Ser Ser Arg Ile Gln Val Ile Tyr Glu Lys
                165                 170                 175
Thr Tyr Cys Val Thr Gly Gln Leu Ile Glu Gly Leu Cys Phe Ile Pro
            180                 185                 190
Thr His Thr Ile Ala Leu Thr Gln Pro Gly His Thr Tyr Asp Thr Met
        195                 200                 205
Thr Leu Pro Val Thr Cys Phe Leu Val Ala Lys Lys Leu Gly Thr Gln
210                 215                 220
Leu Lys Leu Ala Val Glu Leu Glu Lys Leu Ile Thr Gly Val Ser Cys
225                 230                 235                 240
Thr Glu Asn Ser Phe Gln Gly Tyr Tyr Ile Cys Phe Ile Gly Lys His
                245                 250                 255
Ser Glu Pro Leu Phe Val Pro Thr Met Glu Asp Tyr Arg Ser Ala Glu
            260                 265                 270
Leu Phe Thr Arg Met Val Leu Asn Pro Arg Gly Glu Asp His Asp Pro
        275                 280                 285
Asp Gln Asn Gly Gln Gly Leu Met Arg Ile Ala Gly Pro Val Thr Ala
290                 295                 300
Lys Val Pro Ser Thr Glu Thr Thr Glu Thr Met Gln Gly Ile Ala Phe
305                 310                 315                 320
Ala Gly Ala Pro Met Tyr Ser Ser Phe Ser Thr Leu Val Arg Lys Ala
                325                 330                 335
Asp Pro Glu Tyr Val Phe Ser Pro Gly Ile Ile Ala Glu Ser Asn His
            340                 345                 350
Ser Val Cys Asp Lys Lys Thr Val Pro Leu Thr Trp Thr Gly Phe Leu
        355                 360                 365
Ala Val Ser Gly Glu Ile Glu Arg Ile Thr Gly Cys Thr Val Phe Cys
370                 375                 380
Thr Leu Ala Gly Pro Gly Ala Ser Cys Glu Ala Tyr Ser Glu Thr Gly
385                 390                 395                 400
Ile Phe Asn Ile Ser Ser Pro Thr Cys Leu Val Asn Lys Val Gln Lys
                405                 410                 415
Phe Arg Gly Ser Glu Gln Arg Ile Asn Phe Met Cys Gln Arg Val Asp
            420                 425                 430
Gln Asp Val Val Val Tyr Cys Asn Gly Gln Lys Lys Val Ile Leu Thr
        435                 440                 445
Lys Thr Leu Val Ile Gly Gln Cys Ile Tyr Thr Phe Thr Ser Leu Phe
450                 455                 460
Ser Leu Ile Pro Gly Val Ala His Ser Leu Ala Val Glu Leu Cys Val
465                 470                 475                 480
Pro Gly Leu His Gly Trp Ala Thr Thr Ala Leu Leu Ile Thr Phe Cys
                485                 490                 495
Phe Gly Trp Leu Leu Ile Pro Thr Val Thr Leu Ile Ile Leu Lys Ile
            500                 505                 510
Leu Arg Leu Leu Thr Phe Ser Cys Ser His Tyr Ser Thr Glu Ser Lys
```

```
                515                 520                 525
    Phe Lys Val Ile Leu Glu Arg Val Lys Val Glu Tyr Gln Lys Thr Met
    530                 535                 540
    Gly Ser Met Val Cys Asp Ile Cys His His Glu Cys Glu Thr Ala Lys
545                 550                 555                 560
    Glu Leu Glu Thr His Lys Lys Ser Cys Pro Glu Gly Gln Cys Pro Tyr
                    565                 570                 575
    Cys Met Thr Ile Thr Glu Ser Thr Glu Ser Ala Leu Gln Ala His Phe
                580                 585                 590
    Ser Ile Cys Lys Leu Thr Asn Arg Phe Gln Glu Asn Leu Lys Lys Ser
                    595                 600                 605
    Leu Lys Arg Pro Glu Val Arg Lys Gly Cys Tyr Arg Thr Leu Gly Val
                610                 615                 620
    Phe Arg Tyr Lys Ser Arg Cys Tyr Val Gly Leu Val Trp Gly Ile Leu
625                 630                 635                 640
    Leu Thr Thr Glu Leu Ile Ile Trp Ala Ala Ser Ala Asp Thr Pro Leu
                    645                 650                 655
    Met Glu Ser Gly Trp Ser Asp Thr Ala His Gly Val Gly Ile Val Pro
                660                 665                 670
    Met Lys Thr Asp Leu Glu Leu Asp Phe Ala Leu Ala Ser Ser Ser
                    675                 680                 685
    Tyr Ser Tyr Arg Arg Lys Leu Val Asn Pro Ala Asn Gln Glu Thr
                690                 695                 700
    Leu Pro Phe His Phe Gln Leu Asp Lys Gln Val Val His Ala Glu Ile
705                 710                 715                 720
    Gln Asn Leu Gly His Trp Met Asp Gly Thr Phe Asn Ile Lys Thr Ala
                    725                 730                 735
    Phe His Cys Tyr Gly Glu Cys Lys Lys Tyr Ala Tyr Pro Trp Gln Thr
                740                 745                 750
    Ala Lys Cys Phe Phe Glu Lys Asp Tyr Gln Tyr Glu Thr Ser Trp Gly
                    755                 760                 765
    Cys Asn Pro Pro Asp Cys Pro Gly Val Gly Thr Gly Cys Thr Ala Cys
                770                 775                 780
    Gly Val Tyr Leu Asp Lys Leu Arg Ser Val Gly Lys Ala Tyr Lys Ile
785                 790                 795                 800
    Val Ser Leu Lys Tyr Thr Arg Lys Val Cys Ile Gln Leu Gly Thr Glu
                    805                 810                 815
    Gln Thr Cys Lys His Ile Asp Val Asn Asp Cys Leu Val Thr Pro Ser
                820                 825                 830
    Val Lys Val Cys Met Ile Gly Thr Ile Ser Lys Leu Gln Pro Gly Asp
                    835                 840                 845
    Thr Leu Leu Phe Leu Gly Pro Leu Glu Gln Gly Ile Ile Leu Lys
                850                 855                 860
    Gln Trp Cys Thr Thr Ser Cys Val Phe Gly Asp Pro Gly Asp Ile Met
865                 870                 875                 880
    Ser Thr Thr Ser Gly Met Arg Cys Pro Glu His Thr Gly Ser Phe Arg
                    885                 890                 895
    Lys Ile Cys Gly Phe Ala Thr Thr Pro Thr Cys Glu Tyr Gln Gly Asn
                900                 905                 910
    Thr Val Ser Gly Phe Gln Arg Met Met Ala Thr Arg Asp Ser Phe Gln
                    915                 920                 925
    Ser Phe Asn Val Thr Glu Pro His Ile Thr Ser Asn Arg Leu Glu Trp
                930                 935                 940
```

```
Ile Asp Pro Asp Ser Ser Ile Lys Asp His Ile Asn Met Val Leu Asn
945                 950                 955                 960

Arg Asp Val Ser Phe Gln Asp Leu Ser Asp Asn Pro Cys Lys Val Asp
                965                 970                 975

Leu His Thr Gln Ser Ile Asp Gly Ala Trp Gly Ser Gly Val Gly Phe
            980                 985                 990

Thr Leu Val Cys Thr Val Gly Leu Thr Glu Cys Ala Asn Phe Ile Thr
        995                 1000                1005

Ser Ile Lys Ala Cys Asp Ser Ala Met Cys Tyr Gly Ala Thr Val
    1010                1015                1020

Thr Asn Leu Leu Arg Gly Ser Asn Thr Val Lys Val Gly Lys
    1025                1030                1035

Gly Gly His Ser Gly Ser Leu Phe Lys Cys Cys His Asp Thr Asp
    1040                1045                1050

Cys Thr Glu Glu Gly Leu Ala Ala Ser Pro Pro His Leu Asp Arg
    1055                1060                1065

Val Thr Gly Tyr Asn Gln Ile Asp Ser Asp Lys Val Tyr Asp Asp
    1070                1075                1080

Gly Ala Pro Pro Cys Thr Ile Lys Cys Trp Phe Thr Lys Ser Gly
    1085                1090                1095

Glu Trp Leu Leu Gly Ile Leu Asn Gly Asn Trp Val Val Val Ala
    1100                1105                1110

Val Leu Ile Val Ile Leu Ile Leu Ser Ile Leu Leu Phe Ser Phe
    1115                1120                1125

Phe Cys Pro Val Arg Asn Arg Lys Asn Lys Ala Asn
    1130                1135                1140

<210> SEQ ID NO 5
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
atctgcagga attcggcacg agagtagtag actccgcacg aagaagcaaa cactgaataa      60
aggatataca ga                                                         72

<210> SEQ ID NO 6
<211> LENGTH: 223
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
caaacatata tgtaagtaag ggtatgatca tattatatca ttatgcgtat actcttatat      60
ctataatatc tatgtatcct tatactctaa ctatttatat taattttttac ttttatacaa    120 gtattaacta acccattacc agctaaaaaa aacaaaccct taacacctat ataatcccat     180
ttgcttatta cgaggctttt gttcctgcgg agtctactac taa                       223

<210> SEQ ID NO 7
<211> LENGTH: 10
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 7
gcggccgcgg                                                                10

<210> SEQ ID NO 8
<211> LENGTH: 5
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8 gatct                                                                      5

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
atctgcagga attcggcacg ag                                                  22

<210> SEQ ID NO 10
<211> LENGTH: 7913
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
gggggggggg ggcgctgagg tctgcctcgt gaagaaggtg ttgctgactc ataccaggcc         60
tgaatcgccc catcatccag ccagaaagtg agggagccac ggttgatgag agctttgttg        120
taggtggacc agttggtgat tttgaacttt tgctttgcca cggaacggtc tgcgttgtcg        180
ggaagatgcg tgatctgatc cttcaactca gcaaaagttc gatttattca acaaagccgc        240
cgtcccgtca agtcagcgta atgctctgcc agtgttacaa ccaattaacc aattctgatt        300
agaaaaactc atcgagcatc aaatgaaact gcaatttatt catatcagga ttatcaatac        360 catattttg aaaaagccgt ttctgtaatg aaggagaaaa ctcaccgagg cagttccata        420
ggatggcaag atcctggtat cggtctgcga ttccgactcg tccaacatca atacaaccta        480
ttaatttccc ctcgtcaaaa ataaggttat caagtgagaa atcaccatga gtgacgactg        540
aatccggtga gaatggcaaa agcttatgca tttctttcca gacttgttca acaggccagc        600
cattacgctc gtcatcaaaa tcactcgcat caaccaaacc gttattcatt cgtgattgcg        660
cctgagcgag acgaaatacg cgatcgctgt taaaaggaca attacaaaca ggaatcgaat        720
gcaaccggcg caggaacact gccagcgcat caacaatatt ttcacctgaa tcaggatatt        780
cttctaatac ctggaatgct gttttcccgg ggatcgcagt ggtgagtaac catgcatcat        840
caggagtacg gataaaatgc ttgatggtcg gaagaggcat aaattccgtc agccagttta        900
gtctgaccat ctcatctgta acatcattgg caacgctacc tttgccatgt ttcagaaaca        960
actctggcgc atcgggcttc ccatacaatc gatagattgt cgcacctgat tgcccgacat       1020
```

```
tatcgcgagc ccatttatac ccatataaat cagcatccat gttggaattt aatcgcggcc      1080
tcgagcaaga cgtttcccgt tgaatatggc tcataacacc ccttgtatta ctgtttatgt      1140
aagcagacag ttttattgtt catgatgata tattttatc ttgtgcaatg taacatcaga       1200
gattttgaga cacaacgtgg ctttccccc ccccccggca tgcctgcagg tcgacaatat       1260
tggctattgg ccattgcata cgttgtatct atatcataat atgtacattt atattggctc      1320
atgtccaata tgaccgccat gttgacattg attattgact agttattaat agtaatcaat      1380
tacggggtca ttagttcata gcccatatat ggagttccgc gttacataac ttacggtaaa      1440
tggcccgcct ggctgaccgc ccaacgaccc cgcccattg acgtcaataa tgacgtatgt       1500
tcccatagta acgccaatag ggactttcca ttgacgtcaa tgggtggagt atttacggta      1560
aactgcccac ttggcagtac atcaagtgta tcatatgcca agtccgcccc ctattgacgt      1620
caatgacggt aaatggcccg cctggcatta tgcccagtac atgaccttac gggactttcc      1680
tacttggcag tacatctacg tattagtcat cgctattacc atggtgatgc ggttttggca      1740
gtacaccaat gggcgtggat agcggtttga ctcacgggga tttccaagtc tccacccat      1800
tgacgtcaat gggagtttgt tttggcacca aaatcaacgg gactttccaa aatgtcgtaa      1860
taaccccgcc ccgttgacgc aaatgggcgg taggcgtgta cggtgggagg tctatataag      1920
cagagctcgt ttagtgaacc gtcagatcgc ctggagacgc catccacgct gttttgacct      1980
ccatagaaga caccgggacc gatccagcct ccgcggccgg gaacggtgca ttggaacgcg      2040
gattccccgt gccaagagtg acgtaagtac cgcctataga ctctataggc acacccctt       2100
ggctcttatg catgctatac tgttttggc ttggggccta tacaccccg cttccttatg       2160
ctataggtga tggtatagct tagcctatag gtgtgggtta ttgaccatta ttgaccactc      2220
ccctattggt gacgatactt tccattacta atccataaca tggctctttg ccacaactat      2280
ctctattggc tatatgccaa tactctgtcc ttcagagact gacacggact ctgtattttt      2340
acaggatggg gtcccattta ttatttacaa attcacatat acaacaacgc cgtccccgt       2400
gcccgcagtt tttattaaac atagcgtggg atctccacgc gaatctcggg tacgtgttcc      2460
ggacatgggc tcttctccgg tagcggcgga gcttccacat ccgagccctg gtcccatgcc      2520
tccagcggct catggtcgct cggcagctcc ttgctcctaa cagtggaggc cagacttagg      2580
cacagcacaa tgcccaccac caccagtgtg ccgcacaagg ccgtggcggt agggtatgtg      2640
tctgaaaatg agctcggaga ttgggctcgc accgctgacg cagatggaag acttaaggca      2700
gcggcagaag aagatgcagg cagctgagtt gttgtattct gataagagtc agaggtaact      2760
cccgttgcgg tgctgttaac ggtggagggc agtgtagtct gagcagtact cgttgctgcc      2820
gcgcgcgcca ccagacataa tagctgacag actaacagac tgttcctttc catgggtctt      2880
ttctgcagtc agggtccaag cttgcggccg cggatctgca ggaattcggc acgagagtag      2940
tagactccgc acgaagaagc aaaaaattaa agaagtgagt ttaaaatgga agggtggtat      3000
ctggttgttc ttggagtctg ctatacgctg acactggcaa tgcccaagac catttatgag      3060
cttaaaatgg aatgcccgca cactgtgggt ctcggtcaag gttacatcat tggctcaaca      3120
gaactaggtt tgatctcaat tgaggctgca tctgatataa agctcgagag ctcttgcaat      3180
tttgatcttc atacaacatc tatggcccag aagagtttca cccaagttga atggagaaag      3240
aaaagtgaca caactgatac cacaaatgct gcgtccacta cctttgaagc acaaactaaa      3300
actgttaacc ttagagggac ttgtatactg gcacctgaac tctatgatac attgaagaaa      3360
gtaaaaaaga cagtcctgtg ctatgatcta acatgtaatc aaacacattg tcagccaact      3420
```

```
gtctatctga ttgcacctgt attgacatgc atgtcaataa gaagttgtat ggctagtgtg    3480
tttacaagca ggattcaggt gatttatgaa aagacacatt gtgtaacagg tcagctgatt    3540
gagggtcagt gtttcaaccc agcacacaca ttgacattat ctcagcctgc tcacacttat    3600
gatactgtca cccttcctat ctcttgtttt ttcacaccaa agaagtcgga gcaactaaaa    3660
gttataaaaa catttgaagg aattctgacg aagacaggtt gcacggagaa tgcattgcag    3720
ggttattatg tgtgtttttt agggagtcat tcagaaccct taattgttcc gagtttggag    3780
gacatacggt ctgctgaagt tgttagtagg atgcttgtac accctagggg agaagaccat    3840
gatgccatac agaattcaca aagtcactta agaatagtgg gacctatcac agcaaaagtg    3900
ccatcaacta gttccacaga taccctaaag gggacagcct ttgcaggcgt cccaatgtat    3960
agctctttat ctacactagt cagaaatgca gacccagaat ttgtattttc tccaggtata    4020
gtacctgaat ctaatcacag tacatgtgat aagaagacag tacctatcac atggacaggc    4080
tacctaccaa tatcaggtga gatggaaaaa gtgactggat gtacagtttt ttgtacacta    4140
gcaggacctg gtgctagttg tgaggcctat tctgaaaatg gtatatttaa catcagttct    4200
ccaacatgtc ttgtaaacaa agtccaaaga tttcgtggac tgaacagaa  aataaatttt    4260 atctgtcagc gggtagatca ggatgttgtt gtatactgca atgggcaaaa gaaagtcata    4320
ttaaccaaaa ctttggttat tgggcagtgt atttatacat tcacaagcct attttcattg    4380
atgcctgatg tagcccactc attggctgta gaattatgtg tcccgggatt acatgggtgg    4440
gccactgtca tgcttctatc aacattctgc tttgggtggg tcttgattcc tgcggtcaca    4500
ttaataatat taaagtgtct aagggttttg acgttttctt gttcccatta cactaatgag    4560
tcaaaattta aattcatcct ggaaaaagtt aaaattgaat accaaaagac tatgggatca    4620
atggtgtgcg atgtatgtca tcatgagtgt gaaacagcaa agaacttga  atcacataga    4680 cagagttgta tcaatggaca atgtccttat tgcatgacaa taactgaagc aactgaaagt    4740
gccttgcaag cccattattc catttgtaaa ttggcaggaa gatttcagga ggcactgaaa    4800
aagtcactta aaagccaga ggtaaaaaaa ggttgttaca gaacactcgg ggtatttaga    4860
tataaaagta gatgttatgt gggtttggta tggtgcctat tgttgacatg tgaaattgtt    4920
atttgggccg caagtgcaga gactccacta atggagtcag gctggtcaga tacggctcat    4980
ggtgttggtg agattccaat gaagacagac ctcgagctgg acttttcact gccttcttca    5040
tcctcttaca gttataggag aaagctcaca aacccagcca ataaagaaga gtctattccc    5100
ttccacttcc agatggaaaa acaagtaatt catgctgaaa tccaaccct  gggtcattgg    5160 atggatgcga catttaatat taagactgca tttcattgtt atggtgcatg ccagaaatac    5220
tcttatccat ggcagacatc taagtgcttc tttgaaaagg actaccagta tgaaacaggc    5280
tggggctgta atcctggtga ctgcccaggg gttgggactg gatgcactgc ttgtggtgtt    5340
tatctcgata aactaaaatc tgttgggaag gcctataaga taatttctttt aaaatatacc    5400 agaaaggttt gtattcagtt aggaacagaa caaacttgca agcatattga tgcaaatgat    5460
tgtttagtga caccatctgt gaaagtttgc atagtgggca cagtttcaaa acttcaacca    5520
tctgatactc ttttgttctt aggtccacta gaacaagggg gaatcattct taagcaatgg    5580
tgcacaacat catgtgcatt tggggaccct ggtgatatca tgtccactcc cagtggtatg    5640
aggtgtccag agcacactgg atcatttagg aaaatttgcg gttttgctac tacaccagtt    5700
tgtgaatatc aaggaaatac catttctgga tataaaagaa tgatggcaac aaaagattca    5760
```

```
ttccaatcat ttaacttaac agaacctcac atcacaacaa acaagcttga atggatcgac    5820
ccagatggga atacaagaga ccacgtaaac cttgtcttaa atagagatgt ctcatttcag    5880
gatttaagtg ataaccnctg taaagtagac ctacacacac aagcaataga aggggcatgg    5940
ggttctggtg tagggtttac actcacatgt actgtcggat taacagagtg cccaagtttt    6000
atgacatcaa ttaaggcatg tgacctagct atgtgttatg gatcaacagt aacaaacctt    6060
gccaggggct ctaatacagt gaaagtagtt ggtaaaggag gccattcagg gtcctcattt    6120
aaatgctgtc atgatacaga ttgctcctct gaaggtttac ttgcatcagc ccctcatctt    6180
gagagggtaa caggattcaa tcaaattgat tcagataagg tttatgatga tggtgcacca    6240
ccttgcacat tcaaatgctg gttcactaag tcaggtgagt ggcttcttgg gatcttaaac    6300
gggaattgga ttgttgttgt agtgcttgtt gtgatactca ttctctctat cataatgttc    6360
agtgttttgt gtcccaggag agggcacaag aaaactgtct aagcattgac ctcaactcct    6420
acattagatc atatacattt atgcacttcc tcatatttag ctgcactaag atattaataa    6480
actctagtta ttgactttat aagattatta tggaactaac ctcacttaaa aaaaacaaat    6540
actttactca tatataactc catattctct taccgaggat tttgttcctg cggagcatac    6600
tactaggatc tacgtatgat cagcctcgac tgtgccttct agttgccagc catctgttgt    6660
ttgcccctcc cccgtgcctt ccttgaccct ggaaggtgcc actcccactg tcctttccta    6720
ataaaatgag gaaattgcat cgcattgtct gagtaggtgt cattctattc tggggggtgg    6780
ggtggggcag gacagcaagg gggaggattg ggaagacaat agcaggcatg ctggggatgc    6840
ggtgggctct atggcttctg aggcggaaag aaccagctgg ggctcgacag ctcgactcta    6900
gaattgcttc ctcgctcact gactcgctgc gctcggtcgt tcggctgcgg cgagcggtat    6960
cagctcactc aaaggcggta atacggttat ccacagaatc aggggataac gcaggaaaga    7020
acatgtgagc aaaaggccag caaaaggcca ggaaccgtaa aaaggccgcg ttgctggcgt    7080
ttttccatag gctccgcccc cctgacgagc atcacaaaaa tcgacgctca agtcagaggt    7140
ggcgaaaccc gacaggacta taaagatacc aggcgtttcc ccctggaagc tccctcgtgc    7200
gctctcctgt tccgaccctg ccgcttaccg gatacctgtc cgcctttctc ccttcgggaa    7260
gcgtggcgct ttctcatagc tcacgctgta ggtatctcag ttcggtgtag gtcgttcgct    7320
ccaagctggg ctgtgtgcac gaaccccccg ttcagcccga ccgctgcgcc ttatccggta    7380
actatcgtct tgagtccaac ccggtaagac acgacttatc gccactggca gcagccactg    7440
gtaacaggat tagcagagcg aggtatgtag gcggtgctac agagttcttg aagtggtggc    7500
ctaactacgg ctacactaga agaacagtat ttggtatctg cgctctgctg aagccagtta    7560
ccttcgaaaa aagagttggt agctcttgat ccggcaaaca aaccaccgct ggtagcggtg    7620
gtttttttgt ttgcaagcag cagattacgc gcagaaaaaa aggatctcaa gaagatcctt    7680
tgatcttttc tacggggtct gacgctcagt ggaacgaaaa ctcacgttaa gggattttgg    7740
tcatgagatt atcaaaaagg atcttcacct agatcctttt aaattaaaaa tgaagtttta    7800
aatcaatcta agtatatat gagtaaactt ggtctgacag ttaccaatgc ttaatcagtg    7860
aggcacctat ctcagcgatc tgtctatttc gttcatccat agttgcctga ctc           7913
```

<210> SEQ ID NO 11
<211> LENGTH: 7924
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 11

| | | | | | |
|---|---|---|---|---|---|
| gggggggggg | ggcgctgagg | tctgcctcgt | gaagaaggtg | ttgctgactc | ataccaggcc | 60 |
| tgaatcgccc | catcatccag | ccagaaagtg | agggagccac | ggttgatgag | agctttgttg | 120 |
| taggtggacc | agttggtgat | tttgaacttt | tgctttgcca | cggaacggtc | tgcgttgtcg | 180 |
| ggaagatgcg | tgatctgatc | cttcaactca | gcaaaagttc | gatttattca | acaaagccgc | 240 |
| cgtcccgtca | agtcagcgta | atgctctgcc | agtgttacaa | ccaattaacc | aattctgatt | 300 |
| agaaaaactc | atcgagcatc | aaatgaaact | gcaatttatt | catatcagga | ttatcaatac | 360 |
| catatttttg | aaaaagccgt | ttctgtaatg | aaggagaaaa | ctcaccgagg | cagttccata | 420 |
| ggatggcaag | atcctggtat | cggtctgcga | ttccgactcg | tccaacatca | atacaaccta | 480 |
| ttaatttccc | ctcgtcaaaa | ataaggttat | caagtgagaa | atcaccatga | gtgacgactg | 540 |
| aatccggtga | gaatggcaaa | agcttatgca | tttctttcca | gacttgttca | acaggccagc | 600 |
| cattacgctc | gtcatcaaaa | tcactcgcat | caaccaaacc | gttattcatt | cgtgattgcg | 660 |
| cctgagcgag | acgaaatacg | cgatcgctgt | taaaaggaca | attacaaaca | ggaatcgaat | 720 |
| gcaaccggcg | caggaacact | gccagcgcat | caacaatatt | ttcacctgaa | tcaggatatt | 780 |
| cttctaatac | ctggaatgct | gttttcccgg | ggatcgcagt | ggtgagtaac | catgcatcat | 840 |
| caggagtacg | gataaaatgc | ttgatggtcg | gaagaggcat | aaattccgtc | agccagttta | 900 |
| gtctgaccat | ctcatctgta | acatcattgg | caacgctacc | tttgccatgt | tcagaaaca | 960 |
| actctggcgc | atcgggcttc | ccatacaatc | gatagattgt | cgcacctgat | tgcccgacat | 1020 |
| tatcgcgagc | ccatttatac | ccatataaat | cagcatccat | gttggaattt | aatcgcggcc | 1080 |
| tcgagcaaga | cgtttcccgt | tgaatatggc | tcataacacc | ccttgtatta | ctgtttatgt | 1140 |
| aagcagacag | ttttattgtt | catgatgata | tatttttatc | ttgtgcaatg | taacatcaga | 1200 |
| gattttgaga | cacaacgtgg | ctttcccccc | cccccggca | tgcctgcagg | tcgacaatat | 1260 |
| tggctattgg | ccattgcata | cgttgtatct | atatcataat | atgtacattt | atattggctc | 1320 |
| atgtccaata | tgaccgccat | gttgacattg | attattgact | agttattaat | agtaatcaat | 1380 |
| tacggggtca | ttagttcata | gcccatatat | ggagttccgc | gttacataac | ttacggtaaa | 1440 |
| tggcccgcct | ggctgaccgc | ccaacgaccc | ccgcccattg | acgtcaataa | tgacgtatgt | 1500 |
| tcccatagta | acgccaatag | ggactttcca | ttgacgtcaa | tgggtggagt | atttacggta | 1560 |
| aactgcccac | ttggcagtac | atcaagtgta | tcatatgcca | agtccgcccc | ctattgacgt | 1620 |
| caatgacggt | aaatggcccg | cctggcatta | tgcccagtac | atgaccttac | gggactttcc | 1680 |
| tacttggcag | tacatctacg | tattagtcat | cgctattacc | atggtgatgc | ggttttggca | 1740 |
| gtacaccaat | gggcgtggat | agcggtttga | ctcacgggga | tttccaagtc | tccacccat | 1800 |
| tgacgtcaat | gggagtttgt | tttggcacca | aaatcaacgg | gactttccaa | aatgtcgtaa | 1860 |
| taaccccgcc | ccgttgacgc | aaatgggcgg | taggcgtgta | cggtgggagg | tctatataag | 1920 |
| cagagctcgt | ttagtgaacc | gtcagatcgc | ctggagacgc | catccacgct | gttttgacct | 1980 |
| ccatagaaga | caccgggacc | gatccagcct | ccgcggccgg | gaacggtgca | ttggaacgcg | 2040 |
| gattcccgt | gccaagagtg | acgtaagtac | cgcctataga | ctctataggc | acccccttt | 2100 |
| ggctcttatg | catgctatac | tgttttggc | ttggggccta | tacaccccg | cttccttatg | 2160 |
| ctataggtga | tggtatagct | tagcctatag | gtgtgggtta | ttgaccatta | ttgaccactc | 2220 |
| ccctattggt | gacgatactt | tccattacta | atccataaca | tggctctttg | ccacaactat | 2280 |

```
ctctattggc tatatgccaa tactctgtcc ttcagagact gacacggact ctgtattttt   2340
acaggatggg gtcccattta ttatttacaa attcacatat acaacaacgc cgtcccccgt   2400
gcccgcagtt tttattaaac atagcgtggg atctccacgc gaatctcggg tacgtgttcc   2460
ggacatgggc tcttctccgg tagcggcgga gcttccacat ccgagccctg gtcccatgcc   2520
tccagcggct catggtcgct cggcagctcc ttgctcctaa cagtggaggc cagacttagg   2580
cacagcacaa tgcccaccac caccagtgtg ccgcacaagg ccgtggcggt agggtatgtg   2640
tctgaaaatg agctcggaga ttgggctcgc accgctgacg cagatggaag acttaaggca   2700
gcggcagaag aagatgcagg cagctgagtt gttgtattct gataagagtc agaggtaact   2760
cccgttgcgg tgctgttaac ggtggagggc agtgtagtct gagcagtact cgttgctgcc   2820
gcgcgcgcca ccagacataa tagctgacag actaacagac tgttcctttc catgggtctt   2880
ttctgcagtc accgtccaag cttgcggccg cggatctgca ggaattcggc acgagagtag   2940
tagactccgc aagaaacagc aaacacagat aaatatgggc gagctgtccc ctgtgtgcct   3000
gtacctgctg ctgcagggcc tgctgctgtg taacaccgga gccgccagga acctgaacga   3060
gctgaagatg gagtgccccc acaccatcag actgggccag ggcctggtgg tgggcagcgt   3120
ggagctgccc agcctgccca tccagcaggt ggagaccctg aagctggaga gcagctgtaa   3180
cttcgacctg cacaccagca cagccggcca gcagagcttc accaagtgga cctgggagat   3240
caagggcgac ctggccgaga cacccaggc cagcagcacc agcttccaga ccaagagcag   3300
cgaggtgaac ctgagaggcc tgtgcctgat ccccacactg gtggtggaga ccgccgccag   3360
aatgagaaag accatcgcct gctacgacct gagctgtaac cagaccgtgt gtcagcctac   3420
cgtgtacctg atgggcccta tccagacctg tatcaccacc aagagctgcc tgctgtccct   3480
gggcgatcag agaatccagg tgaactacga gaaaacctac tgtgtgagcg ccagctggt   3540 ggagggcatc tgcttcaacc ccatccacac catggccctg agccagccta gccacaccta   3600
cgacatcatg accatgatgg tgagatgctt tctggtgatc aagaaggtga ccagcggcga   3660
cagcatgaag atcgagaaga acttcgagac cctggtgcag aagaatggct gtaccgccaa   3720
caacttccag ggctactaca tctgcctgat cggcagcagc agcgagcccc tgtacgtgcc   3780
cgccctggac gactacagaa gcgccgaggt gctgtccaga atggccttcg cccccacgg   3840 cgaggaccac gacatcgaga aaacgccgt gtccgccatg agaatcgccg gcaaggtgac   3900
cggcaaggcc cccagcaccg agtccagcga caccgtgcag ggcatcgcct tcagcggcag   3960
ccccctgtac acctccaccg gcgtgctgac cagcaaggac gaccccgtgt acatctgggc   4020
ccctggcatc atcatggagg gcaaccacag catctgtgag aagaaaaccc tgccccctgac   4080 ctggaccggc ttcatcagcc tgcccggcga gatcgagaaa accaccccagt gtaccgtgtt   4140 ctgtaccctg gccggacctg gcgccgactg tgaggcctac agcgagaccg catcttcaa   4200 catcagcagc cccacctgcc tgatcaaccg ggtgcagagg ttcagaggca gcgagcagca   4260
gatcaagttt gtgtgccagc gggtggacat ggacatcacc gtgtactgta acggcatgaa   4320
gaaggtgatc ctgaccaaga cactggtgat cggccagtgt atctacacct tcaccagcat   4380 cttctcctg atccccggcg tggcccacag cctggccgtg agctgtgtg tgcccggcct   4440 gcacggctgg gccaccatgc tgctgctgct gaccttctgc ttcggctggg tgctgatccc   4500
taccatcacc atgatcctgc tgaagatcct gatcgccttc gcctaccgt gctccaagta   4560 caacaccgac agcaagttca gaatcctgat cgagaaagtg aagcgggagt accagaaaac   4620
```

```
catgggcagc atggtgtgtg aagtgtgcca gtacgagtgt gagaccgcca aggagctgga    4680
gtcccacaga aagagctgct ccatcggcag ctgcccctac tgcctgaacc ccagcgaggc    4740
caccacctcc gccctgcagg cccacttcaa agtgtgtaag ctgaccagcc ggttccagga    4800
gaacctgagg aagtccctga ccgtgtacga gcccatgcag ggctgctaca gaaccctgag    4860
cctgttccgg tacaggagcc ggttctttgt gggcctggtg tggtgtgtgc tgctggtgct    4920
ggagctgatt gtgtgggccg ccagcgccga gacccagaac ctgaatgccg gctggaccga    4980
caccgcccac ggcagcggca tcatccccat gaaaaccgac ctggagctgg acttcagcct    5040
gcctagcagc gcctcctaca cctacaggcg gcagctgcag aatcctgcca acgagcagga    5100
gaagatcccc ttccacctgc agctgtccaa gcaggtgatc cacgccgaga ttcagcacct    5160
gggccactgg atggacgcca ccttcaacct gaaaaccgcc ttccactgct acggcagctg    5220
tgagaagtac gcctacccct tggcagaccgc cggctgcttc atcgagaagg actacgagta    5280
cgagaccggc tggggctgta atcctcctga ttgccccgga gtgggcaccg gctgtactgc    5340
atgtggcgtg tacctggaca agctgaagtc tgtgggcaag gtgttcaaga tcgtgtccct    5400
gaggtacacc cggaaagtgt gtatccagct gggcaccgag cagacctgta agaccgtgga    5460
cagcaacgat tgcctgatca aaccagcgt gaaagtgtgt ctgatcggca ccatcagcaa    5520
gttccagccc agcgataccc tgctgttttct ggccccctg cagcagggcg gcctgatctt    5580
caagcagtgg tgtaccacca cctgccagtt cggcgatccc ggcgtatatca tgagcacccc    5640
caccggcatg aagtgccctg agctgaacgg cagcttccgg aagaagtgtg ccttcgccac    5700
caccccctgtg tgtcagttcg acggcaacac catcagcggc tacaagcgga tgatcgccac    5760
caaggacagc ttccagtcct tcaacgtgac cgagccccac atcagcacca gcgccctgga    5820
gtggatcgat cccgacagca gcctgaggga ccacatcaac gtgatcgtgt ccagggacct    5880
gagcttccag gacctgagcg agacccctg ccagatcgac ctggccaccg ccagcatcga    5940
tggcgcctgg ggcagcggag tgggcttcaa cctggtgtgt acagtgagcc tgaccgagtg    6000
tagcgccttc ctgaccagca tcaaagcctg tgacgccgcc atgtgttacg gcagcaccac    6060
cgccaacctg gtgagaggcc agaacaccat ccacattgtg gcaaaggcg gccacagcgg    6120
cagcaagttt atgtgctgcc acgacaccaa gtgtagcagc accggcctgg tggccgctgc    6180
cccccacctg gacagagtga ccggctacaa ccaggccgac agcgacaaga ttttcgacga    6240
cggagccccct gagtgtggca tgagttgctg gttcaagaag agcggcgagt ggattctggg    6300
cgtgctgaac gggaattgga tggtggtggc cgtgctggtc gtgctgctga tcctgagcat    6360
cctgctgttc accctgtgct gccctaggag acccagctac cggaaggagc acaagccctg    6420
agtttttgctt actaacataa ttattgtatt ctgtttattg acacaattac catatgatta    6480
actgtattcc cccatcttat atcttatata atattcttta tttaatcact atatagaaaa    6540
aaaactagca ctttactaat taaattaccc cataccgatt atgcctggac ttttgttcct    6600
gcggagcata ctactaggat ctacgtatga tcagcctcga ctgtgccttc tagttgccag    6660
ccatctgttg tttgccccctc ccccgtgcct tccttgaccc tggaaggtgc cactcccact    6720
gtcctttcct aataaaatga ggaaattgca tcgcattgtc tgagtaggtg tcattctatt    6780
ctggggggtg gggtggggca ggacagcaag ggggaggatt gggaagacaa tagcaggcat    6840
gctggggatg cggtgggctc tatggcttct gaggcggaaa gaaccagctg ggctcgaca    6900
gctcgactct agaattgctt cctcgctcac tgactcgctg cgctcggtcg ttcggctgcg    6960
gcgagcggta tcagctcact caaaggcggt aatacggtta tccacagaat caggggataa    7020
```

| | |
|---|---:|
| cgcaggaaag aacatgtgag caaaaggcca gcaaaaggcc aggaaccgta aaaaggccgc | 7080 |
| gttgctggcg ttttccata ggctccgccc ccctgacgag catcacaaaa atcgacgctc | 7140 |
| aagtcagagg tggcgaaacc cgacaggact ataaagatac caggcgtttc ccctggaag | 7200 |
| ctccctcgtg cgctctcctg ttccgaccct gccgcttacc ggatacctgt ccgcctttct | 7260 |
| cccttcggga agcgtggcgc tttctcatag ctcacgctgt aggtatctca gttcggtgta | 7320 |
| ggtcgttcgc tccaagctgg gctgtgtgca cgaaccccc gttcagcccg accgctgcgc | 7380 |
| cttatccggt aactatcgtc ttgagtccaa cccggtaaga cacgacttat cgccactggc | 7440 |
| agcagccact ggtaacagga ttagcagagc gaggtatgta ggcggtgcta cagagttctt | 7500 |
| gaagtggtgg cctaactacg gctacactag aagaacagta tttggtatct gcgctctgct | 7560 |
| gaagccagtt accttcggaa aaagagttgg tagctcttga tccggcaaac aaaccaccgc | 7620 |
| tggtagcggt ggtttttttg tttgcaagca gcagattacg cgcagaaaaa aaggatctca | 7680 |
| agaagatcct ttgatctttt ctacgggtc tgacgctcag tggaacgaaa actcacgtta | 7740 |
| agggattttg gtcatgagat tatcaaaaag gatcttcacc tagatccttt taaattaaaa | 7800 |
| atgaagtttt aaatcaatct aaagtatata tgagtaaact tggtctgaca gttaccaatg | 7860 |
| cttaatcagt gaggcaccta tctcagcgat ctgtctattt cgttcatcca tagttgcctg | 7920 |
| actc | 7924 |

<210> SEQ ID NO 12
<211> LENGTH: 7800
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 12

| | |
|---|---:|
| gggggggggg ggcgctgagg tctgcctcgt gaagaaggtg ttgctgactc ataccaggcc | 60 |
| tgaatcgccc catcatccag ccagaaagtg agggagccac ggttgatgag agctttgttg | 120 |
| taggtggacc agttggtgat tttgaacttt gctttgcca cggaacggtc tgcgttgtcg | 180 |
| ggaagatgcg tgatctgatc cttcaactca gcaaaagttc gatttattca acaaagccgc | 240 |
| cgtcccgtca gtcagcgta atgctctgcc agtgttacaa ccaattaacc aattctgatt | 300 |
| agaaaactc atcgagcatc aaatgaaact gcaatttatt catatcagga ttatcaatac | 360 |
| catattttg aaaagccgt ttctgtaatg aaggagaaaa ctcaccgagg cagttccata | 420 |
| ggatggcaag atcctggtat cggtctgcga ttccgactcg tccaacatca atacaaccta | 480 |
| ttaatttccc ctcgtcaaaa ataaggttat caagtgagaa atcaccatga gtgacgactg | 540 |
| aatccggtga gaatggcaaa agcttatgca tttctttcca gacttgttca acaggccagc | 600 |
| cattacgctc gtcatcaaaa tcactcgcat caaccaaacc gttattcatt cgtgattgcg | 660 |
| cctgagcgag acgaaatacg cgatcgctgt taaaaggaca attacaaaca ggaatcgaat | 720 |
| gcaaccggcg caggaacact gccagcgcat caacaatatt ttcacctgaa tcaggatatt | 780 |
| cttctaatac ctggaatgct gttttccgg ggatcgcagt ggtgagtaac catgcatcat | 840 |
| caggagtacg gataaaatgc ttgatggtcg aagaggcat aaattccgtc agccagttta | 900 |
| gtctgaccat ctcatctgta acatcattgg caacgctacc tttgccatgt ttcagaaaca | 960 |
| actctggcgc atcgggcttc ccatacaatc gatagattgt cgcacctgat tgcccgacat | 1020 |
| tatcgcgagc ccatttatac ccatataaat cagcatccat gttggaattt aatcgcggcc | 1080 |

-continued

```
tcgagcaaga cgtttcccgt tgaatatggc tcataacacc ccttgtatta ctgtttatgt    1140
aagcagacag ttttattgtt catgatgata tattttatc ttgtgcaatg taacatcaga    1200
gattttgaga cacaacgtgg ctttccccc ccccccggca tgcctgcagg tcgacaatat    1260
tggctattgg ccattgcata cgttgtatct atatcataat atgtacattt atattggctc    1320
atgtccaata tgaccgccat gttgacattg attattgact agttattaat agtaatcaat    1380
tacggggtca ttagttcata gcccatatat ggagttccgc gttacataac ttacggtaaa    1440
tggcccgcct ggctgaccgc ccaacgaccc ccgcccattg acgtcaataa tgacgtatgt    1500
tcccatagta acgccaatag ggactttcca ttgacgtcaa tgggtggagt atttacggta    1560
aactgcccac ttggcagtac atcaagtgta tcatatgcca agtccgcccc ctattgacgt    1620
caatgacggt aaatggcccg cctggcatta tgcccagtac atgaccttac ggactttcc    1680
tacttggcag tacatctacg tattagtcat cgctattacc atggtgatgc ggttttggca    1740
gtacaccaat gggcgtggat agcggtttga ctcacgggga tttccaagtc tccacccat    1800
tgacgtcaat gggagtttgt tttggcacca aaatcaacgg gactttccaa aatgtcgtaa    1860
taaccccgcc ccgttgacgc aaatgggcgg taggcgtgta cggtgggagg tctatataag    1920
cagagctcgt ttagtgaacc gtcagatcgc ctggagacgc catccacgct gttttgacct    1980
gcatcgaaga caccgggacc gatccagcct ccgcggccgg gaacggtgca ttggaacgcg    2040
gattcccgt gccaagagtg acgtaagtac cgcctataga ctctataggc acacccttt    2100
ggctcttatg catgctatac tgttttggc ttggggccta tacaccccg cttccttatg    2160
ctataggtga tggtatagct tagcctatag gtgtgggtta ttgaccatta ttgaccactc    2220
ccctattggt gacgatactt tccattacta atccataaca tggctctttg ccacaactat    2280
ctctattggc tatatgccaa tactctgtcc ttcagagact gacacggact ctgtattttt    2340
acaggatggg gtcccatta ttatttacaa attcacatat acaacaacgc cgtcccccgt    2400
gcccgcagtt tttattaaac atagcgtggg atctccacgc gaatctcggg tacgtgttcc    2460
ggacatgggc tcttctccgg tagcggcgga gcttccacat ccgagccctg gtcccatgcc    2520
tccagcggct catggtcgct cggcagctcc ttgctcctaa cagtggaggc cagacttagg    2580
cacagcacaa tgcccaccac caccagtgtg ccgcacaagg ccgtggcggt agggtatgtg    2640
tctgaaaatg agctcggaga ttgggctcgc accgctgacg cagatggaag acttaaggca    2700
gcggcagaag aagatgcagg cagctgagtt gttgtattct gataagagtc agaggtaact    2760
cccgttgcgg tgctgttaac ggtggagggc agtgtagtct gagcagtact cgttgctgcc    2820
gcgcgcgcca ccagacataa tagctgacag actaacagac tgttcctttc catgggtctt    2880
ttctgcagtc accgtccaag cttgcggccg cggatctgca ggaattcggc acgagagtag    2940
tagactccgc aagaaacagc agtcaatcag caacatgggg atatggaagt ggctagtgat    3000
ggccagttta gtatggcctg ttttgacact gagaaatgtc tatgacatga aaattgagtg    3060
cccccataca gtaagttttg ggaaaacag tgtgataggt tatgtagaat taccccccgt    3120
gccattggcc gacacagcac agatggtgcc tgagagttct tgtagcatgg ataatcacca    3180
atcgttgaat acaataacaa aatatacccca agtaagttgg agaggaaagg ctgatcagtc    3240
acagtctagt caaaattcat ttgagacagt gtccactgaa gttgacttga aaggaacatg    3300
tgctctaaaa cacaaaatgg tggaagaatc ataccgtagt aggaaatcag taacctgtta    3360
cgacctgtct tgcaatagca cttactgcaa gccaacacta tacatgattg taccaattca    3420
```

```
tgcatgcaat atgatgaaaa gctgtttgat tgcattggga ccatacagag tacaggtggt    3480
ttatgagaga tcttattgca tgacaggagt cctgattgaa gggaaatgct ttgtcccaga    3540
tcaaagtgtg gtcagtatta tcaagcatgg gatctttgat attgcaagtg ttcatattgt    3600
atgtttcttt gttgcagtta aagggaatac ttataaaatt tttgaacagg ttaagaaatc    3660
ctttgaatca acatgcaatg atacagagaa taaagtgcaa ggatattata tttgtattgt    3720
agggggaaac tctgcaccaa tatatgttcc aacacttgat gatttcagat ccatggaagc    3780
atttacagga atcttcagat caccacatgg ggaagatcat gatctggctg gagaagaaat    3840
tgcatcttat tctatagtcg gacctgccaa tgcaaaagtt cctcatagtg ctagctcaga    3900
tacattgagc ttgattgcct attcaggtat accatcttat tcttccctta gcatcctaac    3960
aagttcaaca gaagctaagc atgtattcag ccctgggttg ttcccaaaac ttaatcacac    4020
aaattgtgat aaaagtgcca taccactcat atggactggg atgattgatt tacctggata    4080
ctacgaagct gtccaccctt gtacagtttt ttgcgtatta tcaggtcctg ggcatcatg    4140 tgaagccttt tctgaaggcg ggattttcaa cataacctct cccatgtgct tagtgtcaaa    4200
acaaaatcga ttccggttaa cagaacagca agtgaatttt gtgtgtcagc gagtggacat    4260
ggacattgtt gtgtactgca acgggcagag gaaagtaata ttaacaaaaa ctctagttat    4320
tggacagtgt atatatacta taacaagctt attctcatta ctacctggag tagcacattc    4380
tattgctgtt gaattgtgtg tacctgggtt ccatggttgg gccacagctg ctctgcttgt    4440
tacattctgt ttcggatggg ttcttatacc agcaattaca tttatcatac taacagtcct    4500
aaagttcatt gctaatattt ttcacacaag taatcaagag ataggctaa aatcagtact    4560 tagaaagata aaggaagagt ttgaaaaaac aaaaggctca atggtatgtg atgtctgcaa    4620
gtatgagtgt gaaacctata agaattaaa ggcacgggg tatcatgcc cccatctca    4680 atgtccttac tgttttactc attgtgaacc cacagaagca gcattccaag ctcattacaa    4740
ggtatgccaa gttactcaca gattcaggga tgatctaag aaaactgtta ctcctcaaaa    4800
ttttacacca ggatgttacc ggacactaaa tttattaga tacaaaagca ggtgctacat    4860
ctttacaatg tggatatttc ttcttgtctt agaatccata ctgtgggctg caagtgcatc    4920
agagacacca ttaactcctg tctggaatga caatgcccat ggggtaggtt ctgttcctat    4980
gcatacagat ttagagcttg atttctcttt aacatccagt tccaagtata cataccgtag    5040
gaggttaaca aacccacttg aggaagcaca atccattgac ctacatattg aaatagaaga    5100
acagacaatt ggtgttgatg tgcatgctct aggacactgg tttgatggtc gtcttaacct    5160
taaaacatcc tttcactgtt atggtgcttg tacaaagtat gaatacctt ggcatactgc    5220 aaagtgccac tatgaaagag attaccaata tgagacgagc tggggttgta atccatcaga    5280
ttgtcctggg gtgggcacag gctgtacagc atgtggttta acctagatc aactgaaacc    5340 agttggtagt gcttataaaa ttatcacaat aaggtacagc aggagagtct gtgttcagtt    5400
tggggaggaa aacctttgta agataataga catgaatgat tgttttgtat ctaggcatgt    5460
taaggtctgc ataattggta cagtatctaa attctctcag ggtgatacct tattgttttt    5520
tggaccgctt gaaggtggtg gtctaatatt taaacactgg tgtacatcca catgtcaatt    5580
tggtgaccca ggagatatca tgagtccaag agacaaaggt ttttatgcc ctgagtttcc    5640 aggtagtttc aggaagaaat gcaactttgc tactacccct atttgtgagt atgatggaaa    5700
tatggtctca ggttacaaga agtgatggc cacaattgat tccttccaat cttttaatac    5760
aagcactatg cacttcactg atgaaaggat agagtggaaa gaccctgatg gaatgctaag    5820
```

```
ggaccatata aacatttttag taacgaagga cattgacttt gataaccttg gtgaaaatcc   5880
ttgcaaaatt ggcctacaaa catcttctat tgagggggcc tggggttctg gtgtggggtt   5940
cacattaaca tgtctggtat cactaacaga atgtcctacc tttttgacct caataaaggc   6000
ttgtgataag gctatctgtt atggtgcaga gagtgtaaca ttgacaagag acaaaatac    6060 agtcaaggta tcagggaaag gtggccatag tggttcaaca tttaggtgtt gccatgggga   6120
ggactgttca caaattggac tccatgctgc tgcacctcac cttgacaagg taaatgggat   6180
ttctgagata gaaaatagta aagtatatga tgatggggca ccgcaatgtg ggataaaatg   6240
ttggtttgtt aaatcagggg aatggatttc agggatattc agtggtaatt ggattgtact   6300
cattgtcctc tgtgtatttc tattgttctc cttggtttta ctaagcattc tctgtcccgt   6360
aaggaagcat aaaaaatcat agctaaattc tgtgactatc ctgttcttat gtatagcttt   6420
aacatatata ctaattttta tattccagta tactctatct aacacactaa aaaaaatagt   6480
agctttctaa ccacaaaacg gatctacgta tgatcagcct cgactgtgcc ttctagttgc   6540
cagccatctg ttgtttgccc ctcccccgtg ccttccttga ccctggaagg tgccactccc   6600
actgtccttt cctaataaaa tgaggaaatt gcatcgcatt gtctgagtag gtgtcattct   6660
attctggggg gtggggtggg gcaggacagc aaggggagg attgggaaga caatagcagg    6720
catgctgggg atgcggtggg ctctatggct tctgaggcgg aaagaaccag ctggggctcg   6780
acagctcgac tctagaattg cttcctcgct cactgactcg ctgcgctcgg tcgttcggct   6840
gcggcgagcg gtatcagctc actcaaaggc ggtaatacgg ttatccacag aatcaggggga  6900 taacgcagga aagaacatgt gagcaaaagg ccagcaaaag gccaggaacc gtaaaaaggc   6960
cgcgttgctg gcgttttcc ataggctccg cccccctgac gagcatcaca aaaatcgacg    7020
ctcaagtcag aggtggcgaa acccgacagg actataaaga taccaggcgt ttccccctgg   7080
aagctccctc gtgcgctctc ctgttccgac cctgccgctt accggatacc tgtccgcctt   7140
tctcccttcg ggaagcgtgg cgctttctca tagctcacgc tgtaggtatc tcagttcggt   7200
gtaggtcgtt cgctccaagc tgggctgtgt gcacgaaccc cccgttcagc ccgaccgctg   7260
cgccttatcc ggtaactatc gtcttgagtc caacccggta agacacgact tatcgccact   7320
ggcagcagcc actggtaaca ggattagcag agcgaggtat gtaggcggtg ctacagagtt   7380
cttgaagtgg tggcctaact acggctacac tagaagaaca gtatttggta tctgcgctct   7440
gctgaagcca gttaccttcg gaaaaagagt tggtagctct tgatccggca aacaaaccac   7500
cgctggtagc ggtggttttt tgtttgcaa gcagcagatt acgcgcagaa aaaaggatc    7560 tcaagaagat cctttgatct tttctacggg gtctgacgct cagtggaacg aaaactcacg   7620
ttaagggatt ttggtcatga gattatcaaa aaggatcttc acctagatcc ttttaaatta   7680
aaaatgaagt tttaaatcaa tctaaagtat atatgagtaa acttggtctg acagttacca   7740
atgcttaatc agtgaggcac ctatctcagc gatctgtcta tttcgttcat ccatagttgc   7800
```

<210> SEQ ID NO 13
<211> LENGTH: 8001
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13

```
gggggggggg ggcgctgagg tctgcctcgt gaagaaggtg ttgctgactc ataccaggcc   60
```

```
tgaatcgccc catcatccag ccagaaagtg agggagccac ggttgatgag agctttgttg    120
taggtggacc agttggtgat tttgaacttt tgctttgcca cggaacggtc tgcgttgtcg    180
ggaagatgcg tgatctgatc cttcaactca gcaaaagttc gatttattca acaaagccga    240
cgtcccgtca agtcagcgta atgctctgcc agtgttacaa ccaattaacc aattctgatt    300
agaaaaactc atcgagcatc aaatgaaact gcaatttatt catatcagga ttatcaatac    360 catattttg aaaaagccgt ttctgtaatg aaggagaaaa ctcaccgagg cagttccata    420
ggatggcaag atcctggtat cggtctgcga ttccgactcg tccaacatca atacaaccta    480
ttaatttccc ctcgtcaaaa ataaggttat caagtgagaa atcaccatga gtgacgactg    540
aatccggtga gaatggcaaa agcttatgca tttctttcca gacttgttca acaggccagc    600
cattacgctc gtcatcaaaa tcactcgcat caaccaaacc gttattcatt cgtgattgcg    660
cctgagcgag acgaaatacg cgatcgctgt taaaaggaca attacaaaca ggaatcgaat    720
gcaaccggcg caggaacact gccagcgcat caacaatatt ttcacctgaa tcaggatatt    780
cttctaatac ctggaatgct gtttttcccgg ggatcgcagt ggtgagtaac catgcatcat    840
caggagtacg gataaaatgc ttgatggtcg gaagaggcat aaattccgtc agccagttta    900
gtctgaccat ctcatctgta acatcattgg caacgctacc tttgccatgt ttcagaaaca    960
actctggcgc atcgggcttc ccatacaatc gatagattgt cgcacctgat tgccccacat    1020
tatcgcgagc ccatttatac ccatataaat cagcatccat gttggaattt aatcgcggcc    1080
tcgagcaaga cgtttcccgt tgaatatggc tcataacacc ccttgtatta ctgtttatgt    1140
aagcagacag ttttattgtt catgatgata tatttttatc ttgtgcaatg taacatcaga    1200
gattttgaga cacaacgtgg ctttcccccc cccccggca tgcctgcagg tcgacataaa    1260
tcaatattgg ctattggcca ttgcatacgt tgtatctata tcataatatg tacatttata    1320
ttggctcatg tccaatatga ccgccatgtt gacattgatt attgactagt tattaatagt    1380
aatcaattac ggggtcatta gttcatagcc catatatgga gttccgcgtt acataactta    1440
cggtaaatgg cccgcctcgt gaccgcccaa cgacccccgc ccattgacgt caataatgac    1500
gtatgttccc atagtaacgc caatagggac tttccattga cgtcaatggg tggagtattt    1560
acggtaaact gcccacttgg cagtacatca agtgtatcat atgccaagtc cggcccccta    1620
ttgacgtcaa tgacggtaaa tggcccgcct ggcattatgc ccagtacatg accttacggg    1680
actttcctac ttggcagtac atctacgtat tagtcatcgc tattaccatg gtgatgcggt    1740
tttggcagta caccaatggg cgtggatagc ggtttgactc acggggattt ccaagtctcc    1800
accccattga cgtcaatggg agtttgtttt ggcaccaaaa tcaacgggac tttccaaaat    1860
gtcgtaataa ccccgccccg ttgacgcaaa tgggcggtag cgtgtacgg tgggaggtct    1920 atataagcag agctcgttta gtgaaccgtc agatcgcctg gagacgccat ccacgctgtt    1980
ttgacctcca tagaagacac cgggaccgat ccagcctccg cggccgggaa cggtgcattg    2040
gaacgcggat tccccgtgcc aagagtgacg taagtaccgc ctatagactc tataggcaca    2100
cccctttggc tcttatgcat gctatactgt ttttggcttg gggcctatac accccgctc    2160 cttatgctat aggtgatggt atagcttagc ctataggtgt gggttattga ccattattga    2220
ccactcccct attggtgacg atactttcca ttactaatcc ataacatggc tctttgccac    2280
aactatctct attggctata tgccaatact ctgtccttca gagactgaca cggactctgt    2340 attttttacag gatggggtcc catttattat ttacaaattc acatatacaa caacgccgtc    2400
```

```
ccccgtgccc gcagtttttta ttaaacatag cgtgggatct ccacgcgaat ctcgggtacg      2460
tgttccggac atgggctctt ctccggtagc ggcggagctt ccacatccga gccctggtcc      2520
catgcctcca gcggctcatg gtcgctcggc agctccttgc tcctaacagt ggaggccaga      2580
cttaggcaca gcacaatgcc caccaccacc agtgtgccgc acaaggccgt ggcggtaggg      2640
tatgtgtctg aaaatgagct cggagattgg gctcgcaccg tgacgcagat ggaagactta      2700
aggcagcggc agaagaagat gcaggcagct gagttgttgt attctgataa gagtcagagg      2760
taactcccgt tgcggtgctg ttaacggtgg agggcagtgt agtctgagca gtactcgttg      2820
ctgccgcgcg cgccaccaga cataatagct gacagactaa cagactgttc ctttccatgg      2880
gtcttttctg cagtcaccgt ccaagcttgc ggccgcggat ctgcaggaat cggcacgag       2940 agtagtagac tccgcaagaa acagcagtta aagaacaata ggatcatgtg gagtttgcta      3000
ttactggccg ctttagttgg ccaaggcttt gcattaaaaa atgtatttga catgagaatt      3060
cagttgcccc actcagtcaa ctttggggaa acaagtgtgt caggctatac agaatttccc      3120
ccactctcat tacaggaggc agaacagcta gtgccagaga gctcatgcaa catggacaac      3180
caccagtcac tctcaacaat aaataaatta accaaggtca tatggcggaa aaaagcaaat      3240
caggaatcag caaaccagaa ttcatttgaa gttgtggaaa gtgaagtcag ctttaaaggg      3300
ttgtgtatgt taaagcatag aatggttgaa gaatcatata gaaataggag atcagtaatc      3360
tgttatgatc tagcctgtaa tagtacattc tgtaaaccaa ctgtttatat gattgttcct      3420
atacatgctt gcaacatgat gaaaagctgt ttgattggcc ttggccccta cagaatccag      3480
gttgtctatg aaaggacata ctgcactacg ggtatattga cagaaggaaa atgctttgtc      3540
cctgacaagg ctgttgtcag tgcattgaaa agaggcatgt atgctatagc aagcatagag      3600
acaatctgct tttttattca tcagaaaggg aatacatata agatagtgac tgccattaca      3660
tcagcaatgg gctccaaatg taataataca gatactaaag ttcaaggata ttatatctgt      3720
attattggtg gaaactccgc ccctgtatat gcccctgctg gtgaagactt cagagcaatg      3780 gaggttttt ctgggattat tacatcacca catggagaag accatgacct acccggcgaa      3840
gaaatcgcaa cgtaccagat ttcagggcag atagaggcaa aaatccctca tacagtgagc      3900
tccaaaaact taaaattgac tgcttttgca ggtattccat catactcatc aactagtata      3960
ttggctgctt cagaagatgg tcgtttcata tttagtcctg gtttatttcc taacctaaat      4020
cagtcagtct gtgacaacaa tgcactccct ttaatctgga ggggcctaat tgatttaacg      4080
ggatactatg aggcagtcca cccttgcaat gtgttctgtg tcttatcagg accaggtgct      4140
tcatgtgagg ccttttcaga aggaggtatt ttcaatatta cttctccaat gtgtctggtg      4200
tctaagcaaa atagatttag agcagctgag cagcagatta gctttgtctg ccaaagagtt      4260
gatatggata ttatagtgta ctgtaatggt cagaaaaaaa caatcctaac aaaaacatta      4320
gttataggcc aatgtattta tactattaca agtctctttt cactgttacc aggggttgcc      4380
cattctattg ctattgagtt gtgtgttcca gggtttcatg gctgggccac agctgcactt      4440
ttgattacat tctgcttcgg ctgggtattg attcctgcat gtacattagc tattctttta      4500
gtccttaagt tctttgcaaa tatccttcat acaagcaatc aagagaaccg attcaaagcc      4560
attctacgga aaataaagga gggagtttgaa aaaacaaagg gttccatggt ttgtgagatc      4620
tgtaagtatg agtgtgaaac attaaaggaa ttgaaggcac ataacctatc atgtgttcaa      4680
ggagagtgcc catattgctt tacccactgt gaaccgacaa aaactgcaat tcaggcacat      4740
tacaaagttt gtcaagccac ccaccgattc agagaagatt taaaaaagac tgtaactcct      4800
```

```
caaaatattg ggccaggctg ttaccgaaca ctaaatcttt ttaggtataa aagtaggtgt    4860
tatattctga caatgtggac tcttcttctc attattgaat ccatcctctg ggcagcaagt    4920
gcagcagaaa tcccccttgt ccctctctgg acagataatg ctcatggcgt tgggagtgtt    4980
cctatgcata cggatcttga attagacttc tctttgccat ccagttctaa gtacacatac    5040
aaaagacatc tcacaaaccc agttaatgac aacagagtg tctcattgca tatagaaatt    5100
gaaagtcaag gcattggtgc tgctgttcat catcttggac attggtatga tgcaagattg    5160
aatctaaaaa cctcatttca ttgttatggt gcctgcacaa aatatcaata cccatggcac    5220
actgcaaaat gccattttga gaaagattat gagtatgaaa atagctgggc ttgcaacccc    5280
ccagattgcc caggggttgg tacaggttgt actgcttgtg gattatatct agatcaattg    5340
aagccggtag gaacagcctt taaaattata agtgtaagat acagtagaaa agtgtgcgtg    5400
cagtttggtg aagaacacct ttgtaaaaca attgatatga atgattgctt tgtgactagg    5460
catgccaaaa tatgtataat tgggactgta tctaagtttt ctcaaggtga cactctacta    5520
tttctggggc ccatggaagg aggtggtata atctttaaac actggtgtac atctacctgt    5580
cactttggag accctggtga tgtcatgggt ccaaaagata aaccatttat ttgccctgaa    5640
ttcccagggc aatttaggaa aaaatgtaac tttgccacaa ctccagtttg tgaatatgat    5700
ggaaacatta tatcaggcta taagaaagta cttgcaacaa ttgattcttt ccaatcattt    5760
aacacaagca atatacactt cactgatgag agaattgaat ggagagaccc tgatggcatg    5820
cttcgggatc atattaatat tgttatttct aaagatattg attttgaaaa tttggctgag    5880
aatccttgta aagtagggct ccaggcagca aacatagaag gtgcctgggg ttcaggtgtc    5940
gggtttacac tcacatgcaa ggtgtctctc acagaatgcc caacatttct tacatcaata    6000
aaggcctgtg acatggcaat ttgttatggt gcagaaagtg tgacactctc acgaggacaa    6060
aatactgtca aaattaccgg gaaggtggc catagtggtt cttcattcaa atgctgtcat    6120
gggaaagaat gttcatcaac tggcctccaa gccagtgcac cacatctgga taaggtaaat    6180
ggtatctctg agttagaaaa cgagaaagtt tatgatgacg gtgcacctga atgtggcatt    6240
acttgttggt ttaaaaaatc aggtgaatgg gttatgggta taatcaatgg gaactgggtt    6300
gtcctaattg tcttgtgtgt actgctgctc ttttctctta tcctgttgag catcttgtgt    6360
cctgttagaa agcataaaaa atcataaatc ccacctaaca atcttcacat catgtatcga    6420
ttttcaaaca ctttatcatt tagaacttaa cttggcacta ctatctgata actgactttc    6480
attttattt ttatatggat taattactaa aaaaaatact ctctcgtgcc gaattcgata    6540
tcaagcttat cgataccgtc gacctcgagg ggggcccgg tacccgggat cctcgcaatc    6600
cctaggagga ttaggcaagg gcttgagctc acgctcttgt gagggacaga aatacaatca    6660
ggggcagtat atgaatactc catggagaaa cccagatcta cgtatgatca gcctcgactg    6720
tgccttctag ttgccagcca tctgttgttt gcccctcccc cgtgccttcc ttgaccctgg    6780
aaggtgccac tcccactgtc ctttcctaat aaaatgagga aattgcatcg cattgtctga    6840
gtaggtgtca ttctattctg ggggtgggg tggggcagga cagcaagggg gaggattggg    6900
aagacaatag caggcatgct ggggatgcgg tgggctctat ggcttctgag gcggaaagaa    6960
ccagctgggg ctcgacagct cgactctaga attgcttcct cgctcactga ctcgctgcgc    7020
tcggtcgttc ggctgcggcg agcggtatca gctcactcaa aggcggtaat acggttatcc    7080
acagaatcag gggataacgc aggaaagaac atgtgagcaa aaggccagca aaggccagg     7140
```

```
aaccgtaaaa aggccgcgtt gctggcgttt tccataggc tccgccccc tgacgagcat    7200 cacaaaaatc gacgctcaag tcagaggtgg cgaaacccga caggactata aagataccag  7260
gcgtttcccc ctggaagctc cctcgtgcgc tctcctgttc cgaccctgcc gcttaccgga  7320
tacctgtccg cctttctccc ttcgggaagc gtggcgcttt ctcaatgctc acgctgtagg  7380
tatctcagtt cggtgtaggt cgttcgctcc aagctgggct gtgtgcacga accccccgtt  7440
cagcccgacc gctgcgcctt atccggtaac tatcgtcttg agtccaaccc ggtaagacac  7500
gacttatcgc cactggcagc agccactggt aacaggatta gcagagcgag gtatgtaggc  7560
ggtgctacag agttcttgaa gtggtggcct aactacggct acactagaag gacagtattt  7620
ggtatctgcg ctctgctgaa gccagttacc ttcggaaaaa gagttggtag ctcttgatcc  7680
ggcaaacaaa ccaccgctgg tagcggtggt ttttttgttt gcaagcagca gattacgcgc  7740
agaaaaaaag gatctcaaga gatcctttg atcttttcta cggggtctga cgctcagtgg   7800
aacgaaaact cacgttaagg gattttggtc atcagattat caaaaaggat cttcacctag  7860
atccttttaa attaaaaatg aagttttaaa tcaatctaaa gtatatatga gtaaacttgg  7920
tctgacagtt accaatgctt aatcagtgag gcacctatct cagcgatctg tctatttcgt  7980
tcatccatag ttgcctgact c                                           8001

<210> SEQ ID NO 14
<211> LENGTH: 3447
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
atgggcgagc tgtcccctgt gtgcctgtac ctgctgctgc agggcctgct gctgtgtaac   60
accggagccg ccaggaacct gaacgagctg aagatggagt gccccacac catcagactg  120 ggccagggcc tggtggtggg cagcgtggag ctgcccagcc tgcccatcca gcaggtggag  180
accctgaagc tggagagcag ctgtaacttc gacctgcaca ccagcacagc cggccagcag  240
agcttcacca gtggacctg ggagatcaag ggcgacctgg ccgagaacac ccaggccagc  300
agcaccagct tccagaccaa gagcagcgag gtgaacctga gaggcctgtg cctgatcccc  360
acactggtgg tggagaccgc cgccagaatg agaaagacca tcgcctgcta cgacctgagc  420
tgtaaccaga ccgtgtgtca gcctaccgtg tacctgatgg cctatcca gacctgtatc   480 accaccaaga gctgcctgct gtccctgggc gatcagagaa tccaggtgaa ctacgagaaa  540
acctactgtg tgagcggcca gctggtggag ggcatctgct tcaaccccat ccacaccatg  600
gccctgagcc agcctagcca cacctacgac atcatgacca tgatggtgag atgctttctg  660
gtgatcaaga aggtgaccag cggcgacagc atgaagatcg agaagaactt cgagaccctg  720
gtgcagaaga tggctgtac cgccaacaac ttccagggc actacatctg cctgatcggc  780
agcagcagcg agcccctgta cgtgcccgcc ctggacgact acagaagcgc cgaggtgctg  840
tccagaatgg ccttcgcccc ccacggcgag gaccacgaca tcgagaaaaa cgccgtgtcc  900
gccatgagaa tcgccggcaa ggtgaccggc aaggccccca gcaccgagtc cagcgacacc  960
gtgcagggca tcgccttcag cggcagcccc ctgtacacct ccaccggcgt gctgaccagc  1020
aaggacgacc ccgtgtacat ctgggccct ggcatcatca tggagggcaa ccacagcatc  1080
tgtgagaaga aaccctgcc cctgacctgg accggcttca tcagcctgcc cggcgagatc  1140
```

-continued

```
gagaaaacca cccagtgtac cgtgttctgt accctggccg gacctggcgc cgactgtgag   1200
gcctacagcg agaccggcat cttcaacatc agcagcccca cctgcctgat caaccgggtg   1260
cagaggttca gaggcagcga gcagcagatc aagtttgtgt gccagcgggt ggacatggac   1320
atcaccgtgt actgtaacgg catgaagaag gtgatcctga ccaagacact ggtgatcggc   1380
cagtgtatct acaccttcac cagcatcttc tccctgatcc ccggcgtggc ccacagcctg   1440
gccgtggagc tgtgtgtgcc cggcctgcac ggctgggcca ccatgctgct gctgctgacc   1500
ttctgcttcg gctgggtgct gatccctacc atcaccatga tcctgctgaa gatcctgatc   1560
gccttcgcct acctgtgctc caagtacaac accgacagca agttcagaat cctgatcgag   1620
aaagtgaagc gggagtacca gaaaaccatg ggcagcatgg tgtgtgaagt gtgccagtac   1680
gagtgtgaga ccgccaagga gctggagtcc cacagaaaga gctgctccat cggcagctgc   1740
ccctactgcc tgaaccccag cgaggccacc acctccgccc tgcaggccca cttcaaagtg   1800
tgtaagctga ccagccggtt ccaggagaac ctgaggaagt ccctgaccgt gtacgagccc   1860
atgcagggct gctacagaac cctgagcctg ttccggtaca ggagccggtt ctttgtgggc   1920
ctggtgtggt gtgtgctgct ggtgctggag ctgattgtgt gggccgccag cgccgagacc   1980
cagaacctga atgccggctg gaccgacacc gcccacggca gcggcatcat ccccatgaaa   2040
accgacctgg agctggactt cagcctgcct agcagcgcct cctacaccta caggcggcag   2100
ctgcagaatc ctgccaacga gcaggagaag atccccttcc acctgcagct gtccaagcag   2160
gtgatccacg ccgagattca gcacctgggc cactggatgg acgccacctt caacctgaaa   2220
accgccttcc actgctacgg cagctgtgag aagtacgcct acccttggca gaccgccggc   2280
tgcttcatcg agaaggacta cgagtacgag accggctggg gctgtaatcc tcctgattgc   2340
cccggagtgg gcaccggctg tactgcatgt ggcgtgtacc tggacaagct gaagtctgtg   2400
ggcaaggtgt tcaagatcgt gtccctgagg tacacccgga agtgtgtat ccagctgggc   2460
accgagcaga cctgtaagac cgtggacagc aacgattgcc tgatcacaac cagcgtgaaa   2520
gtgtgtctga tcggcaccat cagcaagttc cagcccagcg ataccctgct gtttctgggc   2580
ccctgcagc agggcggcct gatcttcaag cagtggtgta ccaccacctg ccagttcggc   2640
gatcccggcg atatcatgag cacccccacc ggcatgaagt gccctgagct gaacggcagc   2700
ttccggaaga agtgtgcctt cgccaccacc cctgtgtgtc agttcgacgg caacaccatc   2760
agcggctaca gcggatgat cgccaccaag gacagcttcc agtccttcaa cgtgaccgag   2820
ccccacatca gcaccagcgc cctggagtgg atcgatcccg acagcagcct gagggaccac   2880
atcaacgtga tcgtgtccag ggacctgagc ttcaggacc tgagcgagac cccctgccag   2940
atcgacctgg ccaccgccag catcgatggc gcctggggca gcggagtggg cttcaacctg   3000
gtgtgtacag tgagcctgac cgagtgtagc gccttcctga ccagcatcaa agcctgtgac   3060
gccgccatgt gttacggcag caccaccgcc aacctggtga gaggcagaa caccatccac   3120
attgtgggca aaggcggcca cagcggcagc aagtttatgt gctgccacga caccaagtgt   3180
agcagcaccg gcctggtggc cgctgccccc cacctggaca gagtgaccgg ctacaaccag   3240
gccgacagcg acaagatttt cgacgacgga gcccctgagt gtggcatgag ttgctggttc   3300
aagaagagcg gcgagtggat tctgggcgtg ctgaacggga attggatggt ggtggccgtg   3360
ctggtcgtgc tgctgatcct gagcatcctg ctgttcaccc tgtgctgccc taggagaccc   3420
agctaccgga aggagcacaa gcccctga                                       3447
```

<210> SEQ ID NO 15
<211> LENGTH: 1140
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 15

```
Met Val Gly Trp Val Cys Ile Phe Leu Val Val Leu Thr Thr Ala Thr
1               5                   10                  15

Ala Gly Leu Thr Arg Asn Leu Tyr Glu Leu Gln Ile Glu Cys Pro His
            20                  25                  30

Thr Val Gly Leu Gly Gln Gly Tyr Val Thr Gly Ser Val Glu Thr Thr
        35                  40                  45

Pro Ile Leu Leu Thr Gln Val Ala Asp Leu Lys Ile Glu Ser Ser Cys
    50                  55                  60

Asn Phe Asp Leu His Val Pro Ala Thr Thr Gln Lys Tyr Asn Gln
65                  70                  75                  80

Val Asp Trp Thr Lys Ser Ser Thr Thr Glu Ser Thr Asn Ala Gly
                85                  90                  95

Ala Thr Thr Phe Glu Ala Lys Thr Lys Glu Val Asn Leu Lys Gly Thr
            100                 105                 110

Cys Asn Ile Pro Pro Thr Thr Phe Glu Ala Ala Tyr Lys Ser Arg Lys
        115                 120                 125

Thr Val Ile Cys Tyr Asp Leu Ala Cys Asn Gln Thr His Cys Leu Pro
    130                 135                 140

Thr Val His Leu Ile Ala Pro Val Gln Thr Cys Met Ser Val Arg Ser
145                 150                 155                 160

Cys Met Ile Gly Leu Leu Ser Ser Arg Ile Gln Val Ile Tyr Glu Lys
                165                 170                 175

Thr Tyr Cys Val Thr Gly Gln Leu Ile Glu Gly Leu Cys Phe Ile Pro
            180                 185                 190

Thr His Thr Ile Ala Leu Thr Gln Pro Gly His Thr Tyr Asp Thr Met
        195                 200                 205

Thr Leu Pro Val Thr Cys Phe Leu Val Ala Lys Lys Leu Gly Thr Gln
    210                 215                 220

Leu Lys Leu Ala Val Glu Leu Glu Lys Leu Ile Thr Gly Val Ser Cys
225                 230                 235                 240

Ala Glu Asn Ser Phe Gln Gly Tyr Tyr Ile Cys Phe Ile Gly Lys His
                245                 250                 255

Ser Glu Pro Leu Phe Val Pro Thr Met Glu Asp Tyr Arg Ser Ala Glu
            260                 265                 270

Leu Phe Thr Arg Met Val Leu Asn Pro Arg Gly Glu Asp His Asp Pro
        275                 280                 285

Asp Gln Asn Gly Gln Gly Leu Met Arg Ile Ala Gly Pro Val Thr Ala
    290                 295                 300

Lys Val Pro Ser Thr Glu Thr Thr Glu Thr Met Gln Gly Ile Ala Phe
305                 310                 315                 320

Ala Gly Ala Pro Met Tyr Ser Ser Phe Ser Thr Leu Val Arg Lys Ala
                325                 330                 335

Asp Pro Glu Tyr Val Phe Ser Pro Gly Ile Ile Ala Glu Ser Asn His
            340                 345                 350

Ser Val Cys Asp Lys Lys Thr Val Pro Leu Thr Trp Thr Gly Phe Leu
        355                 360                 365
```

-continued

```
Ala Val Ser Gly Glu Ile Glu Arg Ile Thr Gly Cys Thr Val Phe Cys
370                 375                 380

Thr Leu Ala Gly Pro Gly Ala Ser Cys Glu Ala Tyr Ser Glu Thr Gly
385                 390                 395                 400

Ile Phe Asn Ile Ser Ser Pro Thr Cys Leu Val Asn Lys Val Gln Lys
                405                 410                 415

Phe Arg Gly Ser Glu Gln Arg Ile Asn Phe Met Cys Gln Arg Val Asp
                420                 425                 430

Gln Gly Val Val Val Tyr Cys Asn Gly Gln Lys Lys Val Ile Leu Thr
            435                 440                 445

Lys Thr Leu Val Ile Gly Gln Cys Ile Tyr Thr Phe Thr Ser Leu Phe
450                 455                 460

Ser Leu Ile Pro Gly Val Ala His Ser Leu Ala Val Glu Leu Cys Val
465                 470                 475                 480

Pro Gly Leu His Gly Trp Ala Thr Thr Ala Leu Leu Ile Thr Phe Cys
                485                 490                 495

Phe Gly Trp Leu Leu Ile Pro Thr Val Thr Leu Ile Ile Leu Lys Ile
                500                 505                 510

Leu Arg Leu Leu Thr Phe Pro Cys Ser His Tyr Ser Thr Glu Ser Lys
                515                 520                 525

Phe Lys Val Ile Leu Glu Arg Val Lys Val Glu Tyr Gln Lys Thr Met
530                 535                 540

Gly Ser Met Val Cys Asp Ile Cys His His Glu Cys Glu Thr Ala Lys
545                 550                 555                 560

Glu Leu Glu Thr His Lys Lys Ser Cys Pro Glu Gly Gln Cys Pro Tyr
                565                 570                 575

Cys Met Thr Ile Thr Glu Ser Thr Glu Ser Ala Leu Gln Ala His Phe
                580                 585                 590

Ser Ile Cys Lys Leu Thr Asn Arg Phe Gln Glu Asn Leu Lys Lys Ser
            595                 600                 605

Leu Lys Arg Pro Glu Val Arg Lys Gly Cys Tyr Arg Thr Leu Gly Val
610                 615                 620

Phe Arg Tyr Lys Ser Arg Cys Tyr Val Gly Leu Val Trp Gly Ile Leu
625                 630                 635                 640

Leu Thr Thr Glu Leu Ile Ile Trp Ala Ala Ser Ala Asp Thr Pro Leu
                645                 650                 655

Met Glu Ser Gly Trp Ser Asp Thr Ala His Gly Val Gly Ile Val Pro
                660                 665                 670

Met Lys Thr Asp Leu Glu Leu Asp Phe Ala Leu Ala Ser Ser Ser Ser
                675                 680                 685

Tyr Ser Tyr Arg Arg Lys Leu Val Asn Pro Ala Asn Gln Glu Glu Thr
690                 695                 700

Leu Pro Phe His Phe Gln Leu Asp Lys Gln Val Val His Ala Glu Ile
705                 710                 715                 720

Gln Asn Leu Gly His Trp Met Asp Gly Thr Phe Asn Ile Lys Thr Ala
                725                 730                 735

Phe His Cys Tyr Gly Glu Cys Lys Lys Tyr Ala Tyr Pro Trp Gln Thr
                740                 745                 750

Ala Lys Cys Phe Phe Glu Lys Asp Tyr Gln Tyr Glu Thr Ser Trp Gly
            755                 760                 765

Cys Asn Pro Pro Asp Cys Pro Gly Val Gly Thr Gly Cys Thr Ala Cys
770                 775                 780

Gly Val Tyr Leu Asp Lys Leu Arg Ser Val Gly Lys Ala Tyr Lys Ile
```

```
                    785                 790                 795                 800
Val Ser Leu Lys Tyr Thr Arg Lys Val Cys Ile Gln Leu Gly Thr Glu
                805                 810                 815

Gln Thr Cys Lys His Ile Asp Val Asn Asp Cys Leu Val Thr Pro Ser
                820                 825                 830

Val Lys Val Cys Met Ile Gly Thr Ile Ser Lys Leu Gln Pro Gly Asp
                835                 840                 845

Thr Leu Leu Phe Leu Gly Pro Leu Glu Gln Gly Ile Ile Leu Lys
            850                 855                 860

Gln Trp Cys Thr Thr Ser Cys Val Phe Gly Asp Pro Gly Asp Ile Met
865                 870                 875                 880

Ser Thr Thr Ser Gly Met Arg Cys Pro Glu His Thr Gly Ser Phe Arg
                885                 890                 895

Lys Ile Cys Gly Phe Ala Thr Thr Pro Thr Cys Glu Tyr Gln Gly Asn
                900                 905                 910

Thr Val Ser Gly Phe Gln Arg Met Met Ala Thr Arg Asp Ser Phe Gln
                915                 920                 925

Ser Phe Asn Val Thr Glu Pro His Ile Thr Ser Asn Arg Leu Glu Trp
            930                 935                 940

Ile Asp Pro Asp Ser Ser Ile Lys Asp His Ile Asn Met Val Leu Asn
945                 950                 955                 960

Arg Asp Val Ser Phe Gln Asp Leu Ser Asp Asn Pro Cys Lys Val Asp
                965                 970                 975

Leu His Thr Gln Ser Ile Asp Gly Ala Trp Gly Ser Gly Val Gly Phe
            980                 985                 990

Thr Leu Val Cys Thr Val Gly Leu  Thr Glu Cys Ala Asn  Phe Ile Thr
            995                 1000                1005

Ser Ile  Lys Ala Cys Asp Ser  Ala Met Cys Tyr Gly  Ala Thr Val
            1010                1015                1020

Thr Asn  Leu Leu Arg Gly Ser  Asn Thr Val Lys Val  Val Gly Lys
            1025                1030                1035

Gly Gly  His Ser Gly Ser Leu  Phe Lys Cys Cys His  Asp Thr Asp
            1040                1045                1050

Cys Thr  Glu Glu Gly Leu Ala  Ala Ser Pro Pro His  Leu Asp Arg
            1055                1060                1065

Val Thr  Gly Tyr Asn Gln Ile  Asp Ser Asp Lys Val  Tyr Asp Asp
            1070                1075                1080

Gly Ala  Pro Pro Cys Thr Ile  Lys Cys Trp Phe Thr  Lys Ser Gly
            1085                1090                1095

Glu Trp  Leu Leu Gly Ile Leu  Asn Gly Asn Trp Val  Val Val Ala
            1100                1105                1110

Val Leu  Ile Val Ile Leu Ile  Leu Ser Ile Leu Leu  Phe Ser Phe
            1115                1120                1125

Phe Cys  Pro Val Arg Asn Arg  Lys Asn Lys Ala Asn
            1130                1135                1140

<210> SEQ ID NO 16
<211> LENGTH: 1140
<212> TYPE: PRT
<213> ORGANISM: Sin Nombre virus
<220> FEATURE:
<223> OTHER INFORMATION: strain Convict Creek 107

<400> SEQUENCE: 16

Met Val Gly Trp Val Cys Ile Phe Leu Val Val Leu Thr Thr Ala Thr
```

-continued

```
1               5                   10                  15
Ala Gly Leu Thr Arg Asn Leu Tyr Glu Leu Lys Ile Glu Cys Pro His
                20                  25                  30

Thr Val Gly Leu Gly Gln Gly Tyr Val Thr Gly Ser Val Glu Thr Thr
                35                  40                  45

Pro Ile Leu Leu Thr Gln Val Ala Asp Leu Lys Ile Glu Ser Ser Cys
                50                  55                  60

Asn Phe Asp Leu His Val Pro Ala Thr Thr Gln Lys Tyr Asn Gln
65                  70                  75                  80

Val Asp Trp Thr Lys Lys Ser Ser Thr Glu Ser Thr Asn Ala Gly
                    85                  90                  95

Ala Thr Thr Phe Glu Ala Lys Thr Lys Glu Val Asn Leu Lys Gly Thr
                100                 105                 110

Cys Asn Ile Pro Pro Thr Thr Phe Glu Ala Ala Tyr Lys Ser Arg Lys
                115                 120                 125

Thr Val Ile Cys Tyr Asp Leu Ala Cys Asn Gln Thr His Cys Leu Pro
                130                 135                 140

Thr Val His Leu Ile Ala Pro Val Gln Thr Cys Met Ser Val Arg Ser
145                 150                 155                 160

Cys Met Ile Gly Leu Leu Ser Ser Arg Ile Gln Val Ile Tyr Glu Lys
                165                 170                 175

Thr Tyr Cys Val Thr Gly Gln Leu Ile Glu Gly Leu Cys Phe Ile Pro
                180                 185                 190

Thr His Thr Ile Ala Leu Thr Gln Pro Gly His Thr Tyr Asp Thr Met
                195                 200                 205

Thr Leu Pro Val Thr Cys Phe Leu Val Ala Lys Lys Leu Gly Thr Gln
                210                 215                 220

Leu Lys Leu Ala Val Glu Leu Glu Lys Leu Ile Thr Gly Val Ser Cys
225                 230                 235                 240

Thr Glu Asn Ser Phe Gln Gly Tyr Tyr Ile Cys Phe Ile Gly Lys His
                245                 250                 255

Ser Glu Pro Leu Phe Val Pro Thr Met Glu Asp Tyr Arg Ser Ala Glu
                260                 265                 270

Leu Phe Thr Arg Met Val Leu Asn Pro Arg Gly Glu Asp His Asp Pro
                275                 280                 285

Asp Gln Asn Gly Gln Gly Leu Met Arg Ile Ala Gly Pro Val Thr Ala
                290                 295                 300

Lys Val Pro Ser Thr Glu Thr Thr Glu Thr Met Gln Gly Ile Ala Phe
305                 310                 315                 320

Ala Gly Ala Pro Met Tyr Ser Ser Phe Ser Thr Leu Val Arg Lys Ala
                325                 330                 335

Asp Pro Glu Tyr Val Phe Ser Pro Gly Ile Ile Ala Glu Ser Asn His
                340                 345                 350

Ser Val Cys Asp Lys Lys Thr Val Pro Leu Thr Trp Thr Gly Phe Leu
                355                 360                 365

Ala Val Ser Gly Glu Ile Glu Arg Ile Thr Gly Cys Thr Val Phe Cys
                370                 375                 380

Thr Leu Ala Gly Pro Gly Ala Ser Cys Glu Ala Tyr Ser Glu Thr Gly
385                 390                 395                 400

Ile Phe Asn Ile Ser Ser Pro Thr Cys Leu Val Asn Lys Val Gln Lys
                405                 410                 415

Phe Arg Gly Ser Glu Gln Arg Ile Asn Phe Met Cys Gln Arg Val Asp
                420                 425                 430
```

-continued

```
Gln Asp Val Val Tyr Cys Asn Gly Gln Lys Lys Val Ile Leu Thr
        435                 440                 445
Lys Thr Leu Val Ile Gly Gln Cys Ile Tyr Thr Phe Thr Ser Leu Phe
    450                 455                 460
Ser Leu Ile Pro Gly Val Ala His Ser Leu Ala Val Glu Leu Cys Val
465                 470                 475                 480
Pro Gly Leu His Gly Trp Ala Thr Thr Ala Leu Leu Ile Thr Phe Cys
                485                 490                 495
Phe Gly Trp Leu Leu Ile Pro Thr Val Thr Leu Ile Ile Leu Lys Ile
                500                 505                 510
Leu Arg Leu Leu Thr Phe Ser Cys Ser His Tyr Ser Thr Glu Ser Lys
                515                 520                 525
Phe Lys Val Ile Leu Glu Arg Val Lys Val Glu Tyr Gln Lys Thr Met
                530                 535                 540
Gly Ser Met Val Cys Asp Ile Cys His His Glu Cys Glu Thr Ala Lys
545                 550                 555                 560
Glu Leu Glu Thr His Lys Lys Ser Cys Pro Glu Gly Gln Cys Pro Tyr
                565                 570                 575
Cys Met Thr Ile Thr Glu Ser Thr Glu Ser Ala Leu Gln Ala His Phe
                580                 585                 590
Ser Ile Cys Lys Leu Thr Asn Arg Phe Gln Glu Ile Leu Lys Lys Ser
                595                 600                 605
Leu Lys Arg Pro Glu Val Arg Lys Gly Cys Tyr Arg Thr Leu Gly Val
                610                 615                 620
Phe Arg Tyr Lys Ser Arg Cys Tyr Val Gly Leu Val Trp Gly Ile Leu
625                 630                 635                 640
Leu Thr Thr Glu Leu Ile Ile Trp Ala Ala Ser Ala Asp Thr Pro Leu
                645                 650                 655
Met Glu Ser Gly Trp Ser Asp Thr Ala His Gly Val Gly Ile Val Pro
                660                 665                 670
Met Lys Thr Asp Leu Glu Leu Asp Phe Ala Leu Ala Ser Ser Ser Ser
                675                 680                 685
Tyr Ser Tyr Arg Arg Lys Leu Val Asn Pro Ala Asn Gln Glu Glu Thr
                690                 695                 700
Leu Pro Phe His Phe Gln Leu Asp Lys Gln Val Val His Ala Glu Ile
705                 710                 715                 720
Gln Asn Leu Gly His Trp Met Asp Gly Thr Phe Asn Ile Lys Thr Ala
                725                 730                 735
Phe His Cys Tyr Gly Glu Cys Lys Lys Tyr Ala Tyr Pro Trp Gln Thr
                740                 745                 750
Ala Lys Cys Phe Phe Glu Lys Asp Tyr Gln Tyr Glu Thr Ser Trp Gly
                755                 760                 765
Cys Asn Pro Pro Asp Cys Pro Gly Val Gly Thr Gly Cys Thr Ala Cys
                770                 775                 780
Gly Val Tyr Leu Asp Lys Leu Arg Ser Val Gly Lys Ala Tyr Lys Ile
785                 790                 795                 800
Val Ser Leu Lys Tyr Thr Arg Lys Val Cys Ile Gln Leu Gly Thr Glu
                805                 810                 815
Gln Thr Cys Lys His Ile Asp Val Asn Asp Cys Leu Val Thr Pro Ser
                820                 825                 830
Val Lys Val Cys Met Ile Gly Thr Ile Ser Lys Leu Gln Pro Gly Asp
                835                 840                 845
```

Thr Leu Leu Phe Leu Gly Pro Leu Glu Gln Gly Gly Ile Ile Leu Lys
            850                 855                 860

Gln Trp Cys Thr Thr Ser Cys Val Phe Gly Asp Pro Gly Asp Ile Met
865                 870                 875                 880

Ser Thr Thr Ser Gly Met Arg Cys Pro Glu His Thr Gly Ser Phe Arg
            885                 890                 895

Lys Ile Cys Gly Phe Ala Thr Thr Pro Thr Cys Glu Tyr Gln Gly Asn
            900                 905                 910

Thr Val Ser Gly Phe Gln Arg Met Met Ala Thr Arg Asp Ser Phe Gln
            915                 920                 925

Ser Phe Asn Val Thr Glu Pro His Ile Thr Ser Asn Arg Leu Glu Trp
930                 935                 940

Ile Asp Pro Asp Ser Ser Ile Lys Asp His Ile Asn Met Val Leu Asn
945                 950                 955                 960

Arg Asp Val Ser Phe Gln Asp Leu Ser Asp Asn Pro Cys Lys Val Asp
            965                 970                 975

Leu His Thr Gln Ser Ile Asp Gly Ala Trp Gly Ser Gly Val Gly Phe
            980                 985                 990

Thr Leu Val Cys Thr Val Gly Leu Thr Glu Cys Ala Asn Phe Ile Thr
            995                1000                1005

Ser Ile Lys Ala Cys Asp Ser Ala Met Cys Tyr Gly Ala Thr Val
    1010                1015                1020

Thr Asn Leu Leu Arg Gly Ser Asn Thr Val Lys Val Val Gly Lys
    1025                1030                1035

Gly Gly His Ser Gly Ser Leu Phe Lys Cys Cys His Asp Thr Asp
    1040                1045                1050

Cys Thr Glu Glu Gly Leu Ala Ala Ser Pro Pro His Leu Asp Arg
    1055                1060                1065

Val Thr Gly Tyr Asn Gln Ile Asp Ser Asp Lys Val Tyr Asp Asp
    1070                1075                1080

Gly Ala Pro Pro Cys Thr Ile Lys Cys Trp Phe Thr Arg Ser Gly
    1085                1090                1095

Glu Trp Leu Leu Gly Ile Leu Asn Gly Asn Trp Val Val Val Ala
    1100                1105                1110

Val Leu Ile Val Ile Leu Leu Ser Ile Leu Leu Phe Ser Phe
    1115                1120                1125

Phe Cys Pro Val Arg Asn Arg Lys Asn Lys Ala Asn
    1130                1135                1140

<210> SEQ ID NO 17
<211> LENGTH: 1140
<212> TYPE: PRT
<213> ORGANISM: Sin Nombre virus
<220> FEATURE:
<223> OTHER INFORMATION: strain Convict Creek 107 isolate 74

<400> SEQUENCE: 17

Met Val Gly Trp Val Cys Ile Phe Leu Val Leu Thr Thr Ala Thr
1               5                   10                  15

Ala Gly Leu Thr Arg Asn Leu Tyr Glu Leu Lys Ile Glu Cys Pro His
            20                  25                  30

Thr Val Gly Leu Gly Gln Gly Tyr Val Thr Gly Ser Val Glu Thr Thr
        35                  40                  45

Pro Ile Leu Leu Thr Gln Val Ala Asp Leu Lys Ile Glu Ser Ser Cys
    50                  55                  60

```
Asn Phe Asp Leu His Val Pro Ala Thr Thr Thr Gln Lys Tyr Asn Gln
 65                  70                  75                  80

Val Asp Trp Thr Lys Lys Ser Ser Thr Thr Glu Ser Thr Asn Ala Gly
                 85                  90                  95

Ala Thr Thr Phe Glu Ala Lys Thr Lys Glu Val Asn Leu Lys Gly Thr
                100                 105                 110

Cys Asn Ile Pro Pro Thr Thr Phe Glu Ala Ala Phe Lys Ser Arg Lys
            115                 120                 125

Thr Val Ile Cys Tyr Asp Leu Ala Cys Asn Gln Thr His Cys Leu Pro
        130                 135                 140

Thr Val His Leu Ile Ala Pro Val Gln Thr Cys Met Ser Val Arg Ser
145                 150                 155                 160

Cys Met Ile Gly Leu Leu Ser Ser Arg Ile Gln Val Ile Tyr Glu Lys
                165                 170                 175

Thr Tyr Cys Val Thr Gly Gln Leu Ile Glu Gly Leu Cys Phe Ile Pro
                180                 185                 190

Thr His Thr Ile Ala Leu Thr Gln Pro Gly His Thr Tyr Asp Thr Met
            195                 200                 205

Thr Leu Pro Val Thr Cys Phe Leu Val Ala Lys Lys Leu Gly Thr Gln
        210                 215                 220

Leu Lys Leu Ala Val Glu Leu Glu Lys Leu Ile Thr Gly Val Ser Cys
225                 230                 235                 240

Thr Glu Asn Ser Phe Gln Gly Tyr Tyr Ile Cys Phe Ile Gly Lys His
                245                 250                 255

Ser Glu Pro Leu Phe Val Pro Thr Met Glu Asp Tyr Arg Ser Ala Glu
                260                 265                 270

Leu Phe Thr Arg Met Val Leu Asn Pro Arg Gly Glu Asp His Asp Pro
            275                 280                 285

Asp Gln Asn Gly Gln Gly Leu Met Arg Ile Ala Gly Pro Val Thr Ala
        290                 295                 300

Lys Val Pro Ser Thr Glu Thr Thr Glu Thr Met Gln Gly Ile Ala Phe
305                 310                 315                 320

Ala Gly Ala Pro Met Tyr Ser Ser Phe Ser Thr Leu Val Arg Lys Ala
                325                 330                 335

Asp Pro Glu Tyr Val Phe Ser Pro Gly Ile Ile Ala Glu Ser Asn His
            340                 345                 350

Ser Val Cys Asp Lys Lys Thr Val Pro Leu Thr Trp Thr Gly Phe Leu
        355                 360                 365

Ala Val Ser Gly Glu Ile Glu Arg Ile Thr Gly Cys Thr Val Phe Cys
        370                 375                 380

Thr Leu Ala Gly Pro Gly Ala Ser Cys Glu Ala Tyr Ser Glu Thr Gly
385                 390                 395                 400

Ile Phe Asn Ile Ser Ser Pro Thr Cys Leu Val Asn Lys Val Gln Lys
                405                 410                 415

Phe Arg Gly Ser Glu Gln Arg Ile Asn Phe Met Cys Gln Arg Val Asp
            420                 425                 430

Gln Asp Val Val Val Tyr Cys Asn Gly Gln Lys Lys Val Ile Leu Thr
        435                 440                 445

Lys Thr Leu Val Ile Gly Gln Cys Ile Tyr Thr Phe Thr Ser Leu Phe
        450                 455                 460

Ser Leu Ile Pro Gly Val Ala His Ser Leu Ala Val Glu Leu Cys Val
465                 470                 475                 480

Pro Gly Leu His Gly Trp Ala Thr Thr Ala Leu Leu Ile Thr Phe Cys
```

```
                485                 490                 495
Phe Gly Trp Leu Leu Ile Pro Thr Val Thr Leu Ile Ile Leu Lys Ile
            500                 505                 510
Leu Arg Leu Leu Thr Phe Ser Cys Ser His Tyr Ser Thr Glu Ser Lys
            515                 520                 525
Phe Lys Val Ile Leu Glu Arg Val Lys Val Glu Tyr Gln Lys Thr Met
            530                 535                 540
Gly Ser Met Val Cys Asp Ile Cys His His Glu Cys Glu Thr Ala Lys
545                 550                 555                 560
Glu Leu Glu Thr His Lys Lys Ser Cys Pro Glu Gly Gln Cys Pro Tyr
                565                 570                 575
Cys Met Thr Ile Thr Glu Ser Thr Glu Ser Ala Leu Gln Ala His Phe
                580                 585                 590
Ser Ile Cys Lys Leu Thr Asn Arg Phe Gln Glu Ile Leu Lys Lys Ser
                595                 600                 605
Leu Lys Arg Pro Glu Val Arg Lys Gly Cys Tyr Arg Thr Leu Gly Val
            610                 615                 620
Phe Arg Tyr Lys Ser Arg Cys Tyr Val Gly Leu Val Trp Gly Ile Leu
625                 630                 635                 640
Leu Thr Thr Glu Leu Ile Ile Trp Ala Ala Ser Ala Asp Thr Pro Leu
                645                 650                 655
Met Glu Ser Gly Trp Ser Asp Thr Ala His Gly Val Gly Ile Val Pro
                660                 665                 670
Met Lys Thr Asp Leu Glu Leu Asp Phe Ala Leu Ala Ser Ser Ser Ser
            675                 680                 685
Tyr Ser Tyr Arg Arg Lys Leu Val Asn Pro Ala Asn Gln Glu Glu Thr
            690                 695                 700
Leu Pro Phe His Phe Gln Leu Asp Lys Gln Val Val His Ala Glu Ile
705                 710                 715                 720
Gln Asn Leu Gly His Trp Met Asp Gly Thr Phe Asn Ile Lys Thr Ala
                725                 730                 735
Phe His Cys Tyr Gly Glu Cys Lys Lys Tyr Ala Tyr Pro Trp Gln Thr
            740                 745                 750
Ala Lys Cys Phe Phe Glu Lys Asp Tyr Gln Tyr Glu Thr Ser Trp Gly
            755                 760                 765
Cys Asn Pro Pro Asp Cys Pro Gly Val Gly Thr Gly Cys Thr Ala Cys
            770                 775                 780
Gly Val Tyr Leu Asp Lys Leu Arg Ser Val Gly Lys Ala Tyr Lys Ile
785                 790                 795                 800
Val Ser Leu Lys Tyr Thr Arg Lys Val Cys Ile Gln Leu Gly Thr Glu
                805                 810                 815
Gln Thr Cys Lys His Ile Asp Val Asn Asp Cys Leu Val Thr Pro Ser
            820                 825                 830
Val Lys Val Cys Met Ile Gly Thr Ile Ser Lys Leu Gln Pro Gly Asp
            835                 840                 845
Thr Leu Leu Phe Leu Gly Pro Leu Glu Gln Gly Gly Ile Ile Leu Lys
            850                 855                 860
Gln Trp Cys Thr Thr Ser Cys Val Phe Gly Asp Pro Gly Asp Ile Met
865                 870                 875                 880
Ser Thr Thr Ser Gly Met Arg Cys Pro Glu His Thr Gly Ser Phe Arg
                885                 890                 895
Lys Ile Cys Gly Phe Ala Thr Thr Pro Thr Cys Glu Tyr Gln Gly Asn
            900                 905                 910
```

```
Thr Val Ser Gly Phe Gln Arg Met Met Ala Thr Arg Asp Ser Phe Gln
        915                 920                 925

Ser Phe Asn Val Thr Glu Pro His Ile Thr Ser Asn Arg Leu Glu Trp
        930                 935                 940

Ile Asp Pro Asp Ser Ser Ile Lys Asp His Ile Asn Met Val Leu Asn
945                 950                 955                 960

Arg Asp Val Ser Phe Gln Asp Leu Ser Asp Asn Pro Cys Lys Val Asp
                965                 970                 975

Leu His Thr Gln Ser Ile Asp Gly Ala Trp Gly Ser Gly Val Gly Phe
                980                 985                 990

Thr Leu Val Cys Thr Val Gly Leu Thr Glu Cys Ala Asn Phe Ile Thr
                995                 1000                1005

Ser Ile Lys Ala Cys Asp Ser Ala Met Cys Tyr Gly Ala Thr Val
        1010                1015                1020

Thr Asn Leu Leu Arg Gly Ser Asn Thr Val Lys Val Val Gly Lys
        1025                1030                1035

Gly Gly His Ser Gly Ser Leu Phe Lys Cys Cys His Asp Thr Asp
        1040                1045                1050

Cys Thr Glu Glu Gly Leu Ala Ala Ser Pro Pro His Leu Asp Arg
        1055                1060                1065

Val Thr Gly Tyr Asn Gln Ile Asp Ser Asp Lys Val Tyr Asp Asp
        1070                1075                1080

Gly Ala Pro Pro Cys Thr Ile Lys Cys Trp Phe Thr Lys Ser Gly
        1085                1090                1095

Glu Trp Leu Leu Gly Ile Leu Asn Gly Asn Trp Val Val Val Ala
        1100                1105                1110

Val Leu Ile Val Ile Leu Ile Leu Ser Ile Leu Leu Phe Ser Phe
        1115                1120                1125

Phe Cys Pro Val Arg Asn Arg Lys Asn Lys Ala Asn
        1130                1135                1140

<210> SEQ ID NO 18
<211> LENGTH: 1140
<212> TYPE: PRT
<213> ORGANISM: Sin Nombre virus
<220> FEATURE:
<223> OTHER INFORMATION: strain NMH10

<400> SEQUENCE: 18

Met Val Gly Trp Val Cys Ile Phe Leu Val Val Leu Thr Thr Ala Thr
1               5                   10                  15

Ala Gly Leu Thr Arg Asn Leu Tyr Glu Leu Lys Ile Glu Cys Pro His
                20                  25                  30

Thr Val Gly Leu Gly Gln Gly Tyr Val Thr Gly Ser Val Glu Ile Thr
        35                  40                  45

Pro Ile Leu Leu Thr Gln Val Ala Asp Leu Lys Ile Glu Ser Ser Cys
    50                  55                  60

Asn Phe Asp Leu His Val Pro Ala Thr Thr Thr Gln Lys Tyr Asn Gln
65                  70                  75                  80

Val Asp Trp Thr Lys Lys Ser Ser Thr Thr Glu Ser Thr Asn Ala Gly
                85                  90                  95

Ala Thr Thr Phe Glu Ala Lys Thr Lys Glu Ile Asn Leu Lys Gly Thr
                100                 105                 110

Cys Asn Ile Pro Pro Thr Thr Phe Glu Ala Ala Tyr Lys Ser Arg Lys
            115                 120                 125
```

-continued

```
Thr Val Ile Cys Tyr Asp Leu Ala Cys Asn Gln Thr His Cys Leu Pro
        130                 135                 140

Thr Val His Leu Ile Ala Pro Val Gln Thr Cys Met Ser Val Arg Ser
145                 150                 155                 160

Cys Met Ile Gly Leu Leu Ser Ser Arg Ile Gln Val Ile Tyr Glu Lys
                    165                 170                 175

Thr Tyr Cys Val Thr Gly Gln Leu Ile Glu Gly Leu Cys Phe Ile Pro
                180                 185                 190

Thr His Thr Ile Ala Leu Thr Gln Pro Gly His Thr Tyr Asp Thr Met
            195                 200                 205

Thr Leu Pro Val Thr Cys Phe Leu Val Ala Lys Lys Leu Gly Thr Gln
        210                 215                 220

Leu Lys Leu Ala Val Glu Leu Glu Lys Leu Ile Thr Gly Val Ser Cys
225                 230                 235                 240

Thr Glu Asn Ser Phe Gln Gly Tyr Tyr Ile Cys Phe Ile Gly Lys His
                    245                 250                 255

Ser Glu Pro Leu Phe Val Pro Thr Met Glu Asp Tyr Arg Ser Ala Glu
                260                 265                 270

Leu Phe Thr Arg Met Val Leu Asn Pro Arg Gly Glu Asp His Asp Pro
            275                 280                 285

Asp Gln Asn Gly Gln Gly Leu Met Arg Ile Ala Gly Pro Val Thr Ala
        290                 295                 300

Lys Val Pro Ser Thr Glu Thr Thr Glu Thr Met Gln Gly Ile Ala Phe
305                 310                 315                 320

Ala Gly Ala Pro Met Tyr Ser Ser Phe Ser Thr Leu Val Arg Lys Ala
                    325                 330                 335

Asp Pro Glu Tyr Val Phe Ser Pro Gly Ile Ile Ala Glu Ser Asn His
                340                 345                 350

Ser Val Cys Asp Lys Lys Thr Val Pro Leu Thr Trp Thr Gly Phe Leu
            355                 360                 365

Ala Val Ser Gly Glu Ile Glu Lys Ile Thr Gly Cys Thr Val Phe Cys
        370                 375                 380

Thr Leu Ala Gly Pro Gly Ala Ser Cys Glu Ala Tyr Ser Glu Thr Gly
385                 390                 395                 400

Ile Phe Asn Ile Ser Ser Pro Thr Cys Leu Val Asn Lys Val Gln Lys
                    405                 410                 415

Phe Arg Gly Ser Glu Gln Arg Ile Asn Phe Met Cys Gln Arg Val Asp
                420                 425                 430

Gln Asp Val Val Tyr Cys Asn Gly Gln Lys Lys Val Ile Leu Thr
            435                 440                 445

Lys Thr Leu Val Ile Gly Gln Cys Ile Tyr Thr Phe Thr Ser Leu Phe
450                 455                 460

Ser Leu Ile Pro Gly Val Ala His Ser Leu Ala Val Glu Leu Cys Val
465                 470                 475                 480

Pro Gly Leu His Gly Trp Ala Thr Thr Ala Leu Leu Ile Thr Phe Cys
                    485                 490                 495

Phe Gly Trp Leu Leu Ile Pro Ala Val Thr Leu Ile Ile Leu Lys Ile
                500                 505                 510

Leu Arg Leu Leu Thr Phe Ser Cys Ser His Tyr Ser Thr Glu Ser Lys
            515                 520                 525

Phe Lys Val Ile Leu Glu Arg Val Lys Val Glu Tyr Gln Lys Thr Met
        530                 535                 540
```

-continued

```
Gly Ser Met Val Cys Asp Ile Cys His His Glu Cys Glu Thr Ala Lys
545                 550                 555                 560

Glu Leu Glu Thr His Lys Lys Ser Cys Pro Glu Gly Gln Cys Pro Tyr
            565                 570                 575

Cys Met Thr Ile Thr Glu Ser Thr Glu Ser Ala Leu Gln Ala His Phe
                580                 585                 590

Ala Ile Cys Lys Leu Thr Asn Arg Phe Gln Glu Asn Leu Lys Lys Ser
            595                 600                 605

Leu Lys Arg Pro Glu Val Arg Lys Gly Cys Tyr Arg Thr Leu Gly Val
    610                 615                 620

Phe Arg Tyr Lys Ser Arg Cys Tyr Val Gly Leu Val Trp Gly Ile Leu
625                 630                 635                 640

Leu Thr Thr Glu Leu Ile Ile Trp Ala Ala Ser Ala Asp Thr Pro Leu
                645                 650                 655

Met Glu Ser Gly Trp Ser Asp Thr Ala His Gly Val Gly Ile Ile Pro
                660                 665                 670

Met Lys Thr Asp Leu Glu Leu Asp Phe Ala Leu Ala Ser Ser Ser Ser
            675                 680                 685

Tyr Ser Tyr Arg Arg Lys Leu Val Asn Pro Ala Asn Gln Glu Glu Thr
    690                 695                 700

Leu Pro Phe His Phe Gln Leu Asp Lys Gln Val Val His Ala Glu Ile
705                 710                 715                 720

Gln Asn Leu Gly His Trp Met Asp Gly Thr Phe Asn Ile Lys Thr Ala
                725                 730                 735

Phe His Cys Tyr Gly Glu Cys Lys Lys Tyr Ala Tyr Pro Trp Gln Thr
            740                 745                 750

Ala Lys Cys Phe Phe Glu Lys Asp Tyr Gln Tyr Glu Thr Ser Trp Gly
            755                 760                 765

Cys Asn Pro Pro Asp Cys Pro Gly Val Gly Thr Gly Cys Thr Ala Cys
    770                 775                 780

Gly Val Tyr Leu Asp Lys Leu Arg Ser Val Gly Lys Ala Tyr Lys Ile
785                 790                 795                 800

Val Ser Leu Lys Tyr Thr Arg Lys Val Cys Ile Gln Leu Gly Thr Glu
                805                 810                 815

Gln Thr Cys Lys His Ile Asp Val Asn Asp Cys Leu Val Thr Pro Ser
            820                 825                 830

Val Lys Val Cys Met Ile Gly Thr Ile Ser Lys Leu Gln Pro Gly Asp
    835                 840                 845

Thr Leu Leu Phe Leu Gly Pro Leu Glu Gln Gly Gly Ile Ile Leu Lys
    850                 855                 860

Gln Trp Cys Thr Thr Ser Cys Val Phe Gly Asp Pro Gly Asp Ile Met
865                 870                 875                 880

Ser Thr Thr Ser Gly Met Arg Cys Pro Glu His Thr Gly Ser Phe Arg
                885                 890                 895

Lys Ile Cys Gly Phe Ala Thr Thr Pro Thr Cys Glu Tyr Gln Gly Asn
            900                 905                 910

Thr Val Ser Gly Phe Gln Arg Met Met Ala Thr Arg Asp Ser Phe Gln
            915                 920                 925

Ser Phe Asn Val Thr Glu Pro His Ile Thr Ser Asn Arg Leu Glu Trp
            930                 935                 940

Ile Asp Pro Asp Ser Ser Ile Lys Asp His Ile Asn Met Val Leu Asn
945                 950                 955                 960

Arg Asp Val Ser Phe Gln Asp Leu Ser Asp Asn Pro Cys Lys Val Asp
```

```
                       965                 970                 975
Leu His Thr Gln Ser Ile Asp Gly Ala Trp Gly Ser Gly Val Gly Phe
                980                 985                 990

Thr Leu Val Cys Thr Val Gly Leu  Thr Glu Cys Ala Asn  Phe Ile Thr
        995                 1000                1005

Ser Ile Lys Ala Cys Asp Ser  Ala Met Cys Tyr Gly  Ala Thr Val
    1010                1015                1020

Thr Asn Leu Leu Arg Gly Ser  Asn Thr Val Lys Val  Val Gly Lys
    1025                1030                1035

Gly Gly His Ser Gly Ser Leu  Phe Lys Cys Cys His  Asp Thr Asp
    1040                1045                1050

Cys Thr Glu Glu Gly Leu Ala  Ala Ser Pro Pro His  Leu Asp Arg
    1055                1060                1065

Val Thr Gly Tyr Asn Gln Ile  Asp Ser Asp Lys Val  Tyr Asp Asp
    1070                1075                1080

Gly Ala Pro Pro Cys Thr Ile  Lys Cys Trp Phe Thr  Lys Ser Gly
    1085                1090                1095

Glu Trp Leu Leu Gly Ile Leu  Asn Gly Asn Trp Val  Val Val Ala
    1100                1105                1110

Val Leu Ile Val Ile Leu Ile  Leu Ser Ile Leu Leu  Phe Ser Phe
    1115                1120                1125

Phe Cys Pro Val Arg Ser Arg  Lys Asn Lys Ala Asn
    1130                1135                1140

<210> SEQ ID NO 19
<211> LENGTH: 1140
<212> TYPE: PRT
<213> ORGANISM: New York virus

<400> SEQUENCE: 19

Met Val Gly Trp Val Cys Ile Ser Leu Val Val Leu Ala Thr Thr Thr
1               5                   10                  15

Ala Gly Leu Thr Arg Asn Leu Tyr Glu Leu Lys Ile Glu Cys Pro His
            20                  25                  30

Thr Val Gly Leu Gly Gln Gly Tyr Val Thr Gly Ser Val Glu Thr Thr
        35                  40                  45

Pro Ile Leu Leu Thr Gln Val Thr Asp Leu Lys Ile Glu Ser Ser Cys
    50                  55                  60

Asn Phe Asp Leu His Val Pro Ser Thr Ser Ile Gln Lys Tyr Asn Gln
65                  70                  75                  80

Val Glu Trp Ala Lys Lys Ser Ser Thr Thr Glu Ser Thr Ser Ala Gly
                85                  90                  95

Ala Thr Thr Phe Glu Ala Lys Thr Lys Glu Val Ser Leu Lys Gly Thr
            100                 105                 110

Cys Asn Ile Pro Val Thr Thr Phe Glu Ala Ala Tyr Lys Ser Arg Lys
        115                 120                 125

Thr Val Ile Cys Tyr Asp Leu Ala Cys Asn Gln Thr His Cys Leu Pro
    130                 135                 140

Thr Val His Leu Ile Ala Pro Val Gln Thr Cys Met Ser Val Arg Ser
145                 150                 155                 160

Cys Met Ile Gly Leu Leu Ser Ser Arg Ile Gln Val Ile Tyr Glu Lys
                165                 170                 175

Thr Tyr Cys Val Thr Gly Gln Leu Val Glu Gly Leu Cys Phe Ile Pro
            180                 185                 190
```

```
Thr His Thr Ile Ala Leu Thr Gln Pro Gly His Thr Tyr Asp Thr Met
        195                 200                 205
Thr Leu Pro Ile Thr Cys Phe Leu Val Ala Lys Lys Leu Gly Thr Gln
    210                 215                 220
Leu Lys Ile Ala Val Glu Leu Glu Lys Leu Ile Thr Ala Ser Gly Cys
225                 230                 235                 240
Thr Glu Asn Ser Phe Gln Gly Tyr Tyr Ile Cys Phe Leu Gly Lys His
                245                 250                 255
Ser Glu Pro Leu Phe Val Pro Met Met Asp Asp Tyr Arg Ser Ala Glu
            260                 265                 270
Leu Phe Thr Arg Met Val Leu Asn Pro Arg Gly Glu Asp His Asp Pro
        275                 280                 285
Asp Gln Asn Gly Gln Gly Leu Met Arg Ile Ala Gly Pro Ile Thr Ala
    290                 295                 300
Lys Val Pro Ser Thr Glu Thr Thr Glu Thr Met Gln Gly Ile Ala Phe
305                 310                 315                 320
Ala Gly Ala Pro Met Tyr Ser Ser Phe Ser Thr Leu Val Arg Lys Ala
                325                 330                 335
Asp Pro Asp Tyr Val Phe Ser Pro Gly Ile Ile Ala Glu Ser Asn His
            340                 345                 350
Ser Val Cys Asp Lys Lys Thr Ile Pro Leu Thr Trp Thr Gly Phe Leu
        355                 360                 365
Ala Val Ser Gly Glu Ile Glu Lys Ile Thr Gly Cys Thr Val Phe Cys
    370                 375                 380
Thr Leu Val Gly Pro Gly Ala Ser Cys Glu Ala Tyr Ser Glu Thr Gly
385                 390                 395                 400
Ile Phe Asn Ile Ser Ser Pro Thr Cys Leu Val Asn Lys Val Gln Lys
                405                 410                 415
Phe Arg Gly Ser Glu Gln Arg Ile Asn Phe Met Cys Gln Arg Val Asp
            420                 425                 430
Gln Asp Val Ile Val Tyr Cys Asn Gly Gln Lys Lys Val Ile Leu Thr
        435                 440                 445
Lys Thr Leu Val Ile Gly Gln Cys Ile Tyr Thr Phe Thr Ser Leu Phe
    450                 455                 460
Ser Leu Ile Pro Gly Val Ala His Ser Leu Ala Val Glu Leu Cys Val
465                 470                 475                 480
Pro Gly Leu His Gly Trp Ala Thr Thr Ala Leu Leu Ile Thr Phe Cys
                485                 490                 495
Phe Gly Trp Leu Leu Ile Pro Thr Ile Thr Met Ile Ile Leu Lys Ile
            500                 505                 510
Leu Arg Leu Leu Thr Phe Ser Cys Ser His Tyr Ser Thr Glu Ser Lys
        515                 520                 525
Phe Lys Ala Ile Leu Glu Arg Val Lys Val Glu Tyr Gln Lys Thr Met
    530                 535                 540
Gly Ser Met Val Cys Asp Val Cys His Glu Cys Glu Thr Ala Lys
545                 550                 555                 560
Glu Leu Glu Thr His Lys Lys Ser Cys Pro Glu Gly Gln Cys Pro Tyr
                565                 570                 575
Cys Met Thr Met Thr Glu Ser Thr Glu Ser Ala Leu Gln Ala His Phe
            580                 585                 590
Ser Ile Cys Lys Leu Thr Asn Arg Phe Gln Glu Asn Leu Lys Lys Ser
        595                 600                 605
Leu Lys Arg Pro Glu Val Lys Gln Gly Cys Tyr Arg Thr Leu Gly Val
```

```
                610                 615                 620
Phe Arg Tyr Lys Ser Arg Cys Tyr Val Gly Leu Val Trp Gly Val Leu
625                 630                 635                 640

Leu Thr Thr Glu Leu Ile Val Trp Ala Ala Ser Ala Asp Thr Pro Leu
                645                 650                 655

Met Glu Ser Gly Trp Ser Asp Thr Ala His Gly Val Gly Ile Val Pro
            660                 665                 670

Met Lys Thr Asp Leu Glu Leu Asp Phe Ala Leu Ala Ser Ser Ser Ser
            675                 680                 685

Tyr Ser Tyr Arg Arg Lys Leu Val Asn Pro Ala Asn Lys Glu Glu Thr
            690                 695                 700

Leu Pro Phe His Phe Gln Leu Asp Lys Gln Val Val His Ala Glu Ile
705                 710                 715                 720

Gln Asn Leu Gly His Trp Met Asp Gly Thr Phe Asn Ile Lys Thr Ala
                725                 730                 735

Phe His Cys Tyr Gly Glu Cys Lys Lys Tyr Ala Tyr Pro Trp Gln Thr
                740                 745                 750

Ala Lys Cys Phe Phe Glu Lys Asp Tyr Gln Tyr Glu Thr Ser Trp Gly
            755                 760                 765

Cys Asn Pro Pro Asp Cys Pro Gly Val Gly Thr Gly Cys Thr Ala Cys
770                 775                 780

Gly Val Tyr Leu Asp Lys Leu Arg Ser Val Gly Lys Ala Tyr Lys Ile
785                 790                 795                 800

Val Ser Leu Lys Phe Thr Arg Lys Val Cys Ile Gln Leu Gly Thr Glu
                805                 810                 815

Gln Thr Cys Lys His Ile Asp Val Asn Asp Cys Leu Val Thr Pro Ser
            820                 825                 830

Val Lys Val Cys Leu Ile Gly Thr Ile Ser Lys Leu Gln Pro Gly Asp
            835                 840                 845

Thr Leu Leu Phe Leu Gly Pro Leu Glu Gln Gly Gly Ile Ile Leu Lys
            850                 855                 860

Gln Trp Cys Thr Thr Ser Cys Val Phe Gly Asp Pro Gly Asp Ile Met
865                 870                 875                 880

Ser Thr Thr Thr Gly Met Lys Cys Pro Glu His Thr Gly Ser Phe Arg
                885                 890                 895

Lys Ile Cys Gly Phe Ala Thr Thr Pro Thr Cys Glu Tyr Gln Gly Asn
            900                 905                 910

Thr Ile Ser Gly Phe Gln Arg Met Met Ala Thr Arg Asp Ser Phe Gln
            915                 920                 925

Ser Phe Asn Val Thr Glu Pro His Ile Thr Ser Asn Arg Leu Glu Trp
930                 935                 940

Ile Asp Pro Asp Ser Ser Ile Lys Asp His Ile Asn Met Val Leu Asn
945                 950                 955                 960

Arg Asp Val Ser Phe Gln Asp Leu Ser Asp Asn Pro Cys Lys Val Asp
                965                 970                 975

Leu His Thr Gln Ser Ile Asp Gly Ala Trp Gly Ser Gly Val Gly Phe
            980                 985                 990

Thr Leu Val Cys Thr Val Gly Leu Thr Glu Cys Ala Asn Phe Ile Thr
            995                 1000                1005

Ser Ile Lys Ala Cys Asp Ser Ala Met Cys Tyr Gly Ala Thr Val
    1010                1015                1020

Thr Asn Leu Leu Arg Gly Ser Asn Thr Val Lys Val Val Gly Lys
    1025                1030                1035
```

```
Gly Gly His Ser Gly Ser Leu Phe Lys Cys Cys His Asp Thr Asp
    1040                1045                1050

Cys Thr Glu Glu Gly Leu Ala Ala Ser Pro Pro His Leu Asp Arg
    1055                1060                1065

Val Thr Gly Tyr Asn Gln Ile Asp Ser Asp Lys Val Tyr Asp Asp
    1070                1075                1080

Gly Ala Pro Pro Cys Thr Ile Lys Cys Trp Phe Thr Lys Ser Gly
    1085                1090                1095

Glu Trp Leu Leu Gly Ile Leu Asn Gly Asn Trp Val Val Val Ala
    1100                1105                1110

Val Leu Ile Val Ile Leu Ile Leu Ser Ile Leu Leu Phe Ser Phe
    1115                1120                1125

Phe Cys Pro Ile Arg Gly Arg Lys Asn Lys Ser Asn
    1130                1135                1140

<210> SEQ ID NO 20
<211> LENGTH: 1140
<212> TYPE: PRT
<213> ORGANISM: New York virus

<400

-continued

```
                260                 265                 270
Leu Phe Thr Arg Met Val Leu Asn Pro Arg Gly Glu Asp His Asp Pro
            275                 280                 285

Asp Gln Asn Gly Gln Gly Leu Met Arg Ile Ala Gly Pro Ile Thr Ala
            290                 295                 300

Lys Val Pro Ser Thr Glu Thr Thr Glu Ala Met Gln Gly Ile Ala Phe
305                 310                 315                 320

Ala Gly Ala Pro Met Tyr Ser Ser Phe Ser Thr Leu Val Arg Lys Ala
            325                 330                 335

Asp Pro Asp Tyr Val Phe Ser Pro Gly Ile Ile Ala Glu Ser Asn His
            340                 345                 350

Ser Val Cys Asp Lys Lys Thr Ile Pro Leu Thr Trp Thr Gly Phe Leu
            355                 360                 365

Ala Val Ser Gly Glu Ile Glu Lys Ile Thr Gly Cys Thr Val Phe Cys
            370                 375                 380

Thr Leu Val Gly Pro Gly Ala Ser Cys Glu Ala Tyr Ser Glu Thr Gly
385                 390                 395                 400

Ile Phe Asn Ile Ser Ser Pro Thr Cys Leu Val Asn Lys Val Gln Lys
            405                 410                 415

Phe Arg Gly Ser Glu Gln Arg Ile Asn Phe Met Cys Gln Arg Val Asp
            420                 425                 430

Gln Asp Val Ile Val Tyr Cys Asn Gly Gln Lys Lys Val Ile Leu Thr
            435                 440                 445

Lys Thr Leu Val Ile Gly Gln Cys Ile Tyr Thr Phe Thr Ser Leu Phe
            450                 455                 460

Ser Leu Ile Pro Gly Val Ala His Ser Leu Ala Val Glu Leu Cys Val
465                 470                 475                 480

Pro Gly Leu His Gly Trp Ala Thr Thr Ala Leu Leu Ile Thr Phe Cys
            485                 490                 495

Phe Gly Trp Leu Leu Ile Pro Thr Ile Thr Met Ile Ile Leu Lys Ile
            500                 505                 510

Leu Arg Leu Leu Thr Phe Ser Cys Ser His Tyr Ser Thr Glu Ser Lys
            515                 520                 525

Phe Lys Ala Ile Leu Glu Arg Val Lys Val Glu Tyr Gln Lys Thr Met
            530                 535                 540

Gly Ser Met Val Cys Asp Val Cys His Glu Cys Glu Thr Ala Lys
545                 550                 555                 560

Glu Leu Glu Thr His Lys Lys Ser Cys Pro Glu Gly Gln Cys Pro Tyr
            565                 570                 575

Cys Met Thr Met Thr Glu Ser Thr Glu Ser Ala Leu Gln Ala His Phe
            580                 585                 590

Ser Ile Cys Lys Leu Thr Asn Arg Phe Gln Glu Asn Leu Lys Lys Ser
            595                 600                 605

Leu Lys Arg Pro Glu Val Lys Gln Gly Cys Tyr Arg Thr Leu Gly Val
            610                 615                 620

Phe Arg Tyr Lys Ser Arg Cys Tyr Val Gly Leu Val Trp Gly Val Leu
625                 630                 635                 640

Leu Thr Thr Glu Leu Ile Val Trp Ala Ala Ser Ala Asp Thr Pro Leu
            645                 650                 655

Met Glu Ser Gly Trp Ser Asp Thr Ala His Gly Val Gly Ile Val Pro
            660                 665                 670

Met Lys Thr Asp Leu Glu Leu Asp Phe Ala Leu Ala Ser Ser Ser Ser
            675                 680                 685
```

-continued

Tyr Ser Tyr Arg Arg Lys Leu Val Asp Pro Ala Asn Lys Glu Glu Thr
    690             695                 700

Leu Pro Phe His Phe Gln Leu Asp Lys Gln Val His Ala Glu Ile
705             710                 715                 720

Gln Asn Leu Gly His Trp Met Asp Gly Thr Phe Asn Ile Lys Thr Ala
                725                 730                 735

Phe His Cys Tyr Gly Glu Cys Lys Lys Tyr Ala Tyr Pro Trp Gln Thr
            740                 745                 750

Ala Lys Cys Phe Phe Glu Lys Asp Tyr Gln Tyr Glu Thr Ser Trp Gly
        755                 760                 765

Cys Asn Pro Pro Asp Cys Pro Gly Val Gly Thr Gly Cys Thr Ala Cys
    770                 775                 780

Gly Val Tyr Leu Asp Lys Leu Arg Ser Val Gly Lys Ala Tyr Lys Ile
785                 790                 795                 800

Val Ser Leu Lys Phe Thr Arg Lys Val Cys Ile Gln Leu Gly Thr Glu
                805                 810                 815

Gln Thr Cys Lys His Ile Asp Val Asn Asp Cys Leu Val Thr Pro Ser
                820                 825                 830

Val Lys Val Cys Leu Ile Gly Thr Ile Ser Lys Leu Gln Pro Gly Asp
            835                 840                 845

Thr Leu Leu Phe Leu Gly Pro Leu Glu Gln Gly Gly Ile Ile Leu Lys
        850                 855                 860

Gln Trp Cys Thr Thr Ser Cys Val Phe Gly Asp Pro Gly Asp Ile Met
865             870                 875                 880

Ser Thr Thr Thr Gly Met Lys Cys Pro Glu His Thr Gly Ser Phe Arg
                885                 890                 895

Lys Ile Cys Gly Phe Ala Thr Thr Pro Thr Cys Glu Tyr Gln Gly Asn
                900                 905                 910

Thr Ile Ser Gly Phe Gln Arg Met Met Ala Thr Arg Asp Ser Phe Gln
            915                 920                 925

Ser Phe Asn Val Thr Glu Pro His Ile Thr Ser Asn Arg Leu Glu Trp
        930                 935                 940

Ile Asp Pro Asp Ser Ser Ile Lys Asp His Ile Asn Met Val Leu Asn
945                 950                 955                 960

Arg Asp Val Ser Phe Gln Asp Leu Ser Asp Asn Pro Cys Lys Val Asp
                965                 970                 975

Leu His Thr Gln Ser Ile Asp Gly Ala Trp Gly Ser Gly Val Gly Phe
            980                 985                 990

Thr Leu Val Cys Thr Val Gly Leu Thr Glu Cys Ala Asn Phe Ile Thr
        995                 1000                1005

Ser Ile Lys Ala Cys Asp Ser Ala Met Cys Tyr Gly Ala Thr Val
    1010                1015                1020

Thr Asn Leu Leu Arg Gly Ser Asn Thr Val Lys Val Val Gly Lys
    1025                1030                1035

Gly Gly His Ser Gly Ser Leu Phe Lys Cys Cys His Asp Thr Asp
    1040                1045                1050

Cys Thr Glu Glu Gly Leu Ala Ala Ser Pro Pro His Leu Asp Arg
    1055                1060                1065

Val Thr Gly Tyr Asn Gln Ile Asp Ser Asp Lys Val Tyr Asp Asp
    1070                1075                1080

Gly Ala Pro Pro Cys Thr Ile Lys Cys Trp Phe Thr Lys Ser Gly
    1085                1090                1095

```
Glu Trp Leu Leu Gly Ile Leu Asn Gly Asn Trp Val Val Ala
    1100                1105                1110

Val Leu Ile Val Ile Leu Ile Leu Ser Ile Leu Leu Phe Ser Phe
1115                1120                1125

Phe Cys Pro Ile Arg Gly Arg Lys Asn Lys Ser Asn
1130                1135                1140

<210> SEQ ID NO 21
<211> LENGTH: 1140
<212> TYPE: PRT
<213> ORGANISM: New York virus
<220> FEATURE:
<223> OTHER INFORMATION: strain Rhode Island-1

```
Ala Gly Ala Pro Thr Tyr Ser Ser Phe Ser Thr Leu Val Arg Lys Ala
            325                 330                 335

Asp Pro Asp Tyr Val Phe Ser Pro Gly Ile Ile Ala Glu Ser Asn His
        340                 345                 350

Ser Val Cys Asp Lys Lys Ala Ile Pro Leu Thr Trp Thr Gly Phe Leu
    355                 360                 365

Ala Val Ser Gly Glu Ile Glu Lys Ile Thr Gly Cys Thr Val Phe Cys
370                 375                 380

Thr Leu Val Gly Pro Gly Ala Ser Cys Lys Ala Tyr Ser Glu Thr Gly
385                 390                 395                 400

Ile Phe Asn Ile Ser Ser Pro Thr Cys Leu Val Asn Lys Val Gln Lys
                405                 410                 415

Phe Arg Gly Ser Glu Gln Arg Ile Asn Phe Met Cys Gln Arg Val Asp
            420                 425                 430

Gln Asp Val Ile Val Tyr Cys Asn Gly Gln Lys Lys Val Ile Leu Thr
        435                 440                 445

Lys Thr Leu Ile Ile Gly Gln Cys Ile Tyr Thr Phe Thr Ser Leu Phe
    450                 455                 460

Ser Leu Ile Pro Gly Val Ala His Ser Leu Ala Val Glu Leu Cys Val
465                 470                 475                 480

Pro Gly Leu His Gly Trp Ala Thr Ala Ala Leu Leu Ile Thr Phe Cys
                485                 490                 495

Phe Gly Trp Leu Leu Ile Pro Thr Ile Thr Met Ile Ile Leu Lys Ile
            500                 505                 510

Leu Arg Leu Leu Thr Phe Ser Cys Ser His Tyr Ser Thr Glu Ser Lys
        515                 520                 525

Phe Lys Ala Ile Leu Glu Arg Val Lys Val Glu Tyr Gln Lys Thr Met
    530                 535                 540

Gly Ser Met Val Cys Asp Ala Cys His His Glu Cys Glu Thr Ala Lys
545                 550                 555                 560

Glu Leu Glu Thr His Lys Lys Ser Cys Pro Gly Gln Cys Pro Tyr
                565                 570                 575

Cys Met Thr Met Thr Glu Ser Thr Glu Ser Ala Leu Leu Ala His Phe
            580                 585                 590

Ser Ile Cys Lys Leu Thr Asn Arg Phe Gln Glu Asn Leu Lys Lys Ser
        595                 600                 605

Leu Lys Arg Pro Glu Val Lys Gln Gly Arg Tyr Arg Thr Leu Gly Val
    610                 615                 620

Phe Arg Tyr Lys Ser Arg Cys Tyr Val Gly Leu Val Trp Gly Val Leu
625                 630                 635                 640

Leu Thr Thr Glu Leu Ile Val Trp Ala Ala Ser Ala Asp Thr Pro Leu
                645                 650                 655

Met Glu Ser Gly Trp Ser Asp Thr Ala His Gly Val Gly Ile Val Pro
            660                 665                 670

Met Lys Thr Asp Leu Glu Leu Asp Phe Ala Leu Ala Ser Ser Ser Ser
        675                 680                 685

Tyr Ser Tyr Arg Arg Lys Leu Val Asn Pro Ala Asn Lys Glu Glu Thr
    690                 695                 700

Leu Pro Phe His Phe Gln Leu Asp Lys Gln Val Val His Ala Glu Ile
705                 710                 715                 720

Gln Asn Leu Gly His Trp Met Asp Gly Thr Phe Asn Ile Lys Thr Ala
                725                 730                 735

Phe His Cys Tyr Gly Glu Cys Lys Lys Tyr Ala Tyr Pro Trp Gln Thr
```

-continued

```
                740                 745                 750
Ala Lys Cys Phe Phe Glu Lys Asp Tyr Gln Tyr Glu Thr Ser Trp Gly
                755                 760                 765

Cys Asn Pro Pro Asp Cys Pro Gly Val Gly Thr Gly Cys Thr Ala Cys
        770                 775                 780

Gly Val Tyr Leu Asp Lys Leu Arg Ser Gly Gly Lys Ala Tyr Lys Ile
785                 790                 795                 800

Val Ser Leu Lys Phe Thr Arg Lys Val Cys Ile Gln Leu Gly Thr Glu
                805                 810                 815

Gln Thr Cys Lys His Ile Asp Val Asn Asp Cys Leu Val Thr Pro Ser
        820                 825                 830

Val Lys Val Cys Leu Ile Gly Thr Ile Ser Lys Leu Gln Pro Gly Asp
        835                 840                 845

Thr Leu Leu Phe Leu Gly Pro Leu Glu Gln Gly Gly Ile Ile Leu Lys
        850                 855                 860

Gln Trp Cys Thr Thr Ser Cys Val Phe Gly Asp Pro Gly Asp Ile Met
865                 870                 875                 880

Ser Thr Thr Thr Gly Met Lys Cys Pro Glu His Thr Gly Ser Phe Arg
                885                 890                 895

Lys Ile Cys Gly Phe Ala Thr Thr Pro Thr Cys Glu Tyr Gln Gly Asn
                900                 905                 910

Thr Ile Ser Gly Phe Gln Arg Met Met Ala Thr Arg Asp Ser Phe Gln
                915                 920                 925

Ser Phe Asn Val Thr Glu Pro His Ile Thr Ser Asn Arg Leu Glu Trp
        930                 935                 940

Ile Asp Pro Asp Ser Ser Ile Lys Asp His Ile Asn Met Val Leu Asn
945                 950                 955                 960

Arg Asp Val Ser Phe Gln Asp Leu Ser Asp Asn Pro Cys Lys Val Asp
                965                 970                 975

Leu His Thr Gln Ser Ile Asp Gly Ala Trp Gly Ser Gly Val Gly Phe
        980                 985                 990

Thr Leu Val Cys Thr Val Gly Leu  Thr Glu Cys Ala Asn  Phe Ile Thr
        995                 1000                1005

Ser Ile  Lys Ala Cys Asp Ser  Ala Met Cys Tyr Gly  Ala Thr Val
        1010                1015                1020

Thr Asn  Leu Leu Arg Gly Ser  Asn Thr Val Lys Val  Val Gly Lys
        1025                1030                1035

Gly Gly  His Ser Ser Ser Leu  Phe Lys Cys Cys His  Asp Thr Asp
        1040                1045                1050

Cys Thr  Glu Glu Gly Leu Ala  Ala Ser Pro Pro His  Leu Asp Arg
        1055                1060                1065

Val Thr  Gly Tyr Asn Gln Ile  Asp Ser Asp Lys Val  Tyr Asp Asp
        1070                1075                1080

Gly Ala  Pro Pro Cys Thr Ile  Lys Cys Trp Phe Thr  Lys Ser Gly
        1085                1090                1095

Glu Trp  Leu Leu Gly Ile Leu  Asn Gly Asn Trp Val  Val Val Ala
        1100                1105                1110

Val Leu  Ile Val Ile Leu Ile  Leu Ser Ile Leu Leu  Phe Ser Phe
        1115                1120                1125

Phe Cys  Pro Ile Arg Gly Arg  Lys Asn Lys Ser Asn
        1130                1135                1140
```

<210> SEQ ID NO 22

<211> LENGTH: 3733
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22

| | | | | | |
|---|---|---|---|---|---|
| gcggccgcgg | atctgcagga | attcggcacg | agagtagtag | actccgcacg | aagaagcaaa | 60 |
| cactgaataa | aggatataca | gaatggtagg | gtgggtttgc | atcttcctcg | tggtccttac | 120 |
| tactgcaact | gctggattga | cacggaatct | ctatgaatta | cagatagaat | gtccacatac | 180 |
| tgtgggtcta | ggtcaaggtt | atgtgacagg | ttctgtagaa | actacaccta | ttctcttaac | 240 |
| acaggtagct | gacctcaaga | ttgagagttc | ttgcaatttt | gacttgcatg | tcccagccac | 300 |
| tactactcag | aaatacaatc | aagttgactg | gactaaaaaa | agttctacta | cagaaagcac | 360 |
| gaatgcaggt | gcaactacat | ttgaggctaa | acaaaagag | gtaaatttaa | aaggcacatg | 420 |
| taatattcct | ccaactacgt | ttgaggctgc | atacaagtca | aggaagacag | tgatttgtta | 480 |
| tgatttggcc | tgtaatcaaa | cacattgtct | tcctacagtc | catctgattg | ctcctgttca | 540 |
| aacatgtatg | tctgtacgga | gctgtatgat | aggtctgtta | tctagcagga | tccaggttat | 600 |
| ctacgagaag | acatattgtg | tcacgggtca | gttaatagaa | gggctatgtt | tcattccaac | 660 |
| acatacaatt | gcacttacac | agcctggtca | tacttatgat | actatgacat | tgcctgtgac | 720 |
| ttgtttttta | gtagccaaaa | agttggggac | gcagcttaag | ctggctgttg | agttagagaa | 780 |
| attgattact | ggtgtgagct | gcgcagagaa | tagcttccaa | ggttattaca | tctgttttat | 840 |
| tggaaaacat | tcagagccct | tatttgtacc | aacaatggaa | gattatagat | cagctgagtt | 900 |
| atttactcgt | atggttttaa | atccaagagg | tgaagatcat | gaccctgatc | aaaatggaca | 960 |
| agggttgatg | agaatagctg | gacctgttac | tgccaaggta | ccatctacag | aaacgactga | 1020 |
| aacaatgcaa | ggaattgcat | ttgctggggc | accaatgtat | agttcattct | caactcttgt | 1080 |
| gagaaaagct | gatcctgaat | atgtcttttc | tccaggtata | attgcagaat | caaatcatag | 1140 |
| tgtttgtgat | aaaagacag | tgcccctaac | atggactggg | tttctagcag | tttcaggaga | 1200 |
| gatagaaagg | ataacaggct | gtacagtttt | ctgtacattg | gctggacctg | gtgccagttg | 1260 |
| tgaagcatac | tcagaaacag | gaatcttcaa | cataagctcc | ccaacttgct | tggtaaataa | 1320 |
| agtccaaaaa | tttagaggtt | cagaacaaag | aattaatttt | atgtgtcaaa | gggttgatca | 1380 |
| aggtgttgtg | gtttactgta | atggacagaa | gaaagtcatt | cttaccaaaa | ccctagtaat | 1440 |
| aggtcaatgt | atctacacat | ttactagtct | gttttcactg | atccctggag | ttgctcattc | 1500 |
| ccttgctgtg | gagttatgtg | ttccaggtct | tcatggctgg | gctacaacag | cactacttat | 1560 |
| tactttctgc | tttggctggc | ttctcatacc | aacagttact | ttaattatac | taaaaatctt | 1620 |
| aaggctattg | accttcccat | gctcgcacta | ttctacagaa | tcaaaattca | aagtcatttt | 1680 |
| agaaagagtc | aaggtggagt | atcaaaagac | aatgggttca | atggtgtgtg | acatttgtca | 1740 |
| ccatgaatgt | gagacggcaa | aagagctcga | acacataag | aaaagttgcc | cagaaggtca | 1800 |
| atgcccatac | tgcatgacaa | taactgagtc | cactgagagt | gcattacaag | ctcatttttc | 1860 |
| aatctgtaag | ctaacgaaca | ggttccagga | aaatctaaaa | aaatcattaa | aacgtccaga | 1920 |
| agtaaggaaa | ggttgttaca | ggacattagg | agtattccgc | tacaagagca | ggtgctatgt | 1980 |
| tggcttagta | tgggggatcc | tcttgacgac | agagctgatt | atatgggctg | ctagtgcaga | 2040 |
| taccccctcta | atggagtctg | gttggtcaga | tacagcacat | ggtgtaggta | tagtccctat | 2100 |

```
gaaaacagat ttagagcttg actttgcctt ggcctcatca tcttcttata gttatagaag    2160
aaagcttgta aaccctgcca atcaagagga gacactccct tttcatttcc agttagataa    2220
gcaagtagtg catgcagaaa tacagaacct agggcattgg atggatggca cattcaacat    2280
aaagactgct ttccattgct atggagaatg taaaaaatat gcctatcctt ggcagacagc    2340
caagtgtttc tttgaaaaag attatcagta tgaaacaagc tggggctgta acccaccaga    2400
ttgcccagga gtagggacag gttgtacagc ctgtggggta tacttagaca agctccgttc    2460
agttgggaaa gcctataaaa ttgtatcact caaatacacg cgaaaggtgt gtattcaatt    2520
ggggacagaa caaacctgta aacatataga tgttaatgat tgtttggtca ccccgtctgt    2580
taaagtttgc atgataggta ccatctcgaa gcttcagcca ggtgacacct tattgttttt    2640 gggccctta gagcaaggtg ggattattct aaaacaatgg tgcacaacat catgtgtgtt    2700
tggagaccct ggtgatatca tgtcaacaac aagtgggatg agatgccctg agcacacagg    2760
gtcttttaga aaaatctgtg gatttgctac aacacctaca tgtgaatatc aaggtaatac    2820
agtgtctgga ttccaacgca tgatggcaac tcgagattct tttcaatcat tcaatgtgac    2880
agaaccacat attaccagca atcgactgga atggattgat ccagatagta gtattaaaga    2940
ccatatcaac atggttttga atagagatgt ttccttccaa gatctaagtg ataatccatg    3000
taaggttgat ttgcatacac aatctattga tggggcttgg ggatcaggag tgggctttac    3060
attagtatgt actgtaggtc ttacagagtg tgcaaatttc ataacttcaa ttaaggcgtg    3120
tgattctgct atgtgttatg gggccacagt tacaaatcta ctcagagggt ctaacacagt    3180
taaagttgtc ggtaaaggtg ggcattctgg gtccttgttc aagtgctgcc atgatactga    3240
ctgtactgaa gaaggtttag cagcatcacc acctcattta gatagggtta ctggttacaa    3300
tcaaatagat tctgataagg tttatgatga cggtgcaccg ccctgtacaa ttaaatgttg    3360
gttcacaaag tcaggtgagt ggttgctagg aattcttaat ggcaattggg tagtagttgc    3420
tgttttgatt gtaattttga tactatcaat actcctgttc agcttctttt gtcctgttag    3480
aaatagaaaa aataaggcca attagcaaac atatatgtaa gtaagggtat gatcatatta    3540
tatcattatg cgtatactct tatatctata atatctatgt atccttatac tctaactatt    3600
tatattaatt tttacttta tacaagtatt aactaaccca ttaccagcta aaaaaaacaa    3660
acccttaaca cctatataat cccatttgct tattacgagg cttttgttcc tgcggagtct    3720
actactattc gaa                                                       3733
```